United States Patent
Zhou et al.

(10) Patent No.: US 9,884,863 B2
(45) Date of Patent: Feb. 6, 2018

(54) STAT3 INHIBITOR

(71) Applicant: Board of Regents, The University of Texas System, Austin, TX (US)

(72) Inventors: Jia Zhou, League City, TX (US); Haijun Chen, Fuzhou (CN); Qiang Shen, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/380,798

(22) Filed: Dec. 15, 2016

(65) Prior Publication Data

US 2017/0152260 A1 Jun. 1, 2017

Related U.S. Application Data

(62) Division of application No. 14/760,711, filed as application No. PCT/US2014/011674 on Jan. 15, 2014, now Pat. No. 9,562,002.

(60) Provisional application No. 61/752,866, filed on Jan. 15, 2013.

(51) Int. Cl.
*C07D 471/04* (2006.01)
*C07D 409/12* (2006.01)
*C07D 333/64* (2006.01)

(52) U.S. Cl.
CPC ......... *C07D 471/04* (2013.01); *C07D 333/64* (2013.01); *C07D 409/12* (2013.01)

(58) Field of Classification Search
CPC .................................................. C07D 471/04
USPC ......................................................... 549/53
See application file for complete search history.

(56) References Cited

FOREIGN PATENT DOCUMENTS

| SU | 591474 | * | 2/1978 |
|---|---|---|---|
| WO | WO 1999/065449 | | 12/1999 |
| WO | WO 2004/006906 | | 1/2004 |
| WO | WO 2006/093832 | | 9/2006 |
| WO | WO 2010/101648 | | 9/2010 |
| WO | WO 2012/143377 | | 10/2012 |

OTHER PUBLICATIONS

PubChem datasheets, retrieved Apr. 23, 2014.*
Submitted by applicant in U.S. Appl. No. 14/760,711.*
Khaidarov et al., Tezisy Dokl. Nauchn. Sess. Khim. Tekhnol. Org. Soedin. Sery Sernistykh Neftei, (1976) 14th Meeting 1975, 75-76, Riga USSR.*
Numanov et al., Doklady Akademii Nauk Tadzhikskoi, USSR (1979), vol. 22(3), pp. 177-179.*
Numanov et al., Doklady Akademii Nauk Tadzhikskoi, USSR (1977), vol. 20(6), pp. 40-43.*
Numanov et al., Doklady Akademii Nauk Tadzhikskoi, USSR (1978), vol. 21(2), pp. 32-35.*
Becker et al., "Three-dimensional structure of the Stat3beta homodimer bound to DNA," *Nature*, 394:145-151, 1998.
Bergström et al., "Poorly soluble marketed drugs display solvation limited solubility," *J. Med. Chem.*, 50:5858-5862, 2007.
Bowman et al., "STATs in oncogenesis," *Oncogene*, 19:2474-2488, 2000.
Bromberg et al., "Stat3 as an oncogene," *Cell*, 98:295-303, 1999.
Bromberg et al., "The role of STATs in transcriptional control and their impact on cellular function," *Oncogene*, 19:2468-2473, 2000.
Buettner et al., "Activated STAT signaling in human tumors provides novel molecular targets for therapeutic intervention," *Clin. Cancer Res.*, 8:945-954, 2002.
Chapman et al., "Suppression of epithelial apoptosis and delayed mammary gland involution in mice with a conditional knockout of Stat3," *Genes Dev*, 13(19):2604-2616, 1999.
Chen et al., "Structure-based design of conformationally constrained, cell-permeable STAT3 inhibitors." *ACS Med. Chem. Lett.*, 1:85-89, 2010.
Colletta et al., "Transcriptional control of the cell cycle in mammary gland development and tumorigenesis," *J Mammary Gland Biol Neoplasia*, 9(1):39-53, 2004.
Compound Summaries, PubChemCompound, datasheets located at http://pubchem.ncbi.nlm.nih.gov/search/search.cgi, retrieved Apr. 23, 2014.
Costantino, et al., "STAT3 as a target for cancer drug discovery," *Curr. Med. Chem.*, 15:834-843, 2008.
Darnell, "STATs and gene regulation," *Science*, 277:1630-1635, 1997.
Darnell, "Transcription factors as targets for cancer therapy," *Nat. Rev. Cancer*, 2:740-749, 2002.
Darnell, "Validating Stat3 in cancer therapy," *Nat. Med.*, 11:595-596, 2005.
Debnath et al., "Small molecule inhibitors of signal transducer and activator of transcription 3 (Stat3) protein," *J. Med. Chem.*, 55:6645-6668, 2012.
Deng et al., "Small molecule inhibitors of Stat3 signaling pathway," *Curr. Cancer Drug Targets*, 7:91-107, 2007.
Elkihel et al., "Synthesis and orally macrofilaricidal evaluation of niclosamide lymphotropic prodrugs," *Arznemittelforschung*, 44:1259-1264, 1994.
Germain et al., "Targeting the cytoplasmic and nuclear functions of signal transducers and activators of transcription 3 for cancer therapy," *Clin. Cancer Res.*, 13:5665-5669, 2007.
Haftchenary et al., "Inhibiting aberrant Stat3 function with molecular therapeutics: a progress report," *Anticancer Drugs*, 22:115-127, 2011.
Hann et al., "Finding the sweet spot: the role of nature and nurture in medicinal chemistry," *Nat. Rev. Drug Discov.*, 11:355-365, 2012.
Haura et al., "Mechanisms of disease: Insights into the emerging role of signal transducers and activators of transcription in cancer," *Nat. Clin. Pract. Oncol.*, 2:315-324, 2005.

(Continued)

*Primary Examiner* — Taofiq A Solola
(74) *Attorney, Agent, or Firm* — Parker Highlander PLLC

(57) ABSTRACT

Provided are STAT3 inhibitors and methods of treating inflammation or a hyperproliferative disease such as, e.g., cancer. In some aspects, compounds may be used to treat breast cancer, a head/neck cancer, a lung cancer, a prostate cancer, or pancreatic cancer.

18 Claims, 23 Drawing Sheets

(56) References Cited

OTHER PUBLICATIONS

Hsieh et al., "Evaluation of potential Stat3-regulated genes in human breast cancer," *Biochem Biophys Res Commun*, 335:292-299, 2005.
Ishikawa et al., "Improvement in aqueous solubility in small molecule drug discovery programs by disruption of molecular planarity and symmetry," *J. Med. Chem.*, 54:1539-1554, 2011.
Jin et al., "Antineoplastic mechanisms of niclosamide in acute myelogenous leukemia stem cells: inactivation of the NF-kappaB pathway and generation of reactive oxygen species," *Cancer Res.*, 70:2516-2527, 2010.
Lavecchia et al., "STAT-3 inhibitors: state of the art and new horizons for cancer treatment," *Curr. Med. Chem.*, 18:2359-2375, 2011.
Leach et al., "Matched molecular pairs as a guide in the optimization of pharmaceutical properties; a study of aqueous solubility, plasma protein binding and oral exposure," *J. Med. Chem.*, 49:6672-6682, 2006.
Lipinski, "Drug-like properties and the causes of poor solubility and poor permeability," *J. Pharmacol. Toxicol. Methods*, 44:235-249, 2000.
Liu et al., "Stat5a is mandatory for adult mammary gland development and lactogenesis," *Genes Dev*, 11(2):179-186, 1997.
Mandal et al., "Potent and selective phosphopeptide mimetic prodrugs targeted to the Src Homology 2 (SH2) domain of signal transducer and activator of transcription 3," *J. Med. Chem.*, 54:3549-3563, 2011.
Mandal et al., "Structure-affinity relationships of glutamine mimics incorporated into phosphopeptides targeted to the SH2 domain of signal transducer and activator of transcription 3," *J. Med. Chem.*, 52:6126-6141, 2009.
Mankan et al., "Inhibiting signal transducer and activator of transcription 3: rationality and rationale design of inhibitors," *Expert Opin. Invest. Drugs*, 20:1263-1275, 2011.
Navab et al., "A novel method for oral delivery of apolipoprotein mimetic peptides synthesized from all L-amino acids," *J. Lipid Res.*, 50:1538-1547, 2009.
Office Action issued in U.S. Appl. No. 14/760,711, dated Apr. 12, 2016.
Office Action issued in U.S. Appl. No. 14/760,711, dated Jun. 7, 2016.
O'Neill et al., "Oral cancer treatment: developments in chemotherapy and beyond," *Br. J. Cancer*, 87:933-937, 2002.
Osada et al., "Antihelminth compound niclosamide downregulates Wnt signaling and elicits antitumor responses in tumors with activating APC mutations," *Cancer Res.*, 71:4172-4182, 2011.
Page et al., "Signal transducer and activator of transcription 3 inhibitors: a patent review," *Expert Opin. Ther. Pat.*, 21:65-83, 2011.
Park et al., "Niclosamide induces mitochondria fragmentation and promotes both apoptotic and autophagic cell death," *BMB Rep*, 44:517-522, 2011.
PCT International Preliminary Report on Patentability issued in International Application No. PCT/US2014/011674, dated Jul. 30, 2015.
PCT International Search Report and Written Opinion issued in International Application No. PCT/US2014/011674, dated May 21, 2014.
Ranger et al., "Identification of a Stat3-dependent transcription regulatory network involved in metastatic progression," *Cancer Res.*, 69(17):6823-6830, 2009.
Ren et al., "Identification of Niclosamide as a New Small-Molecule Inhibitor of the STAT3 Signaling Pathway," *ACS Med. Chem. Lett.*, 1:454-459, 2010.
Schindler, "Series introduction. JAK-STAT signaling in human disease," *J. Clin. Invest.*, 109:1133-1137, 2002.
Schott et al., "Acceptance of oral chemotherapy in breast cancer patients—a survey study," *BMC Cancer*, 11:129, 2011.
Schust et al., "Stattic: a small-molecule inhibitor of STAT3 activation and dimerization," *Chemistry & Biology*, 13:1235-1242, 2006.
Siddiquee et al., "STAT3 as a target for inducing apoptosis in solid and hematological tumors," *Cell Res.*, 18:254-267, 2008.
Takeda et al., "Enhanced Th1 activity and development of chronic enterocolitis in mice devoid of Stat3 in macrophages and neutrophils," *Immunity*, 10(1):39-49, 1999.
Takeda et al., "Stat3 activation is responsible for IL-6-dependent T cell proliferation through preventing apoptosis: generation and characterization of T cell-specific Stat3-deficient mice," *J Immunol*, 161(9):4652-4660, 1998.
Turkson et al., "STAT proteins: novel molecular targets for cancer drug discovery," *Oncogene*, 19:6613-6626, 2000.
Turkson, "STAT proteins as novel targets for cancer drug discovery," *Expert Opin Ther Targets*, 8(5):409-422, 2004.
Watson, "Stat transcription factors in mammary gland development and tumorigenesis," *J Mammary Gland Biol Neoplasia*, 6(1):115-127, 2001.
Xiong et al., "Discovery and structure-activity relationship of 3-methoxy-N-(3-(1-methyl-1H-pyrazol-5-yl)-4-(2-morpholinoethoxy)phenyl)benzamide (APD791): a highly selective 5-hydroxytryptamine2A receptor inverse agonist for treatment of arterial thrombosis," *J. Med. Chem.*, 53:4412-4421, 2010.
Yeh et al., "STAT3 ser727 phosphorylation and its association with negative estrogen receptor status in breast infiltrating ductal carcinoma," *Int J Cancer*, 118(12):2943-2947, 2006.
Yu and Jove, "The STATs of cancer—new molecular targets come of age," *Nat Rev Cancer*, 4(2):97-105, 2004.
Yu et al., "Crosstalk between cancer and immune cells: role of STAT3 in the tumour microenvironment," *Nat. Rev. Immunol.*, 7:41-51, 2007.
Yu et al., "STATs in cancer inflammation and immunity: a leading role for STAT3," *Nat. Rev. Cancer*, 9:798-809, 2009.
Yu et al., "The STATs of cancer—new molecular targets come of age," *Nat Rev Cancer*, 4(2):97-105, 2004.
Yue et al., "Targeting STAT3 in cancer: how successful are we?" *Expert Opin. Investig. Drugs*, 18:45-56, 2009.
Zhang et al., "Orally bioavailable small-molecule inhibitor of transcription factor Stat3 regresses human breast and lung cancer xenografts," *Proc. Natl. Acad. Sci. U.S.A.*, 109:9623-9628, 2012.
Zhao et al., "Small molecule inhibitors of STAT3 for cancer therapy," *Curr. Med. Chem.*, 18:4012-4018, 2011.
Bishop et al., "The multifaceted roles of STAT3 signaling in the progression of prostate cancer," *Cancers*, 6:829-859, 2014.
Dutta et al., "Role of STAT3 in lung cancer," *JAKSTAT*, 3(4):e999503, 2015.
Fan et al., "NF-κB and STAT3 signaling pathways collaboratively link inflammation to cancer," *Protein Cell*, 4(3):176-185, 2013.
Geiger et al., "The STAT3 pathway as a therapeutic target in head and neck cancer: barriers and innovations," *Oral Oncol.*, 56:84-92, 2016.
Haftchenary et al., "Potent targeting of the STAT3 protein in brain cancer stem cells: a promising route for treating glioblastoma," *ACS Med. Chem. Lett.*, 4:1102-1107, 2013.
Munoz et al.,"STAT3 inhibitors: finding a home in lymphoma and leukemia," *The Oncologist*, 19:536-544, 2014.

* cited by examiner

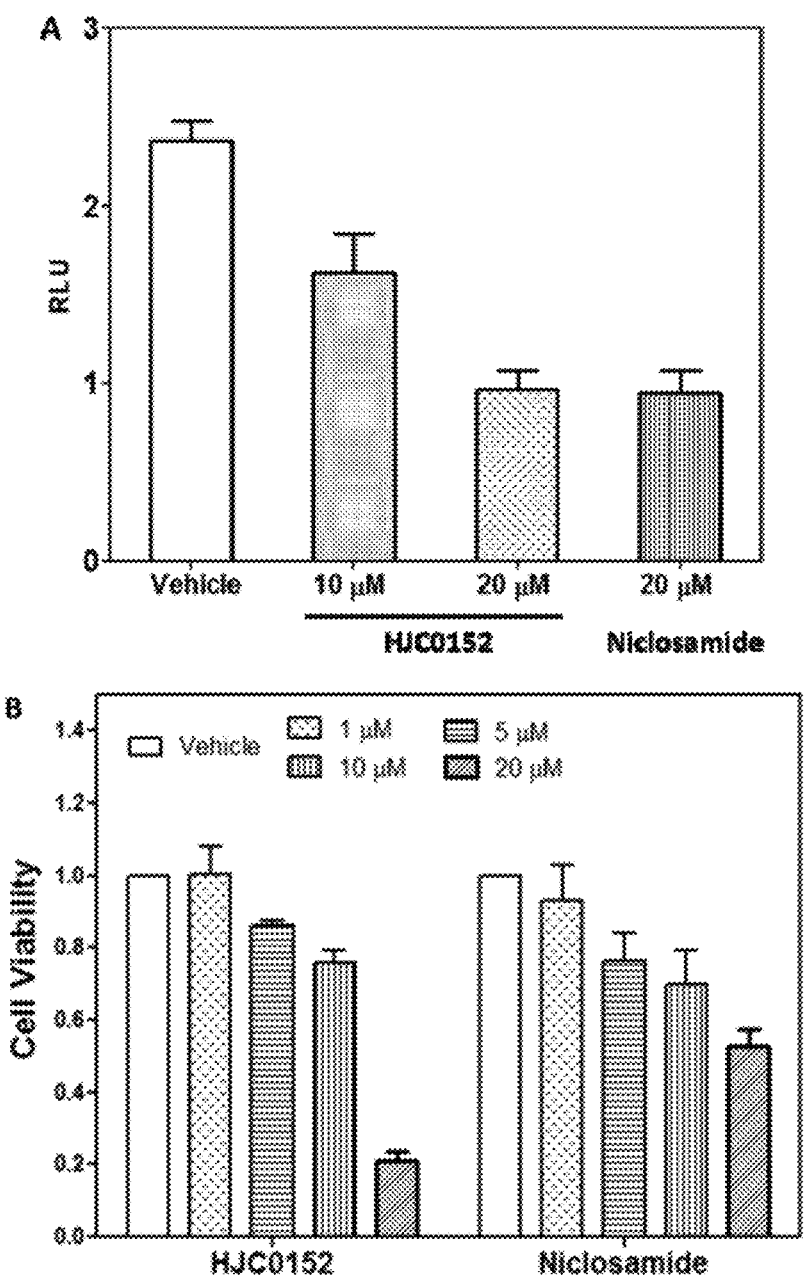
FIGS. 6A-B

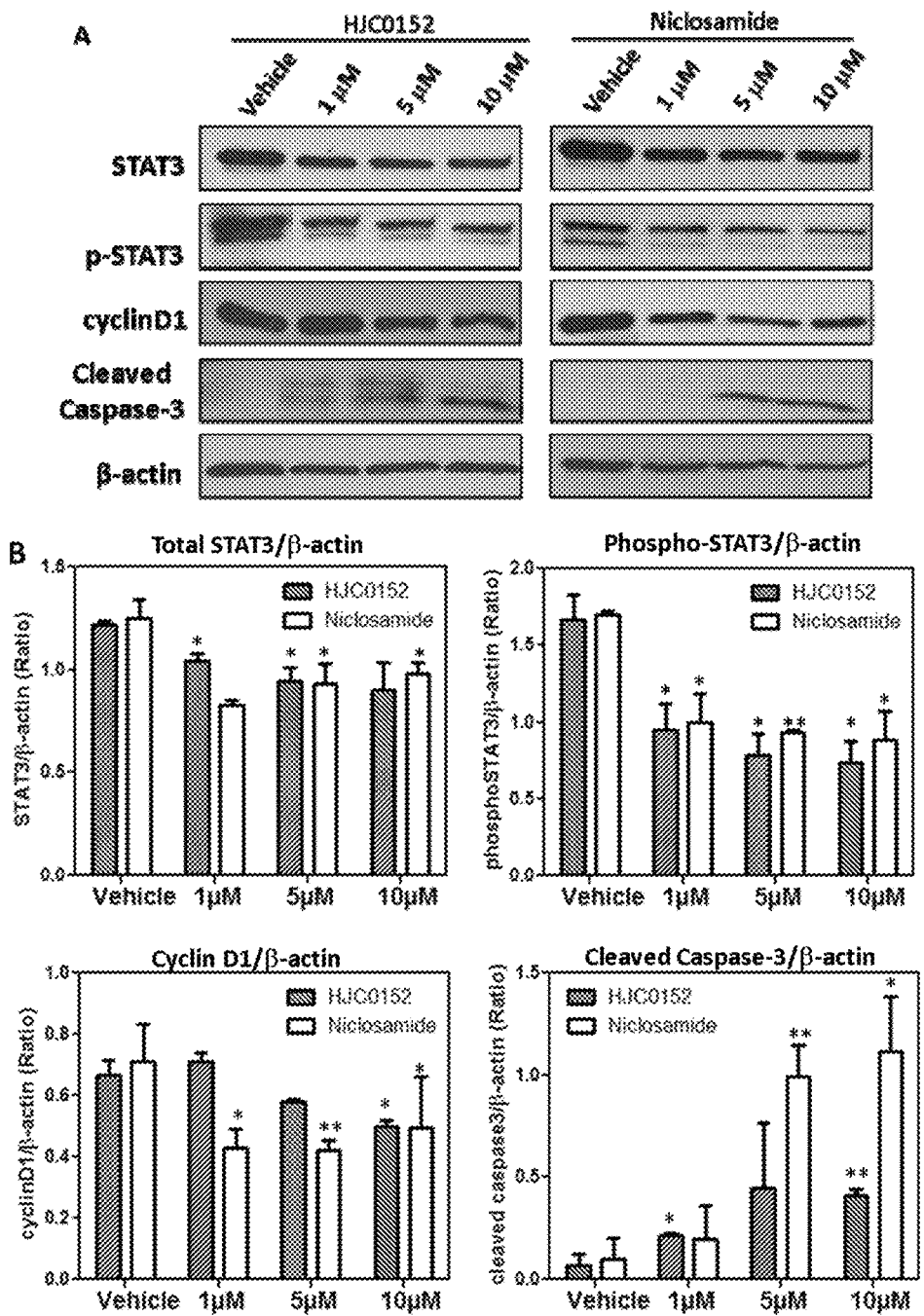
FIGS. 7A-B

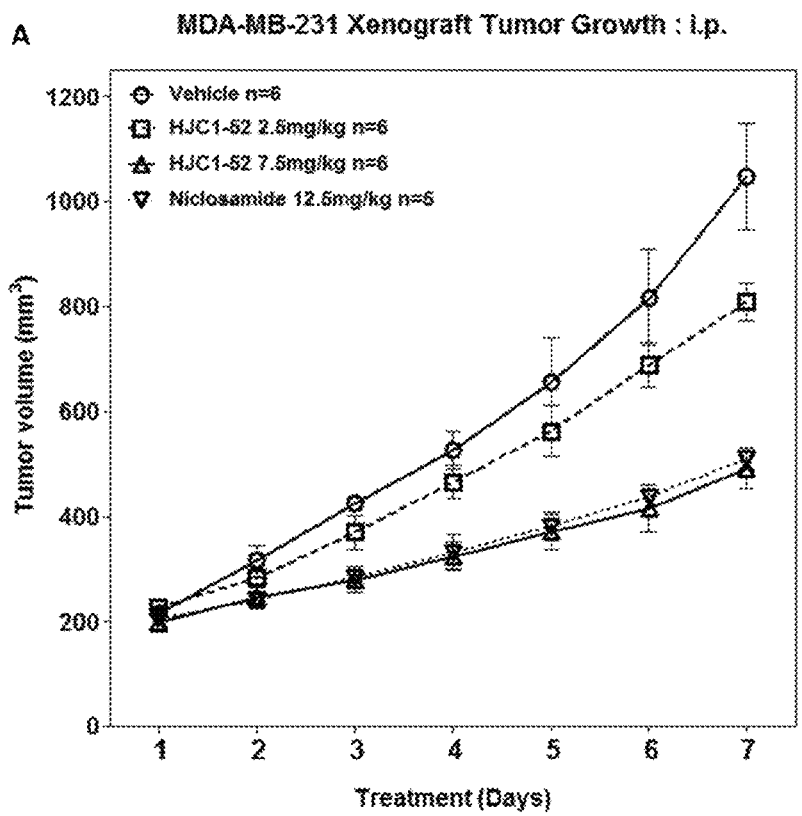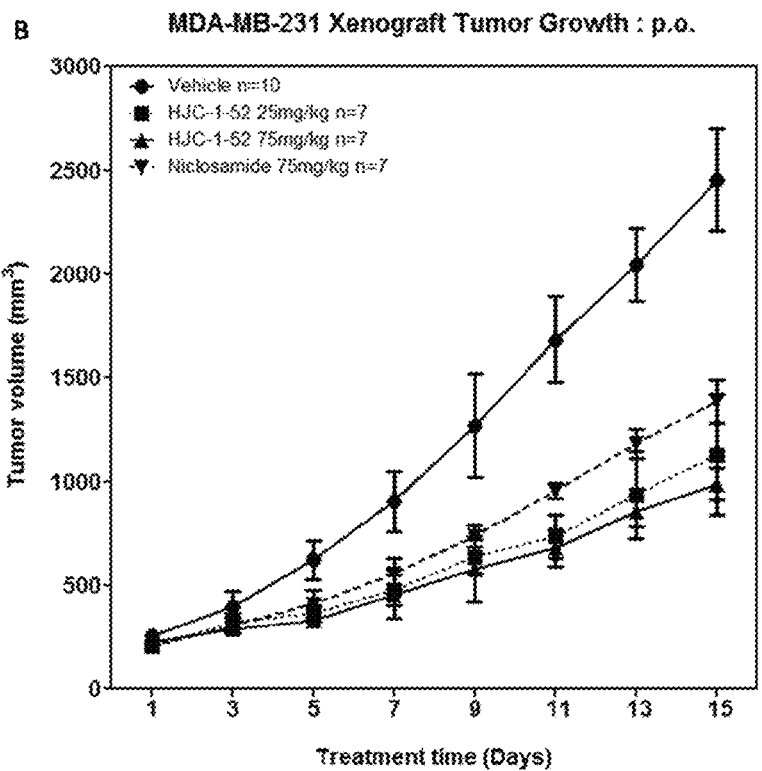
FIGS. 8A-B

FIGS. 11A-B

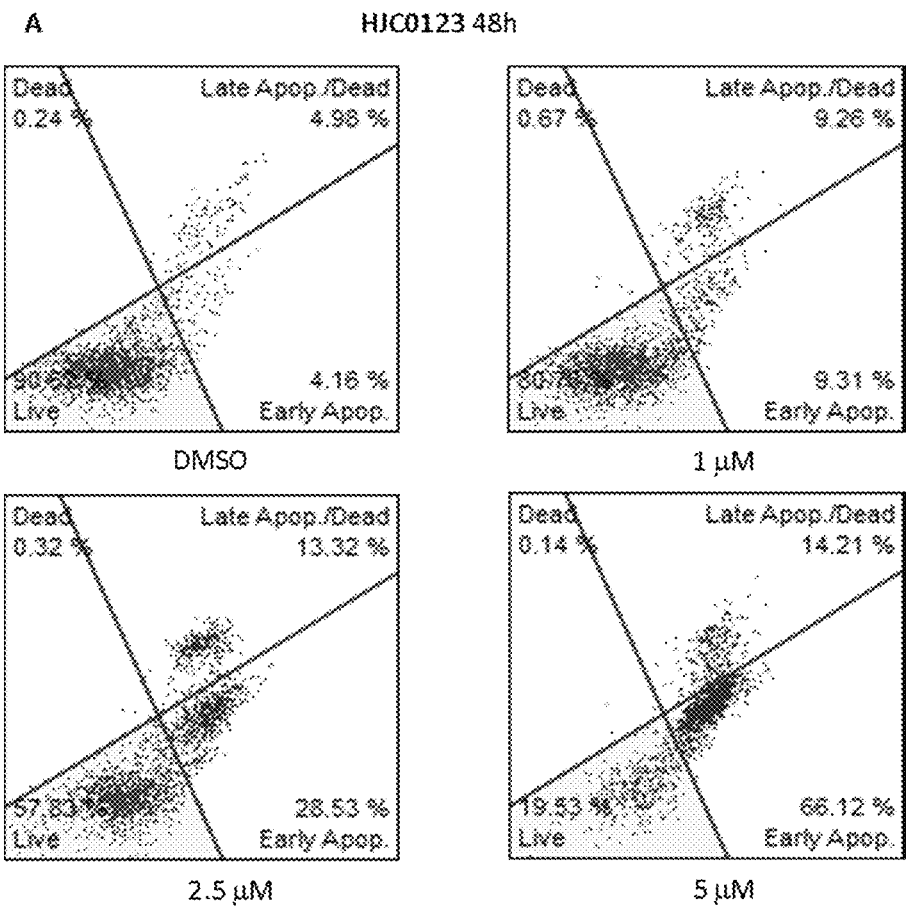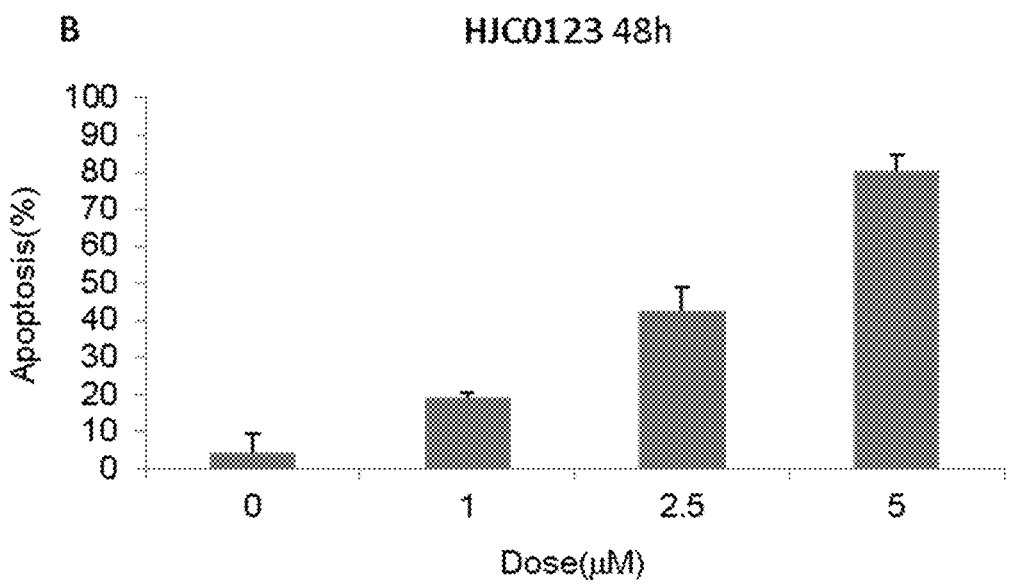
FIGS. 16A-B

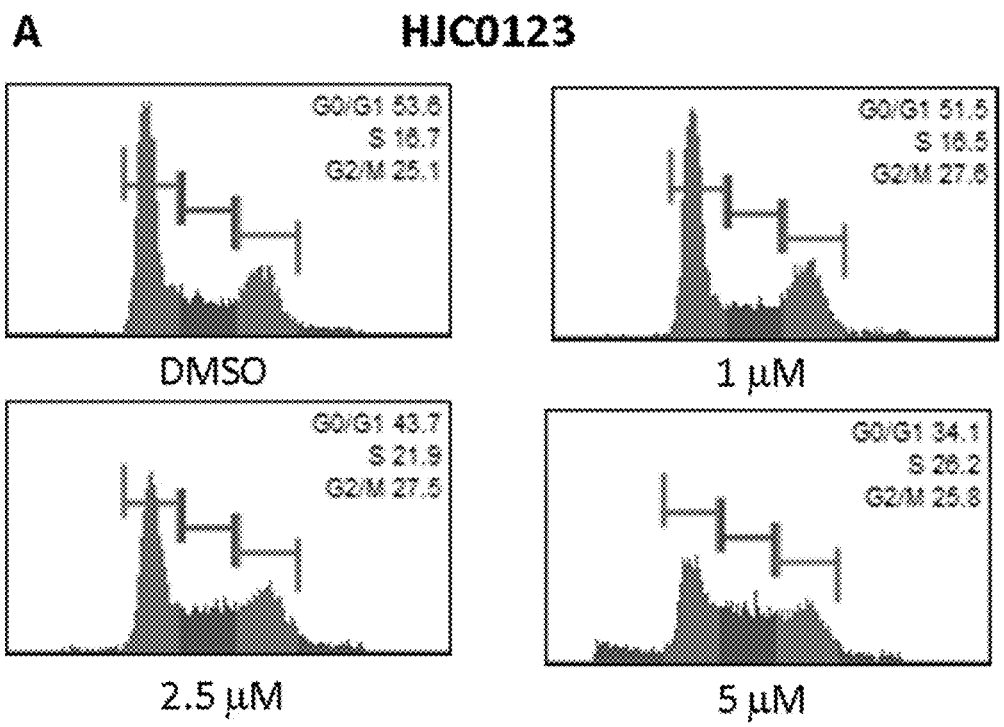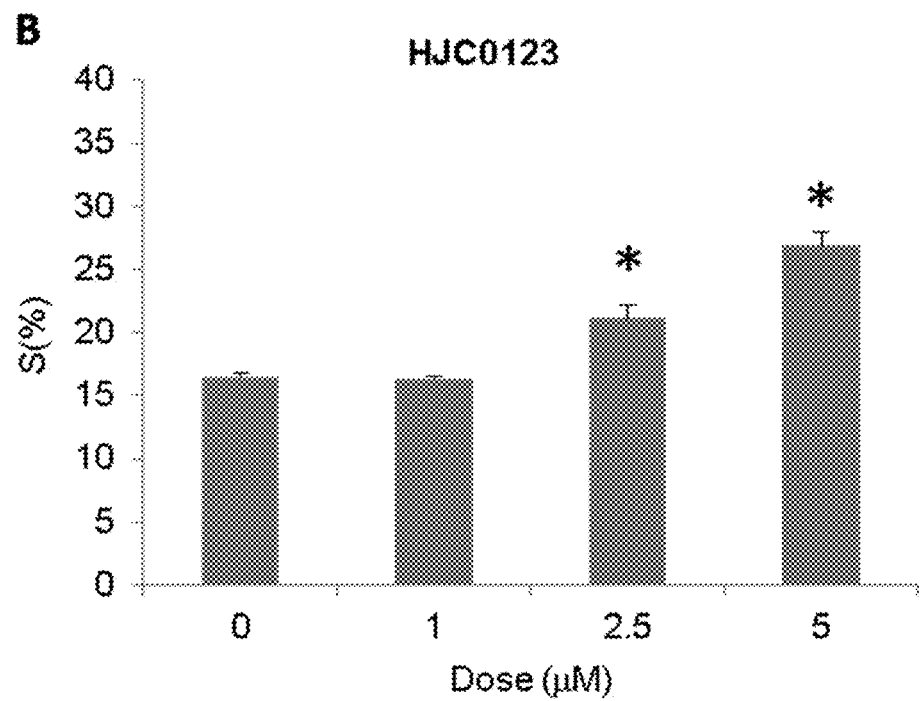
FIGS. 17A-B

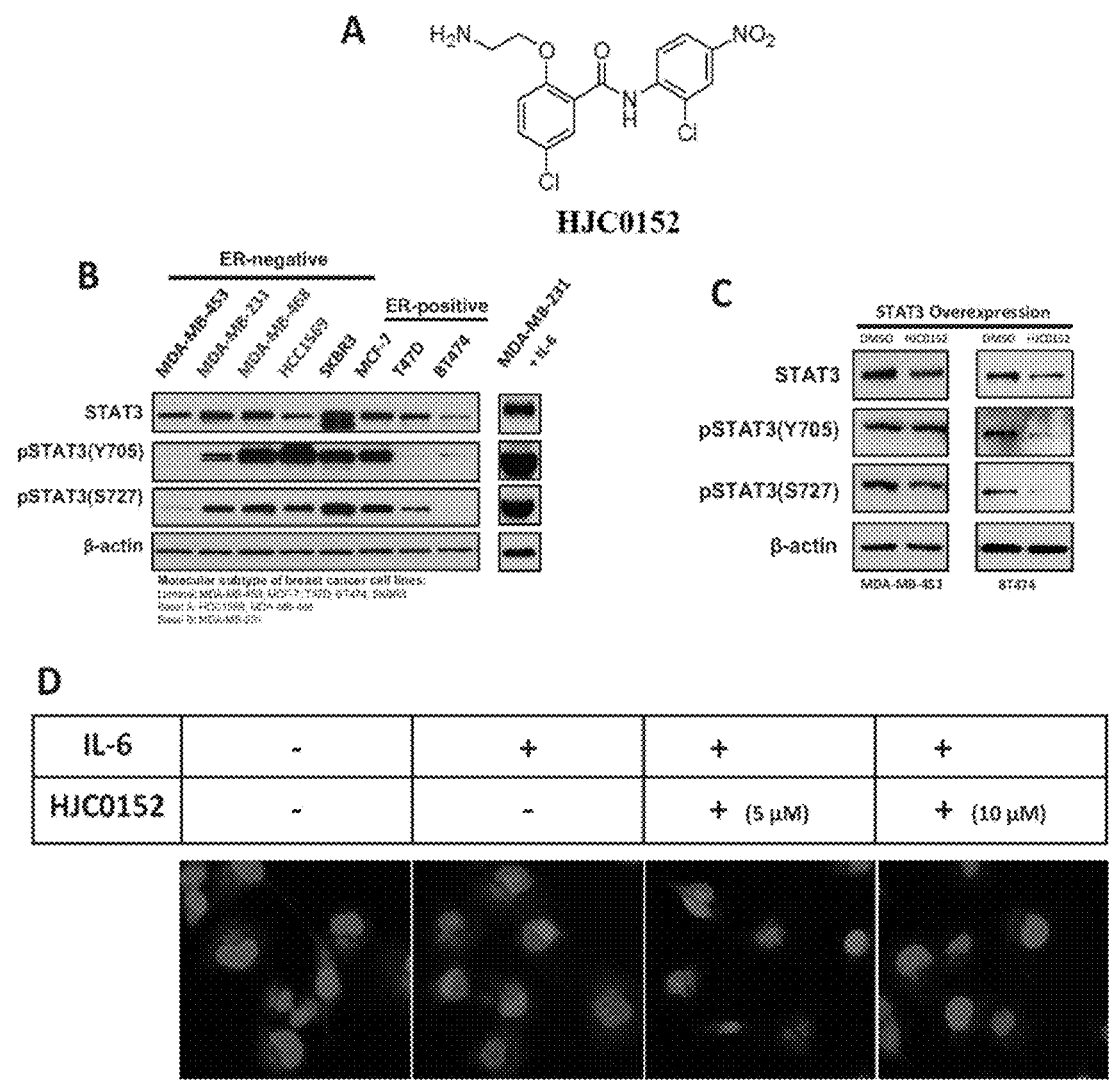
FIGS. 18A-D

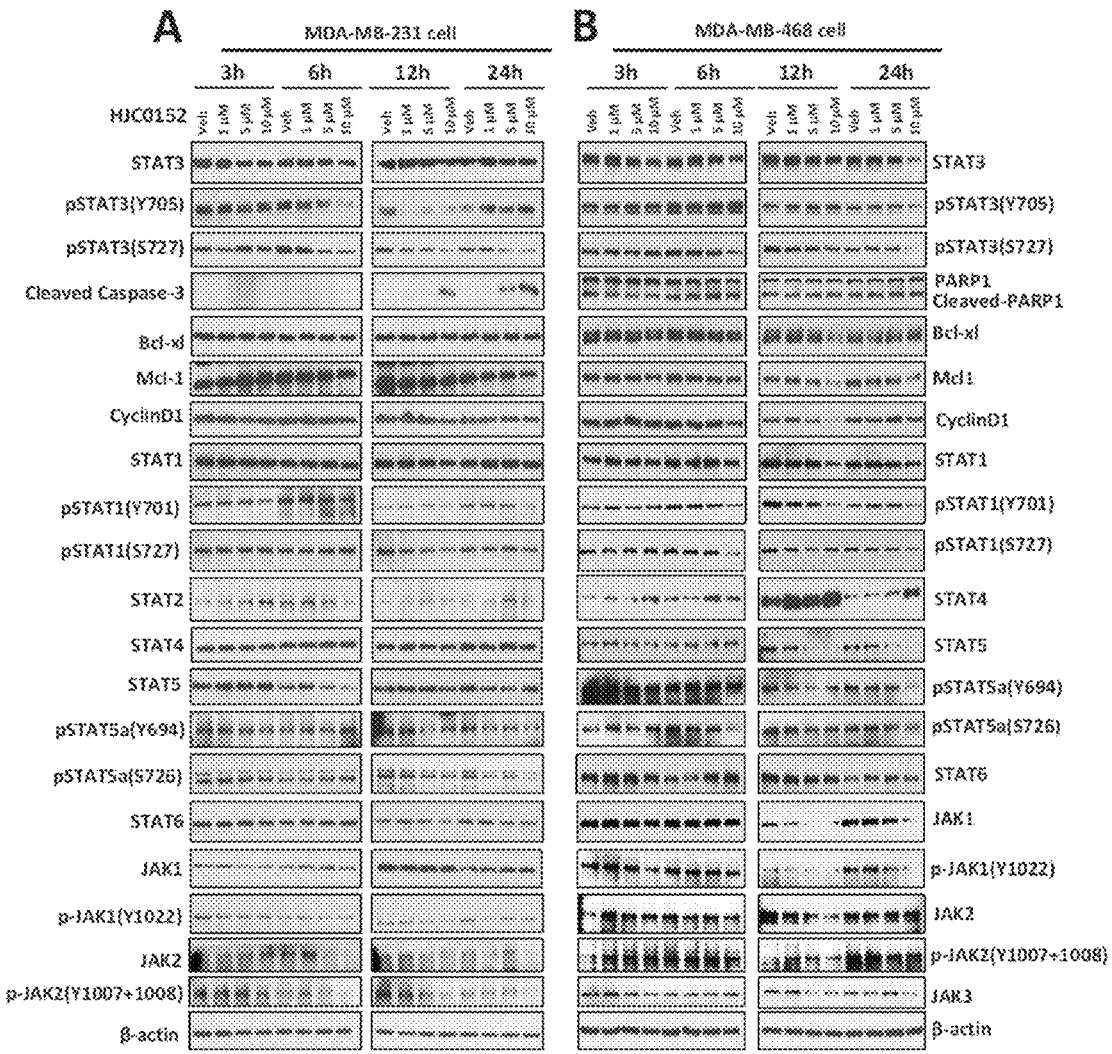
FIGS. 19A-B

FIGS. 20B-C

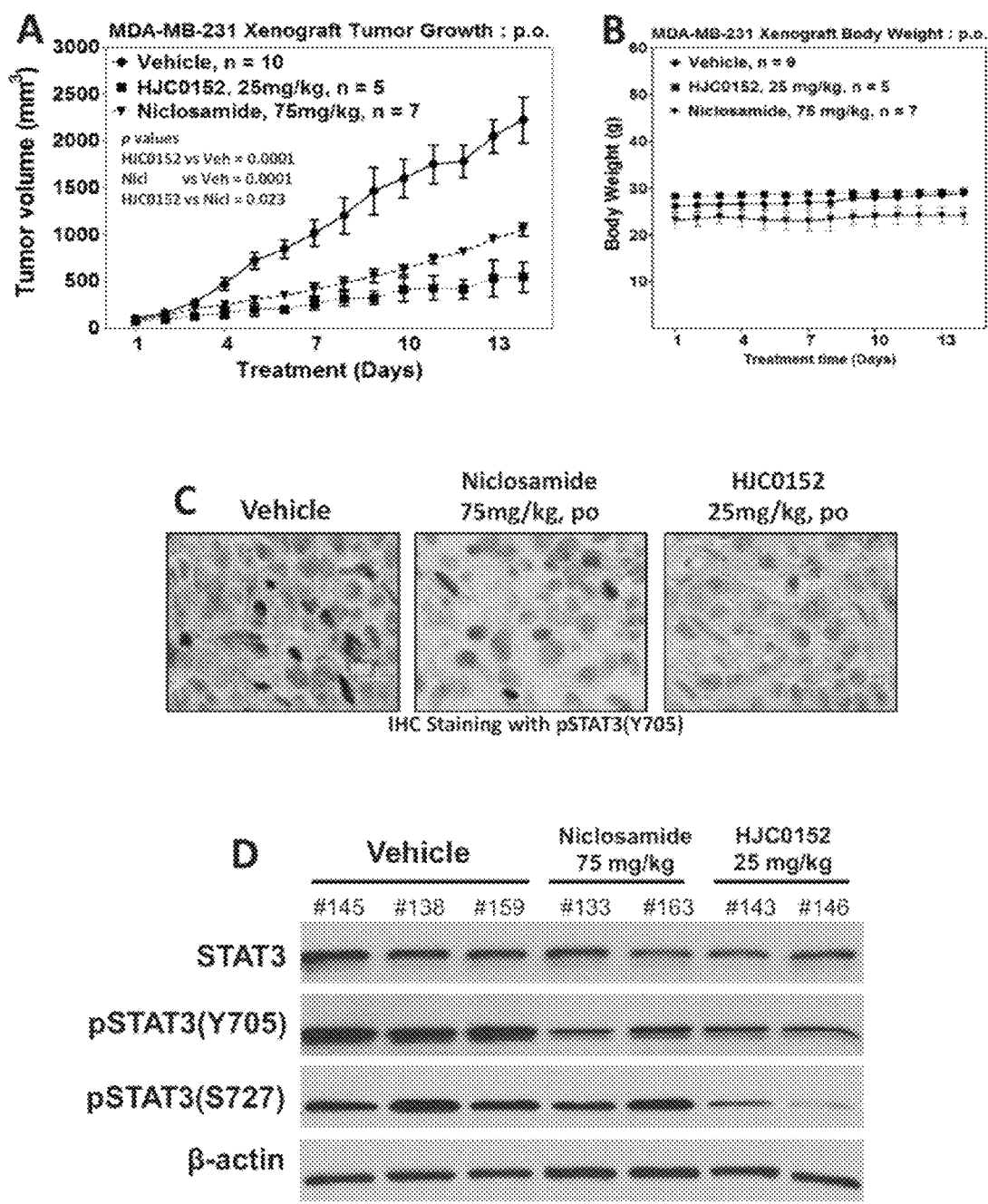
FIGS. 21A-D

STAT3 INHIBITOR

This application is a divisional of U.S. application Ser. No. 14/760,711, filed Jul. 14, 2015, which is a national phase application under 35 U.S.C. § 371 of International Application No. PCT/US2014/011674, filed Jan. 15, 2014, which claims the benefit of U.S. Provisional Patent Application No. 61/752,866, filed Jan. 15, 2013, the entirety of each of which is incorporated herein by reference.

The invention was made with government support under Grant Nos. P50 CA097007, P30DA028821, R21MH093844, awarded by the National Institutes of Health. The government has certain rights in the invention.

BACKGROUND OF THE INVENTION

1. Field of the Invention

The present invention relates generally to the field of molecular biology and medicine. More particularly, it concerns compounds for the treatment of cancer or inflammation.

2. Description of Related Art

Although a large portion of estrogen receptor (ER)-positive breast cancer can be prevented and treated with ER modulators (such as tamoxifen and raloxifene) and aromatase inhibitors (such as anastrozole and letrozole) as preventive and therapeutic drug, these available drugs fail to prevent or treat the rest ER-positive breast cancers (approximately 45% of all ER-positive) and all ER-negative breast cancers (both accounting for approximately 60% of all breast cancer cases, including triple-negative breast cancer). In particular, ER-negative breast cancer including triple negative breast cancer does not respond to hormonal therapy and incline to develop metastasis. Thus, effective targets and agents are urgently needed to prevent and treat the resistant ER-positive breast cancer and all ER-negative including triple negative breast cancers.

Signal Transducers and Activators of Transcription (STATs) are a family of transcription factors involved in the regulation of early embryonic development, the immune response, cell proliferation, differentiation, and apoptosis (Takeda et al. 1999; Takeda et al. 1998). Previous studies have shown that STAT1 regulates remodeling of the mammary gland during involution, STAT3 regulates lobuloalveolar apoptosis during involution, and STAT5 regulates lobuloalveolar proliferation, differentiation, and expansion in the normal mammary gland development (Chapman et al. 1999; Watson, 2001). Sufficient data also demonstrate that STATs play an important role in breast carcinogenesis (Yu et al. 2004). Particularly, STAT3 activation promotes growth and survival of mammary tumors by upregulating Bcl-xL, Bcl-2, and surviving. Stimulating epidermal growth factor receptor (EGFR), Src, and Jaks will activate STAT3 (Turkson 2004). Increased STAT3 transcriptional activity was found to correlate with ER-negative phenotype in breast cancer cell lines and in primary human invasive ductal breast carcinomas (Yeh et al. 2006). High levels of activated STAT3 are often found to correlate with poor prognosis in human breast cancer patients in terms of metastatic progression (Ranger et al. 2009). Therefore, STAT3 represents a promising target for the prevention and treatment of both ER-positive and ER-negative breast cancer and also other cancers such as pancreatic, head/neck, prostate and lung cancers. However, current strategies of inhibiting STAT3 activity by means of blocking peptides, blockade of translocation, disrupting dimerization, or modulating phosphatase activity have not sufficiently inhibit STAT3 activity in cancer cells.

Despite substantial effort in the design of both peptidic and non-peptidic inhibitors that target STAT3, only a limited number of STAT3 inhibitors have been developed into a clinical trial. While peptide-based inhibitors can bind to STAT3 with high affinities, they suffer from the lack of cellular permeability due to both their peptidic nature and the negative charges on the phosphotyrosine group. Non-peptidic small-molecule inhibitors are relatively more cell-permeable, but most of the reported compounds such as Stattic bind to STAT3 with weak affinities ($IC_{50}$=5.1 µM) and the cellular activity cannot be clearly attributed to STAT3 targeting (Schust et al. 2006). Recently, niclosamide has been identified to potently inhibit the activation, nuclear translocation, and transactivation of STAT3 ($IC_{50}$=0.25 µM) but have no obvious effects on the closely related STAT1 and STAT5 proteins, the upstream JAK1, JAK2, and Src kinases, or other receptor tyrosine kinases (Ren et al. 2010). Unfortunately, niclosamide does not have an ideal pharmacokinetic profile in humans as an anticestodal drug, displaying poor oral bioavailability. Thus, its clinical use as anticancer agent is limited because of its moderate potency, poor solubility, and poor bioavailability. Clearly, there is a need for new STAT3 inhibitors that could be further developed as clinical candidates for molecular mechanism-based apoptosis, such as the treatment of cancer.

SUMMARY OF THE INVENTION

The present invention overcomes limitations in the prior art by providing synthetic low molecular-weight compounds that specifically block STAT3 activation, e.g., in cancer cells. In certain aspects and as shown in the below examples, compounds were observed to display improved potency, specificity, and/or better drug-like properties such as water solubility and bioavailability. In some embodiments, these small molecules may be used as potent, orally active STAT3 inhibitors for the therapy, prevention, or treatment of various cancers including but not limited to breast cancers, pancreatic cancer, brain tumors, head/neck cancer, prostate and lung cancers as well as inflammation.

An aspect of the present invention relates to a compound having one of the following structures:

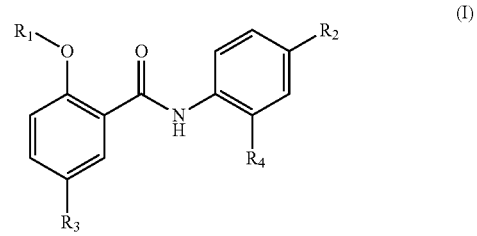

wherein $R_1$ is selected from the group consisting of hydrogen, substituted or unsubstituted alkyl$_{(C1-12)}$, substituted or unsubstituted heterocycloalkyl$_{(C4-12)}$, acyl$_{(C1-C6)}$, alkylamino$_{(C1-6)}$, alkoxyamino$_{(C1-6)}$,

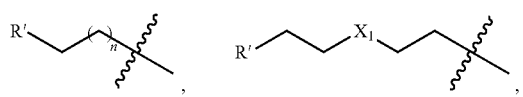

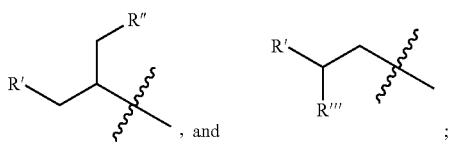, and wherein $X_1$ is —O— or —NH—; wherein n=0, 1, 2, 3, 4, or 5; wherein R' is selected from the group consisting of substituted or unsubstituted alkyl$_{(C1-6)}$, alkylamino$_{(C1-6)}$, halogen, —OH, amido$_{(C1-12)}$, alkyl sulfonylamino$_{(C1-12)}$,

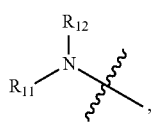

substituted or unsubstituted heterocycloalkyl$_{(C4-12)}$; wherein $R_{11}$ and $R_{12}$ are each independently —H or alkyl$_{(C1-6)}$; wherein R'' is —H, —OH, —NH$_2$, or halogen; wherein R''' is alkyl$_{(C1-6)}$;

wherein if $R_2$ is —NO$_2$, and $R_3$ and $R_4$ are —Cl, then $R_1$ is not —H; wherein $R_2$ is selected from the group consisting of —NO$_2$, —NH$_2$, H, amido$_{(C1-12)}$, substituted amido$_{(C1-12)}$, alkylsulfonylamino$_{(C1-12)}$, dialkylsulfonylamino$_{(C1-12)}$, and halogen; wherein $R_3$ and $R_4$ are halogen;

(II)

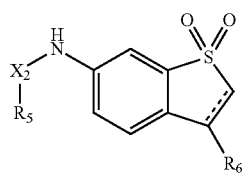

wherein $R_5$ is selected from the group consisting of alkyl$_{(C1-14)}$, substituted alkyl$_{(C1-14)}$, —H,

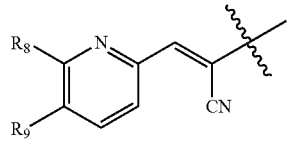,

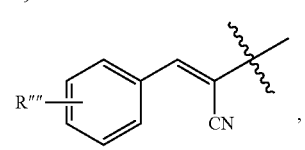,

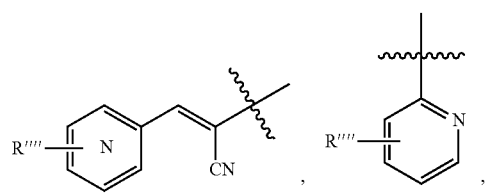,

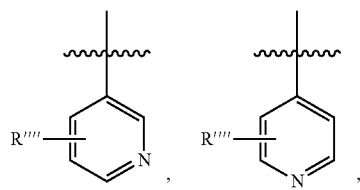,

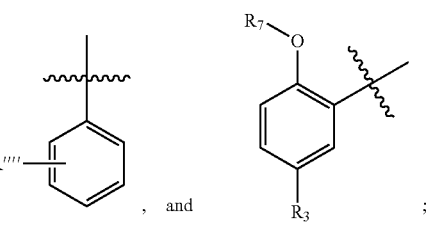, and 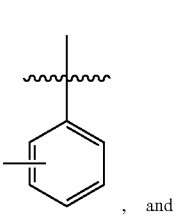;

wherein $R_3$ is halogen, —OH, or —H; wherein $R_7$ is —H or $R_1$; wherein $R_8$ and $R_9$ are each independently —H or halogen; wherein $R_6$ is —H or —O—CH$_3$; wherein $X_2$ is —C(O)— or —S(O)$_2$—; wherein R'''' is —H, —CF$_3$, —NO$_2$, —CN, halogen, alkyl$_{(C1-12)}$, alkoxy$_{(C1-12)}$, aryl$_{(C6-12)}$, heteroaryl$_{(C4-12)}$, substituted carboxylates$_{(C1-C12)}$, amido$_{(C1-C12)}$, substitutedalkyl amino$_{(C1-C12)}$, or —S(O)$_2$—X$_3$; wherein X$_3$ is —OH, —NH$_2$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, or —OC(O)CH$_3$;

(III)

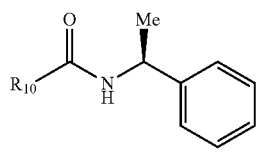

wherein $R_{10}$ is substituted or unsubstituted aryl$_{(C6-18)}$, substituted or unsubstituted heteroaryl$_{(C6-18)}$, or $R_5$; or (IV)

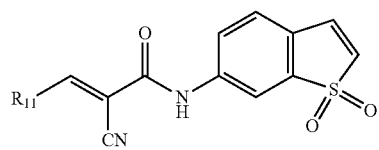

wherein $R_{11}$ is substituted or unsubstituted aryl$_{(C6-18)}$, substituted or unsubstituted heteroaryl$_{(C6-18)}$, cycloalkyl$_{(C6-12)}$, or $R_5$; or a salt thereof. The compound may have structure (I). $R_2$ may be —NO$_2$. $R_3$ and $R_4$ may be —Cl. $R_1$ may be selected from the group consisting of:

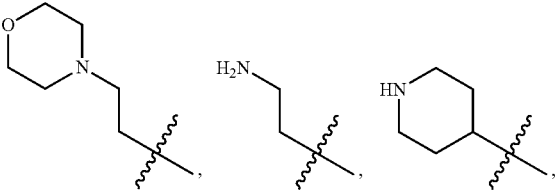

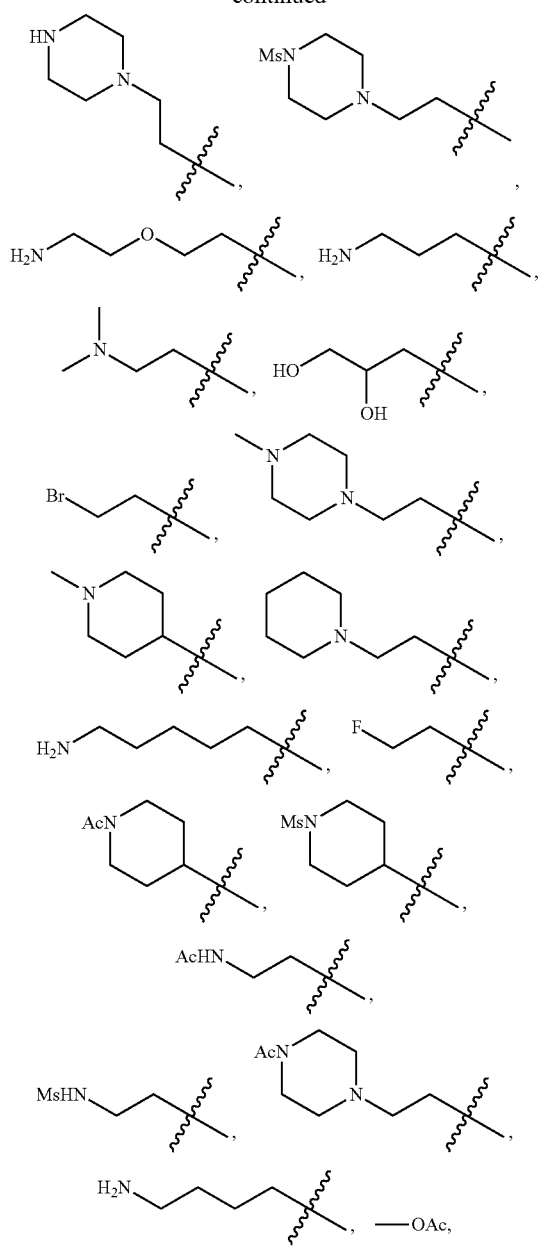
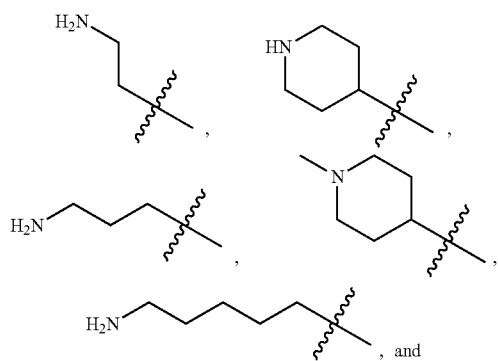
and —OH. R₁ may be selected from the group consisting of:
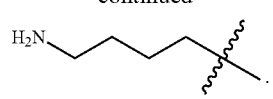
R₂ may be selected from the group consisting of: —NH₂,
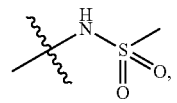
—H, —NHAc, —N(Ms)₂, and —NHMs.
In some embodiments, the compound has a structure selected from the group consisting of:
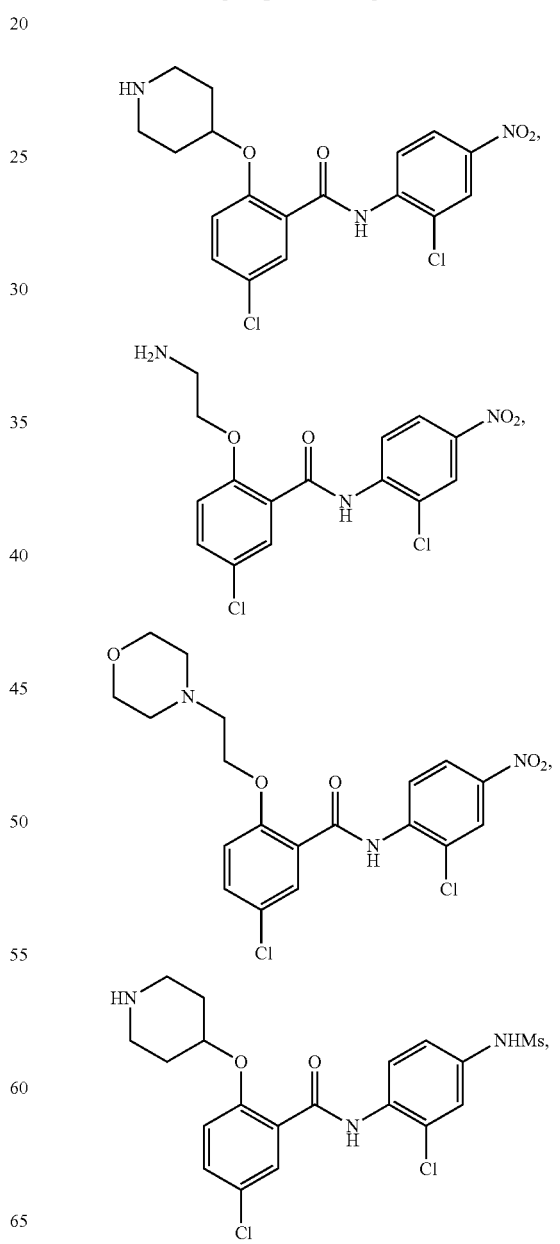

-continued
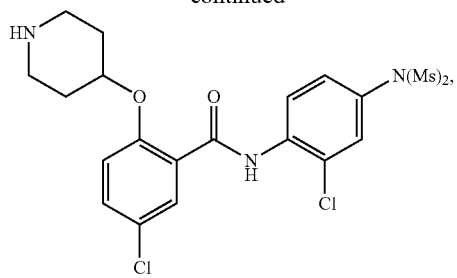
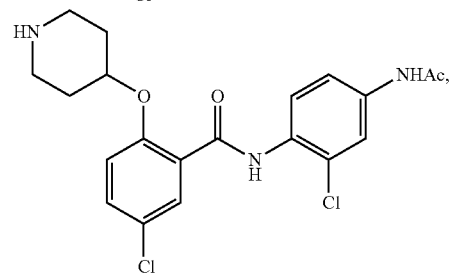
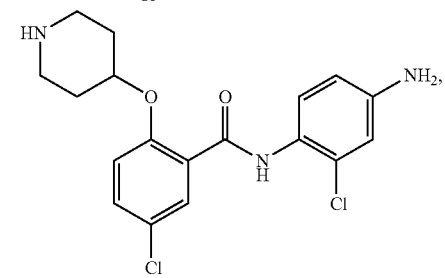
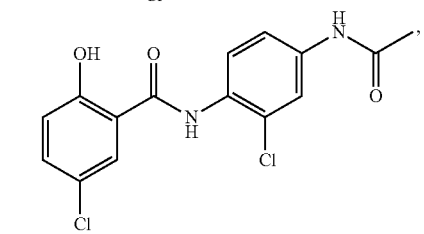
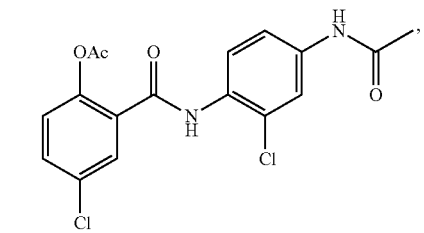
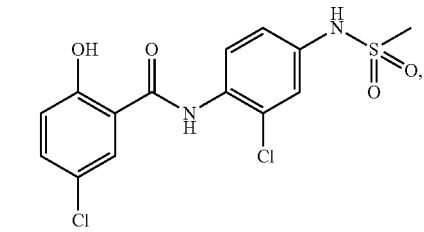
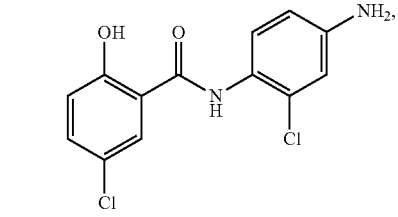
-continued
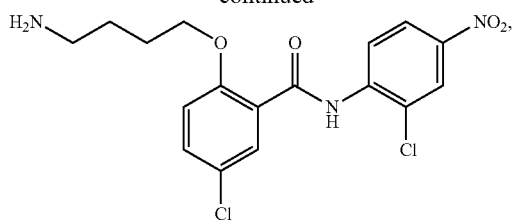
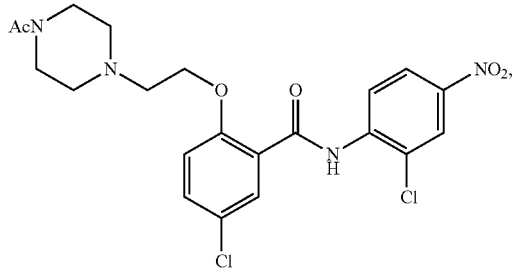
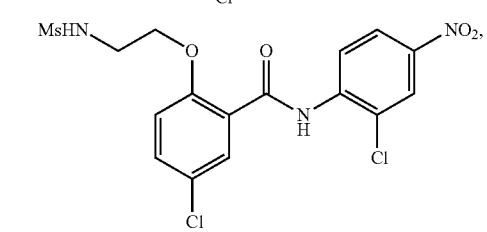
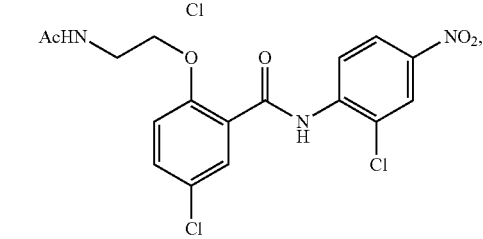
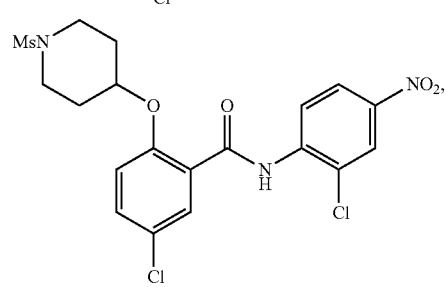
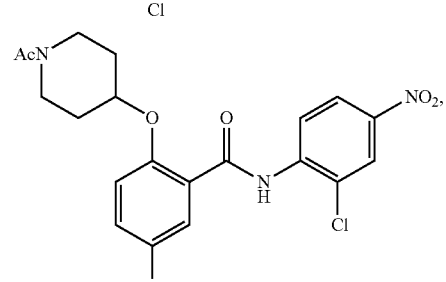
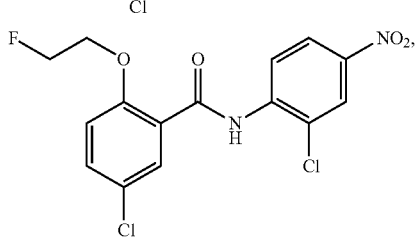

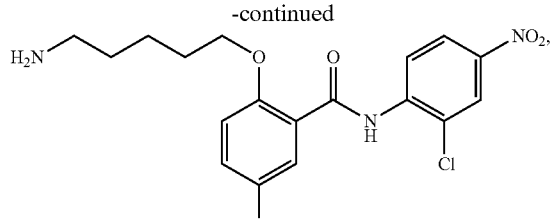
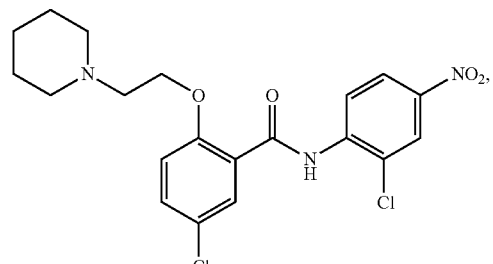
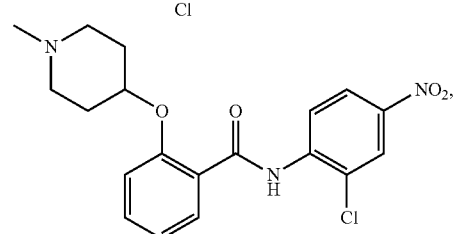
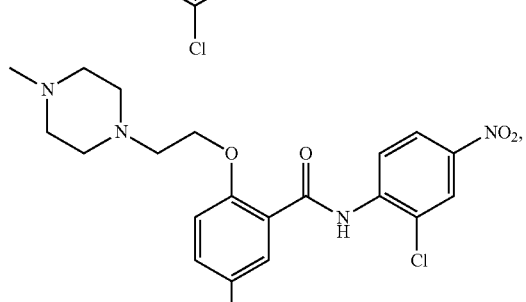
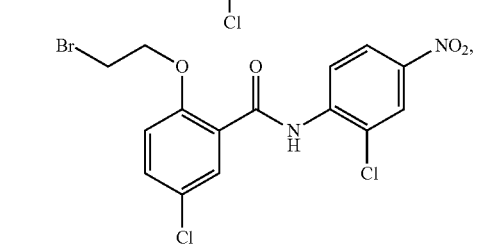
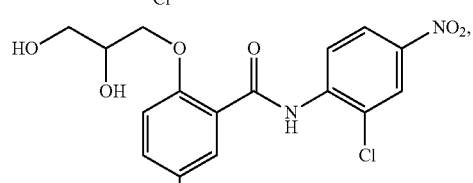
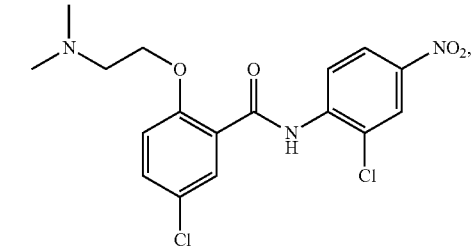
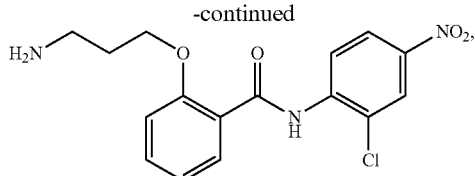
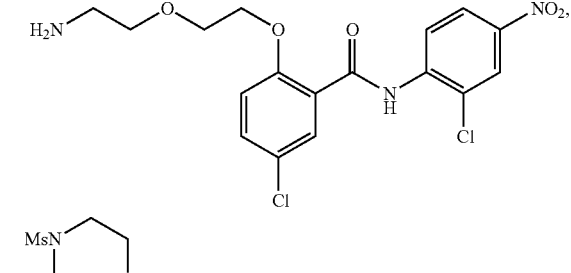
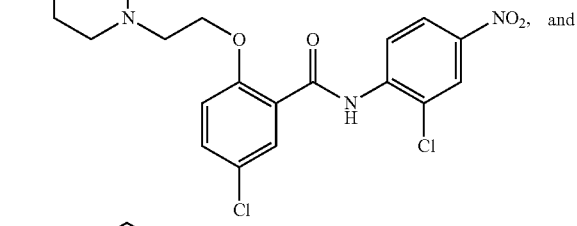
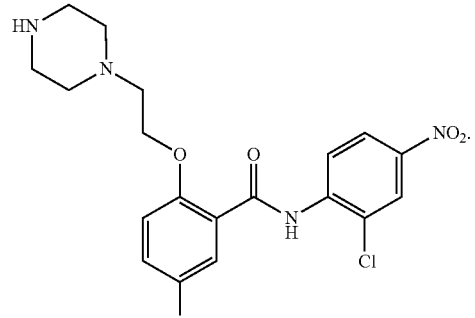
The compound may have a structure selected from the group consisting of:
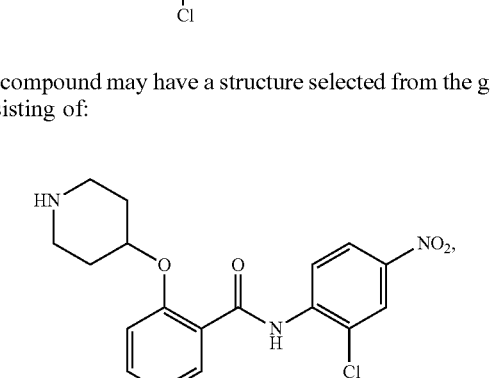
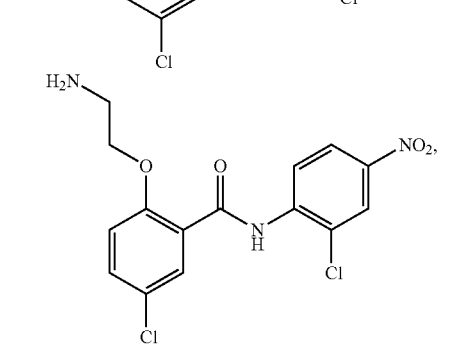

-continued

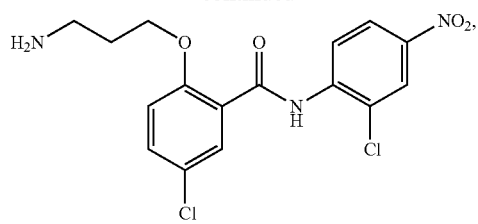

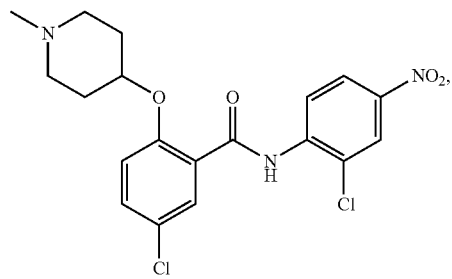

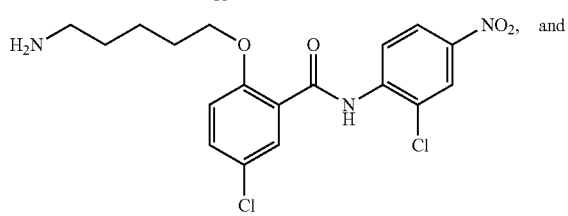

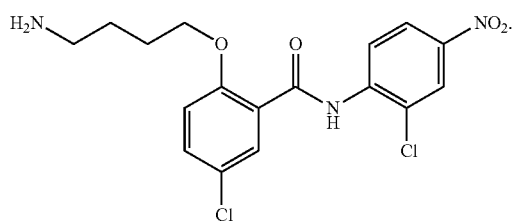

In some embodiments, the compound is comprised in a pharmaceutical composition or a pharmaceutically acceptable carrier.

The compound may have structure (II). The compound may have the structure

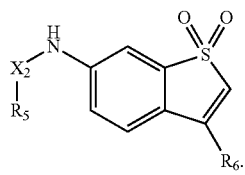

$R_6$ may be —H. $R_5$ may be aryl$_{(C6-20)}$ or heteroaryl$_{(C6-20)}$. $R_5$ may be aryl$_{(C6-18)}$ or heteroaryl$_{(C6-18)}$. $R_5$ may be -continued

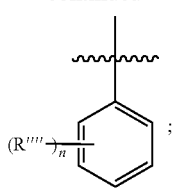

wherein n is 1, 2, 3, or 4. R"" may be aryl$_{(C6-12)}$ or heteroaryl$_{(C4-12)}$, wherein said aryl$_{(C6-12)}$ or heteroaryl$_{(C4-12)}$ is fused or unfused. $R_5$ may be selected form the group consisting of

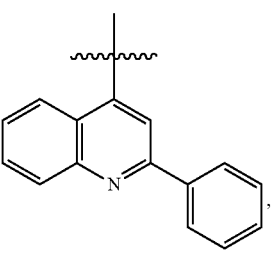

$R_5$ may be selected form the group consisting of

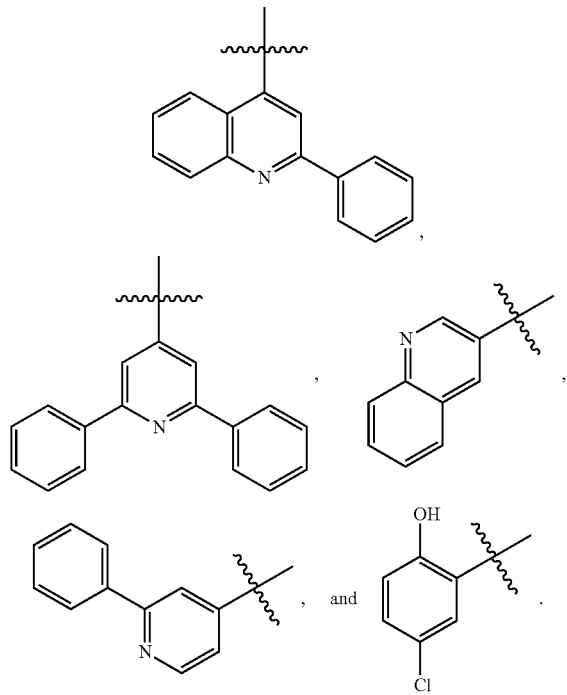

$R_5$ may be

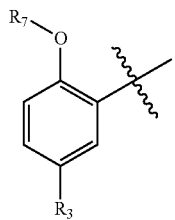

$R_3$ may be —Cl. $R_7$ may be selected from the group consisting of —H, substituted alkyl$_{(C1-14)}$, substituted heterocycloalkyl$_{(C4-12)}$, substituted or unsubstituted alkylamino$_{(C1-14)}$, or alkoxyamino$_{(C1-12)}$. $R_7$ may be selected from the group consisting of —H,

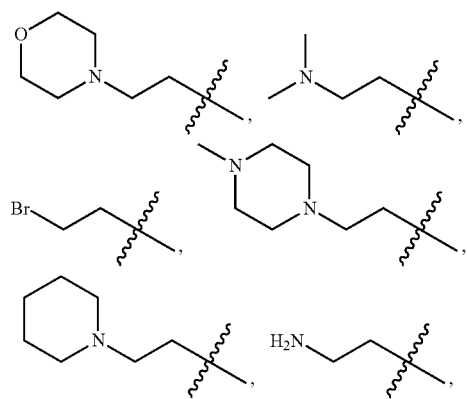

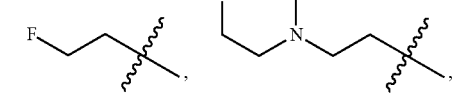

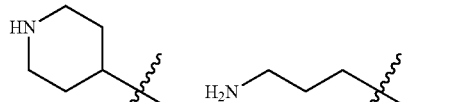

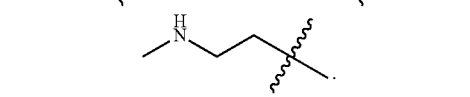

$R_7$ may be selected from the group consisting of —H,

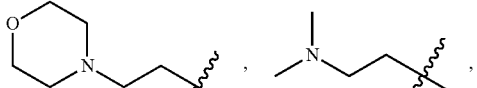

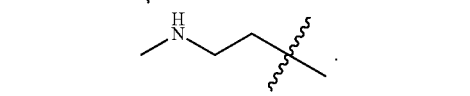

In some embodiments, the compound is:

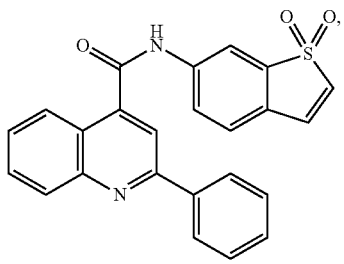

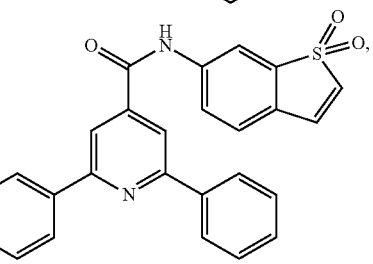

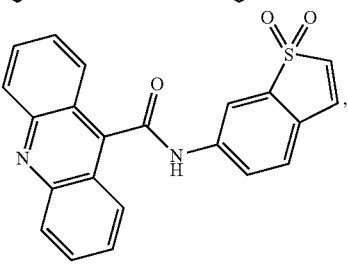

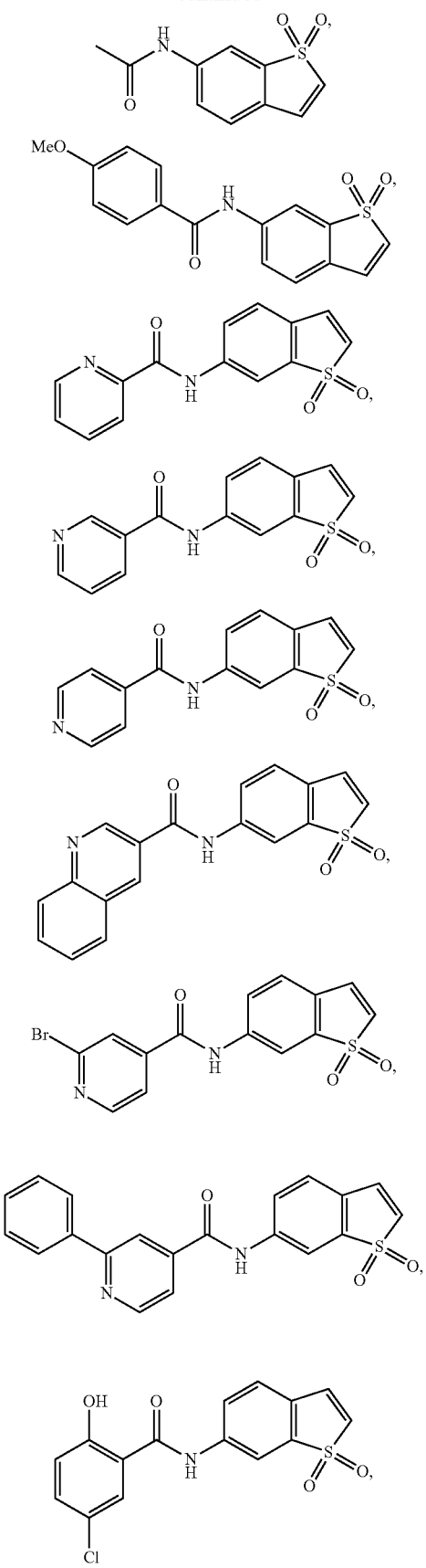
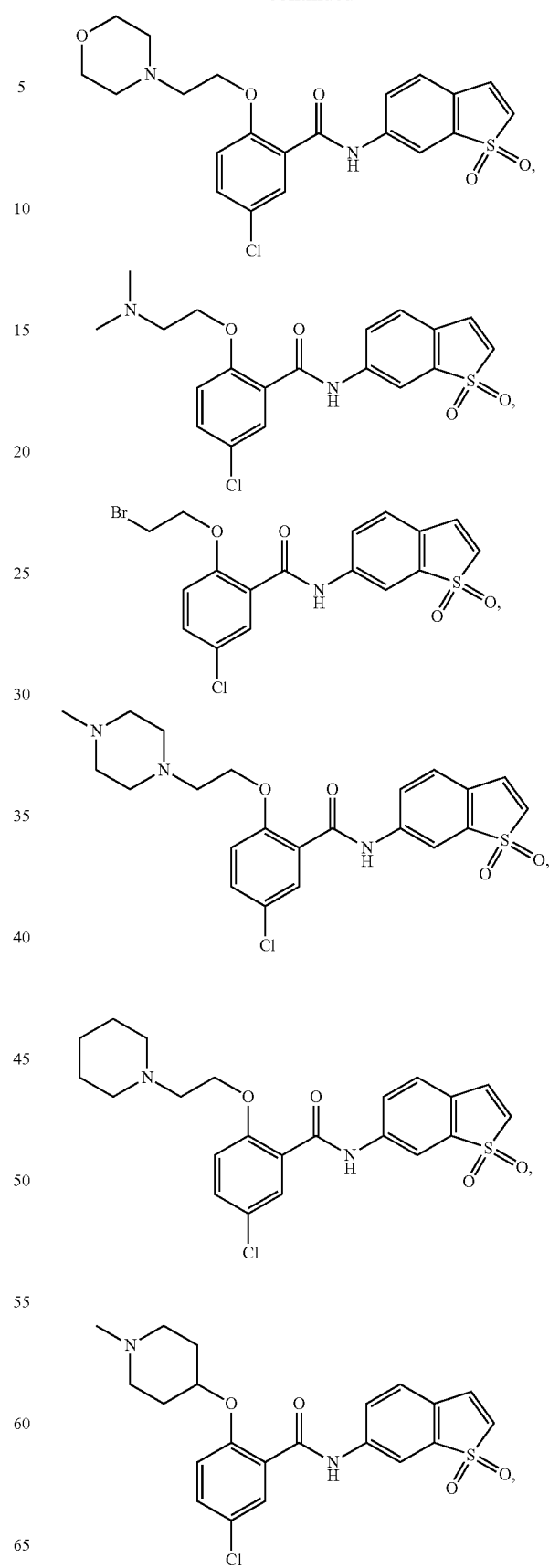

-continued
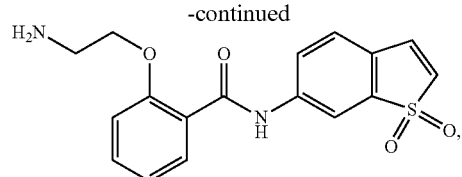
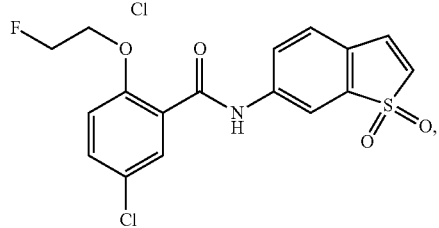
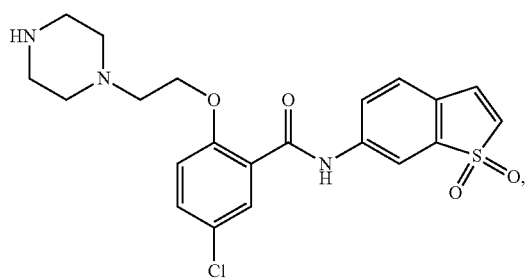
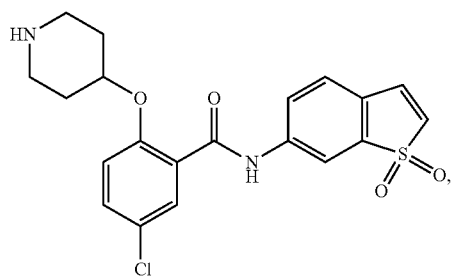
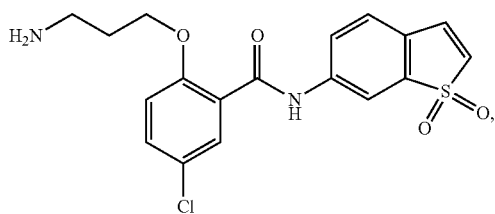
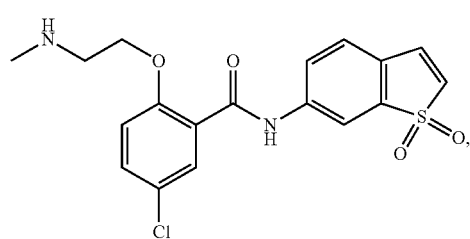
or a salt thereof. In some embodiments, the compound is:
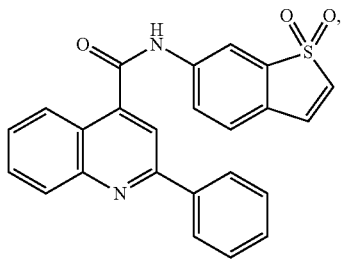
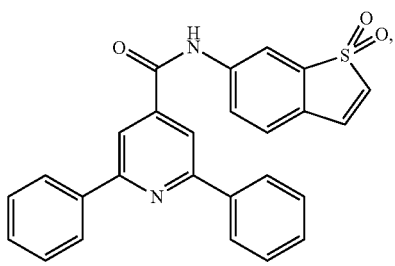
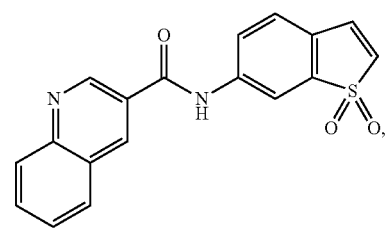
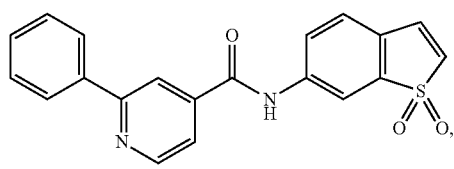
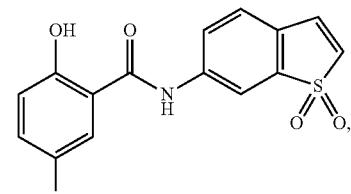
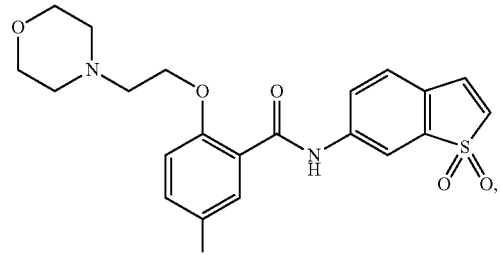
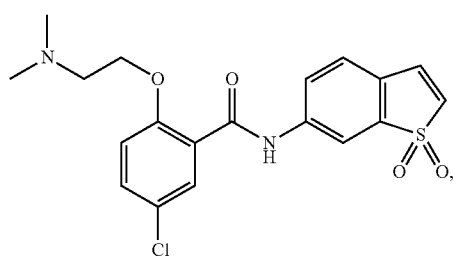

-continued
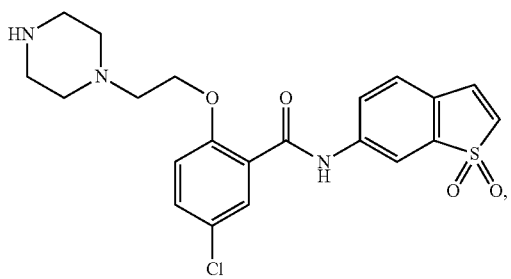
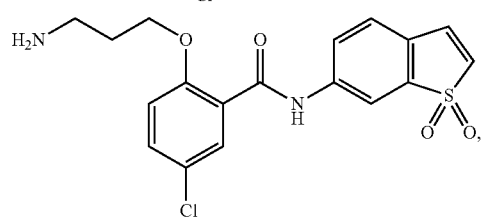
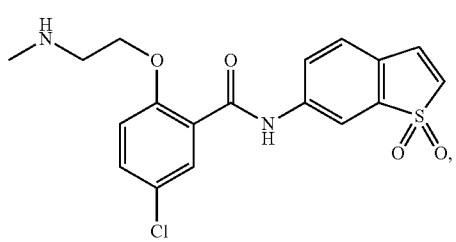
or a salt thereof. R₅ may be
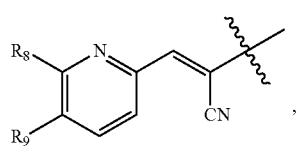
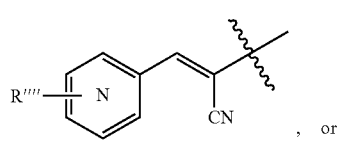
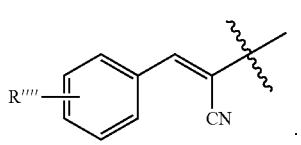
In some embodiments, R₈ is halogen and R₉ is —H. R₈ may be —Br. The compound may be:
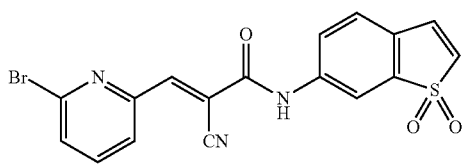
or a salt thereof. The compound may have the structure
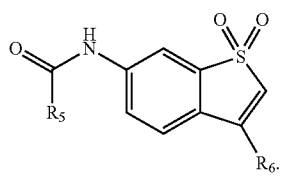
The compound may have the structure
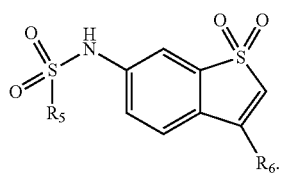
The compound may be
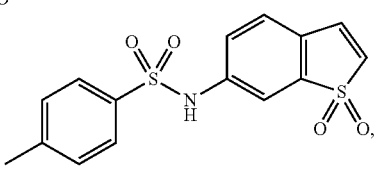
or a salt thereof. R₆ may be —O—CH₃. The compound may have the structure:
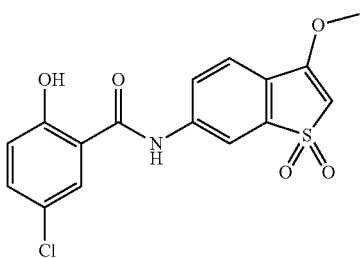
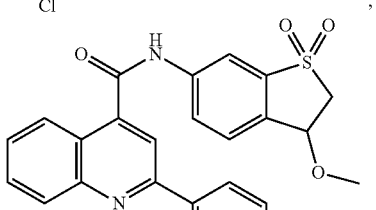
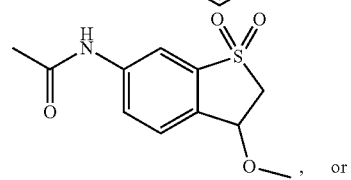

-continued

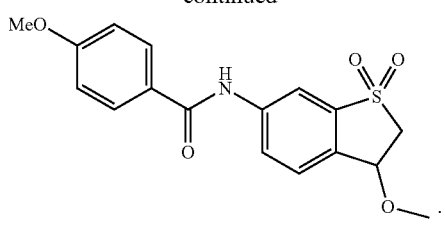

In some embodiments, the compound has structure (III). The compound may have the structure

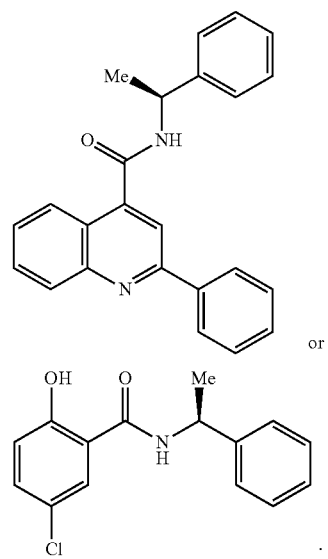

In some embodiments, compound has structure (I) or structure (II); wherein $R_1$ is

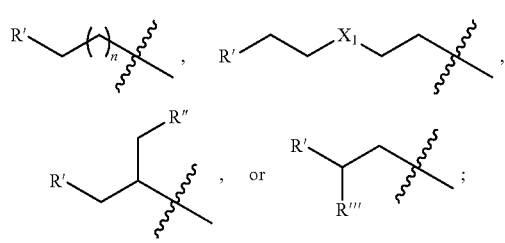

and wherein R' is —NMe₂, —NHMe, —NHAc,

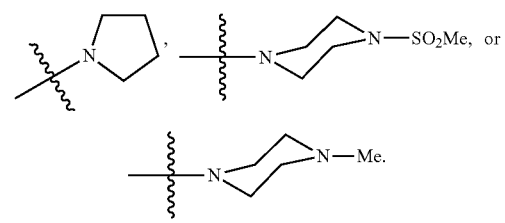

In some embodiments, the compound has the structure:

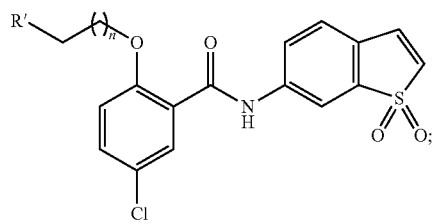

wherein n=1, 2, 3, or 4; wherein R' is —NMe₂, —NHMe, —NHAc,

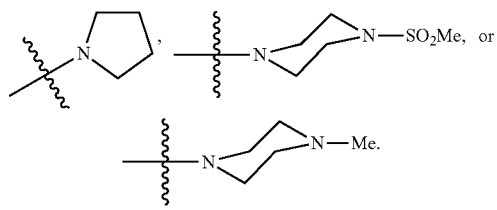

In some embodiments, the compound has the structure:

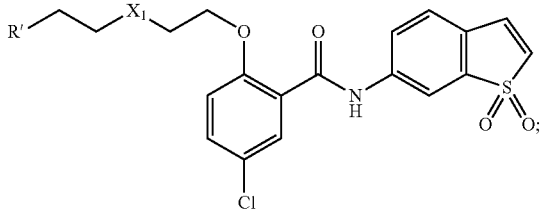

wherein R' is —NMe₂, —NHMe, —NHAc,

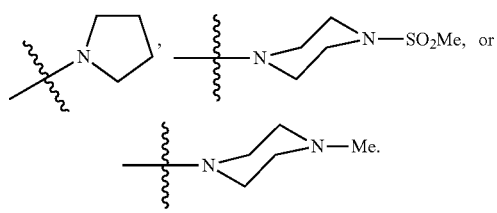

In some embodiments, the compound has the structure:

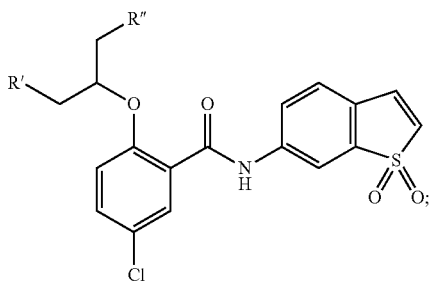

wherein R' is —NMe₂, —NHMe, —NHAc,

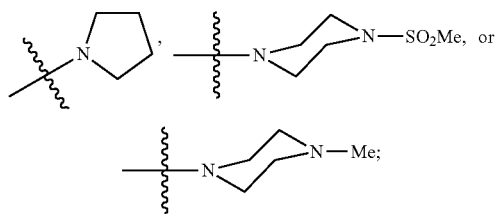

and wherein R" is —H, —NH₂, or —Cl. In some embodiments, the compound has the structure:

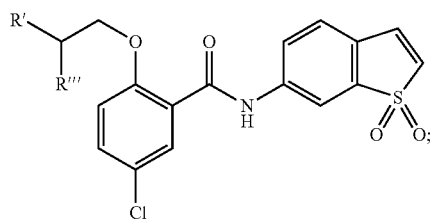

wherein R' is —NMe₂, —NHMe, —NHAc,

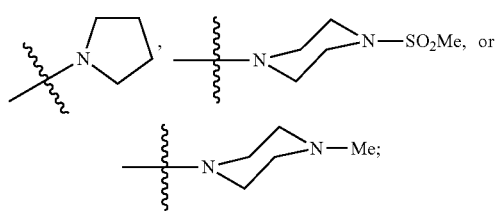

and wherein R'" is -Et or -i—Pr. In some embodiments, the compound has the structure:

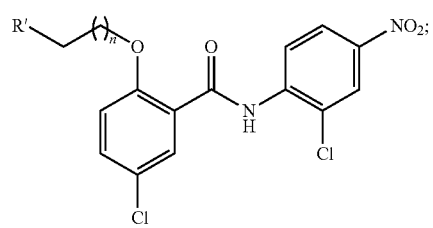

wherein n=1, 2, 3, or 4; wherein R' is —NMe₂, —NHMe, —NHAc,

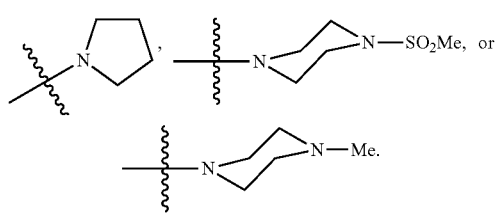

In some embodiments, the compound has the structure:

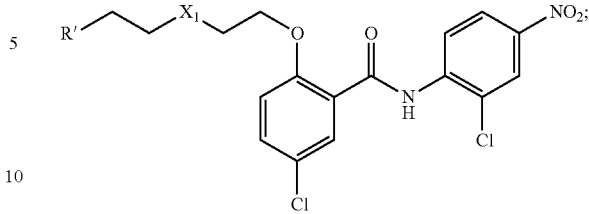

wherein R' is —NMe₂, —NHMe, —NHAc,

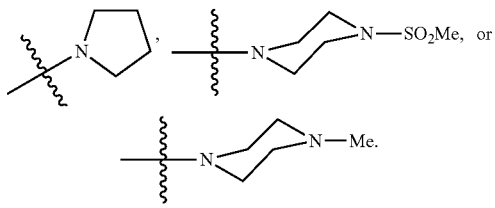

In some embodiments, the compound has the structure:

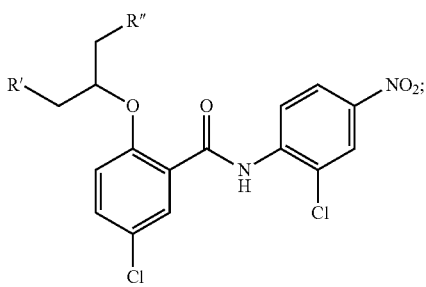

wherein R' is —NMe₂, —NHMe, —NHAc,

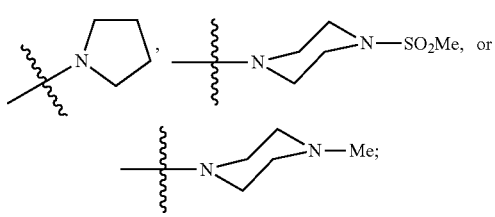

and wherein R" is —H, —NH₂, or —Cl. In some embodiments, the compound has the structure:

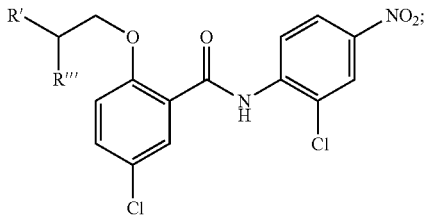

wherein R' is —NMe$_2$, —NHMe, —NHAc,
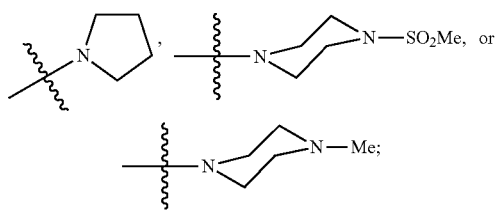
and wherein R''' is -Et or -i-Pr.
In some embodiments, the compound has structure (I) or structure (II), and wherein R$_1$ is selected form the group consisting of
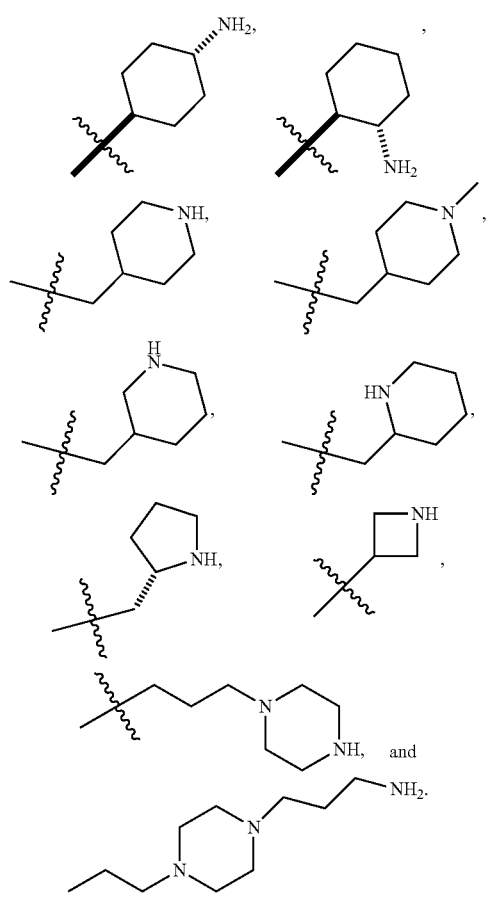
The compound may have the structure
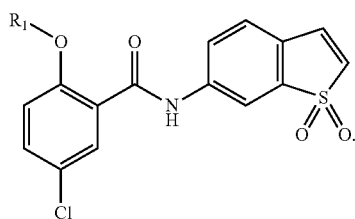
The compound may have the structure
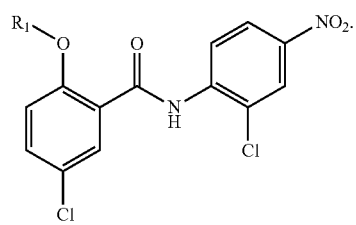
In some embodiments, the compound has the structure
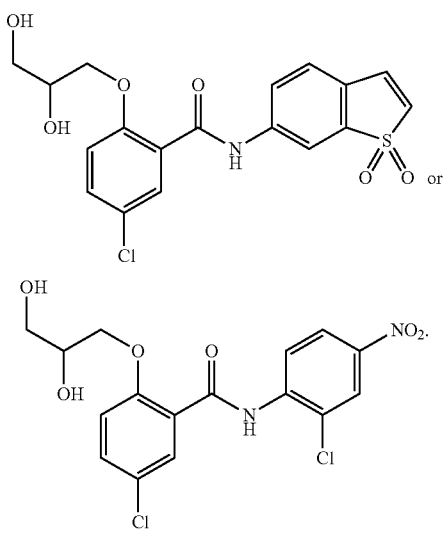
In some embodiments, the compound has the structure
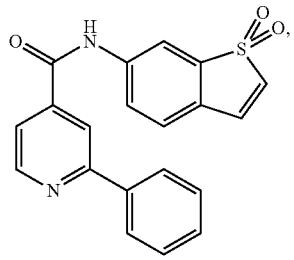
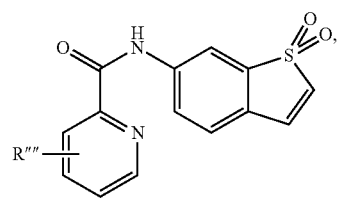
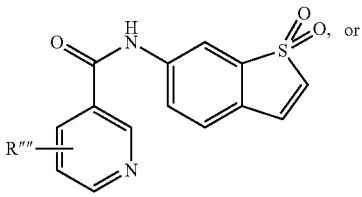

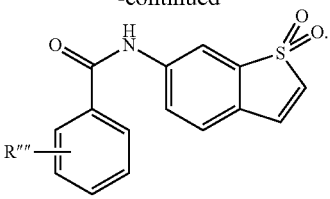
The compound may have the structure
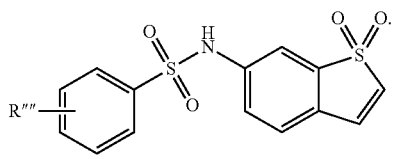
In some embodiments, the compound has structure (IV). The compound may have the structure
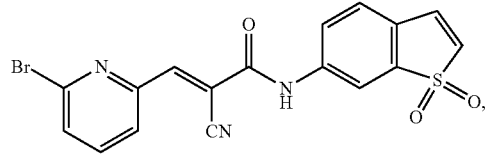
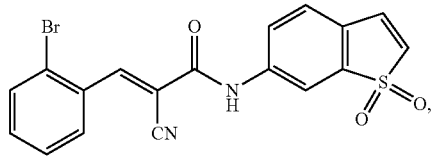
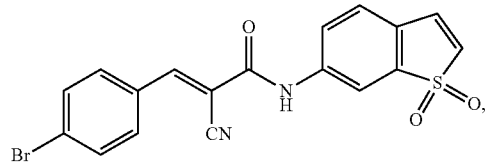
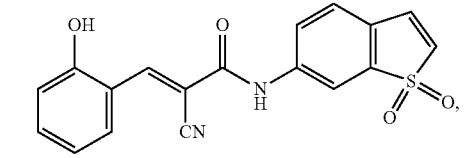
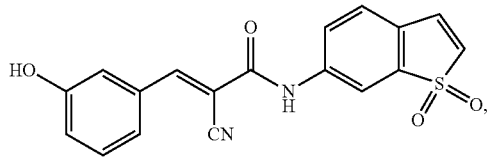
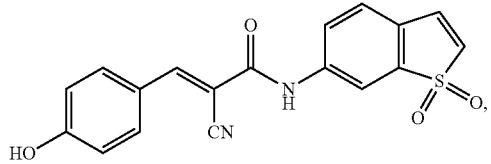
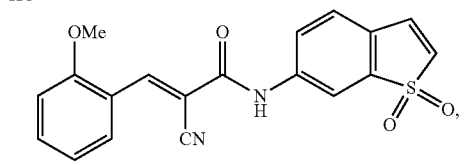
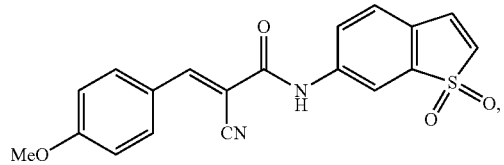
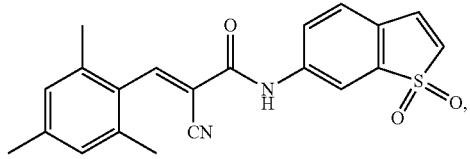
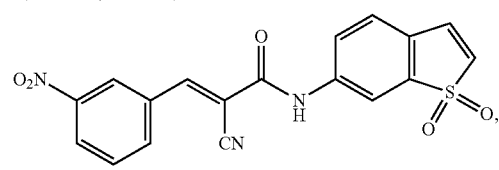
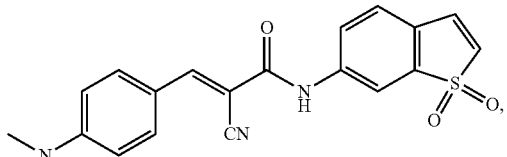
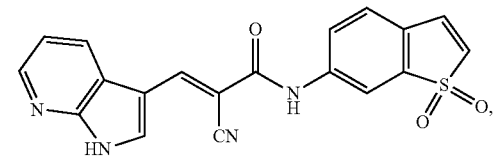
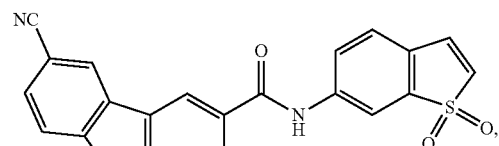
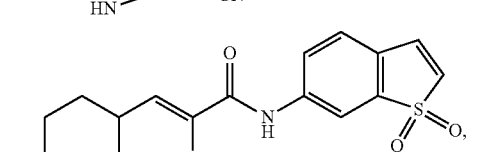
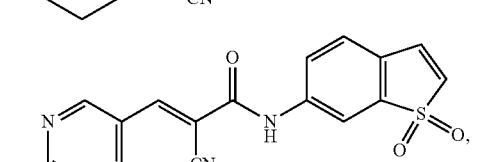
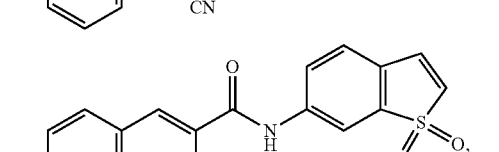
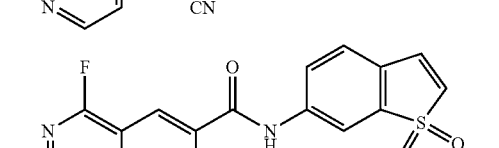

-continued
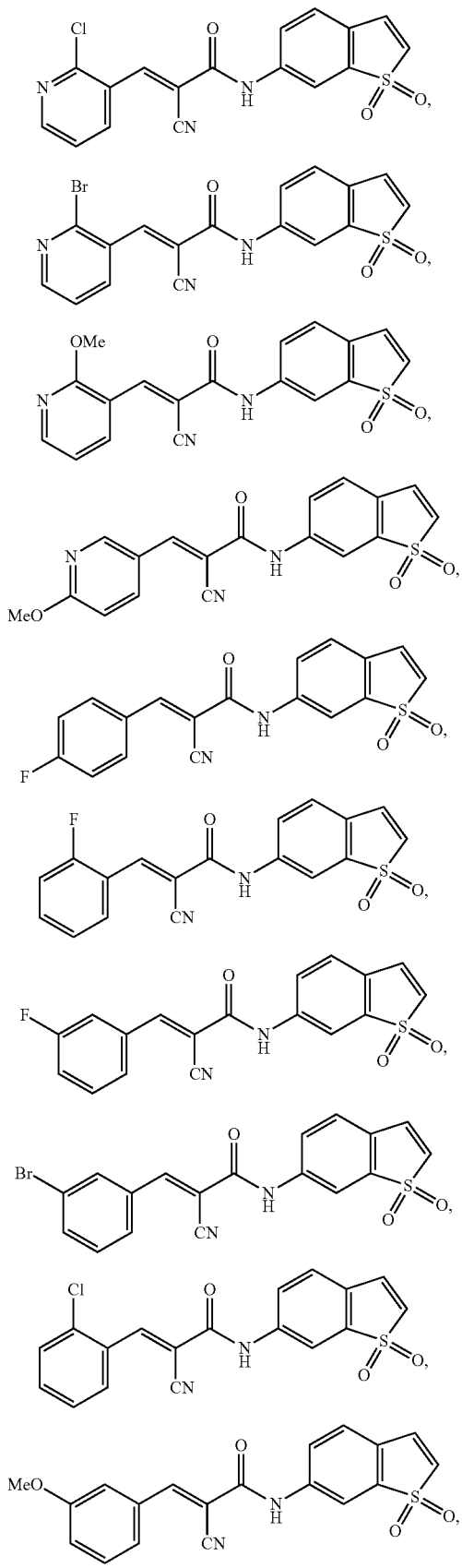
-continued
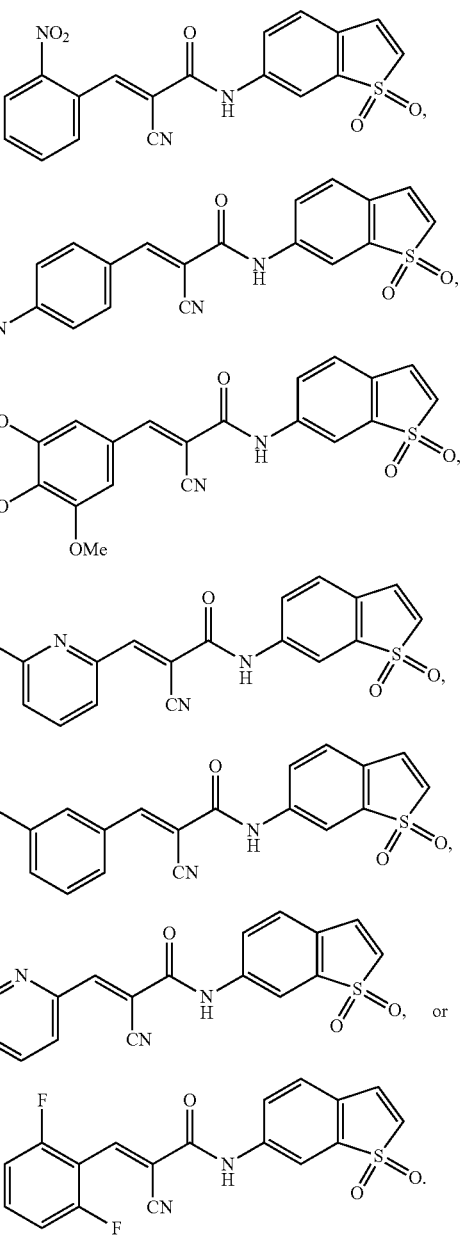
Another aspect of the present invention relates to a compound having the formula:

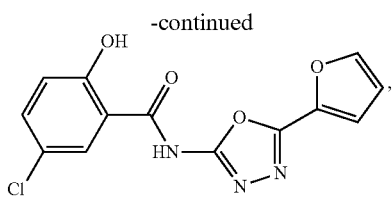

or a salt thereof.

Yet another aspect of the present invention relates to a method of treating cancer in a subject comprising administering a pharmaceutically effective amount of a compound of the present invention to treat the cancer. The cancer may be a breast cancer, pancreatic cancer, brain cancer, head/neck cancer, prostate cancer, lung cancer, colon cancer, or skin cancer. In some embodiments, the cancer is an ER-positive breast cancer or an ER-negative breast cancer. In some embodiments, the cancer is a triple negative breast cancer. Triple-negative breast cancer (TNBC) is a breast cancer subtype that lacks expression of estrogen receptor (ER), progesterone receptor and HER2/Neu receptor. The subject may be a human, mouse, rat, primate, cat, or dog. The compound may be administered to the subject in an amount of about 1-500 mg/kg. The administration may be oral, intravenous, intratumoral, intraperitoneal, subcutaneous, or intramuscular. The method may further comprise administering a second anti-cancer therapy such as, e.g., a chemotherapy, and immunotherapy, a radiotherapy, a gene therapy, or a surgery.

Another aspect of the present invention relates to a method of treating inflammation in a subject comprising administering a pharmaceutically effective amount of a compound of the present invention to treat the inflammation. The inflammation may result from pancreatitis or an inflammatory disease.

Yet another aspect of the present invention relates to a pharmaceutical composition comprising a compound or STAT3 inhibitor of the present invention and an excipient. Another aspect of the present invention relates to a composition comprising a compound or STAT3 inhibitor of the present invention for use in the treatment of inflammation or cancer. The cancer may be a breast cancer, pancreatic cancer, brain cancer, head/neck cancer, prostate cancer, lung cancer, colon cancer, or skin cancer. In some embodiments, the cancer is a breast cancer such as, e.g., a triple negative breast cancer.

It is anticipated that STAT3 inhibitors of the present invention may be used to treat a wide variety of cancers. For example, the cancer may be oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer. The cancer may be deficient in, or have a mutated or inactivated gene such as, e.g., p53, PTEN, ARF, pRB. The cancer may express or overexpress a gene such as, e.g., Her2/Neu. The cancer may comprise cancer stem cells or cancer initiating cells. In some embodiments a STAT3 inhibitor of the present invention may be used as a triple-negative breast cancer (TNBC) treatment.

As shown in the below examples, anticancer activity was observed for compounds, such as on growth of TNBC cells and xenograft tumors using the orally active HJC0152 inhibitor. The effects of HJC0152 on activation and expression of STAT3 and associated proteins in STAT/JAK signaling pathway, growth of TNBC cells and TNBC xenograft tumors in mice, and alterations in signal transduction pathways and networks were analyzed. In vitro, HJC0152 suppressed STAT3 phosphorylation and its nuclear translocation. Inhibition of STAT3 phosphorylation at Y705 and S727 residues started 6 hours after treatment. HJC0152 had minimal effect on STAT1, STAT2, STAT4, STAT6 and their phosphorylation. STAT5 was moderately affected at 6 hours at a higher dose, and recovered at 12 hours in MDA-MB-231 cells. JAK2 and phospho-JAK2 were reduced at 6 hours of treatment, similar to that of STAT3 in MDA-MB-231 cells. HJC0152 also induced apoptosis and apoptotic markers. In vivo, HJC0152 was given orally for a consecutive 14 days. HJC0152 significantly inhibited the growth of TNBC xenografts than the positive control at a lower dose. The expression of STAT3 and phospho-STAT3 was verified in xenograft tumors. Signal transduction pathways and signal proteins that mediate the effect from HJC0152 were analyzed and networks generated. Without wishing to be bound by any theory, these data support the idea that HJC0152 inhibits the growth of TNBC cells and TNBC xenograft tumors via inhibiting STAT3/JAK2 signaling pathway. The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 6A-B: (FIG. 6A) HJC0152 inhibited the STAT3 mediated luciferase reporter activity in MDA-MB-231 cells. (FIG. 6B) Proliferation of MDA-MB-231 cells treated with HJC0152 and Niclosamide for 24 h.

FIGS. 7A-B: (FIG. 7A) Western blot analysis of biochemical markers for apoptosis induction and inhibition of STAT3 activity by HJC0152 in the MDA-MB-231 cell line. (FIG. 7B) Densitometric analysis of three independent experiments for the expression level of total STAT3, phospho-STAT3, cyclin D1 and caspase 3. * represents $p<0.01$, ** represents $p<0.001$.

FIGS. 8A-B: In vivo efficacy of compound 11 (HJC0152) in inhibiting growth of xenograft tumors (Breast cancer MDA-MB-231) in mice. (A) i.p.; (B) p.o.

(FIG. 11A) Surface of the electrostatic map. (FIG. 11B) Residues of STAT3. Compound 5 is shown in small sticks and in pink color. Hydrogen bonds are indicated by dashed lines. The figures were generated using Pymol.

FIGS. 16A-B. Induction of apoptosis on MDA-MB-231 cells by HJC0123. Cells were not treated or treated with 1 µM, 2.5 µM, and 5 µM concentration of HJC0123 for 48 h.

FIGS. 17A-B. Changes of cell cycle distribution in MDA-MB-231 cells after treatment with HJC0123. (FIG. 17A) Cell cycle profiles of MDA-MB-231 cells after treated with HJC0123 for 24 h. (FIG. 17B) The cell cycle distribution expressed in percentage. Cells were not treated or treated with 1 µM, 2.5 µM, and 5 µM concentration of HJC0123. Error bar represents standard deviations. * represents: $p\leq0.05$.

FIGS. 18A-D: Small-molecule inhibitor HJC0152 inhibits STAT3 expression and nuclear translocation. FIG. 18A, Chemical structure of HJC0152. FIG. 18B, Protein levels of STAT3 and phospho-STAT3 in breast cancer cells, analyzed by Western blots. Breast cancer cell lines were grouped as ER-positive, ER-negative and molecular subtypes. MDA-MB-231 cell with IL-6 stimulation was used as control. FIG. 18C, HJC0152 suppresses STAT3 expression and activation in STAT3-low MDA-MB-453 and BT474 cells. Exogenous STAT3 was overexpressed via STATC expression vector. FIG. 18D, Pretreatment of HJC0152 attenuates IL-6 induced-pSTAT3 nuclear translocation. IL-6 treatment lasted 1 h.

FIGS. 19A-B: Dynamic changes in protein level of STAT family, STAT3-dependent genes, and JAKs family. Cells were treated as described in the method section. FIG. 19A, Western blot analyses in MDA-MB-231 cells. FIG. 19B, Western blot analyses in MDA-MB-468 cells.

FIGS. 20A-D: Effect of HJC0152 on mammary cell growth, colony formation and apoptosis. FIG. 20A, MDA-MB-231 cells were grown in 6-well dishes and treated with HJC0152 or niclosamide for 72 h. Morphology was compared at multiple concentrations. FIG. 20B, Proliferation data from 3 cell lines: MDA-MB-231, HMEC and MCF-10A cells were treated with HJC0152 and niclosamide for 72 h and then cell growth compared. FIG. 20C, MDA-MB-231 or MDA-MB-468 cells were seeded in 6-well tissue culture plates with a density of 800 or 3,000 cells to compare colony formation ability in the presence of STAT3 inhibitor shown MDA-MB-568 cell). Image results at the end of 2-week experiments. Representative colony formation results were shown. FIG. 20D, Apoptosis was analyzed with combined data from 3 independent experiments. MDA-MB-231 cells were treated as described in method section. Percentage of cells underwent apoptosis, early or late apoptotic phases, was analyzed with flow cytometry using Muse Cell Analyzed, % changes were shown inside the panels.

FIGS. 21A-D: HJC0152 by oral gavage suppresses the growth of xenograft tumors arose from TNBC MDA-MB-231 cells. Cells were maintained in full potential grow and collected to generate xenograft tumors. FIG. 21A, Oral treatment with HJC0152, niclosamide and vehicle for a continuous 14 days when the tumor reach 100 mm³. FIG. 21B, Body weight and toxicity signs were measured and recorded daily. FIG. 21C, IHC staining with pSTAT3(Y705) antibody in the sections of xenograft tumors. FIG. 21D, Western blot analysis of the total tissue lysates from the tumors in mice treated with HJC0152, niclosamide or vehicle from panel FIG. 21A.

DESCRIPTION OF ILLUSTRATIVE EMBODIMENTS

The present invention overcomes limitations in the prior art by providing synthetic low molecular-weight compounds that specifically block STAT3 activation in breast cancer cells as well as other cancers. As shown in the below examples, the STAT3 inhibitors displayed activity in 4 breast and 3 pancreatic cancer cell lines. Several of these compounds were found to be effective in suppressing cell growth and display improved drug-like properties. The STAT3 inhibitors may be used as drug candidates for preclinical and clinical trials. The compounds may be used as preventive or therapeutic agents for various cancers including but not limited to breast cancers, pancreatic cancer, brain tumors, head/neck cancer, prostate and lung cancers as well as inflammation.

Figure 1:
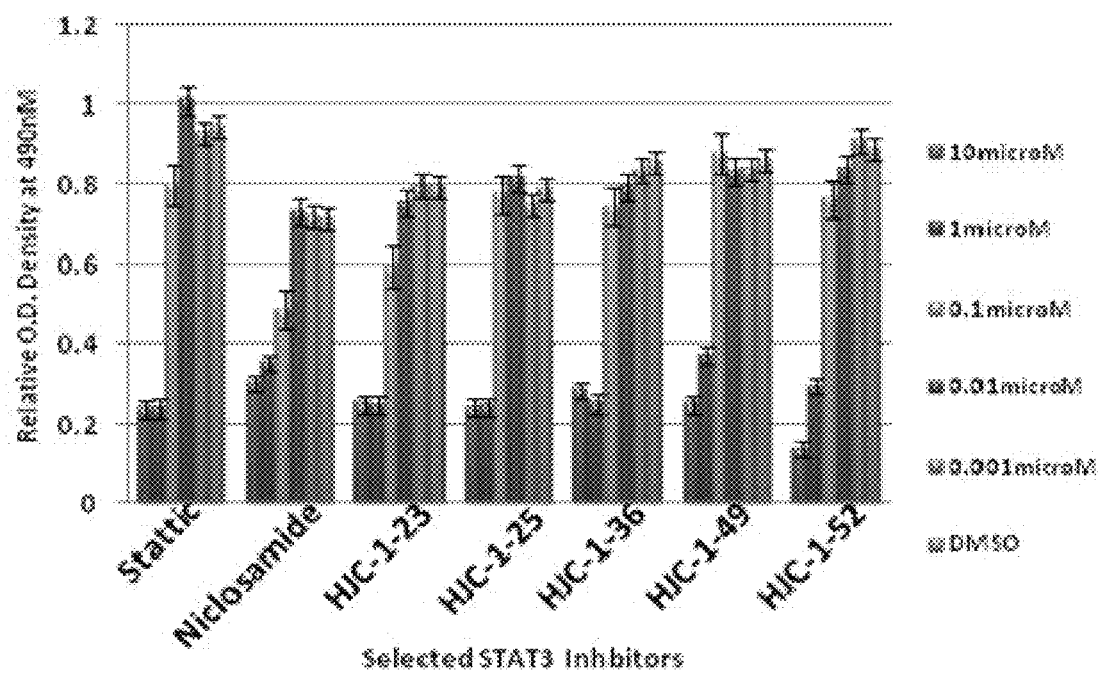
FIG. 1: Selected novel STAT3 inhibitors significantly reduced proliferation of MCF-7 breast cancer cells 48 hr after treatment at µM concentrations. The effect of selected STAT3 inhibitors on the proliferation of MCF-7 breast cancer cells are shown.

High levels of activated STAT3 are often correlated with poor outcome in human breast cancer patients in terms of metastatic progression. Furthermore, increased STAT3 transcriptional activity was correlated with ER-negative phenotype in breast cancer cell lines and in primary human invasive ductal breast carcinomas. Therefore, inhibition of STAT3 may be used for the prevention and treatment of both ER-positive and ER-negative breast cancer. The inventors hypothesized that the specific STAT3 inhibitors will block STAT3 activation in mammary epithelial cells, premalignant breast cells and breast cancer cells, resulting in blockade of malignant transformation of mammary epithelial cells and reduction of breast cancer development in transgenic models. As shown in the below examples, compounds were synthesized and shown to inhibit STAT3 in breast cancer and pancreatic cancer cells. A number of compounds demonstrated significant inhibition on breast cancer cell proliferation in vitro (e.g., Table 1, Table 2, and FIG. 1) and tumor growth in vivo (FIG. 3), accompanied with morphological changed in cellular appearance (FIG. 2), as well as significant inhibition on pancreatic cancer cell proliferation (e.g., Table 1, Table 2).

I. Chemical Group Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO₂H); "halo" means independently —F, —Cl, —Br or —I; "amino" means —NH₂; "hydroxyamino" means —NHOH; "nitro" means —NO₂; imino means =NH; "cyano" means —CN; "isocyanate" means —N=C=O; "azido" means —N₃; in a monovalent context "phosphate" means —OP(O)(OH)₂ or a deprotonated form thereof; in a divalent context "phosphate" means —OP(O)(OH)O— or a deprotonated form thereof; "mercapto" means —SH; and "thio" means =S; "sulfonyl" means —S(O)₂—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⩵" represents a single bond or a double bond. Thus, for example, the structure

includes the structures

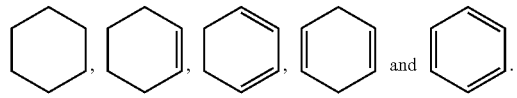

As will be understood by a person of skill in the art, no one such ring atom forms part of more than one double bond. The symbol "⁓", when drawn perpendicularly across a bond indicates a point of attachment of the group. It is noted that the point of attachment is typically only identified in this manner for larger groups in order to assist the reader in rapidly and unambiguously identifying a point of attachment. The symbol "◢" means a single bond where the group attached to the thick end of the wedge is "out of the page." The symbol "◣" means a single bond where the group attached to the thick end of the wedge is "into the page". The symbol "⁓" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

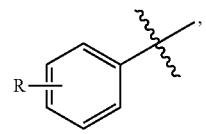

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

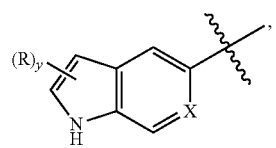

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). Where the term "aliphatic" is used without the "substituted" modifier, then only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

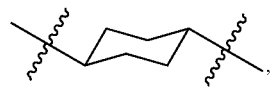 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH═CH—, —CH═C(CH$_3$)CH$_2$—, —CH═CHCH$_2$—, and

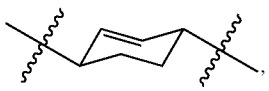 [SMILES: *C1C=CC(*)CC1]

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$CH$_3$, or —S(O)$_2$NH$_2$. The groups, —CH═CHF, —CH═CHCl and —CH═CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

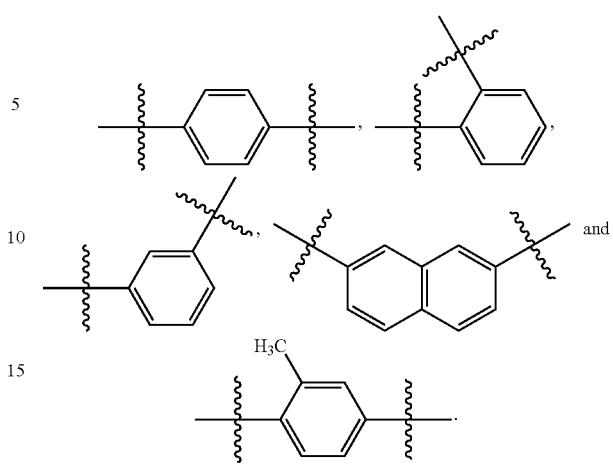

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$CH$_3$, or —S(O)$_2$NH$_2$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

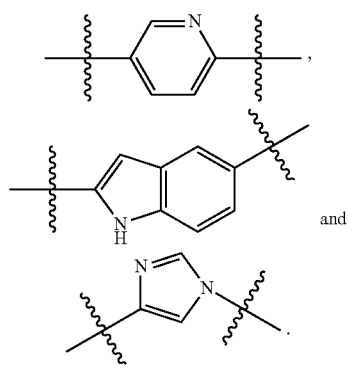

and

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O) CH$_3$, —NHCH$_3$, —NHCH$_2$CH$_3$, —N(CH$_3$)$_2$, —C(O)NH$_2$, —OC(O)CH$_3$, —S(O)$_2$CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. As used herein, the term does not preclude the presence of one or more double bonds in the ring or ring system, provided that the resulting groups remains non-aromatic. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$CH$_3$, —S(O)$_2$NH$_2$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH (CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "carboxylate" when used without the "substituted" modifier refers to the group —C(O)OR, in which R is a hydrogen, alkyl, aryl, aralkyl or heteroaryl, as those terms are defined above. The groups, —C(O)OH, —C(O)OCH$_3$, —C(O)OCH$_2$CH$_3$, and —C(O)OC(CH$_3$)$_3$ are non-limiting examples of carboxylate groups. When this term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted carboxylate groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "aryl sulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—CH$_2$CH$_2$—]$_n$—, the repeat unit is —CH$_2$CH$_2$—. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$), benzyloxycarbonyl, p-methoxybenzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Compounds of the Invention

The compounds provided by the present disclosure are shown, for example, above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

In some embodiments, compounds may be synthesized according to one or more of the below schemes.

Scheme 1$^a$

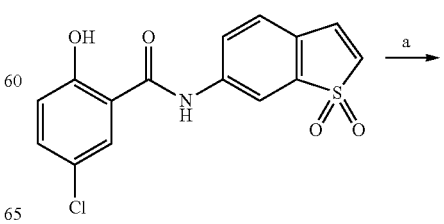

1

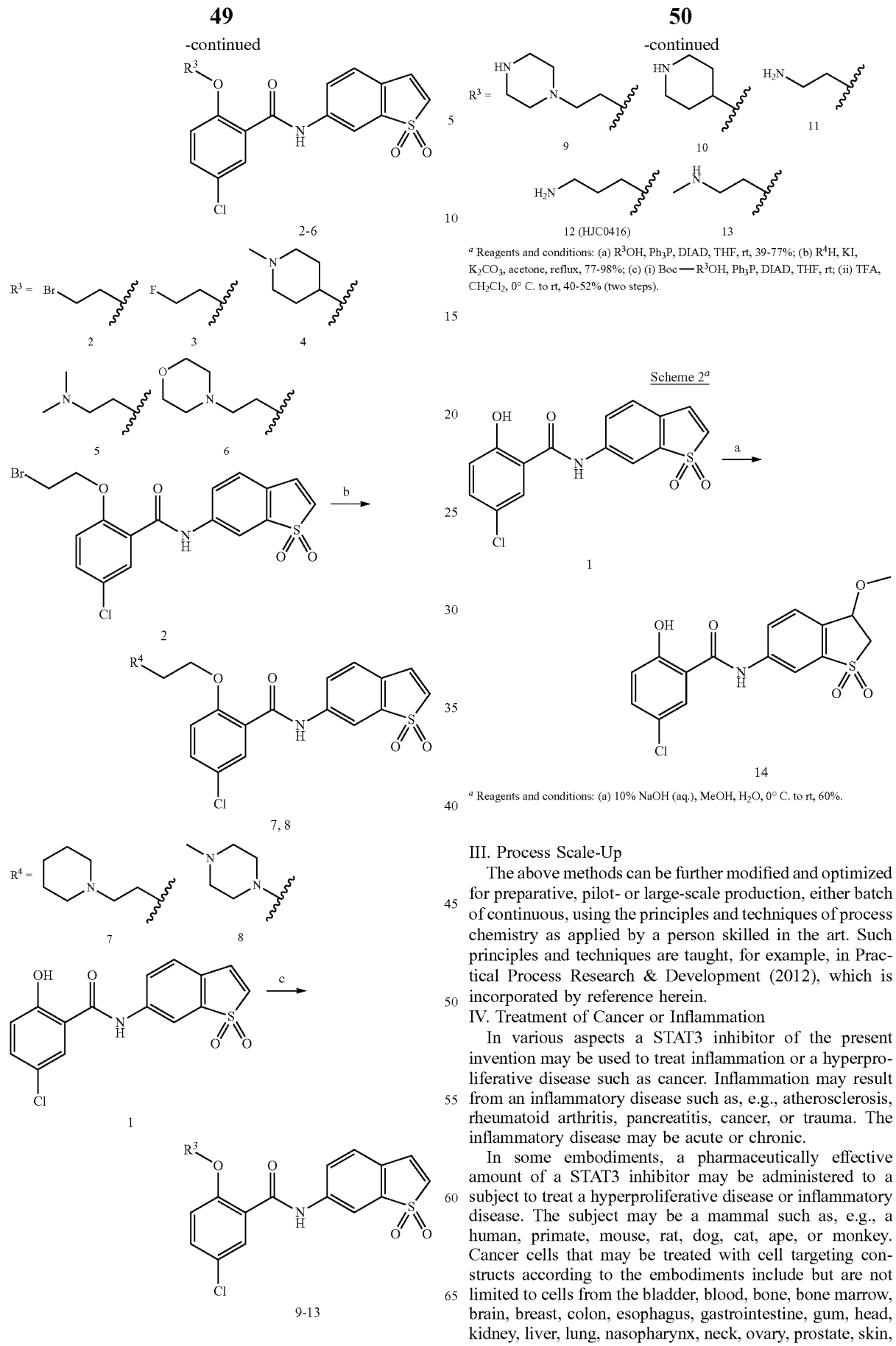

III. Process Scale-Up

The above methods can be further modified and optimized for preparative, pilot- or large-scale production, either batch of continuous, using the principles and techniques of process chemistry as applied by a person skilled in the art. Such principles and techniques are taught, for example, in Practical Process Research & Development (2012), which is incorporated by reference herein.

IV. Treatment of Cancer or Inflammation

In various aspects a STAT3 inhibitor of the present invention may be used to treat inflammation or a hyperproliferative disease such as cancer. Inflammation may result from an inflammatory disease such as, e.g., atherosclerosis, rheumatoid arthritis, pancreatitis, cancer, or trauma. The inflammatory disease may be acute or chronic.

In some embodiments, a pharmaceutically effective amount of a STAT3 inhibitor may be administered to a subject to treat a hyperproliferative disease or inflammatory disease. The subject may be a mammal such as, e.g., a human, primate, mouse, rat, dog, cat, ape, or monkey. Cancer cells that may be treated with cell targeting constructs according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

V. Pharmaceutical Compositions

Pharmaceutical compositions of the present invention comprise an effective amount of one or more compounds of the present invention, e.g., a STAT3 inhibitor, or additional agent dissolved or dispersed in a pharmaceutically acceptable carrier. In some embodiments, a STAT3 inhibitor of the present invention may be conjugated with a pharmaceutically acceptable carrier such as a nanoparticle or biotin. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one compound or STAT3 inhibitor or additional active ingredient will be known to those of skill in the art in light of the present disclosure, as exemplified by *Remington: The Science and Practice of Pharmacy*, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, conjugates, antioxidants, preservatives (e.g., antibacterial agents, antifungal agents), isotonic agents, absorption delaying agents, salts, preservatives, drugs, drug stabilizers, gels, polymers, nanoparticles, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18$^{th}$ Ed. Mack Printing Company, 1990, pp. 1289-1329, incorporated herein by reference). Except insofar as any conventional carrier is incompatible with the active ingredient, its use in the pharmaceutical compositions is contemplated.

The compound or STAT3 inhibitor of the present invention may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18$^{th}$ Ed. Mack Printing Company, 1990, incorporated herein by reference).

The compound or STAT3 inhibitor of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, polymers, nanoparticles, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include a compound or STAT3 inhibitor of the present invention, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the compound or STAT3 inhibitor of the present invention may be dispersed in a solution containing a lipid, dissolved with a lipid, emulsified with a lipid, mixed with a lipid, combined with a lipid, covalently bonded to a lipid, contained as a suspension in a lipid, contained or complexed with or conjugated with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the compound or STAT3 inhibitor of the present invention is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, a compound or STAT3 inhibitor of the present invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound or STAT3 inhibitor may be formulated for administration via various miscellaneous routes, for example, topical or transdermal administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Compounds

The following experimental procedures were used to generate the following compounds.

5-Chloro-N-(2-chloro-4-nitro-phenyl)-2-(2-morpholin-4-yl-ethoxy)benzamide (HJC-1-14)

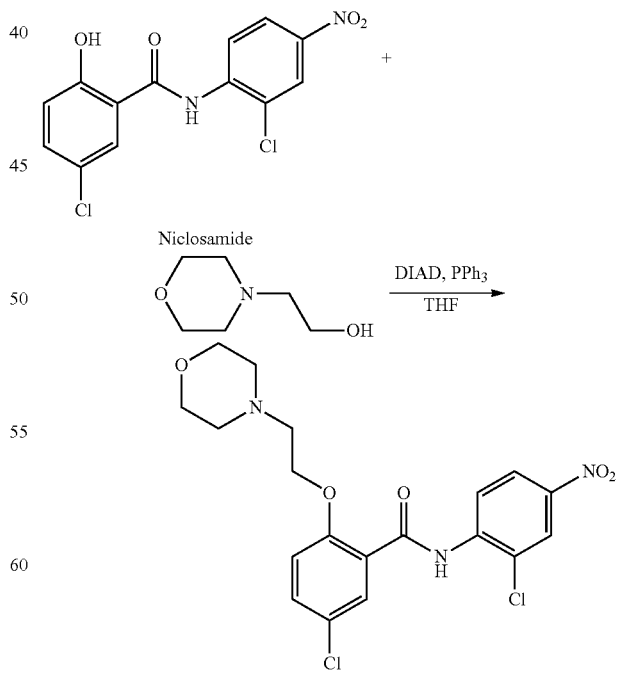

To a solution of niclosamide (150 mg, 0.46 mmol) and PPh$_3$ (217 mg, 0.83 mmol) in THF (8 mL) was added 2-morpholin-4-yl-ethanol (108 mg, 0.83 mmol) and DIAD (168 mg, 0.83 mmol). The mixture was stirred at r.t. for 1 h. The mixture was partitioned between EtOAc (50 mL) and H$_2$O (30 mL). The organic layer was added 10% HCl (3 mL). A white suspension formed during the course of addition. The solid was filtrated and washed with EtOAc (20 mL). The solid was suspended in EtOAc (50 mL), and basified with 10% NaHCO$_3$. The organic layer was dried with anhydrous Na$_2$SO$_4$, concentrated to give a yellow solid. The crude product was purified with silica gel column (DCM/MeOH=50/1) to obtain HJC-1-14 (119 mg, 59%) as a pale yellow solid. $^1$H NMR (600 MHz, CDCl$_3$) δ 10.63 (s, 1H), 8.75 (d, 1H, J=9.6 Hz), 8.31 (s, 1H), 8.20 (s, 1H), 8.19 (d, 1H, J=9.6 Hz), 7.47 (d, 1H, J=9.0 Hz), 7.05 (d, 1H, J=9.0 Hz), 4.40 (t, 2H, J=6.0 Hz), 3.39-3.41 (m, 4H), 2.84 (d, 1H, J=6.0 Hz), 2.43-2.45 (m, 4H). $^{13}$C NMR (150 MHz, CDCl$_3$) δ 162.5, 155.2, 143.2, 141.1, 133.8, 132.4, 127.6, 124.7, 123.5, 123.4, 122.8, 122.0, 115.2, 67.5, 66.7, 56.8, 53.7.

4-[4-Chloro-2-(2-chloro-4-nitro-phenylcarbamoyl)phenoxyl]piperidine-1-carboxylic acid tert-butyl ester (HJC-1-16)

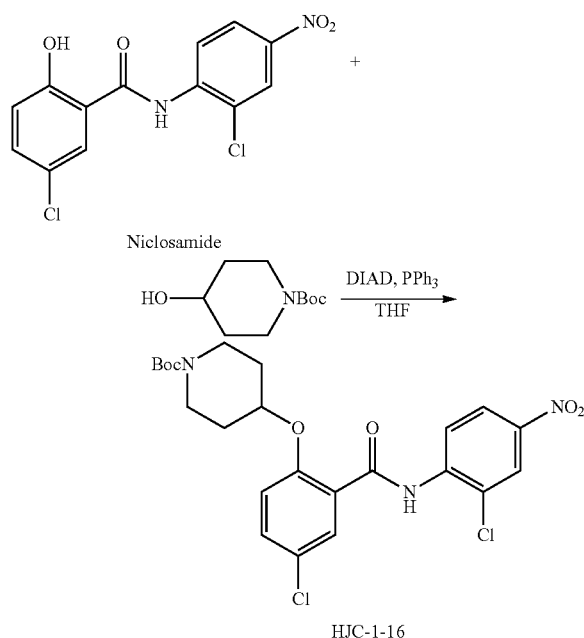

To a solution of niclosamide (200 mg, 0.6 mmol) and PPh$_3$ (288 mg, 1.1 mmol) in THF (10 mL) was added tert-butyl 4-hydroxypiperidine-1-carboxylate (222 mg, 1.1 mmol) and DIAD (222 mg, 1.1 mmol). The reaction mixture was stirred at r.t. for 4 h, and then it was partitioned between EtOAc (50 mL) and H$_2$O (20 mL). The organic layer was washed with brine (10 mL), dried with anhydrous Na$_2$SO$_4$, and concentrated to give the crude product. This residue was purified with silica gel column (hexane/EtOAc=3/1) to afford HJC-1-16 (180 mg, 58%) as a white solid. $^1$H NMR (600 MHz, CDCl$_3$) δ 10.17 (s, 1H), 8.85 (d, 1H, J=9.6 Hz), 8.32 (s, 1H), 8.20 (d, 1H, J=6.0 Hz), 8.17 (s, 1H), 7.46 (d, 1H, J=8.4 Hz), 7.03 (d, 1H, J=6.0 Hz), 4.61-4.63 (m, 1H), 3.99-3.41 (m, 2H), 2.98-3.02 (m, 2H), 210-2.12 (m, 2H), 1.81-1.83 (m, 2H), 1.45 (s, 9H).

5-Chloro-N-(2-chloro-4-nitro-phenyl)-2-(piperidin-4-yloxy)benzamide (HJC-1-25)

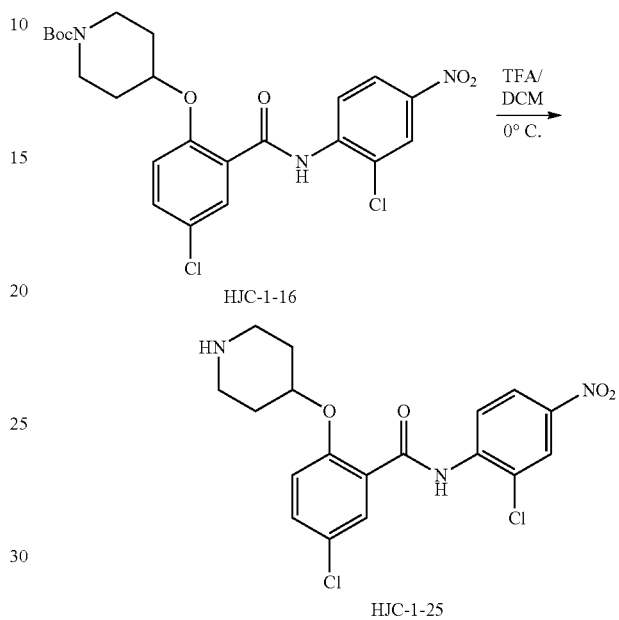

To a solution of HJC-1-16 (150 mg, 0.29 mmol) in DCM (4 mL) was added TFA (1 mL) at 0° C. The mixture was stirred at 0° C. for 1 h. The reaction mixture was concentrated, and the residue was partitioned between EtOAc (50 mL) and 1 N NaHCO$_3$ (10 mL). The organic layer was washed with brine (10 mL), dried with anhydrous Na$_2$SO$_4$, and concentrated to give the crude product. This residue was purified with silica gel column (DCM/MeOH=10/1) to provide HJC-1-25 (70 mg, 58%) as a pale yellow solid. $^1$H NMR (600 MHz, CD$_3$OD) δ 8.71 (d, 1H, J=9.6 Hz), 8.39 (s, 1H), 8.24 (d, 1H, J=9.6 Hz), 7.96 (s, 1H), 7.55 (d, 1H, J=9.0 Hz), 7.33 (d, 1H, J=9.0 Hz), 4.91-4.94 (m, 1H), 3.40-3.43 (m, 2H), 3.13-3.18 (m, 2H), 2.32-2.35 (m, 2H), 2.04-2.10 (m, 2H). $^{13}$C NMR (150 MHz, CD$_3$OD) δ 164.8, 154.6, 145.1, 141.9, 134.6, 132.3, 128.3, 126.1, 125.9, 125.0, 124.3, 123.5, 117.6, 73.6, 42.9, 29.1.

2-Phenyl-quinoline-4-carboxylic acid (2-chloro-4-nitro-phenyl)amide (HJC-1-17)

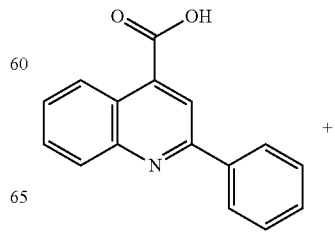

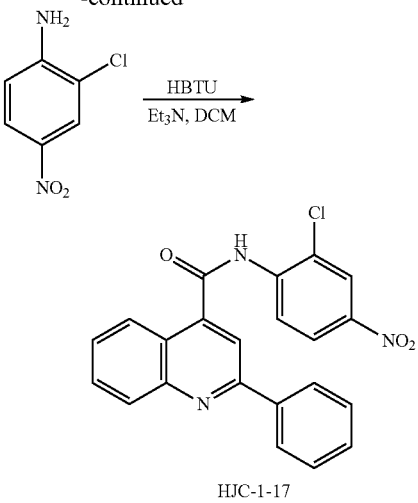

To a solution of 2-phenyl-quinoline-4-carboxylic acid (249 mg, 1.0 mmol) and 2-chloro-4-nitrobenzenamine (173 mg, 1.0 mmol) in 10 mL of DCM was added Et$_3$N (304 mg, 3.0 mmol). HBTU (606 mg, 1.6 mmol) was added at 0° C. The resulting mixture was stirred at r.t. for 28 h. A white suspension formed during the reaction. The precipitate was collected by filtration and washed with DCM (50 mL) and EtOAc (50 mL). The desired product was obtained as a white solid (150 mg, 37%). $^1$H NMR (600 MHz, DMSO-d6) δ 8.62-8.64 (m, 1H), 8.51-8.53 (m, 1H), 8.32-8.36 (m, 1H), 7.94-7.97 (m, 4H), 7.75-7.77 (m, 1H), 7.50-7.53 (m, 5H), 7.19-7.21 (m, 1H).

2-Phenyl-quinoline-4-carboxylic acid (1,1-dioxo-1H-1λ$^6$-benzo[b]thiophen-6-yl)-amide (HJC-1-23)

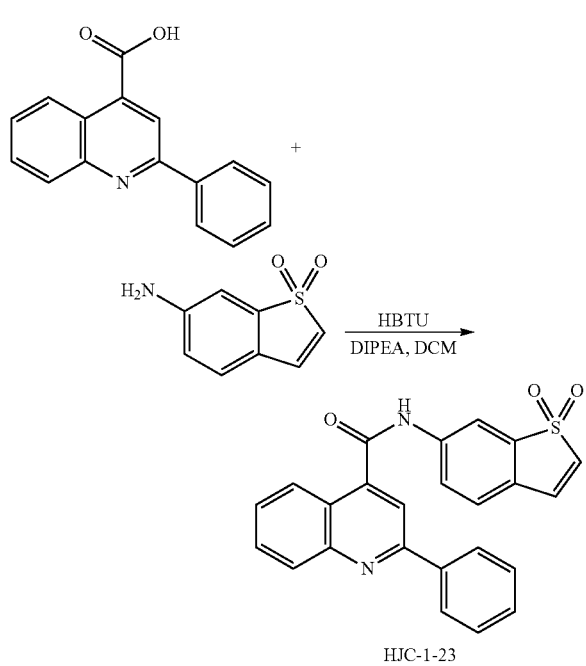

To a solution of 2-phenyl-quinoline-4-carboxylic acid (249 mg, 1.0 mmol) and 1,1-dioxo-1H-1λ$^6$-benzo[b]thiophen-6-ylamine (181 mg, 1.0 mmol) in 10 mL of DCM was added DIPEA (388 mg, 3.0 mmol). HBTU (569 mg, 1.5 mmol) was added at 0° C. The resulting mixture was stirred at r.t. for 28 h. An additional amount of HBTU (190 mg, 0.5 mmol) was added to the solution at 0° C., and the resulting mixture was stirred at r.t. for 24 h. A white suspension formed during the reaction. The precipitate was dissolved in DMF (10 mL). The solution was added to the stirring water dropwise. A yellow solid was formed. The solid was filtered and washed with H$_2$O. 160 mg of the desired product was obtained as a yellow solid (39% yield). $^1$H NMR (600 MHz, DMSO-d6) δ 11.29 (s, 1H), 8.44 (s, 1H), 8.38 (d, 2H, J=7.2 Hz), 8.34 (s, 1H), 8.20 (dd, 2H, J=5.4 Hz, 13.8 Hz), 7.98 (d, 1H, J=7.8 Hz), 7.88 (t, 1H, J=7.2 Hz), 7.54-7.70 (m, 6H), 7.34 (d, 1H, J=6.6 Hz). $^{13}$C NMR (150 MHz, DMSO-d6) δ 165.8, 155.8, 147.9, 142.2, 141.2, 138.0, 137.2, 132.9, 130.5, 130.4, 130.0, 129.7, 129.0, 127.6, 127.3, 126.6, 126.3, 125.1, 124.2, 123.0, 117.1, 117.1, 112.3, 112.3.

2-Phenyl-quinoline-4-carboxylic acid (1-phenyl-ethyl)amide (HJC-1-28)

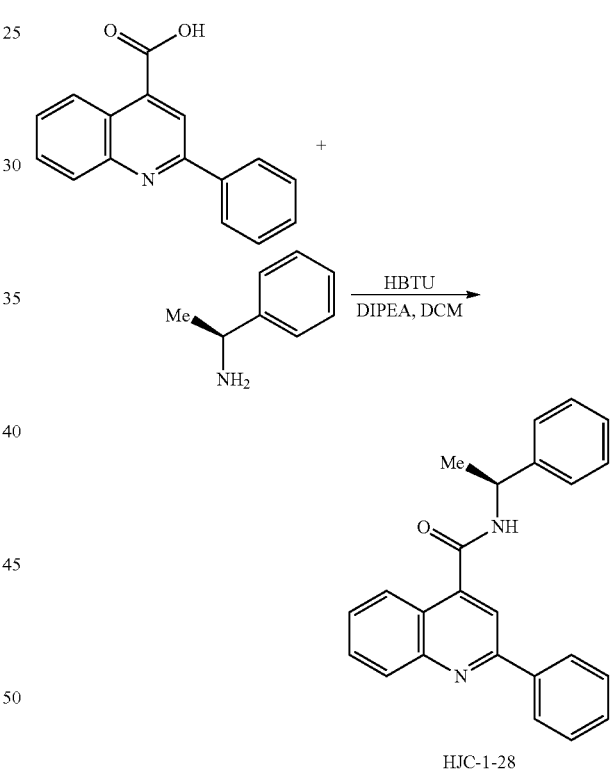

To a solution of 2-phenyl-quinoline-4-carboxylic acid (249 mg, 1.0 mmol) and L(−)-α-methylbenzylamine (127 mg, 1.05 mmol) in 10 mL of DCM was added DIPEA (388 mg, 3.0 mmol). HBTU (569 mg, 1.5 mmol) was added at 0° C. The resulting mixture was stirred at r.t. for 3 h. The reaction mixture was diluted with DCM (80 mL) and washed with water (20 mL). The organic layer was separated and dried with anhydrous Na$_2$SO$_4$. The solution was concentrated to give a crude product, which was purified with silica gel column (EtOAc/hexane=1/3) to obtain HJC-1-28 (330 mg, 94%) as a white solid. $^1$H NMR (600 MHz, DMSO-d6) δ 8.03-8.07 (m, 3H), 7.97 (d, 1H, J=8.4 Hz), 7.71 (s, 1H), 7.67 (t, 1H, J=7.2 Hz), 7.28-7.48 (m, 9H), 6.78

(d, 1H, J=7.2 Hz), 5.38-5.43 (m, 1H), 1.66 (d, 3H, J=6.6 Hz). <sup>13</sup>C NMR (150 MHz, DMSO-d6) δ 166.8, 156.7, 148.6, 142.9, 142.7, 138.8, 130.1, 130.0, 130.0, 129.8, 128.9, 127.8, 127.6, 127.3, 126.4, 125.0, 125.0, 123.4, 116.4, 116.3, 49.7, 22.0.

N-(4-Amino-2-chloro-phenyl)-5-chloro-2-hydroxy-benzamide (HJC-1-29)

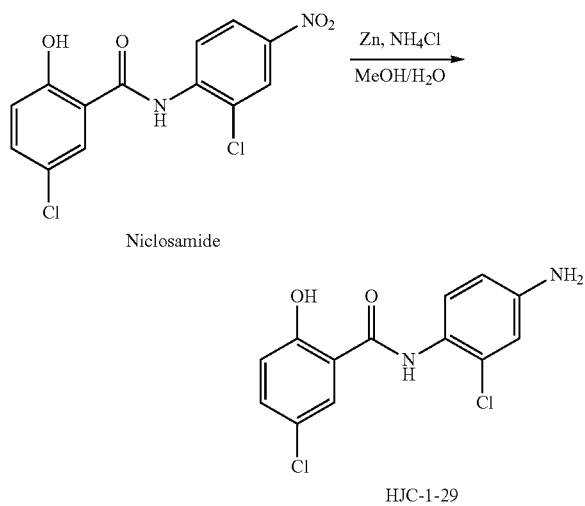

HJC-1-29

To a solution of niclosamide (500 mg, 1.53 mmol) in 20 mL of MeOH was added 4 mL of saturated NH₄Cl (a.q.). Zinc dust (994 mg, 15.3 mmol) was added into the solution at 0° C. The reaction was stirred at r.t. for 16 h. TLC indicated that the starting material was gone. 100 mL of MeOH was added to the solution. The Zinc solid was filtered, and the filtrate was concentrated under vacuum to give a yellow solid. The desired product (455 mg, 100%) was filtered as a pale yellow solid. <sup>1</sup>H NMR (600 MHz, DMSO-d6) δ 11.94 (s, 1H), 7.83-7.87 (m, 2H), 7.11 (s, 1H), 6.96 (d, 1H, J=7.8 Hz), 6.64 (s, 1H), 6.51 (d, 1H, J=8.4 Hz), 5.05-5.15 (bs, 2H), 3.23 (s, 1H).

5-Chloro-2-hydroxy-N-(1-phenyl-ethyl)benzamide (HJC-1-30)

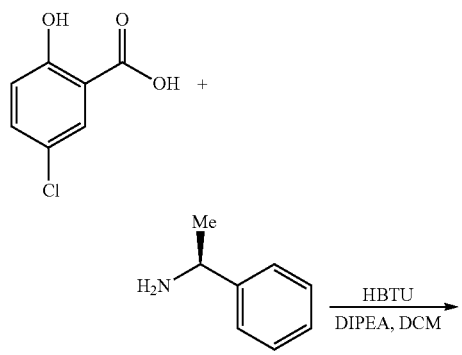

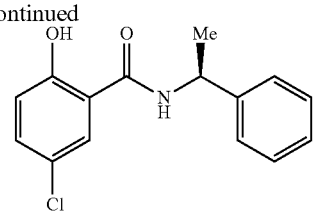

HJC-1-30

To a solution of 5-chloro-2-hydroxy-benzoic acid (173 mg, 1.0 mmol) and L(−)-α-methylbenzylamine (122 mg, 1.0 mmol) in 10 mL of DCM was added DIPEA (388 mg, 3.0 mmol). HBTU (569 mg, 1.5 mmol) was added at 0° C. The resulting mixture was stirred at r.t. for 16 h. The reaction mixture was diluted with DCM (80 mL) and washed with water (20 mL). The organic layer was separated and dried with anhydrous Na₂SO₄. The solution was concentrated to give a crude product. This residue was purified with silica gel column (EtOAc/hexane=1/10) to afford HJC-1-30 (108 mg, 39%) as a white solid. <sup>1</sup>H NMR (600 MHz, CDCl₃) δ 12.22 (s, 1H), 7.28-7.48 (m, 7H), 6.93 (d, 1H, J=9.0 Hz), 6.55 (d, 1H, J=6.6 Hz), 5.29-5.34 (m, 1H), 1.64 (d, 3H, J=7.2 Hz). <sup>13</sup>C NMR (150 MHz, CDCl₃) δ 168.2, 160.2, 142.3, 134.2, 129.0, 129.0, 127.9, 126.3, 126.3, 125.2, 123.4, 120.2, 115.4, 49.5, 21.8.

N-(1,1-Dioxo-1H-1λ⁶-benzo[b]thiophen-6-yl)-2,6-diphenyl-isonicotinamide (HJC-1-36)

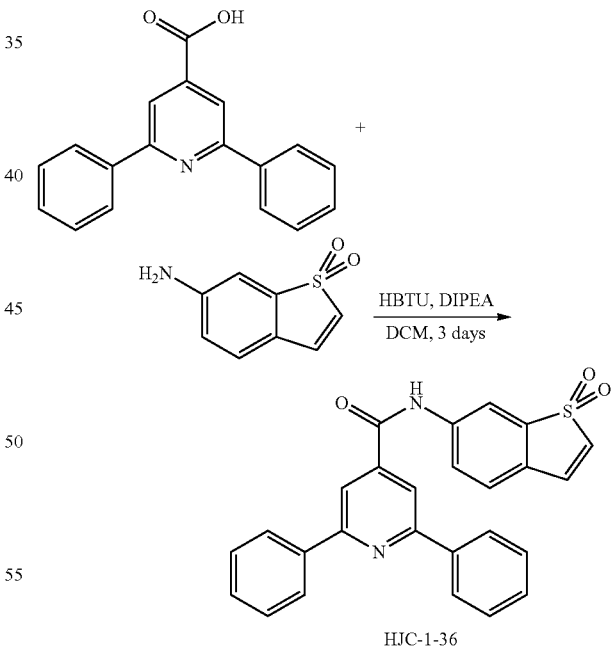

HJC-1-36

To a solution of 2,6-diphenylisonicotinic acid (150 mg, 0.6 mmol) and 1,1-dioxo-1H-1λ⁶-benzo[b]thiophen-6-ylamine (119 mg, 0.7 mmol) in 10 mL of DCM was added DIPEA (211 mg, 1.6 mmol). HBTU (330 mg, 0.9 mmol) was added at 0° C. The resulting mixture was stirred at r.t. for 28 h. An additional amount of HBTU (190 mg, 0.5 mmol) was added to the solution at 0° C., and the resulting mixture was stirred at r.t. for 24 h. The mixture was diluted with DCM (50 mL) and washed with water (20 mL). The organic layer was separated and dried with anhydrous Na$_2$SO$_4$. The solution was concentrated to give a crude product. This residue was purified with silica gel column (EtOAc/hexane=1/2) to provide HJC-1-36 (120 mg, 50%) as a pale yellow solid. $^1$H NMR (600 MHz, CDCl$_3$) δ 8.76 (s, 1H), 8.34 (d, 1H, J=6.6 Hz), 8.23 (d, 4H, J=7.2 Hz), 8.14 (s, 2H) 7.93 (s, 1H), 7.41-7.55 (m, 6H), 7.40 (d, 1H, J=8.4 Hz), 7.13-7.15 (m, 1H), 6.26-6.28 (m, 1H). $^{13}$C NMR (150 MHz, DMSO-d6) δ 164.7, 156.6, 143.9, 141.1, 138.1, 137.1, 132.8, 130.4, 129.7, 129.0, 126.9, 126.6, 126.3, 124.6, 116.7, 112.7.

5-Chloro-N-(2-chloro-4-methanesulfonylaminophenyl)-2-hydroxybenzamide (HJC-1-31)

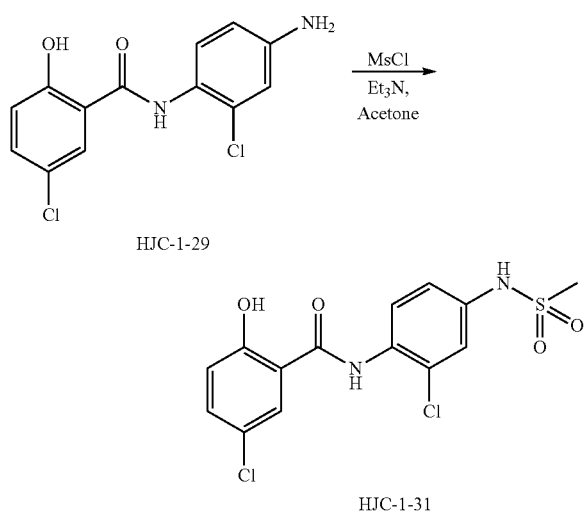

To a solution of N-(4-amino-2-chlorophenyl)-5-chloro-2-hydroxybenzamide (HJC-1-29) (120 mg, 0.4 mmol) in 10 mL of acetone was added Et$_3$N (61 mg, 0.6 mmol). MsCl (51 mg, 0.44 mmol) was added at 0° C. The resulting mixture was stirred at r.t. for 4 h. The mixture was concentrated. The residue was diluted with EtOAc (75 mL) and washed with water (20 mL). The organic layer was separated and dried with anhydrous Na$_2$SO$_4$. The solution was concentrated to give a crude product. This residue was purified with silica gel column (DCM/MeOH=30/1) to obtain HJC-1-31 (105 mg, 69%) as a pale yellow solid. $^1$H NMR (600 MHz, CDCl$_3$) δ 8.28 (s, 1H), 8.10 (d, 1H, J=8.4 Hz), 7.90 (s, 1H), 7.53 (d, 1H, J=9.0 Hz), 7.48 (d, 1H, J=8.4 Hz), 6.77 (s, 1H), 6.65 (d, 1H, J=9.0 Hz), 3.70 (s, 1H), 3.22 (s, 3H). $^{13}$C NMR (150 MHz, CDCl$_3$) δ 161.9, 145.3, 144.2, 133.6, 132.3, 130.7, 130.6, 126.2, 125.1, 124.9, 124.7, 115.3, 114.2, 38.2.

Acetic acid 2-(4-acetylamino-2-chloro-phenylcarbamoyl)-4-chlorophenyl ester (HJC-1-37)

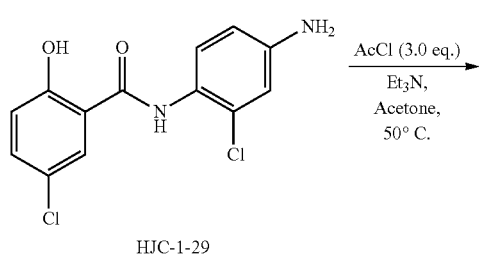

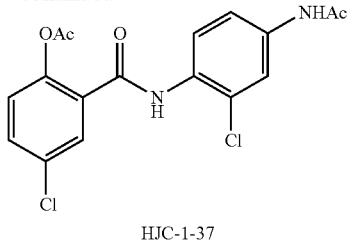

To the mixture of N-(4-amino-2-chlorophenyl)-5-chloro-2-hydroxybenzamide (HJC-1-29) (200 mg, 0.67 mmol) in 10 mL of acetone was added Et$_3$N (341 mg, 3.4 mmol). AcCl (159 mg, 2.0 mmol) was added at 0° C. The resulting mixture was stirred at 50° C. for 2 h. The mixture was concentrated and then the residue was washed with acetone (3 mL). The desired product was filtered as a pale yellow solid (250 mg, 98%). $^1$H NMR (600 MHz, CDCl$_3$) δ 8.65 (s, 1H), 8.45 (d, 1H, J=9.0 Hz), 7.98 (s, 1H), 7.96 (s, 1H), 7.50 (d, 1H, J=8.4 Hz), 7.14-7.17 (m, 3H), 2.37 (s, 3H), 2.17 (s, 3H). $^{13}$C NMR (150 MHz, DMSO-d6) δ 168.7, 168.6, 162.9, 146.9, 138.3, 131.4, 130.4, 129.9, 129.1, 129.0, 128.8, 128.2, 125.5, 119.3, 117.8, 24.0, 20.8.

N-(4-Acetylamino-2-chlorophenyl)-5-chloro-2-hydroxybenzamide (HJC-1-40)

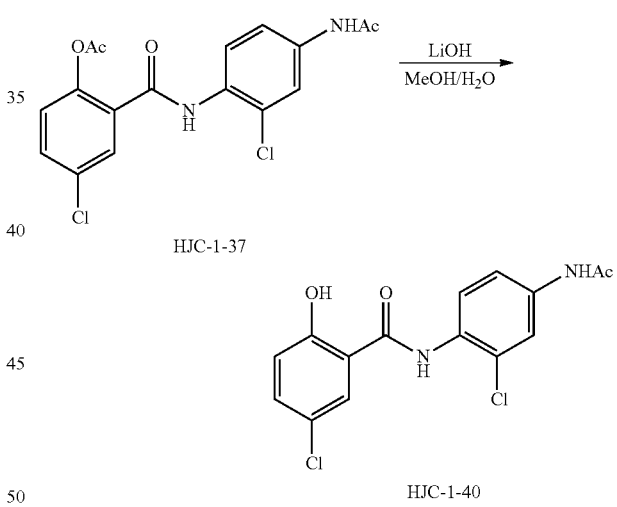

To a solution of acetic acid 2-(4-acetylamino-2-chlorophenylcarbamoyl)-4-chloro-phenyl ester (HJC-1-37) (150 mg, 0.4 mmol) in 10 mL of MeOH and 2.5 mL of H$_2$O was added LiOH (66 mg, 1.6 mmol) at 0° C. The resulting mixture was stirred at r.t. for 1 h. The mixture was diluted with EtOAc (100 mL) and washed with water (20 mL) and 2 N HCl (5 mL). The organic layer was separated and dried with anhydrous Na$_2$SO$_4$. The solution was concentrated to give the desired product (130 mg, 97%) as a yellow solid. $^1$H NMR (600 MHz, DMSO-d6) δ 12.23 (s, 1H), 10.75 (s, 1H), 10.14 (s, 1H), 8.21 (d, 1H, J=8.4 Hz), 7.99 (s, 1H), 7.96 (s, 1H), 7.50 (d, 1H, J=9.0 Hz), 7.43 (d, 1H, J=9.0 Hz), 7.06 (d, 1H, J=9.0 Hz), 2.05 (s, 3H). $^{13}$C NMR (150 MHz, DMSO-d6) δ 168.5, 162.9, 156.1, 136.6, 133.3, 130.0, 129.5, 123.9, 123.5, 123.1, 119.5, 119.2, 119.2, 118.0, 24.0.

Acridine-9-carboxylic acid (1,1-dioxo-1H-1λ⁶-benzo[b]thiophen-6-yl)amide (HJC-1-41)

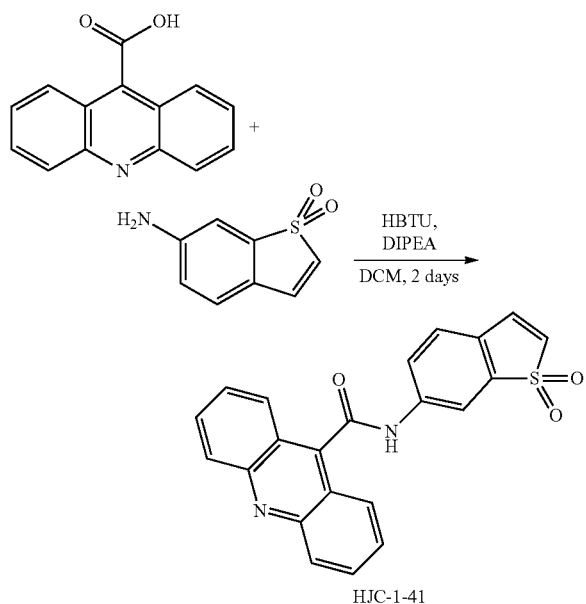

To a solution of acridine-9-carboxylic acid (150 mg, 0.67 mmol) and 1,1-dioxo-1H-1λ⁶-benzo[b]thiophen-6-ylamine (146 mg, 0.81 mmol) in 10 mL of DCM was added DIPEA (434 mg, 3.36 mmol). HBTU (637 mg, 1.68 mmol) was added at 0° C. The resulting mixture was stirred at r.t. for 2 days. A yellow suspension formed during the reaction. The mixture was filtered. The precipitate was dissolved in DMF (10 mL). The solution was added to the stirring water dropwise. A yellow solid was formed. The solid was filtered and washed with H$_2$O (100 mL). 100 mg of the desired product was obtained as a yellow solid (39% yield). $^1$H NMR (600 MHz, DMSO-d6) δ 8.71 (d, 1H, J=8.4 Hz), 8.32 (d, 2H, J=8.4 Hz), 8.08-8.13 (m, 5H), 7.97 (t, 2H, J=7.8 Hz), 7.82 (t, 1H, J=8.4 Hz), 7.68 (t, 2H, J=7.8 Hz). $^{13}$C NMR (150 MHz, DMSO-d6) δ 163.4, 147.9, 136.1, 133.9, 132.9, 131.1, 129.5, 128.0, 128.0, 125.2, 121.7, 116.5, 115.5.

5-Chloro-N-(1,1-dioxo-1H-1λ⁶-benzo[b]thiophen-6-yl)-2-hydroxybenzamide (HJC-1-49)

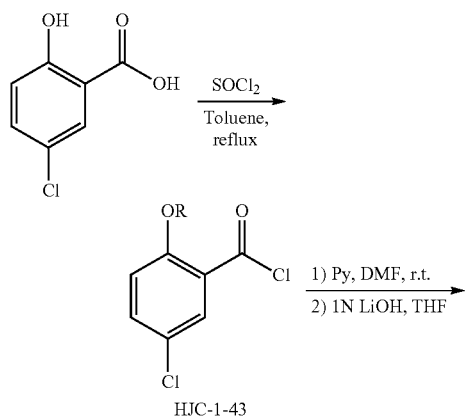

A solution of 5-chloro-2-hydroxybenzoic acid (2.0 g, 11 mmol) and 4 mL of SOCl$_2$ in 4 mL of toluene was stirred at 110° C. overnight. The mixture was concentrated to give a crude product as a pale yellow oil. To the solution of pyridine (869 mg, 11 mmol) and 1,1-dioxo-1H-1λ⁶-benzo[b]thiophen-6-ylamine (200 mg, 1.1 mmol) was added the solution of the acid chloride (500 mg, 2.6 mmol) in DMF (15 mL) dropwise at 0° C. The mixture was stirred at r.t. for 4 h. The mixture was added to the water solution dropwise. The yellow solid was formed and filtrated. To the mixture of one half of the crude product in THF (8 mL) was added 1 N LiOH (0.7 mL, 0.7 mmol) at 0° C. The mixture was stirred at 0° C. for 30 min. The mixture was diluted with EtOAc (50 mL) and washed with 2 N HCl (10 mL). The organic layer was separated and dried with anhydrous Na$_2$SO$_4$. The solution was concentrated to afford the crude product, which was washed with DCM (20 mL) to give the desired product (40 mg, 22%) as a yellow solid. $^1$H NMR (600 MHz, DMSO-d6) δ 11.50 (s, 1H), 10.74 (s, 1H), 8.25 (s, 1H), 7.92 (d, 1H, J=8.4 Hz), 7.86 (d, 1H, J=2.4 Hz), 7.59-7.62 (m, 2H), 7.48 (d, 1H, J=9.0 Hz), 7.31 (d, 1H, J=6.6 Hz), 7.04 (d, 1H, J=8.4 Hz). $^{13}$C NMR (150 MHz, DMSO-d6) δ 165.1, 156.2, 140.7, 137.1, 133.1, 132.8, 130.3, 128.6, 126.5, 126.2, 124.6, 122.8, 120.4, 119.0, 112.7.

5-(5-Chloro-2-hydroxybenzoylamino)-2-vinylbenzenesulfonic acid methyl ester (HJC-1-47)

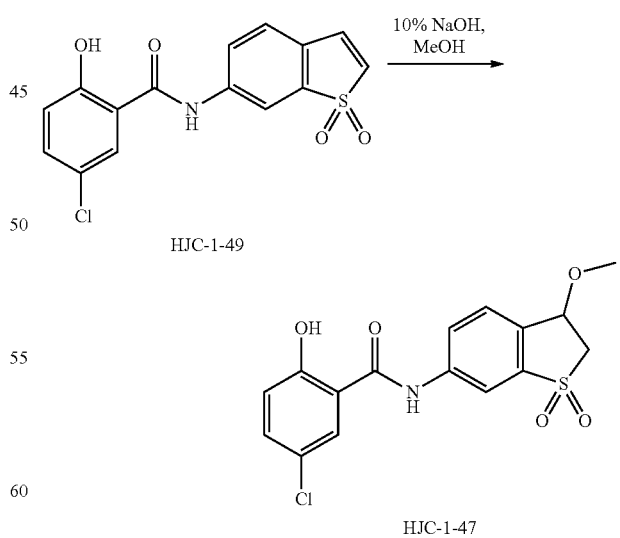

To the solution of HJC-1-49 (400 mg, 0.82 mmol) in MeOH (8 mL) was added 10% NaOH (2 mL, 4.9 mmol) at 0° C. The mixture was stirred at r.t. for 15 min. The mixture was diluted with EtOAc (100 mL) and washed with 2 N HCl (20 mL) and brine (20 mL). The organic layer was separated and dried with anhydrous Na$_2$SO$_4$. The solution was concentrated to afford the crude product, which was washed with DCM (20 mL) to give the desired product (90 mg, 30%). $^1$H NMR (600 MHz, DMSO-d6) δ 11.52 (s, 1H), 10.73 (s, 1H), 8.24 (s, 1H), 7.95 (d, 1H, J=8.4 Hz), 7.88 (s, 1H), 7.70 (d, 1H, J=9.0 Hz), 7.49 (d, 1H, J=9.0 Hz), 7.03 (d, 1H, J=8.4 Hz), 5.17-5.18 (m, 1H), 3.96-3.99 (m, 1H), 3.65-3.67 (dd, 1H, J=3.0, 13.8 Hz), 3.40 (s, 3H). $^{13}$C NMR (150 MHz, DMSO-d6) δ 165.2, 156.3, 140.5, 139.8, 133.1, 132.7, 128.6, 128.3, 125.7, 122.8, 120.2, 119.0, 111.1, 74.5, 56.8, 56.0.

5-Chloro-N-(5-furan-2-yl-[1,3,4]oxadiazol-2-yl)-2-hydroxybenzamide (HJC-1-51)

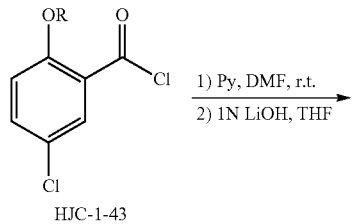

HJC-1-43

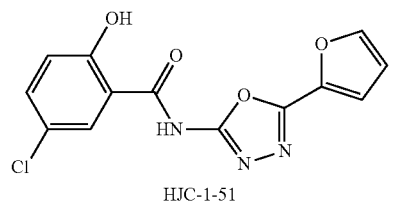

HJC-1-51

To the solution of pyridine (1.05 g, 13.2 mmol) and 5-furan-2-yl-[1,3,4]oxadiazol-2-ylamine (100 mg, 0.66 mmol) in DMF (5 mL) was added the solution of the acid chloride (400 mg, 2.1 mmol) in DMF (5 mL) dropwise at 0° C. The mixture was stirred at r.t. for 2 h. The reaction mixture was then added to the water solution dropwise. The yellow solid was formed and filtered. To the mixture of one half of the crude product in THF (20 mL) and H$_2$O (2 mL) was added 1 N LiOH (2.7 mL, 2.7 mmol) at 0° C. The mixture was stirred at r.t. for 30 min. Then the mixture was diluted with EtOAc (20 mL) and washed with 2 N HCl (10 mL). The organic layer was separated and dried with anhydrous Na$_2$SO$_4$. The solution was concentrated to afford the crude product, which was washed with DCM (10 mL) to provide the desired product (80 mg, 50%) as a white solid. $^1$H NMR (600 MHz, CDCl$_3$) δ 10.11 (s, 1H), 8.13 (d, 1H, J=2.4 Hz), 8.02 (d, 1H, J=2.4 Hz), 7.64 (dd, 1H, J=2.4 Hz and 8.4 Hz), 7.49 (dd, 1H, J=2.4 Hz and 8.4 Hz), 7.21 (d, 1H, J=9.0 Hz), 6.99 (d, 1H, J=9.0 Hz). $^{13}$C NMR (150 MHz, DMSO-d6) δ 164.4, 158.4, 148.3, 135.2, 133.6, 130.8, 130.6, 130.2, 126.2, 125.9, 122.6, 119.7, 115.4.

{2-[4-Chloro-2-(2-chloro-4-nitro-phenylcarbamoyl)-phenoxy]-ethyl}-carbamic acid tert-butyl ester (HJC-1-50)

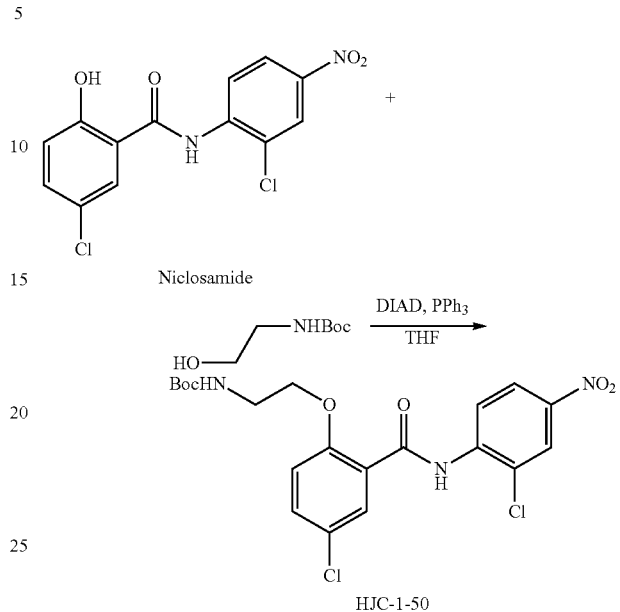

To a solution of niclosamide (327 mg, 1.0 mmol) and PPh$_3$ (341 mg, 1.3 mmol) in THF (10 mL) was added (2-hydroxyethyl)-carbamic acid tert-butyl ester (193 mg, 1.2 mmol) in THF (10 mL) and DIAD (263 mg, 1.3 mmol). The mixture was stirred at r.t. overnight, and then was concentrated to give the crude product. This residue was washed with DCM (20 mL) to obtain HJC-1-50 (290 mg, 71%) as a white solid. $^1$H NMR (600 MHz, CDCl$_3$) δ 10.45 (s, 1H), 8.90 (d, 1H, J=9.6 Hz), 8.34 (d, 1H, J=2.4 Hz), 8.21-8.24 (m, 2H), 7.49 (d, 1H, J=8.4 Hz), 7.08 (d, 1H, J=8.4 Hz), 4.84-4.85 (m, 1H), 4.41 (t, 2H, J=5.4 Hz), 3.62 (t, 2H, J=5.4 Hz), 1.40 (s, 9H).

2-(2-Aminoethoxy)-5-chloro-N-(2-chloro-4-nitrophenyl)benzamide (HJC-1-52)

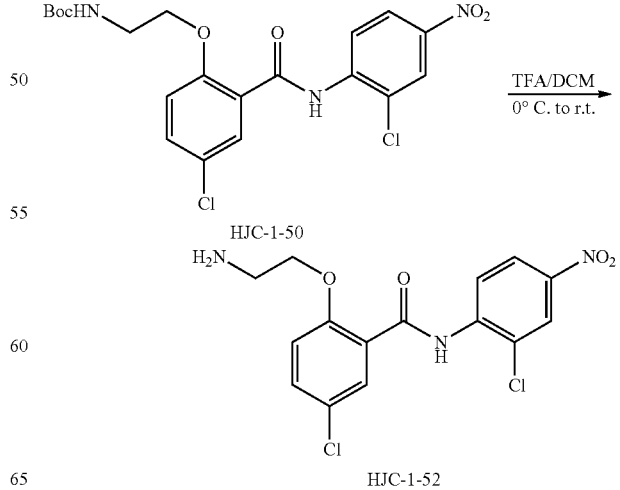

To a solution of HJC-1-50 (230 mg, 0.57 mmol) in DCM (10 mL) was added TFA (2.5 mL) at 0° C. The mixture was stirred at r.t. for 2 h, and then was concentrated. The residue was partitioned between EtOAc (250 mL) and 1 N NaHCO$_3$ (10 mL). The organic layer was washed with H$_2$O (10 mL) and dried with Na$_2$SO$_4$. The organic layer was concentrated. The residue was washed with EtOAc (20 mL) to give HJC-1-52 (140 mg, 77%) as a pale yellow solid. $^1$H NMR (600 MHz, CDCl$_3$) δ 8.85 (d, 1H, J=9.0 Hz), 8.32 (s, 1H), 8.18-8.20 (m, 2H), 7.47 (dd, 1H, J=3.0 Hz and 9.0 Hz), 7.05 (d, 1H, J=9.0 Hz), 4.31 (t, 2H, J=6.0 Hz), 3.22 (t, 2H, J=6.0 Hz), 1.89-1.93 (bs, 2H). $^{13}$C NMR (150 MHz, DMSO-d6) δ 162.7, 154.5, 143.4, 141.1, 133.7, 130.9, 125.7, 124.9, 124.6, 123.6, 123.6, 122.8, 115.8, 66.4, 38.1.

2-Phenyl-quinoline-4-carboxylic acid (3-methoxy-1,1-dioxo-2,3-dihydro-1H-1λ$^6$-benzo[b]thiophen-6-yl)amide (HJC-1-57)

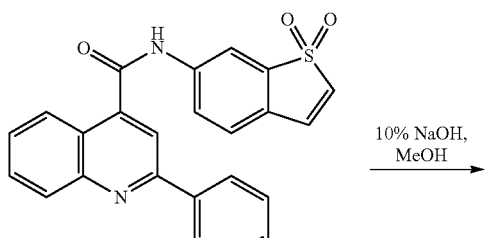

To the solution of HJC-1-23 (15 mg, 0.036 mmol) in MeOH (4 mL) was added 10% NaOH (0.2 mL, 0.5 mmol) at 0° C. The mixture was stirred at r.t. for 5 h. The mixture was diluted with EtOAc (50 mL) and washed with 2 N HCl (10 mL) and brine (20 mL). The organic layer was separated and dried with anhydrous Na$_2$SO$_4$. The solution was concentrated to afford the desired product (17 mg, 100%). $^1$H NMR (600 MHz, CDCl$_3$) δ 8.46 (d, 1H, J=7.8 Hz), 8.23-8.29 (m, 2H), 8.11-8.18 (m, 3H), 8.08 (s, 1H), 7.79 (t, 1H, J=8.4 Hz), 7.69 (d, 1H, J=8.4 Hz), 7.62 (t, 1H, J=7.2 Hz), 7.46-7.50 (m, 3H), 5.11-5.13 (m, 1H), 3.62-3.66 (m, 1H), 3.50 (s, 3H), 3.33-3.35 (m, 1H).

N-(1,1-Dioxo-1H-1λ$^6$-benzo[b]thiophen-6-yl)acetamide (HJC-1-62)

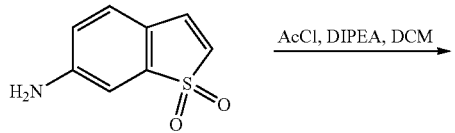

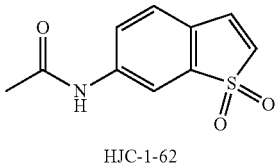

To the solution of DIPEA (713 mg, 5.5 mmol) and 1,1-dioxo-1H-1λ$^6$-benzo[b]thiophen-6-ylamine (500 mg, 2.8 mmol) in 10 mL of DCM was added the solution of AcCl (260 mg, 3.3 mmol) in DCM (15 mL) dropwise at 0° C. The mixture was stirred at r.t. for 10 min. The mixture was diluted with DCM (50 mL) and washed with H$_2$O (10 mL). The organic layer was separated and dried with anhydrous Na$_2$SO$_4$. The solution was concentrated to afford the crude product, which was purified with silica gel column (EtOAc/hexane=1/1) to afford the desired product (400 mg, 65%) as a pale yellow solid. $^1$H NMR (600 MHz, DMSO-d6) δ 10.44 (s, 1H), 8.12 (s, 1H), 7.68 (d, 1H, J=7.8 Hz), 7.56 (d, 1H, J=6.6 Hz), 7.51 (d, 1H, J=7.8 Hz), 7.25 (d, 1H, J=6.6 Hz), 2.10 (s, 3H). $^{13}$C NMR (150 MHz, DMSO-d6) δ 169.1, 141.7, 137.2, 132.9, 129.8, 126.5, 125.2, 122.9, 111.0, 24.1.

N-(3-Methoxy-1,1-dioxo-2,3-dihydro-1H-1λ$^6$-benzo[b]thiophen-6-yl)acetamide (HJC-1-63)

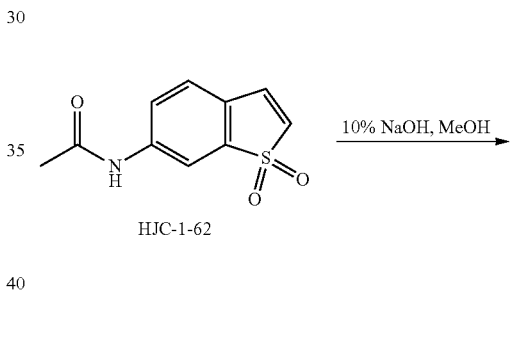

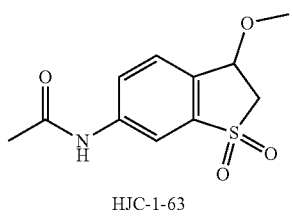

To the solution of HJC-1-62 (30 mg, 0.13 mmol) in MeOH (2 mL) was added 10% NaOH (0.22 mL, 0.54 mmol) at 0° C. The mixture was stirred at r.t. for 4 h. The mixture was diluted with EtOAc (25 mL) and washed with 2 N HCl (2 mL) and brine (20 mL). The organic layer was separated and dried with anhydrous Na$_2$SO$_4$. The solution was concentrated to afford the desired product (33 mg, 97%). $^1$H NMR (600 MHz, CDCl$_3$/CD$_3$OD 2:1) δ 7.84 (d, 1H, J=9.0 Hz), 7.82 (s, 1H), 7.42 (d, 1H, J=8.4 Hz), 4.99-5.01 (m, 1H), 3.69-3.72 (m, 1H), 3.38-3.40 (m, 1H), 3.37 (s, 3H), 2.05 (s, 3H). $^{13}$C NMR (150 MHz, CDCl$_3$/CD$_3$OD 2:1) δ 170.1, 141.3, 139.5, 132.0, 127.5, 125.0, 110.9, 74.9, 57.1, 56.7, 23.7.

N-(1,1-Dioxo-1H-1λ⁶-benzo[b]thiophen-6-yl)-4-methoxybenzamide (HJC-2-15)

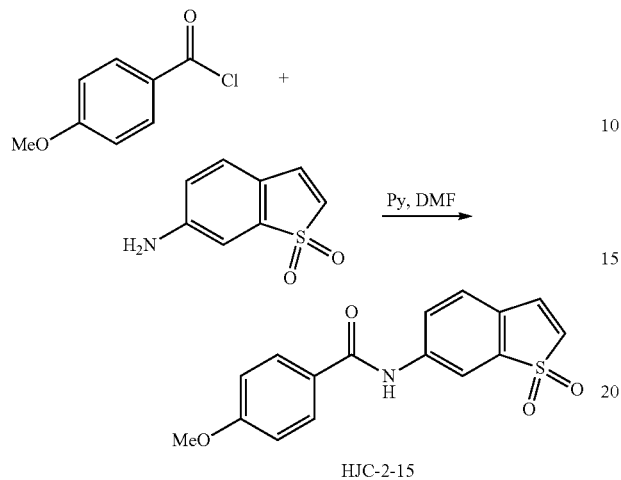

HJC-2-15

To a solution of pyridine (395 mg, 5.0 mmol) and 1,1-dioxo-1H-1λ⁶-benzo[b]-thiophen-6-ylamine (181 mg, 1.0 mmol) in 5 mL of DMF was added the solution of 4-methoxy-benzoyl chloride (170 mg, 1.0 mmol) in DMF (5 mL) dropwise at 0° C. The mixture was stirred at r.t. for 16 h. The mixture was diluted with EtOAc (100 mL) and washed with H₂O (10 mL). The organic layer was separated and dried with anhydrous Na₂SO₄. The solution was concentrated to afford the crude product, which was washed with DCM (30 mL) to give the desired product (120 mg, 38%) as a yellow solid. ¹H NMR (600 MHz, DMSO-d6) δ 10.52 (s, 1H), 8.28 (s, 1H), 7.98-8.01 (m, 3H), 7.56-7.61 (m, 2H), 7.28 (d, 1H, J=6.0 Hz), 7.09 (d, 2H, J=8.4 Hz), 3.85 (s, 3H).

4-Methoxy-N-(3-methoxy-1,1-dioxo-2,3-dihydro-1H-1λ⁶-benzo[b]thiophen-6-yl)benzamide (HJC-2-20)

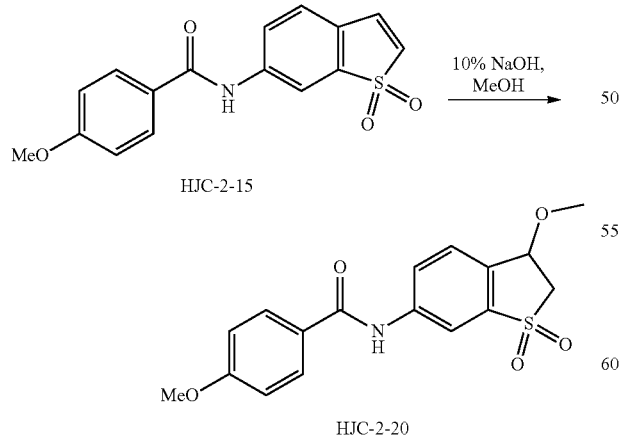

HJC-2-15

HJC-2-20

To the solution of HJC-2-15 (50 mg, 0.16 mmol) in MeOH (10 mL) was added 10% NaOH (0.26 mL, 0.64 mmol) at 0° C. The mixture was stirred at r.t. for 18 h. The mixture was diluted with EtOAc (25 mL) and washed with 2 N HCl (2 mL) and brine (20 mL). The organic layer was separated and dried with anhydrous Na₂SO₄. The solution was concentrated to afford the crude product, which was purified with silica gel column (EtOAc/hexane=1/1) to afford the desired product (40 mg, 73%) as a pale yellow solid. ¹H NMR (600 MHz, DMSO-d6) δ 10.51 (s, 1H), 8.27 (s, 1H), 8.05 (d, 1H, J=7.8 Hz), 7.99 (d, 2H, J=7.8 Hz), 7.68 (d, 1H, J=9.0 Hz), 7.09 (d, 2H, J=7.2 Hz), 5.14-5.17 (m, 1H), 3.95-3.98 (m, 1H), 3.85 (s, 3H), 3.63-3.66 (m, 1H), 3.38 (s, 3H).

4-{2-[4-Chloro-2-(2-chloro-4-nitro-phenylcarbamoyl)-phenoxy]-ethyl}-piperazine-1-carboxylic acid tert-butyl ester (HJC-2-50)

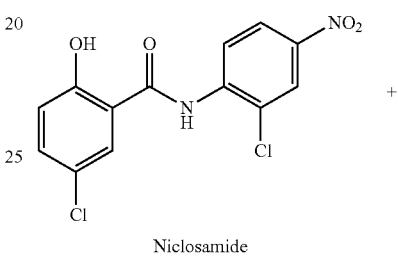

Niclosamide

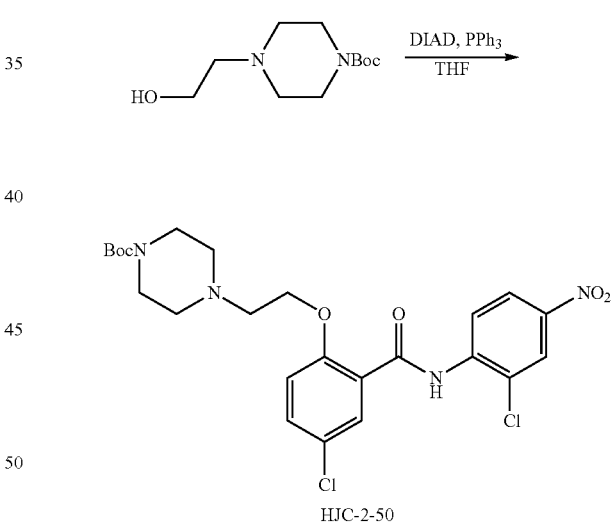

HJC-2-50

To a solution of niclosamide (200 mg, 0.61 mmol) and PPh₃ (288 mg, 1.1 mmol) in THF (5 mL) was added 4-(2-hydroxy-ethyl)-piperazine-1-carboxylic acid tert-butyl ester (253 mg, 1.1 mmol) in THF (5 mL) and DIAD (222 mg, 1.1 mmol). The mixture was stirred at r.t. for 2 h, and then was concentrated to give the crude product. This residue was purified with silica gel column (EtOAc/hexane=3/1) to afford the desired product (300 mg, 91%) as a white solid. ¹H NMR (600 MHz, CDCl₃) δ 10.62 (s, 1H), 8.80 (d, 1H, J=9.0 Hz), 8.34 (s, 1H), 8.24 (s, 1H), 8.22 (d, 1H, J=9.0 Hz), 7.49 (d, 1H, J=9.0 Hz), 7.07 (d, 1H, J=9.0 Hz), 4.42 (t, 2H, J=6.0 Hz), 3.26-3.29 (m, 4H), 2.87 (d, 2H, J=6.0 Hz), 2.40-2.44 (m, 4H), 1.43 (s, 9H).

5-Chloro-N-(2-chloro-4-nitro-phenyl)-2-(2-piperazin-1-yl-ethoxy)benzamide (HJC-2-52)

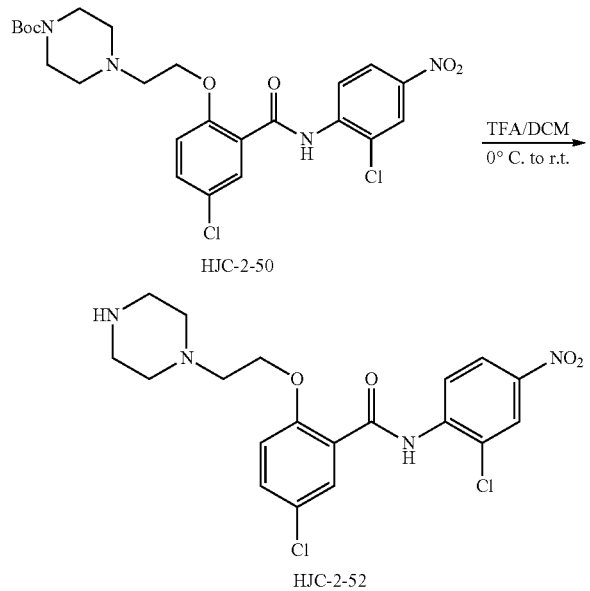

To a solution of HJC-2-50 (300 mg, 0.56 mmol) in DCM (10 mL) was added TFA (3 mL) at 0° C. The mixture was stirred at r.t. for 3 h, and then was concentrated. The residue was partitioned between EtOAc (250 mL) and 1 N NaHCO$_3$ (10 mL). The organic layer was washed with H$_2$O (10 mL) and dried with Na$_2$SO$_4$. The organic layer was concentrated. The residue was washed with EtOAc (20 mL) to give HJC-2-52 (200 mg, 81%) as a pale yellow solid. $^1$H NMR (600 MHz, DMSO-d6) δ 10.48 (s, 1H), 9.70-9.80 (bs, 1H), 8.44 (d, 2H, J=7.2 Hz), 8.30 (d, 1H, J=8.4 Hz), 7.85 (s, 1H), 7.68 (d, 1H, J=9.0 Hz), 7.39 (d, 1H, J=8.4 Hz), 4.65-4.68 (m, 2H), 3.39-3.65 (m, 10H). $^{13}$C NMR (150 MHz, DMSO-d6) δ 163.2, 154.1, 143.9, 140.9, 132.9, 130.1, 125.9, 125.7, 124.9, 124.8, 124.4, 123.4, 115.9, 64.0, 58.9, 54.3, 48.5.

(2-{2-[4-Chloro-2-(2-chloro-4-nitro-phenylcarbamoyl)-phenoxy]-ethoxy}-ethyl)-carbamic acid tert-butyl ester (HJC-2-56)

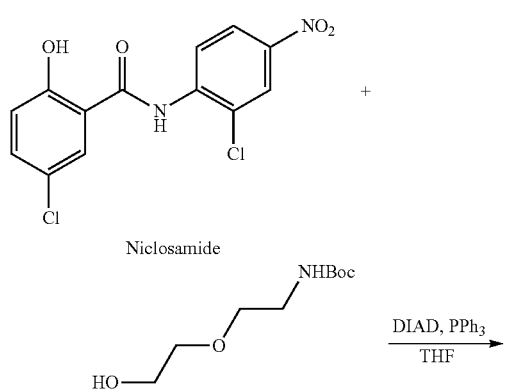

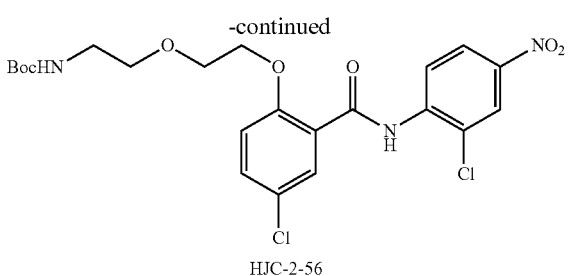

To a solution of niclosamide (327 mg, 1.0 mmol) and PPh$_3$ (524 mg, 2.0 mmol) in THF (5 mL) was added [2-(2-hydroxy-ethoxy)-ethyl]-carbamic acid tert-butyl ester (410 mg, 2.0 mmol) in THF (5 mL) and DIAD (404 mg, 2.0 mmol). The mixture was stirred at r.t. for 2 h, and then was concentrated to give the crude product. This residue was purified with silica gel column (EtOAc/hexane=1/1) to afford the desired product (480 mg, 93%) as a white solid. $^1$H NMR (600 MHz, CDCl$_3$) δ 10.61 (s, 1H), 8.87 (d, 1H, J=9.6 Hz), 8.34 (s, 1H), 8.26 (s, 1H), 8.21 (d, 1H, J=9.6 Hz), 7.49 (d, 1H, J=9.0 Hz), 7.10 (d, 1H, J=8.4 Hz), 4.65-4.68 (m, 1H), 4.45-4.47 (m, 2H), 3.87-3.90 (m, 2H), 3.51-3.53 (m, 2H), 3.20-3.25 (m, 2H), 1.40 (s, 9H).

2-[2-(2-Amino-ethoxy)-ethoxy]-5-chloro-N-(2-chloro-4-nitro-phenyl)benzamide (HJC-2-58)

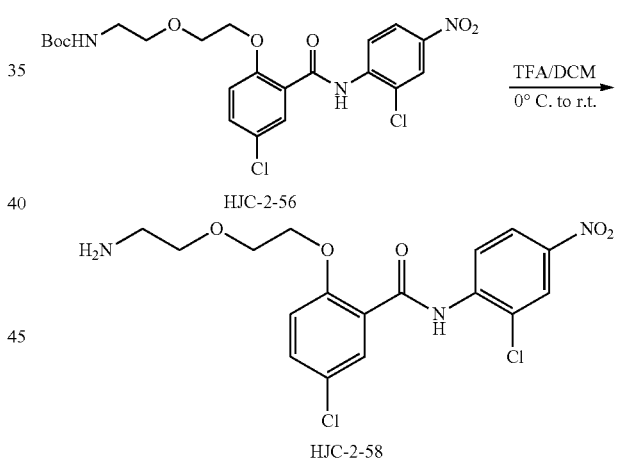

To a solution of HJC-2-56 (400 mg, 0.78 mmol) in DCM (10 mL) was added TFA (2.5 mL) at 0° C. The mixture was stirred at r.t. for 3 h, and then was concentrated. The residue was partitioned between EtOAc (300 mL) and 1 N NaHCO$_3$ (10 mL). The organic layer was washed with H$_2$O (10 mL) and dried with Na$_2$SO$_4$. The organic layer was concentrated. The residue was washed with EtOAc (20 mL) to give HJC-2-58 (280 mg, 87%) as a pale yellow solid. $^1$H NMR (600 MHz, DMSO-d6) δ 10.59 (s, 1H), 8.63 (d, 1H, J=9.0 Hz), 8.43 (s, 1H), 8.29 (d, 1H, J=7.2 Hz), 7.97 (s, 1H), 7.78-7.83 (m, 2H), 7.68 (d, 1H, J=8.4 Hz), 7.42 (d, 1H, J=8.4 Hz), 4.48-4.52 (m, 2H), 3.86-3.89 (m, 2H), 3.58-3.62 (m, 2H), 2.86-2.90 (m, 2H). $^{13}$C NMR (150 MHz, DMSO-d6) δ 162.2, 155.4, 143.0, 140.7, 133.8, 130.6, 125.5, 124.7, 123.6, 123.4, 122.5, 122.0, 116.4, 69.5, 68.2, 66.7, 38.3.

Pyridine-2-carboxylic acid (1,1-dioxo-1H-1λ⁶-benzo[b]thiophen-6-yl)amide (HJC-3-20)

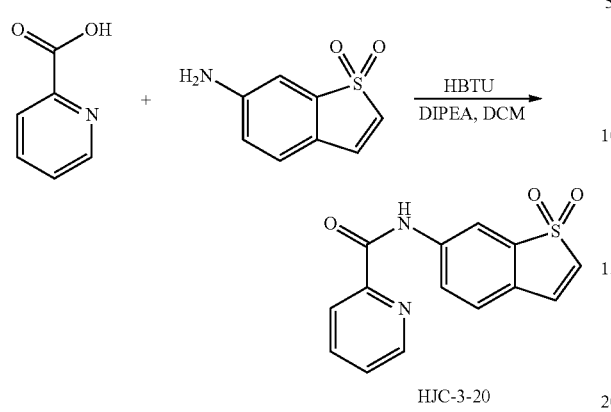

To a solution of pyridine-2-carboxylic acid (148 mg, 1.2 mmol) and 1,1-dioxo-1H-1λ⁶-benzo[b]thiophen-6-ylamine (181 mg, 1.0 mmol) in 10 mL of DCM was added DIPEA (388 mg, 3.0 mmol). HBTU (570 mg, 1.5 mmol) was added at 0° C. The resulting mixture was stirred at r.t. for 24 h and then was concentrated. The residue was dissolved in DMF (10 mL). The solution was added to the stirring water (50 mL) dropwise. A yellow solid was formed. The solid was filtered and washed with $H_2O$ (50 mL). 130 mg of the desired product was obtained as a yellow solid (45% yield). ¹H NMR (600 MHz, DMSO-d6) δ 11.17 (s, 1H), 8.77 (d, 1H, J=4.2 Hz), 8.46 (s, 1H), 8.20 (d, 1H, J=2.4 Hz), 8.19 (d, 1H, J=1.8 Hz), 8.08-8.11 (m, 1H), 7.70-7.72 (m, 1H), 7.58-7.61 (m, 2H), 7.31 (d, 1H, J=6.6 Hz). ¹³C NMR (150 MHz, DMSO-d6) δ 163.3, 149.3, 148.6, 141.0, 138.3, 137.1, 132.8, 130.3, 127.3, 126.4, 126.0, 124.6, 122.8, 112.6.

2-Cyano-N-(1,1-dioxo-1H-1λ⁶-benzo[b]thiophen-6-yl)acetamide (HJC-3-61)

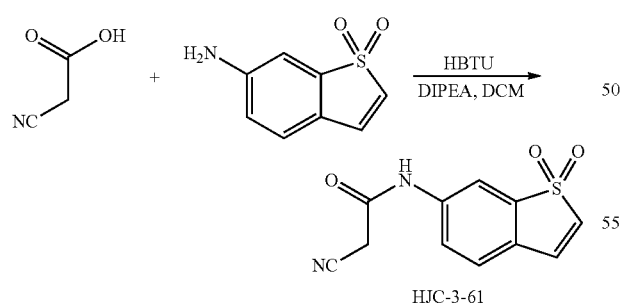

The general procedure was the same as HJC-3-20 by using cyanoacetic acid as reactant. Obtained as a pale yellow solid (81% yield); ¹H NMR (600 MHz, acetone-d6) δ 9.96 (s, 1H), 8.12 (s, 1H), 7.76-7.79 (m, 1H), 7.54 (d, 1H, J=8.4 Hz), 7.50 (d, 1H, J=7.8 Hz), 6.99 (d, 1H, J=7.2 Hz), 3.90 (s, 2H). ¹³C NMR (150 MHz, acetone-d6) δ 162.4, 141.8, 139.1, 133.0, 131.5, 127.7, 127.2, 124.3, 115.2, 112.8, 27.5.

N-(1,1-Dioxo-1H-1λ⁶-benzo[b]thiophen-6-yl)-nicotinamide (HJC-3-76)

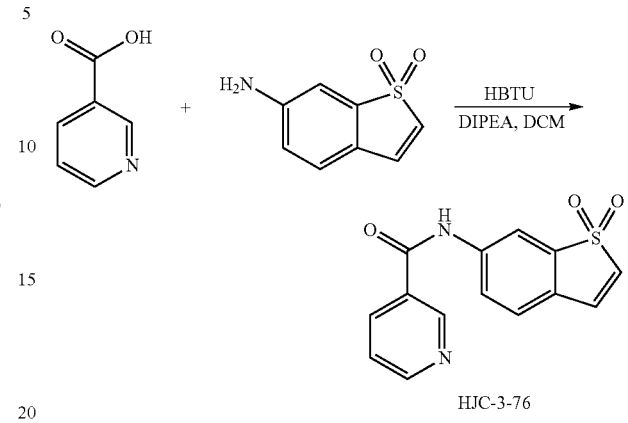

The general procedure was the same as HJC-3-20 by using pyridine-3-carboxylic acid as reactant. Obtained as a pale yellow solid (52% yield); ¹H NMR (600 MHz, DMSO-d6) δ 10.87 (s, 1H), 9.13 (d, 1H, J=1.8 Hz), 8.79 (t, 1H, J=2.4 Hz), 8.32 (d, 1H, J=8.4 Hz), 8.27 (s, 1H), 7.99-8.00 (m, 1H), 7.59-7.63 (m, 3H), 7.32 (d, 1H, J=7.2 Hz). ¹³C NMR (150 MHz, DMSO-d6) δ 164.6, 152.5, 148.8, 141.3, 137.1, 135.6, 132.8, 130.3, 130.0, 126.5, 126.1, 124.3, 123.6, 112.4.

N-(1,1-Dioxo-1H-1λ⁶-benzo[b]thiophen-6-yl)-isonicotinamide (HJC-3-80)

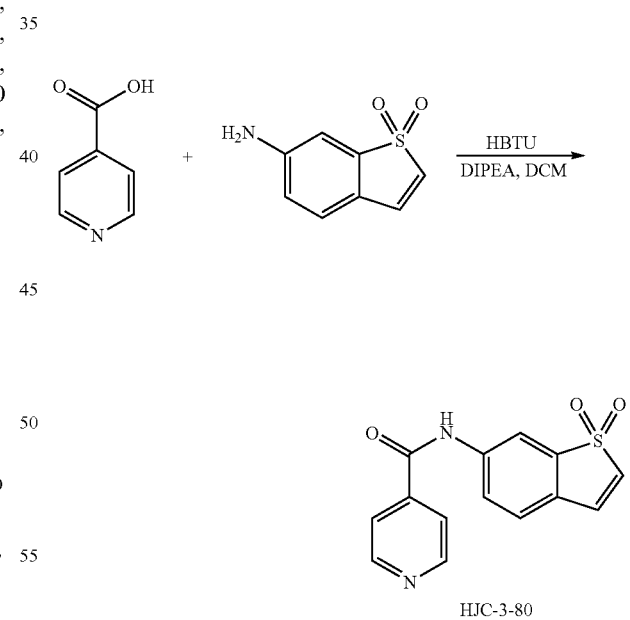

The general procedure was the same as HJC-3-20 by using pyridine-4-carboxylic acid as reactant. Obtained as a pale yellow solid (56% yield); ¹H NMR (600 MHz, DMSO-d6) δ 10.92 (s, 1H), 8.81-8.82 (m, 1H), 8.27 (s, 1H), 8.00 (d, 1H, J=7.8 Hz), 7.88 (t, 2H, J=2.4 Hz), 7.62 (t, 2H, J=6.6 Hz), 7.33 (d, 1H, J=6.6 Hz). ¹³C NMR (150 MHz, DMSO-d6) δ 164.6, 150.4, 141.3, 141.1, 137.1, 132.8, 130.4, 126.5, 126.3, 124.5, 121.6, 112.6.

Quinoline-3-carboxylic acid (1,1-dioxo-1H-1λ⁶-benzo[b]thiophen-6-yl)amide (HJC-3-91)

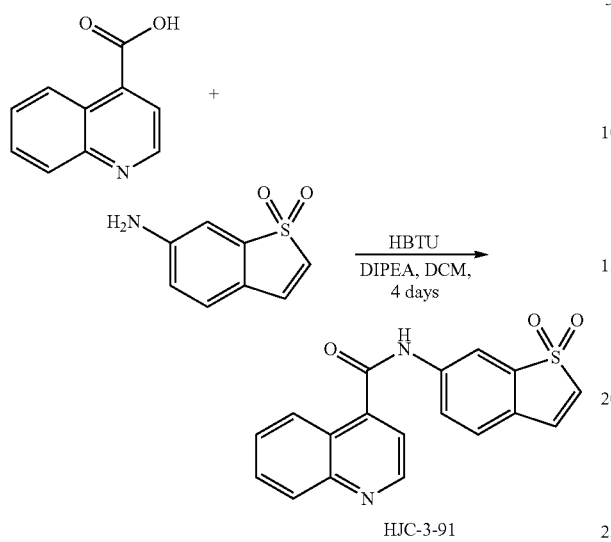

HJC-3-91

The general procedure was the same as HJC-3-20 by using quinoline-3-carboxylic acid as reactant. Obtained as a pale yellow solid (48% yield); $^1$H NMR (600 MHz, DMSO-d6) δ 11.25 (s, 1H), 9.08 (d, 1H, J=4.2 Hz), 8.31 (s, 1H), 8.18 (d, 1H, J=8.4 Hz), 8.14 (d, 1H, J=7.2 Hz), 7.93-7.95 (m, 1H), 7.85-7.88 (m, 1H), 7.79 (d, 1H, J=4.2 Hz), 7.70-7.72 (m, 1H), 7.63-7.65 (m, 2H), 7.34 (d, 1H, J=6.6 Hz). $^{13}$C NMR (150 MHz, DMSO-d6) δ 166.7, 151.0, 149.7, 142.4, 139.1, 133.1, 131.6, 130.7, 128.5, 127.7, 127.2, 126.3, 125.1, 124.8, 124.7, 120.0, 113.3, 113.2.

2-Bromo-N-(1,1-dioxo-1H-1λ⁶-benzo[b]thiophen-6-yl)-isonicotinamide (HJC-3-95)

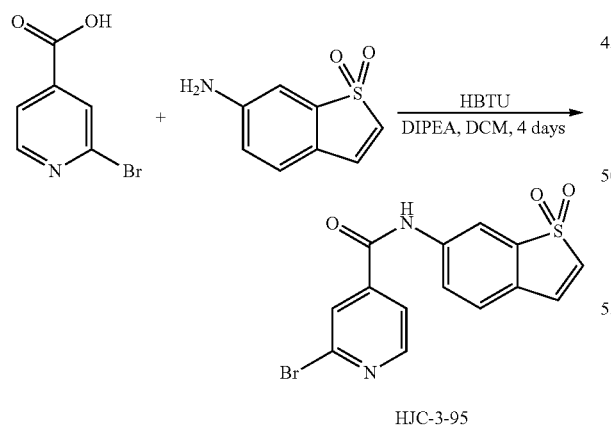

HJC-3-95

The general procedure was the same as HJC-3-20 by using 2-bromo-isonicotinic acid as reactant. Obtained as a pale yellow solid (82% yield); $^1$H NMR (600 MHz, DMSO-d6) δ 10.96 (s, 1H), 8.63 (d, 1H, J=4.8 Hz), 8.23 (s, 1H), 8.15 (s, 1H), 7.97-7.99 (m, 1H), 7.91 (d, 1H, J=4.8 Hz), 7.61-7.63 (m, 2H), 6.33 (d, 1H, J=7.2 Hz). $^{13}$C NMR (150 MHz, DMSO-d6) δ 162.9, 151.3, 144.4, 141.8, 140.8, 137.1, 132.8, 130.5, 126.5, 126.5, 125.9, 124.6, 121.6, 112.6.

N-(1,1-Dioxo-1H-1λ⁶-benzo[b]thiophen-6-yl)-2-phenyl-isonicotinamide (HJC-4-30)

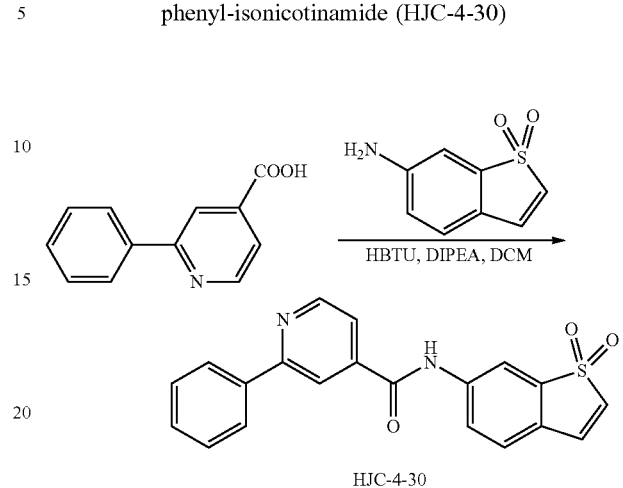

HJC-4-30

The general procedure was the same as HJC-3-20 by using 2-phenyl-isonicotinic acid as reactant. Obtained as a pale yellow solid (46% yield); $^1$H NMR (600 MHz, DMSO-d6) δ 10.97 (s, 1H), 8.89 (d, 1H, J=4.8 Hz), 8.42 (s, 1H), 8.28 (s, 1H), 8.19 (d, 1H, J=7.8 Hz), 8.03-8.05 (m, 1H), 7.82 (d, 1H, J=4.8 Hz), 7.63 (d, 2H, J=7.8 Hz), 7.56 (t, 1H, J=7.2 Hz), 7.51 (t, 2H, J=7.2 Hz), 7.34 (d, 1H, J=6.6 Hz). $^{13}$C NMR (150 MHz, DMSO-d6) δ 164.6, 156.9, 150.4, 142.6, 141.1, 138.1, 137.1, 132.8, 130.4, 129.6, 128.9, 126.8, 126.5, 126.3, 124.6, 120.5, 118.0, 112.7.

2-(3-Aminopropoxy)-5-chloro-N-(2-chloro-4-nitrophenyl)benzamide (HJC-3-8)

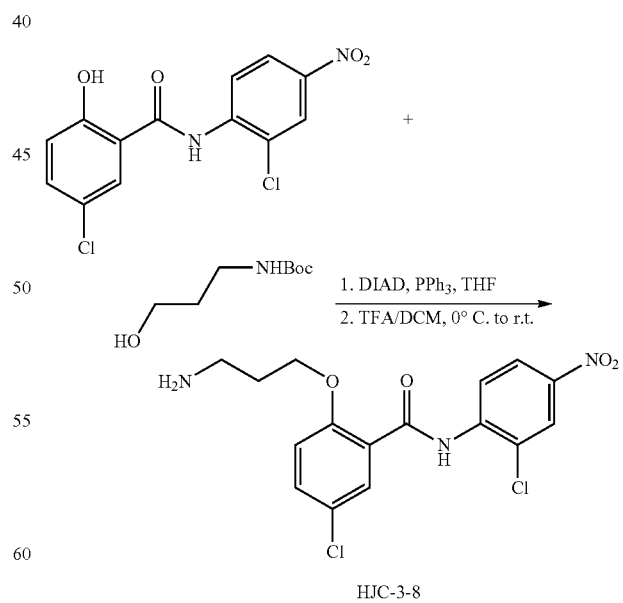

HJC-3-8

The general procedure was the same as HJC-1-50/HJC-1-52. Obtained as a pale yellow solid (two steps, 52% yield); $^1$H NMR (600 MHz, DMSO-d6) δ 10.40 (bs, 1H), 8.61 (d, 1H, J=9.6 Hz), 8.45 (d, 1H, J=1.8 Hz), 8.31 (d, 1H, J=9.0

Hz), 7.93 (d, 1H, J=2.4 Hz), 7.69-7.83 (m, 2H), 7.70 (d, 1H, J=9.0 Hz), 7.36 (d, 1H, J=8.4 Hz), 4.42 (t, 1H, J=6.0 Hz), 2.96 (t, 2H, J=7.2 Hz), 2.08-2.13 (m, 2H). $^{13}$C NMR (150 MHz, DMSO-d6) δ 162.7, 154.9, 143.2, 140.7, 133.4, 130.4, 125.2, 124.9, 123.8, 123.6, 123.2, 122.5, 115.7, 66.8, 36.1, 26.5.

2-(5-Amino-pentyloxy)-5-chloro-N-(2-chloro-4-nitro-phenyl)benzamide (HJC-3-89)

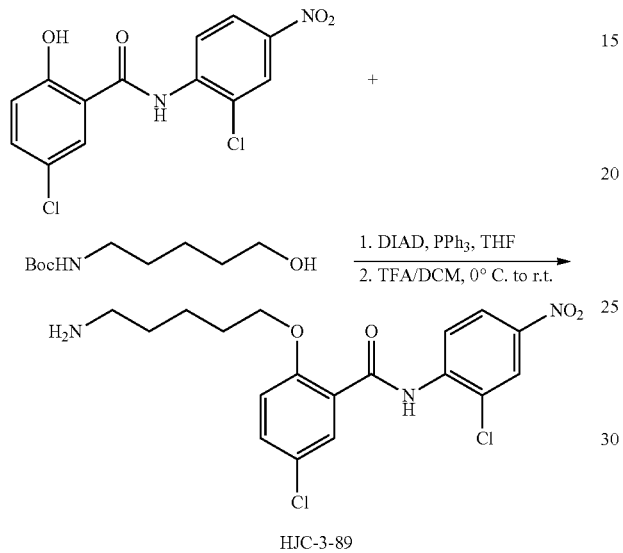

HJC-3-89

The general procedure was the same as HJC-1-50/HJC-1-52. Obtained as a white solid (two steps, 73% yield); $^{1}$H NMR (600 MHz, DMSO-d6) δ 10.54 (s, 1H), 8.68 (d, 1H, J=9.6 Hz), 8.43 (d, 1H, J=2.4 Hz), 8.29-8.31 (m, 1H), 7.97 (d, 1H, J=2.4 Hz), 7.66-7.68 (m, 3H), 7.38 (d, 1H, J=9.0 Hz), 4.35 (t, 2H, J=6.6 Hz), 2.74-2.76 (m, 2H), 1.84-1.89 (m, 2H), 1.55-1.60 (m, 2H), 1.42-1.55 (m, 2H). $^{13}$C NMR (150 MHz, DMSO-d6) δ 162.3, 155.3, 143.0, 140.7, 133.6, 130.5, 125.1, 124.7, 123.6, 123.0, 122.5, 121.8, 115.9, 69.8, 38.6, 27.7, 26.5, 22.1.

2-(2-Amino-ethoxy)-5-chloro-N-(1,1-dioxo-1H-1λ$^{6}$-benzo[b]thiophen-6-yl)benzamide (HJC-3-93)

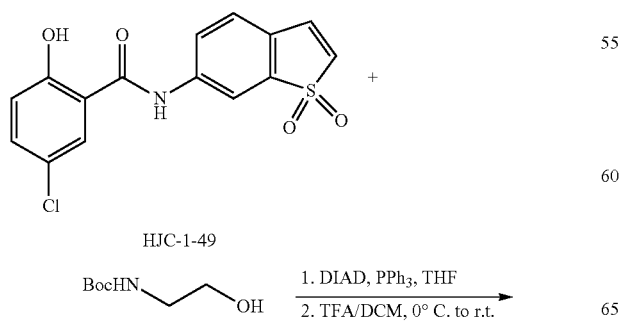

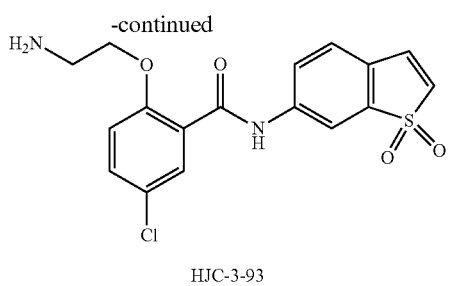

HJC-3-93

The general procedure was the same as HJC-1-50/HJC-1-52. Obtained as a pale yellow solid (two steps, 40% yield); $^{1}$H NMR (600 MHz, acetone-d6) δ 10.85 (s, 1H), 8.19 (s, 1H), 8.13-8.15 (m, 1H), 8.06 (d, 1H, J=3.0 Hz), 7.55-7.59 (m, 2H), 7.51-7.52 (m, 1H), 7.33 (d, 1H, J=8.4 Hz), 6.99 (d, 1H, J=7.2 Hz), 4.52 (t, 2H, J=4.8 Hz), 3.80 (t, 2H, J=4.8 Hz), 1.92-1.96 (m, 2H). $^{13}$C NMR (150 MHz, DMSO-d6) δ 163.4, 154.8, 141.2, 137.1, 132.6, 132.1, 130.1, 129.5, 126.4, 125.8, 125.8, 124.6, 124.1, 116.0, 112.1, 71.2, 40.4.

5-Chloro-N-(1,1-dioxo-1H-1λ$^{6}$-benzo[b]thiophen-6-yl)-2-(2-piperazin-1-yl-ethoxy) benzamide (HJC-4-13)

HJC-4-13

The general procedure was the same as HJC-1-50/HJC-1-52. Obtained as a pale yellow solid (two steps, 48% yield); $^{1}$H NMR (600 MHz, DMSO-d6) δ 10.71 (s, 1H), 8.52 (s, 1H), 8.21 (s, 1H), 7.87-7.89 (m, 1H), 7.69 (d, 1H, J=2.4 Hz), 7.58-7.63 (m, 3H), 7.32 (d, 1H, J=7.2 Hz), 7.26 (d, 1H, J=8.4 Hz), 4.24 (t, 2H, J=4.8 Hz), 2.96 (t, 4H, J=4.8 Hz), 2.82 (t, 2H, J=4.8 Hz), 2.62-2.64 (m, 4H). $^{13}$C NMR (150 MHz, DMSO-d6) δ 163.6, 154.6, 141.1, 137.2, 132.9, 132.0, 130.2, 129.1, 126.6, 126.0, 126.0, 124.6, 123.8, 115.2, 111.9, 66.9, 55.8, 49.4, 42.9.

5-Chloro-N-(1,1-dioxo-1H-1λ⁶-benzo[b]thiophen-6-yl)-2-(piperidin-4-yloxy)benzamide (HJC-4-15)

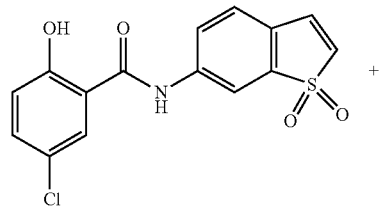

HJC-1-49

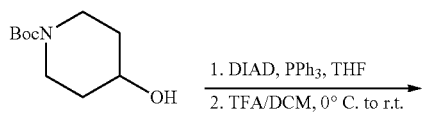

1. DIAD, PPh₃, THF
2. TFA/DCM, 0° C. to r.t.

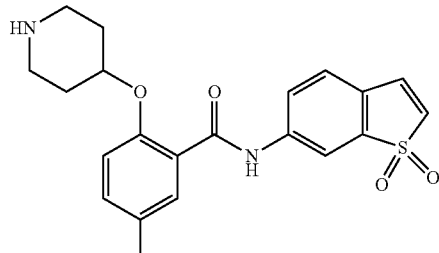

HJC-4-15

The general procedure was the same as HJC-1-50/HJC-1-52. Obtained as a pale yellow solid (two steps, 52% yield); ¹H NMR (600 MHz, DMSO-d6) δ 10.73 (s, 1H), 8.26 (s, 1H), 7.81-7.82 (m, 1H), 7.58-7.63 (m, 3H), 7.54-7.61 (m, 1H), 7.29-7.31 (m, 2H), 4.72-4.73 (m, 1H), 3.03-3.07 (m, 2H), 2.87-2.90 (m, 2H), 1.98-2.01 (m, 2H), 1.74-1.77 (m, 2H). ¹³C NMR (150 MHz, DMSO-d6) δ 164.2, 152.8, 141.3, 137.2, 132.9, 131.4, 130.2, 128.9, 128.2, 126.6, 125.9, 124.6, 123.6, 116.7, 111.6, 71.7, 41.1, 28.5.

2-(3-Aminopropoxy)-5-chloro-N-(1,1-dioxo-1H-1λ⁶-benzo[b]thiophen-6-yl)benzamide (HJC-4-16)

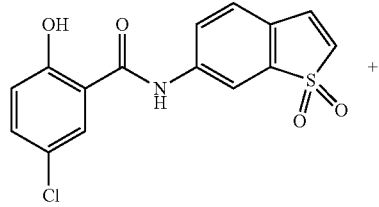

HJC-1-49

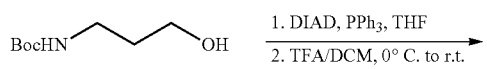

1. DIAD, PPh₃, THF
2. TFA/DCM, 0° C. to r.t.

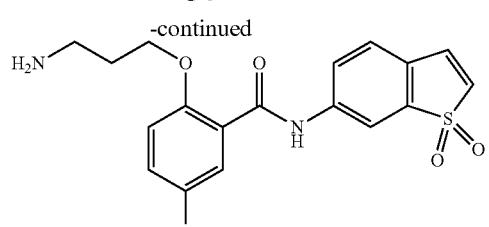

HJC-4-16

The general procedure was the same as HJC-1-50/HJC-1-52. Obtained as a pale yellow solid (two steps, 51% yield); ¹H NMR (600 MHz, DMSO-d6) δ 10.76 (s, 1H), 8.31 (s, 1H), 7.78-7.80 (m, 1H), 7.75 (s, 2H), 7.57-7.64 (m, 4H), 7.31 (d, 1H, J=6.6 Hz), 7.21 (d, 1H, J=8.4 Hz), 4.18 (t, 2H, J=6.0 Hz), 2.95 (t, 2H, J=6.6 Hz), 2.00-2.02 (m, 2H). ¹³C NMR (150 MHz, DMSO-d6) δ 164.3, 154.3, 141.3, 137.2, 132.8, 131.6, 130.2, 128.8, 126.8, 126.6, 125.9, 124.3, 123.8, 114.8, 111.8, 66.0, 36.5, 26.5.

5-Chloro-N-(1,1-dioxo-1H-1λ⁶-benzo[b]thiophen-6-yl)-2-(2-methylaminoethoxy)benzamide (HJC-4-28)

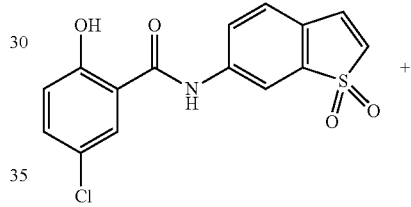

HJC-1-49

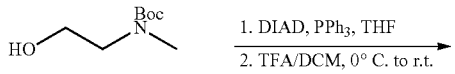

1. DIAD, PPh₃, THF
2. TFA/DCM, 0° C. to r.t.

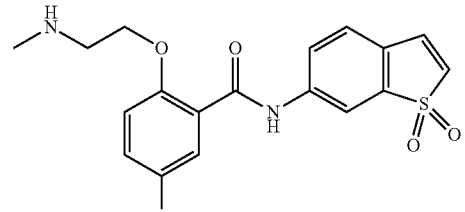

HJC-4-28

The general procedure was the same as HJC-1-50/HJC-1-52. Obtained as a white solid (two steps, 43% yield); ¹H NMR (600 MHz, CDCl₃) δ 10.77 (s, 1H), 8.36-8.38 (m, 1H), 8.21 (d, 1H, J=2.4 Hz), 8.10 (s, 1H), 7.44-7.46 (m, 1H), 7.35 (d, 1H, J=8.4 Hz), 7.21-7.22 (m, 1H), 6.98 (d, 1H, J=9.0 Hz), 6.67 (d, 1H, J=6.6 Hz), 4.31 (t, 2H, J=4.8 Hz), 3.18 (t, 2H, J=5.4 Hz), 2.64 (s, 3H). ¹³C NMR (150 MHz, CDCl₃) δ 162.6, 155.2, 141.8, 137.6, 133.3, 132.5, 132.4, 129.6, 127.4, 126.0, 124.5, 123.3, 114.3, 114.1, 68.3, 50.8, 36.5.

2-(4-Aminobutoxy)-5-chloro-N-(2-chloro-4-nitrophenyl)benzamide (HJC-4-31)

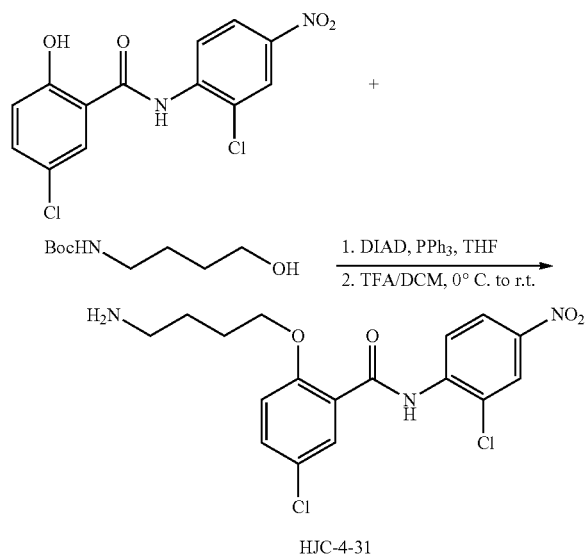

HJC-4-31

The general procedure was the same as HJC-1-50/HJC-1-52. Obtained as a white solid (two steps, 46% yield); $^1$H NMR (600 MHz, DMSO-d6) δ 8.70 (d, 1H, J=9.6 Hz), 8.46 (d, 1H, J=2.4 Hz), 8.30-8.32 (m, 1H), 7.97 (d, 1H, J=3.0 Hz), 7.68-7.70 (m, 1H), 7.40 (d, 1H, J=9.0 Hz), 4.40 (t, 2H, J=6.6 Hz), 2.81 (t, 2H, J=7.2 Hz), 1.87-1.90 (m, 2H), 1.64-1.67 (m, 2H). $^{13}$C NMR (150 MHz, DMSO-d6) δ 162.4, 155.2, 143.0, 140.8, 133.7, 130.6, 125.2, 124.8, 123.8, 123.2, 122.6, 121.9, 116.0, 69.3, 38.6, 25.2, 24.0.

5-Chloro-N-(1,1-dioxo-1H-1λ$^6$-benzo[b]thiophen-6-yl)-2-(2-morpholin-4-yl-ethoxy) benzamide (HJC-3-9)

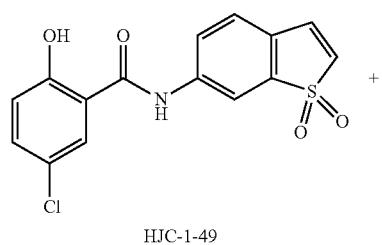

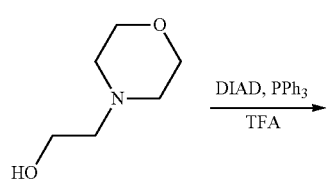

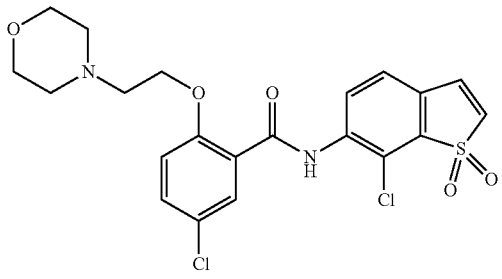

HJC-3-9

The general procedure was the same as HJC-1-14. Obtained as a white solid (67% yield); $^1$H NMR (600 MHz, DMSO-d6) δ 10.72 (s, 1H), 8.18 (s, 1H), 7.90 (d, 1H, J=8.4 Hz), 7.73 (d, 1H, J=2.4 Hz), 7.58-7.62 (m, 3H), 7.27-7.32 (m, 2H), 4.26-4.28 (m, 2H), 3.43-3.45 (m, 4H), 2.74-2.76 (m, 2H), 2.42-2.50 (m, 4H). $^{13}$C NMR (150 MHz, DMSO-d6) δ 163.4, 154.8, 141.0, 137.2, 132.8, 132.1, 130.2, 129.2, 126.5, 126.0, 125.5, 124.7, 124.1, 115.4, 112.1, 66.7, 66.0, 56.6, 53.3.

5-Chloro-N-(2-chloro-4-nitro-phenyl)-2-(2-dimethylamino-ethoxy)benzamide (HJC-3-57)

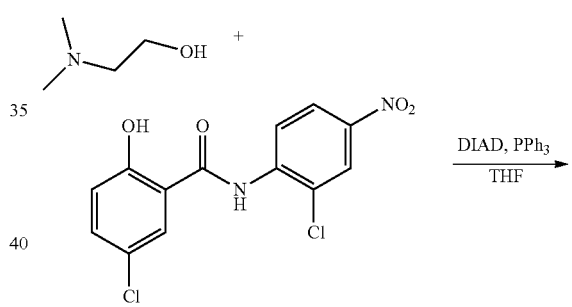

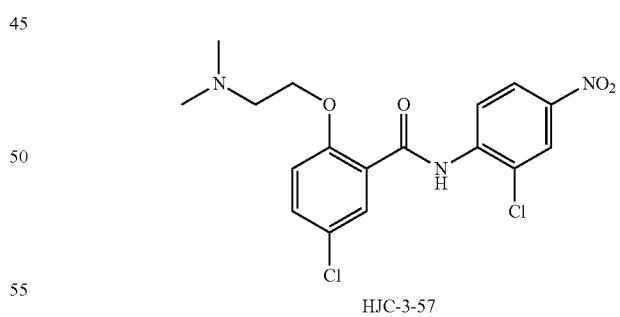

HJC-3-57

The general procedure was the same as HJC-1-14. Obtained as a pale yellow solid (50% yield); $^1$H NMR (600 MHz, CDCl$_3$) δ 10.59 (s, 1H), 8.76 (d, 1H, J=9.0 Hz), 8.33 (d, 1H, J=2.4 Hz), 8.22 (d, 1H, J=2.4 Hz), 8.20 (d, 1H, J=9.0 Hz), 7.48 (dd, 1H, J=2.4, 8.4 Hz), 7.06 (d, 1H, J=9.0 Hz), 4.36 (t, 2H, J=6.6 Hz), 2.80 (t, 2H, J=6.0 Hz), 2.26 (s, 6H). $^{13}$C NMR (150 MHz, CDCl$_3$) δ 162.8, 155.5, 143.4, 141.4, 133.9, 132.6, 127.6, 125.0, 123.8, 123.5, 123.0, 122.3, 115.1, 68.6, 57.8, 45.8.

2-(2-Bromoethoxy)-5-chloro-N-(2-chloro-4-nitrophenyl)benzamide (HJC-3-64)

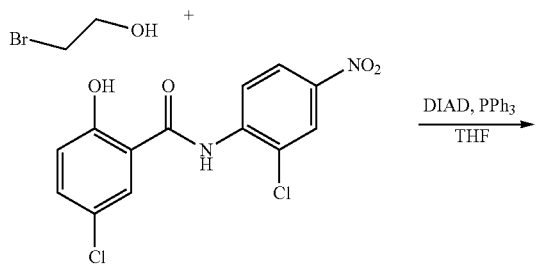

HJC-3-64

The general procedure was the same as HJC-1-14. Obtained as a pale yellow solid (75% yield); $^1$H NMR (600 MHz, DMSO-d6) δ 10.51 (s, 1H), 8.62 (d, 1H, J=9.0 Hz), 8.45 (d, 1H, J=2.4 Hz), 8.28-8.30 (m, 1H), 7.97 (d, 1H, J=2.4 Hz), 7.68-7.70 (m, 1H), 7.40 (d, 1H, J=9.6 Hz), 4.70 (t, 2H, J=6.6 Hz), 3.92 (t, 1H, J=6.0 Hz). $^{13}$C NMR (150 MHz, DMSO-d6) δ 162.2, 154.6, 143.2, 140.7, 133.8, 130.7, 125.8, 124.8, 123.8, 123.6, 122.8, 122.3, 116.4, 69.9, 30.9.

5-Chloro-2-(2-dimethylaminoethoxy)-N-(1,1-dioxo-1H-1λ$^6$-benzo[b]thiophen-6-yl) benzamide (HJC-3-69)

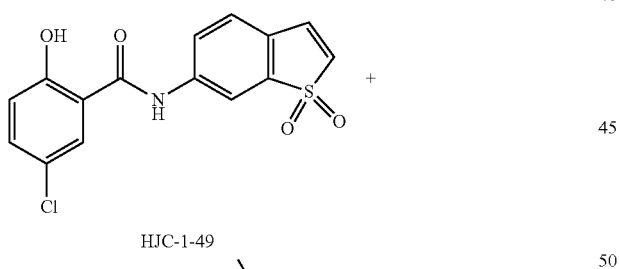

HJC-3-69

The general procedure was the same as HJC-1-14. Obtained as a pale yellow solid (62% yield); $^1$H NMR (600 MHz, CDCl$_3$) δ 10.77 (s, 1H), 8.41 (d, 1H, J=7.8 Hz), 8.24 (d, 1H, J=1.8 Hz), 7.99 (s, 1H), 7.43-7.45 (m, 1H), 7.33 (d, 1H, J=8.4 Hz), 7.20 (d, 1H, J=6.6 Hz), 6.97 (d, 1H, J=9.0 Hz), 6.64 (d, 1H, J=7.2 Hz), 4.26 (t, 2H, J=5.4 Hz), 2.84 (t, 2H, J=4.2 Hz), 2.39 (s, 6H). $^{13}$C NMR (150 MHz, CDCl$_3$) δ 162.4, 155.3, 141.9, 137.6, 133.4, 132.5, 132.5, 129.7, 127.5, 126.0, 124.5, 123.0, 114.3, 66.1, 57.9, 45.2.

2-(2-Bromo-ethoxy)-5-chloro-N-(1,1-dioxo-1H-1λ$^6$-benzo[b]thiophen-6-yl)benzamide (HJC-3-77)

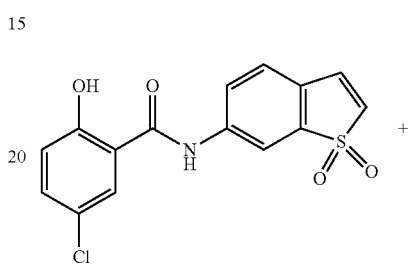

HJC-3-77

The general procedure was the same as HJC-1-14. Obtained as a pale yellow solid (75% yield); $^1$H NMR (600 MHz, DMSO-d6) δ 10.59 (s, 1H), 8.26 (s, 1H), 7.89 (d, 1H, J=7.8 Hz), 7.70 (d, 1H, J=2.4 Hz), 7.58-7.61 (m, 3H), 7.26-7.31 (m, 2H), 4.47 (t, 2H, J=5.4 Hz), 3.87 (t, 2H, J=5.4 Hz). $^{13}$C NMR (150 MHz, DMSO-d6) δ 163.4, 154.1, 141.1, 137.2, 132.8, 132.0, 130.2, 129.3, 126.5, 126.2, 125.9, 125.0, 123.9, 115.5, 112.0, 69.1, 31.1.

5-Chloro-N-(2-chloro-4-nitrophenyl)-2-(1-methylpiperidin-4-yloxy)benzamide (HJC-3-81)

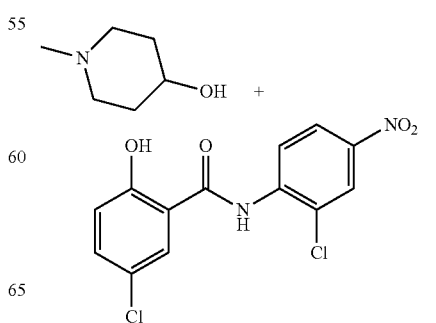

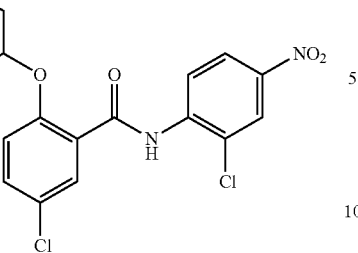

HJC-3-81

The general procedure was the same as HJC-1-14. Obtained as a pale yellow solid (57% yield); $^1$H NMR (600 MHz, DMSO-d6) δ 10.33 (s, 1H), 8.63 (d, 1H, J=9.0 Hz), 8.44 (d, 1H, J=2.4 Hz), 8.30 (d, 1H, J=9.0 Hz), 7.91 (s, 1H), 7.64 (d, 1H, J=9.0 Hz), 7.44 (d, 1H, J=9.0 Hz), 4.69-4.71 (m, 1H), 2.67-2.69 (m, 2H), 2.16 (s, 3H), 2.14-2.16 (m, 2H), 2.03-2.05 (m, 2H), 1.79-1.81 (m, 2H). $^{13}$C NMR (150 MHz, DMSO-d6) δ 162.6, 154.0, 143.1, 140.5, 133.5, 130.6, 125.2, 124.9, 123.7, 123.6, 123.3, 122.2, 117.4, 75.8, 52.6, 45.4, 30.5.

5-Chloro-N-(1,1-dioxo-1H-1λ$^6$-benzo[b]thiophen-6-yl)-2-(1-methyl-piperidin-4-yloxy) benzamide (HJC-3-82)

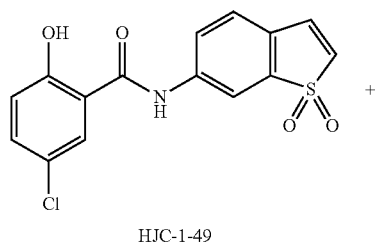

HJC-1-49

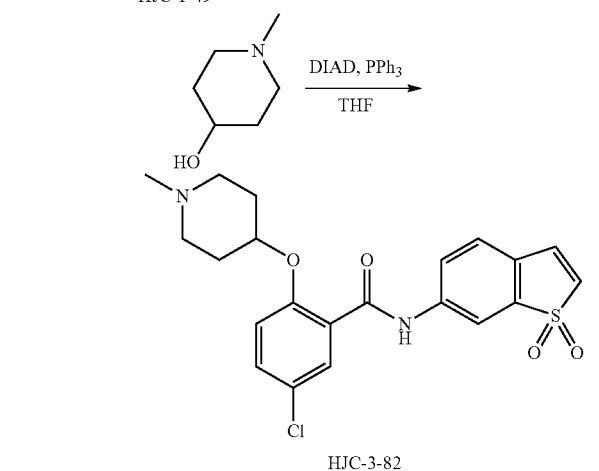

HJC-3-82

The general procedure was the same as HJC-1-14. Obtained as a pale yellow solid (39% yield); $^1$H NMR (600 MHz, DMSO-d6) δ 10.63 (s, 1H), 8.22 (s, 1H), 7.85 (d, 1H, J=7.2 Hz), 7.58-7.61 (m, 3H), 7.51-7.53 (m, 1H), 7.27-7.30 (m, 2H), 4.53-4.55 (m, 1H), 2.42-2.44 (m, 2H), 2.19-2.21 (m, 2H), 2.06 (s, 3H), 1.89-1.91 (m, 2H), 1.69-1.71 (m, 2H). $^{13}$C NMR (150 MHz, DMSO-d6) δ 164.1, 153.2, 141.2, 137.2, 132.8, 131.5, 130.1, 128.8, 128.0, 126.6, 125.8, 124.4, 123.5, 116.8, 111.6, 79.2, 51.6, 45.8, 30.0.

5-Chloro-N-(2-chloro-4-nitro-phenyl)-2-(2-fluoro-ethoxy)benzamide (HJC-3-98)

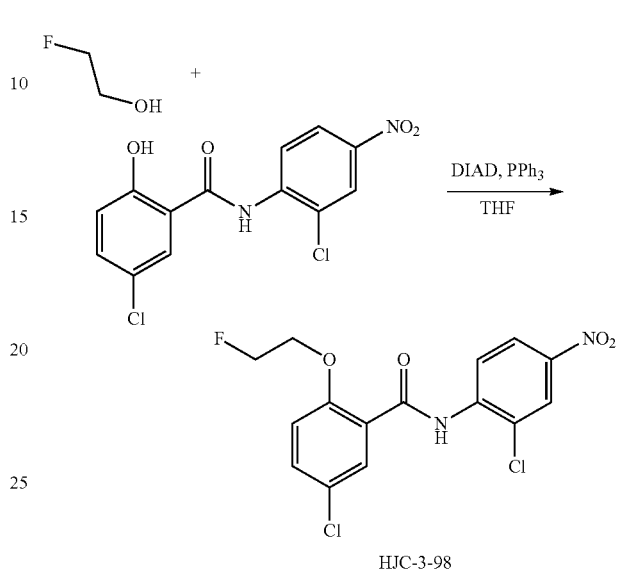

HJC-3-98

The general procedure was the same as HJC-1-14. Obtained as a white solid (86% yield); $^1$H NMR (600 MHz, DMSO-d6) δ 10.53 (s, 1H), 8.66 (d, 1H, J=9.6 Hz), 8.43 (d, 1H, J=3.0 Hz), 8.28-8.30 (m, 1H), 7.98 (d, 1H, J=3.0 Hz), 7.69-7.70 (m, 1H), 7.40 (d, 1H, J=9.0 Hz), 4.82-4.91 (m, 2H), 4.60-4.66 (m, 2H). $^{13}$C NMR (150 MHz, DMSO-d6) δ 162.2, 155.0, 143.1, 140.7, 133.7, 130.7, 125.7, 124.8, 123.6, 123.3, 122.7, 122.0, 116.3, 81.6 (d, J=166 Hz), 69.6 (d, J=19 Hz).

5-Chloro-N-(1,1-dioxo-1H-1λ$^6$-benzo[b]thiophen-6-yl)-2-(2-fluoroethoxy)benzamide (HJC-3-99)

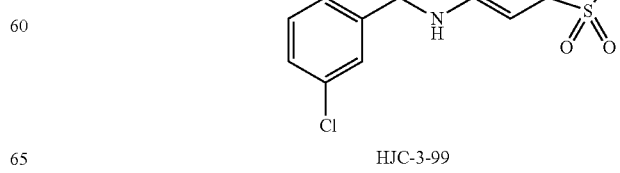

HJC-3-99

The general procedure was the same as HJC-1-14. Obtained as a pale yellow solid (77% yield); $^1$H NMR (600 MHz, DMSO-d6) δ 10.63 (s, 1H), 8.21 (s, 1H), 7.85-7.86 (m, 1H), 7.68 (d, 1H, J=2.4 Hz), 7.58-7.61 (m, 3H), 7.26-7.31 (m, 2H), 4.74-4.83 (m, 2H), 4.37-4.43 (m, 2H). $^{13}$C NMR (150 MHz, DMSO-d6) δ 163.6, 154.3, 141.1, 137.2, 132.8, 131.9, 130.2, 129.1, 126.6, 126.4, 125.9, 124.9, 123.7, 115.5, 111.7, 82.1 (d, J=166 Hz), 68.5 (d, J=18 Hz).

5-Chloro-N-(2-chloro-4-nitrophenyl)-2-[2-(4-methanesulfonylpiperazin-1-yl)-ethoxy]benzamide (HJC-2-55)

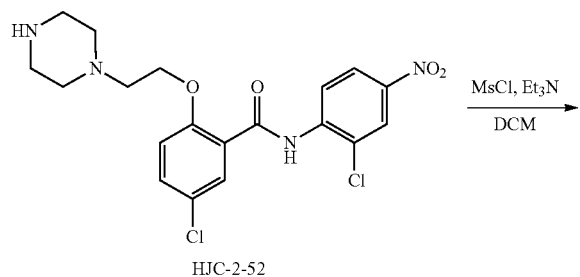

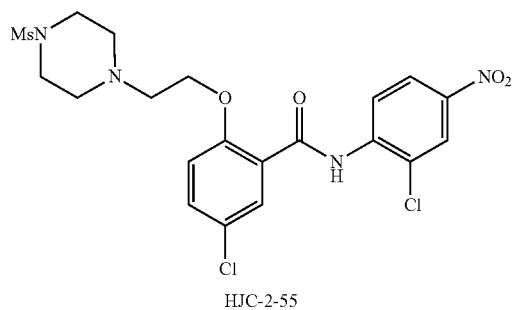

The general procedure was the same as HJC-1-31. Obtained as a pale yellow solid (100% yield); $^1$H NMR (600 MHz, DMSO-d6) δ 10.71 (s, 1H), 8.54 (d, 1H, J=9.0 Hz), δ 8.45 (d, 1H, J=2.4 Hz), 8.28 (d, 1H, J=9.0 Hz), δ 7.97 (d, 1H, J=3.0 Hz), 7.68 (d, 1H, J=9.0 Hz), 7.43 (d, 1H, J=9.0 Hz), 4.48 (t, 2H, J=6.0 Hz), 2.81-2.87 (m, 6H), 2.66 (s, 3H), 2.48-2.51 (m, 4H). $^{13}$C NMR (150 MHz, DMSO-d6) δ 162.1, 155.4, 143.4, 140.7, 133.6, 130.4, 125.5, 124.8, 124.4, 124.0, 123.1, 122.8, 117.0, 67.3, 55.3, 51.7, 45.1, 33.3.

5-Chloro-N-(2-chloro-4-nitrophenyl)-2-(1-methanesulfonylpiperidin-4-yloxy)benzamide (HJC-4-24)

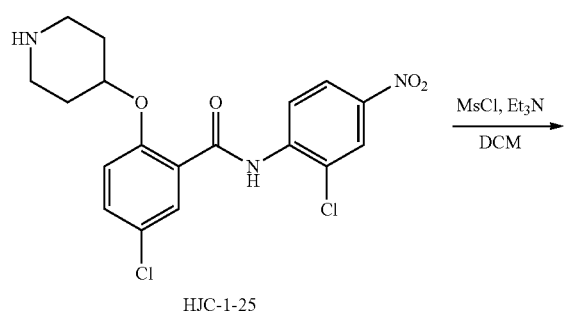

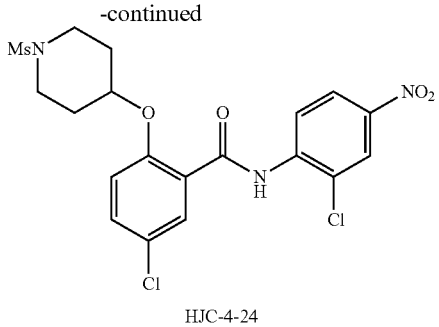

The general procedure was the same as HJC-1-31. Obtained as a pale yellow solid (95% yield); $^1$H NMR (600 MHz, CDCl$_3$) δ 9.99 (s, 1H), 8.87 (d, 1H, J=9.0 Hz), 8.34 (d, 1H, J=1.8 Hz), 8.21-8.23 (m, 1H), 8.16 (d, 1H, J=2.4 Hz), 7.48-7.50 (m, 1H), 7.03 (d, 1H, J=9.0 Hz), 4.64-4.66 (m, 1H), 3.66-3.69 (m, 2H), 3.04-3.09 (m, 2H), 2.77 (s, 3H), 2.21-2.24 (m, 2H), 2.03-2.07 (m, 2H). $^{13}$C NMR (150 MHz, CDCl$_3$) δ 162.9, 153.4, 143.5, 140.8, 133.8, 132.8, 128.2, 125.1, 124.7, 123.8, 122.8, 121.6, 116.3, 76.0, 43.7, 36.0, 30.9.

5-Chloro-N-(2-chloro-4-nitrophenyl)-2-(2-methanesulfonylaminoethoxy)benzamide (HJC-4-26)

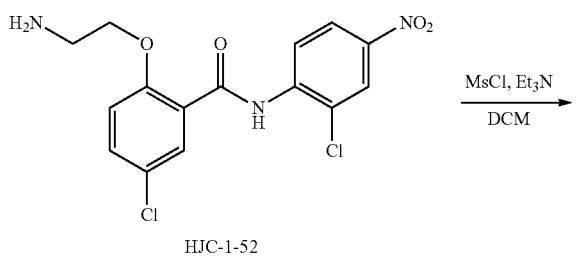

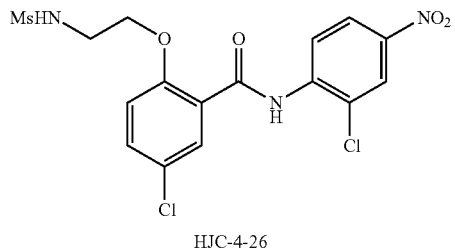

The general procedure was the same as HJC-1-31. Obtained as a pale yellow solid (89% yield); $^1$H NMR (600 MHz, DMSO-d6) δ 10.54 (s, 1H), 8.65 (d, 1H, J=9.0 Hz), 8.45 (s, 1H), 8.30 (d, 1H, J=7.8 Hz), 7.97 (s, 1H), 7.69 (d, 1H, J=7.8 Hz), 7.38-7.40 (m, 2H), 4.42-4.45 (m, 2H), 3.43-3.45 (m, 2H), 2.89 (s, 3H). $^{13}$C NMR (150 MHz, DMSO-d6) δ 162.4, 155.0, 143.1, 140.9, 133.6, 130.7, 125.4, 124.8, 123.9, 123.6, 122.9, 122.2, 115.9, 69.3, 41.3, 38.3.

HJC-4-35-1 and HJC-4-35-2

5-Chloro-N-(2-chloro-4-nitrophenyl)-2-(2,3-dihydroxypropoxy)benzamide (HJC-3-60)

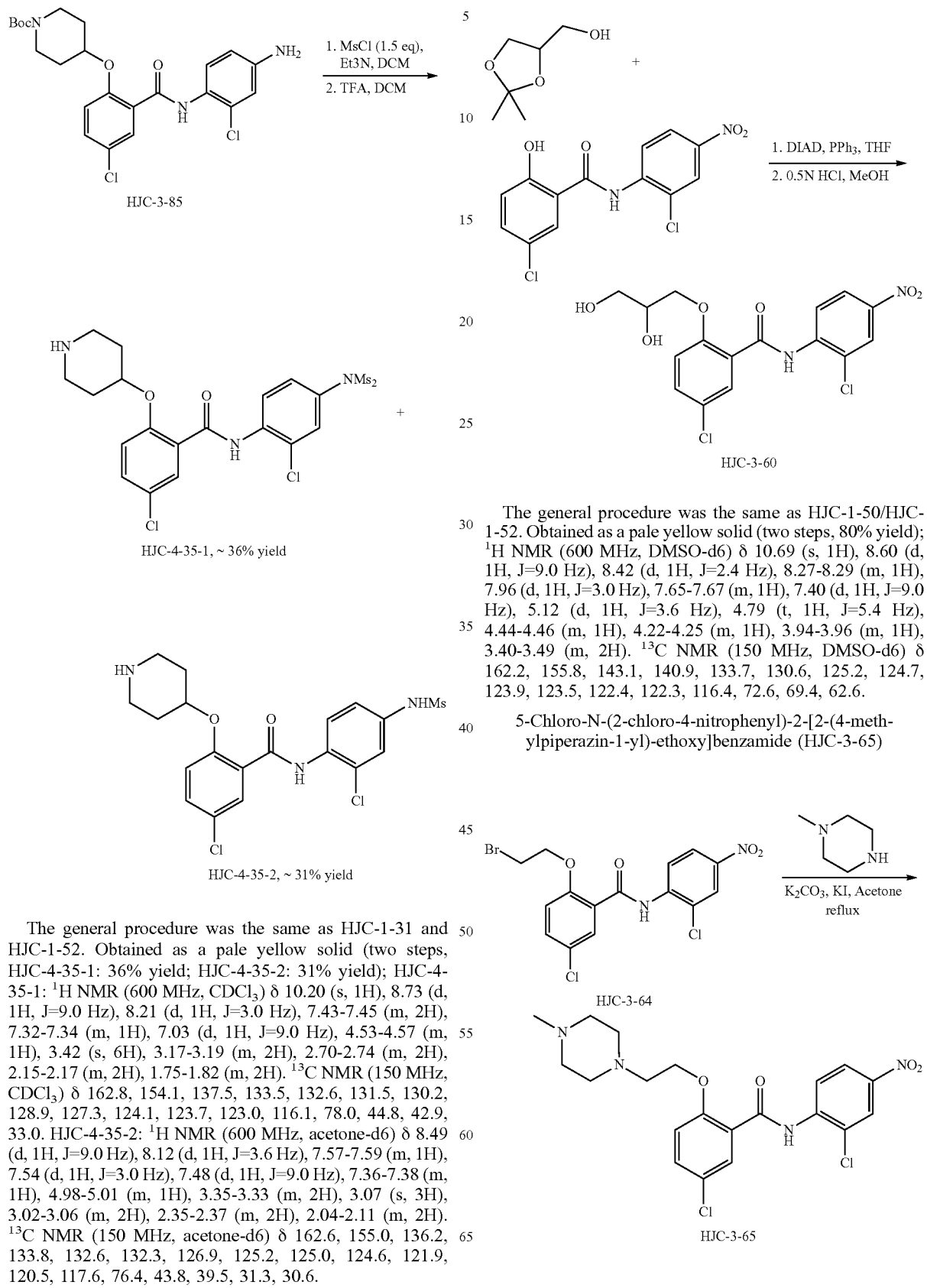

The general procedure was the same as HJC-1-50/HJC-1-52. Obtained as a pale yellow solid (two steps, 80% yield); $^1$H NMR (600 MHz, DMSO-d6) δ 10.69 (s, 1H), 8.60 (d, 1H, J=9.0 Hz), 8.42 (d, 1H, J=2.4 Hz), 8.27-8.29 (m, 1H), 7.96 (d, 1H, J=3.0 Hz), 7.65-7.67 (m, 1H), 7.40 (d, 1H, J=9.0 Hz), 5.12 (d, 1H, J=3.6 Hz), 4.79 (t, 1H, J=5.4 Hz), 4.44-4.46 (m, 1H), 4.22-4.25 (m, 1H), 3.94-3.96 (m, 1H), 3.40-3.49 (m, 2H). $^{13}$C NMR (150 MHz, DMSO-d6) δ 162.2, 155.8, 143.1, 140.9, 133.7, 130.6, 125.2, 124.7, 123.9, 123.5, 122.4, 122.3, 116.4, 72.6, 69.4, 62.6.

5-Chloro-N-(2-chloro-4-nitrophenyl)-2-[2-(4-methylpiperazin-1-yl)-ethoxy]benzamide (HJC-3-65)

The general procedure was the same as HJC-1-31 and HJC-1-52. Obtained as a pale yellow solid (two steps, HJC-4-35-1: 36% yield; HJC-4-35-2: 31% yield); HJC-4-35-1: $^1$H NMR (600 MHz, CDCl$_3$) δ 10.20 (s, 1H), 8.73 (d, 1H, J=9.0 Hz), 8.21 (d, 1H, J=3.0 Hz), 7.43-7.45 (m, 2H), 7.32-7.34 (m, 1H), 7.03 (d, 1H, J=9.0 Hz), 4.53-4.57 (m, 1H), 3.42 (s, 6H), 3.17-3.19 (m, 2H), 2.70-2.74 (m, 2H), 2.15-2.17 (m, 2H), 1.75-1.82 (m, 2H). $^{13}$C NMR (150 MHz, CDCl$_3$) δ 162.8, 154.1, 137.5, 133.5, 132.6, 131.5, 130.2, 128.9, 127.3, 124.1, 123.7, 123.0, 116.1, 78.0, 44.8, 42.9, 33.0. HJC-4-35-2: $^1$H NMR (600 MHz, acetone-d6) δ 8.49 (d, 1H, J=9.0 Hz), 8.12 (d, 1H, J=3.6 Hz), 7.57-7.59 (m, 1H), 7.54 (d, 1H, J=3.0 Hz), 7.48 (d, 1H, J=9.0 Hz), 7.36-7.38 (m, 1H), 4.98-5.01 (m, 1H), 3.35-3.33 (m, 2H), 3.07 (s, 3H), 3.02-3.06 (m, 2H), 2.35-2.37 (m, 2H), 2.04-2.11 (m, 2H). $^{13}$C NMR (150 MHz, acetone-d6) δ 162.6, 155.0, 136.2, 133.8, 132.6, 132.3, 126.9, 125.2, 125.0, 124.6, 121.9, 120.5, 117.6, 76.4, 43.8, 39.5, 31.3, 30.6.

To a solution of HJC-3-64 (100 mg, 0.23 mmol), KI (58 mg, 0.35 mmol) and K$_2$CO$_3$ (48 mg, 0.35 mmol) in acetone (5 mL) was added 1-methyl-piperazine (46 mg, 0.46 mmol) at 0° C. The mixture was stirred at 75° C. for 18 h. The solution was diluted with EtOAc (100 mL), washed with 0.1 N HCl (aq.) (10 mL) and brine (10 mL). The organic layer was dried over anhydrous Na$_2$SO$_4$, and then concentrated under reduced pressure. The residue was purified by silica gel column chromatography (hexane/EtOAc=1/1 to 1/3) to give the desired product as a pale yellow solid (57 mg, 55%). $^1$H NMR (600 MHz, CDCl$_3$) δ 10.66 (s, 1H), 8.75 (d, 1H, J=9.0 Hz), 8.33 (d, 1H, J=3.0 Hz), 8.22 (d, 1H, J=2.4 Hz), 8.20-8.21 (m, 1H), 7.47-7.49 (m, 1H), 7.06 (d, 1H, J=8.4 Hz), 4.39 (t, 2H, J=6.0 Hz), 2.85 (t, 2H, J=6.6 Hz), 2.21-2.50 (m, 8H), 2.14 (s, 3H). $^{13}$C NMR (150 MHz, CDCl$_3$) δ 162.7, 155.5, 143.4, 141.4, 133.9, 132.5, 127.7, 125.0, 124.0, 123.5, 123.0, 122.4, 115.5, 68.1, 56.5, 55.0, 53.4, 46.1.

5-Chloro-N-(1,1-dioxo-1H-1λ$^6$-benzo[b]thiophen-6-yl)-2-[2-(4-methylpiperazin-1-yl)-ethoxy]benzamide (HJC-3-78)

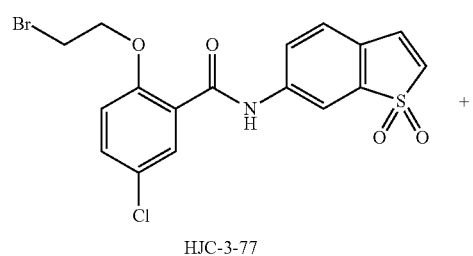

HJC-3-77

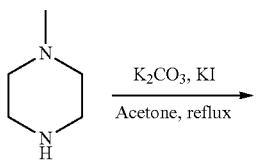

K$_2$CO$_3$, KI
Acetone, reflux

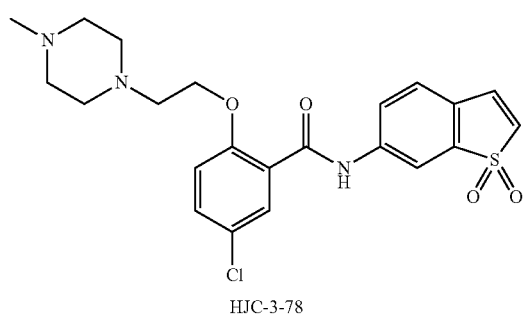

HJC-3-78

The general procedure was the same as HJC-3-65. Obtained as a pale yellow solid (77% yield); $^1$H NMR (600 MHz, DMSO-d6) δ 10.70 (s, 1H), 8.17 (s, 1H), 7.89-7.90 (m, 1H), 7.73 (d, 1H, J=3.0 Hz), 7.58-7.62 (m, 3H), 7.26-7.31 (m, 2H), 4.25 (t, 2H, J=5.4 Hz), 2.73 (t, 2H, J=4.8 Hz), 2.42-2.50 (m, 4H), 2.12-2.22 (m, 4H), 2.03 (s, 3H). $^{13}$C NMR (150 MHz, DMSO-d6) δ 163.3, 154.9, 141.0, 137.2, 132.8, 132.2, 130.2, 129.2, 126.5, 126.0, 125.4, 124.7, 124.2, 115.4, 112.2, 66.9, 56.2, 54.5, 52.7, 45.6.

5-Chloro-N-(1,1-dioxo-1H-1λ$^6$-benzo[b]thiophen-6-yl)-2-(2-piperidin-1-yl-ethoxy)benzamide (HJC-3-79)

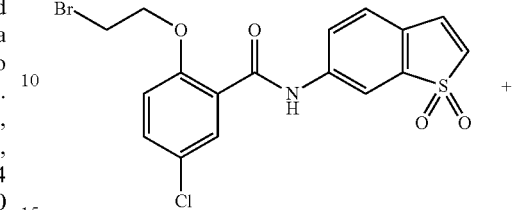

HJC-3-77

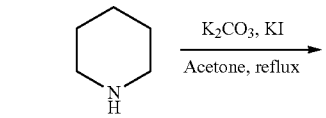

K$_2$CO$_3$, KI
Acetone, reflux

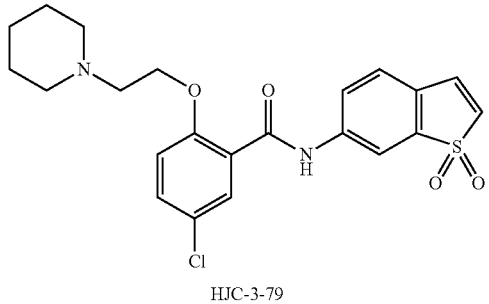

HJC-3-79

The general procedure was the same as HJC-3-65. Obtained as a pale yellow solid (98% yield); $^1$H NMR (600 MHz, DMSO-d6) δ 10.71 (s, 1H), 8.20 (s, 1H), 7.89 (d, 1H, J=7.8 Hz), 7.74 (d, 1H, J=2.4 Hz), 7.59-7.62 (m, 3H), 7.27-7.31 (m, 2H), 4.25 (t, 2H, J=5.4 Hz), 2.70-2.72 (m, 2H), 2.38-2.40 (m, 4H), 1.35-1.38 (m, 4H), 1.22-1.24 (m, 2H). $^{13}$C NMR (150 MHz, DMSO-d6) δ 163.3, 155.0, 141.0, 137.2, 132.8, 132.2, 130.2, 129.3, 126.5, 126.0, 125.3, 124.7, 124.1, 115.4, 112.2, 66.9, 56.9, 54.1, 25.4, 23.8.

5-Chloro-N-(2-chloro-4-nitrophenyl)-2-(2-piperidin-1-yl-ethoxy)benzamide (HJC-3-84)

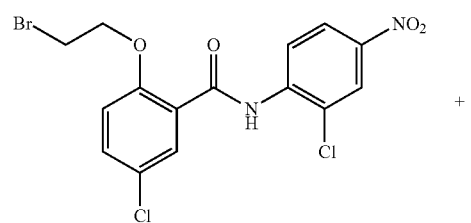

HJC-3-64

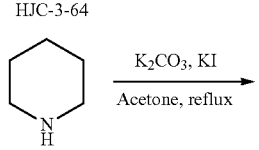

K$_2$CO$_3$, KI
Acetone, reflux

97

-continued

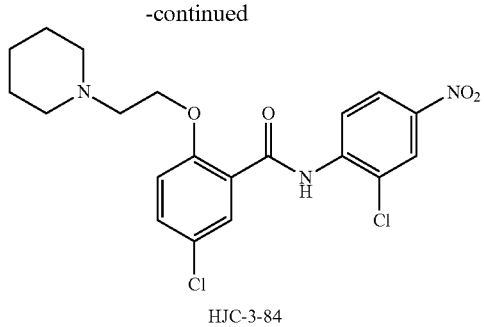

HJC-3-84

The general procedure was the same as HJC-3-65. Obtained as a pale yellow solid (91% yield); ¹H NMR (600 MHz, DMSO-d6) δ 10.80 (s, 1H), 8.54 (d, 1H, J=9.0 Hz), 8.45 (s, 1H), 8.28-8.30 (m, 1H), 7.97 (s, 1H), 7.66-7.68 (m, 1H), 7.42 (d, 1H, J=8.4 Hz), 4.44-4.46 (m, 2H), 2.68-2.70 (m, 2H), 2.30-2.32 (m, 4H), 1.22-1.24 (m, 6H). ¹³C NMR (150 MHz, DMSO-d6) δ 162.1, 155.6, 143.3, 140.9, 133.7, 130.5, 125.5, 124.7, 124.5, 123.5, 123.0, 122.6, 117.2, 67.6, 56.6, 53.9, 25.3, 23.7.

N-(1,1-Dioxo-1H-1λ⁶-benzo[b]thiophen-6-yl)-4-methoxybenzenesulfonamide (HJC-3-68)

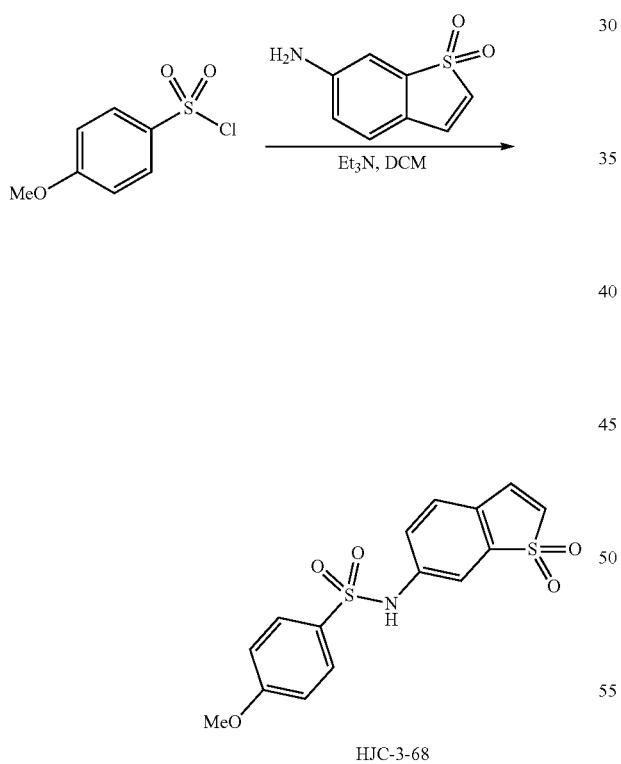

HJC-3-68

The general procedure was the same as HJC-1-62. Obtained as a yellow solid (46% yield); ¹H NMR (600 MHz, DMSO-d6) δ 7.74 (d, 2H, J=9.0 Hz), 7.69 (d, 1H, J=7.2 Hz), 7.66 (d, 1H, J=7.8 Hz), 7.53 (d, 1H, J=7.2 Hz), 7.42 (d, 1H, J=1.2 Hz), 7.26-7.28 (m, 1H), 7.18 (d, 2H, J=9.0 Hz), 3.90 (s, 3H). ¹³C NMR (150 MHz, DMSO-d6) δ 164.0, 137.2, 137.1, 135.6, 133.1, 132.8, 132.0, 130.7, 129.1, 126.9, 123.8, 114.8, 56.0.

98

N-(1,1-Dioxo-1H-1λ⁶-benzo[b]thiophen-6-yl)-4-methylbenzenesulfonamide (HJC-3-70)

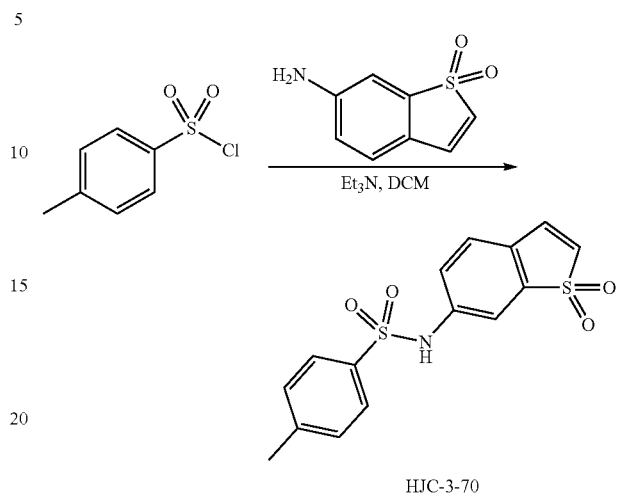

HJC-3-70

The general procedure was the same as HJC-1-62. Obtained as a yellow solid (30% yield); ¹H NMR (600 MHz, DMSO-d6) δ 7.65-7.72 (m, 5H), 7.54 (d, 1H, J=6.6 Hz), 7.49 (d, 2H, J=7.8 Hz), 7.26-7.28 (m, 1H), 2.46 (s, 3H). ¹³C NMR (150 MHz, DMSO-d6) δ 145.9, 137.2, 135.3, 135.0, 133.2, 133.0, 132.0, 130.1, 128.2, 127.0, 123.8, 21.2.

3-(6-Bromo-pyridin-2-yl)-2-cyano-N-(1,1-dioxo-1H-1λ⁶-benzo[b]thiophen-6-yl)-acrylamide (HJC-3-71)

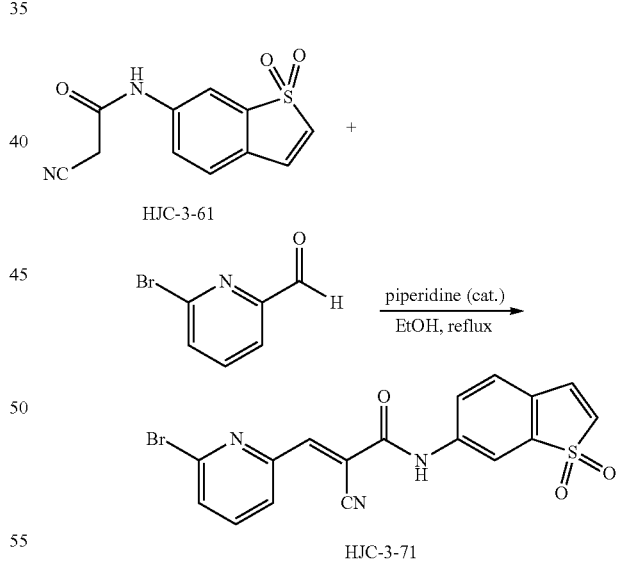

HJC-3-71

To a solution of HJC-3-61 (100 mg, 0.40 mmol) and 6-bromo-pyridine-2-carbaldehyde (112 mg, 0.60 mmol) in EtOH (5 mL) was added piperidine (3 mg, 0.04 mmol) at 0° C. The mixture was stirred at 90° C. for 0.5 h. A yellow suspension formed during the reaction. The solid was filtered and washed with H₂O. 120 mg of the desired product was obtained as a yellow solid (72% yield). ¹H NMR (600 MHz, DMSO-d6) δ 10.94 (s, 1H), 8.24 (s, 1H), 8.14 (s, 1H), 7.98 (t, 1H, J=7.8 Hz), 7.91-7.93 (m, 2H), 7.84 (d, 1H, J=7.8 Hz), 7.62 (t, 2H, J=7.2 Hz), 7.34 (d, 1H, J=7.2 Hz). ¹³C NMR (150 MHz, DMSO-d6) δ 160.7, 150.8, 147.2, 141.3, 140.8, 140.6, 137.1, 132.7, 130.9, 130.5, 126.7, 126.6, 126.6, 124.8, 114.6, 112.8, 110.8.

2-Cyano-3-(3,4-dihydroxy-phenyl)-N-(1,1-dioxo-1H-1λ⁶-benzo[b]thiophen-6-yl)-acrylamide (HJC-4-11)

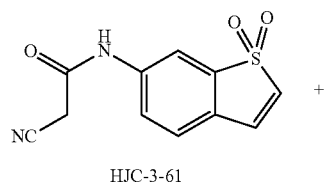

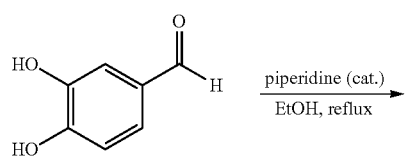

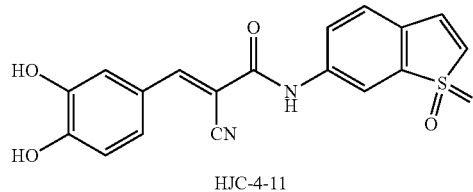

The general procedure was the same as HJC-1-62. Obtained as a yellow solid (75% yield); $^1$H NMR (600 MHz, DMSO-d6) δ 10.62 (s, 1H), 9.50-10.20 (bs, 2H), 8.12 (s, 1H), 8.10 (s, 1H), 7.89-7.91 (m, 1H), 7.58-7.62 (m, 3H), 7.36-7.37 (m, 1H), 7.31 (d, 2H, J=7.2 Hz), 6.92 (d, 1H, J=9.0 Hz). $^{13}$C NMR (150 MHz, DMSO-d6) δ 161.9, 151.8, 151.3, 145.8, 141.0, 137.0, 132.8, 130.4, 126.4, 126.2, 125.8, 124.6, 123.1, 116.8, 116.3, 116.1, 112.7, 101.0.

2-(1-Acetylpiperidin-4-yloxy)-5-chloro-N-(2-chloro-4-nitrophenyl)benzamide (HJC-4-22)

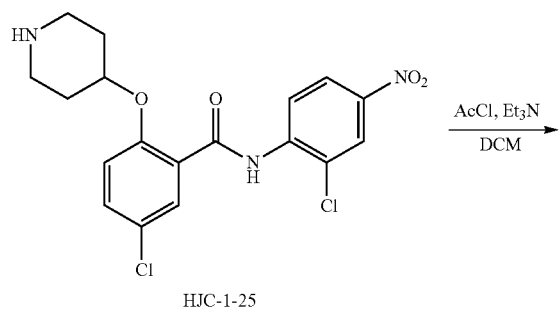

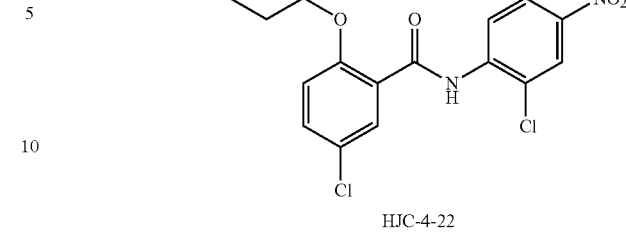

The general procedure was the same as HJC-1-62. Obtained as a pale yellow solid (91% yield); $^1$H NMR (600 MHz, CDCl₃) δ 10.07 (s, 1H), 8.87 (d, 1H, J=9.0 Hz), 8.33 (d, 1H, J=2.4 Hz), 8.21-8.23 (m, 1H), 8.18 (d, 1H, J=3.0 Hz), 7.48-7.50 (m, 1H), 7.05 (d, 1H, J=9.0 Hz), 4.69-4.73 (m, 1H), 4.33-4.35 (m, 1H), 3.80-3.82 (m, 1H), 3.28 (t, 1H, J=10.8 Hz), 3.05-3.08 (m, 1H), 2.16-2.18 (m, 2H), 2.11 (s, 3H), 1.82-1.92 (m, 2H). $^{13}$C NMR (150 MHz, CDCl₃) δ 169.1, 162.9, 153.6, 143.5, 140.9, 133.9, 132.9, 128.1, 125.0, 124.5, 123.8, 122.8, 121.7, 116.2, 44.0, 39.3, 31.8, 31.0, 21.5.

2-(2-Acetylaminoethoxy)-5-chloro-N-(2-chloro-4-nitrophenyl)benzamide (HJC-4-25)

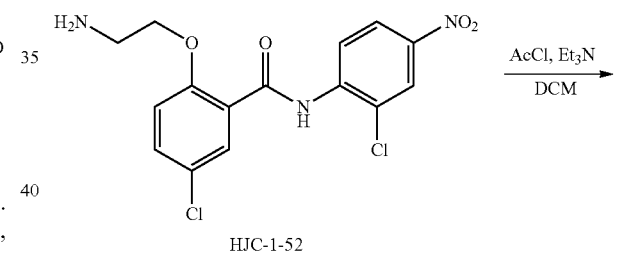

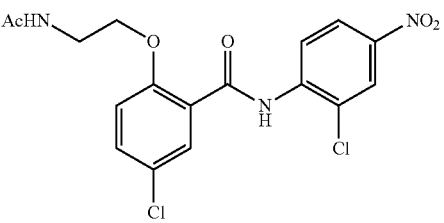

The general procedure was the same as HJC-1-62. Obtained as a pale yellow solid (90% yield); $^1$H NMR (600 MHz, DMSO-d6) δ 10.60 (s, 1H), 8.67 (d, 1H, J=9.0 Hz), 8.43 (d, 1H, J=3.0 Hz), 8.28-8.30 (m, 1H), 8.04-8.06 (m, 1H), 7.99 (d, 1H, J=3.0 Hz), 7.66-7.68 (m, 1H), 7.39 (d, 1H, J=9.0 Hz), 4.41 (t, 2H, J=6.0 Hz), 3.49-3.51 (m, 2H), 1.72 (s, 3H). $^{13}$C NMR (150 MHz, DMSO-d6) δ 169.5, 162.2, 155.0, 143.0, 140.8, 133.6, 130.6, 125.3, 124.6, 123.5, 122.6, 121.9, 115.8, 68.6, 37.6, 22.3.

2-[2-(4-Acetylpiperazin-1-yl)-ethoxy]-5-chloro-N-(2-chloro-4-nitrophenyl)benzamide (HJC-4-27)

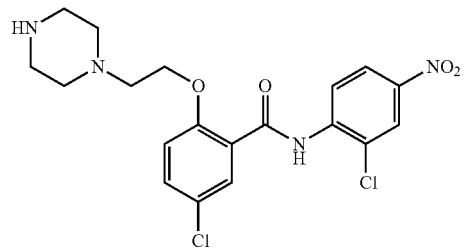

HJC-2-52

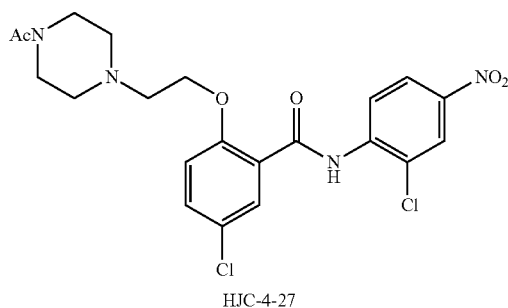

HJC-4-27

The general procedure was the same as HJC-1-62. Obtained as a pale yellow solid (91% yield); $^1$H NMR (600 MHz, CDCl$_3$) δ 10.60 (s, 1H), 8.81 (d, 1H, J=9.0 Hz), 8.34 (d, 1H, J=1.8 Hz), 8.21-8.24 (m, 2H), 7.49-7.51 (m, 1H), 7.07 (d, 1H, J=8.4 Hz), 4.43 (t, 2H, J=5.4 Hz), 3.46-3.48 (m, 2H), 3.31-3.33 (m, 2H), 2.89 (t, 2H, J=5.4 Hz), 2.44-2.48 (m, 4H), 2.03 (s, 3H). $^{13}$C NMR (150 MHz, CDCl$_3$) δ 168.8, 162.5, 155.2, 143.3, 141.1, 133.9, 132.5, 127.8, 124.8, 123.7, 123.2, 123.0, 121.9, 115.2, 67.7, 56.4, 53.6, 52.9, 46.0, 41.1, 21.3.

N-(4-Acetylamino-2-chloro-phenyl)-5-chloro-2-(piperidin-4-yloxy)benzamide (HJC-4-32)

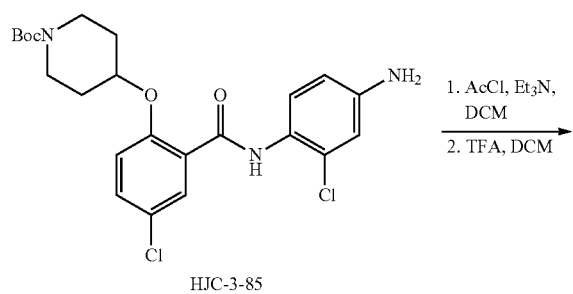

HJC-3-85

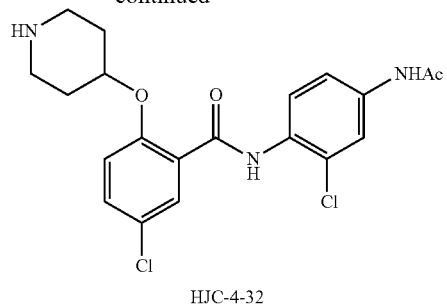

HJC-4-32

The general procedure was the same as HJC-1-62 and HJC-1-52. Obtained as a pale yellow solid (two steps, 66% yield); $^1$H NMR (600 MHz, acetone-d6) δ 8.37-8.40 (m, 1H), 8.07-8.08 (m, 1H), 7.55-7.56 (m, 1H), 7.45-7.48 (m, 2H), 5.04-5.06 (m, 1H), 3.45-3.49 (m, 2H), 3.16-3.20 (m, 2H), 2.41-2.45 (m, 2H), 2.14-2.20 (m, 2H), 1.95 (s, 3H). $^{13}$C NMR (150 MHz, acetone-d6) δ 169.0, 162.5, 154.8, 137.5, 133.7, 132.2, 131.1, 127.0, 125.5, 124.5, 124.1, 120.2, 118.7, 117.4, 75.1, 43.1, 30.6, 24.2.

N-(4-Amino-2-chlorophenyl)-5-chloro-2-(piperidin-4-yloxy)benzamide (HJC-4-23)

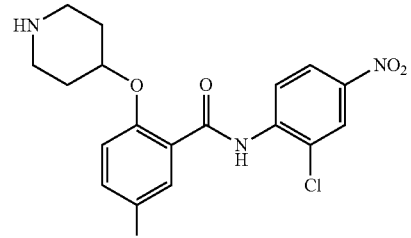

HJC-1-25

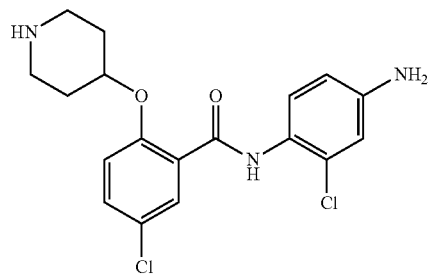

HJC-4-23

The general procedure was the same as HJC-1-29. Obtained as a pale yellow solid (72% yield); $^1$H NMR (600 MHz, DMSO-d6) δ 9.60 (s, 1H), 7.74 (d, 1H, J=2.4 Hz), 7.51-7.56 (m, 2H), 7.34 (d, 1H, J=9.0 Hz), 6.70 (d, 1H, J=1.8 Hz), 6.55 (d, 1H, J=9.0 Hz), 5.31-5.32 (m, 2H), 4.84-4.86 (m, 1H), 3.26-3.29 (m, 3H), 3.00-3.02 (m, 2H), 2.13-2.15 (m, 2H), 1.90-1.92 (m, 2H). $^{13}$C NMR (150 MHz, DMSO-d6) δ 162.5, 152.9, 147.7, 131.6, 129.6, 127.3, 126.9, 126.6, 124.9, 122.5, 116.7, 113.3, 112.7, 71.6, 40.9, 27.6.

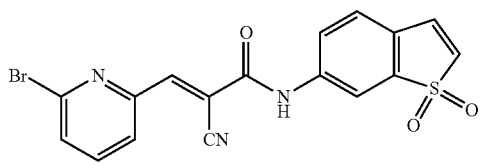

HJC0371

The following general procedure was used to generate HJC0371 analogues:

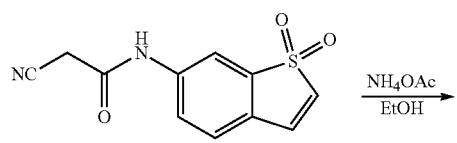

To the solution of 2-cyano-N-(1,1-dioxo-1H-1λ⁶-benzo[b]thiophen-6-yl)acetamide (0.1 mmol) and the appropriate aldehyde (0.15 mmol) in EtOH (4 mL) was added ammonium acetate (0.05 mmol) was stirred at room temperature for 16 h. The separated solid was isolated by simple filtration and dried.

3-(2-Bromophenyl)-2-cyano-N-(1,1-dioxo-1H-1λ⁶-benzo[b]thiophen-6-yl)acrylamide (RMF-1-7)

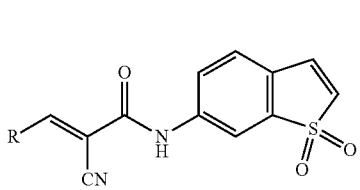

The title compound was obtained as a yellow solid (mp 226-227° C.) in 94% yield. HPLC purity 98.4% ($t_R$=20.19 min). $^1$H NMR (600 MHz, DMSO-d6) δ 10.90 (s, 1H), 8.44 (s, 1H), 8.15 (s, 1H), 8.03 (t, 1H, J=1.2 Hz), 7.92-7.94 (m, 1H), 7.86-7.88 (m, 1H), 7.61-7.65 (m, 3H), 7.53-7.56 (m, 1H), 7.34 (d, 1H, J=6.6 Hz). $^{13}$C NMR (150 MHz, DMSO-d6) δ 160.0, 150.5, 140.4, 137.0, 133.6, 133.4, 132.7, 132.1, 130.6, 130.1, 128.4, 126.7, 126.5, 125.1, 124.5, 115.0, 113.1, 111.0. HRMS (ESI) calcd for $C_{18}H_{12}BrN_2O_3S$ 414.9747 (M+H)⁺, found 414.9746.

3-(4-Bromophenyl)-2-cyano-N-(1,1-dioxo-1H-1λ⁶-benzo[b]thiophen-6-yl)acrylamide (RMF-1-8)

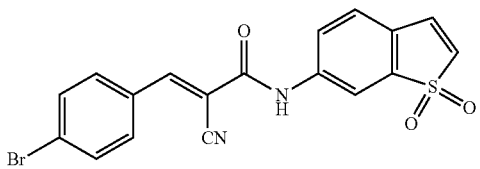 [SMILES: N#C/C(=C\c1ccc(Br)cc1)C(=O)Nc1ccc2c(c1)S(=O)(=O)C=C2]

The title compound was obtained as a yellow solid (mp 289-290° C.) in 90% yield. $^1$H NMR (600 MHz, DMSO-d6) δ 10.86 (s, 1H), 8.32 (s, 1H), 8.13 (s, 1H), 7.90-7.94 (m, 3H), 7.85 (d, 2H, J=8.4 Hz), 7.61-7.63 (m, 2H), 7.33 (d, 1H, J=6.6 Hz). $^{13}$C NMR (150 MHz, DMSO-d6) δ 160.9, 150.4, 140.7, 137.1, 132.8, 132.5, 131.9, 130.9, 130.5, 126.5, 126.5, 126.5, 126.4, 124.7, 115.7, 112.7, 107.5. HRMS (ESI) calcd for $C_{18}H_{12}BrN_2O_3S$ 414.9747 (M+H)⁺, found 414.9746.

2-Cyano-N-(1,1-dioxo-1H-1λ⁶-benzo[b]thiophen-6-yl)-3-(2-hydroxyphenyl)acrylamide (RMF-1-9)

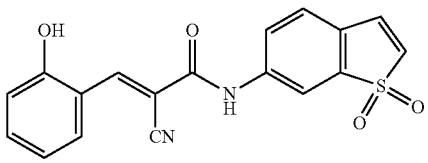 [SMILES: N#C/C(=C\c1ccccc1O)C(=O)Nc1ccc2c(c1)S(=O)(=O)C=C2]

The title compound was obtained as a yellow solid (mp 284-285° C.) in 96% yield. HPLC purity 99.2% ($t_R$=20.92 min). $^1$H NMR (600 MHz, DMSO-d6) δ 13.29 (s, 1H), 9.33 (s, 1H), 8.60 (s, 1H), 8.37 (s, 1H), 7.85 (d, 1H, J=7.8 Hz), 7.69-7.71 (m, 1H), 7.59-7.62 (m, 3H), 7.27-7.33 (m, 3H). $^{13}$C NMR (150 MHz, DMSO-d6) δ 160.5, 155.6, 153.5, 142.1, 140.5, 137.4, 133.5, 132.6, 130.3, 126.7, 126.2, 124.3, 124.0, 119.7, 118.4, 115.0, 111.8. HRMS (ESI) calcd for $C_{18}H_{13}N_2O_4S$ 353.0591 (M+H)⁺, found 353.0590.

2-Cyano-N-(1,1-dioxo-1H-1λ⁶-benzo[b]thiophen-6-yl)-3-(3-hydroxyphenyl)acrylamide (RMF-1-10)

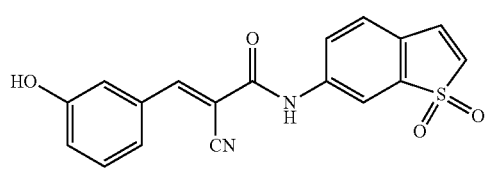 [SMILES: N#C/C(=C\c1cccc(O)c1)C(=O)Nc1ccc2c(c1)S(=O)(=O)C=C2]

The title compound was obtained as a white solid (mp 262-263° C.) in 96% yield. HPLC purity 98.1% ($t_R$=17.84 min). $^1$H NMR (600 MHz, DMSO-d6) δ 10.81 (s, 1H), 9.99 (s, 1H), 8.23 (s, 1H), 8.13 (s, 1H), 7.90-7.92 (m, 1H), 7.60-7.63 (m, 2H), 7.44 (s, 1H), 7.40-7.41 (m, 2H), 7.33 (d, 1H, J=7.2 Hz), 7.02-7.04 (m, 1H). $^{13}$C NMR (150 MHz, DMSO-d6) δ 161.2, 157.8, 151.7, 140.8, 137.1, 132.9, 132.8, 130.5, 130.4, 126.5, 126.4, 124.7, 121.6, 120.1, 116.0, 115.9, 112.7, 106.4. HRMS (ESI) calcd for $C_{18}H_{13}N_2O_4S$ 353.0591 (M+H)⁺, found 353.0595.

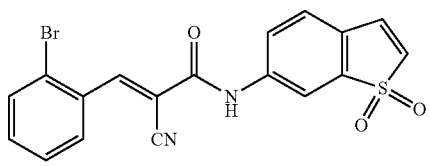

2-Cyano-N-(1,1-dioxo-1H-1λ⁶-benzo[b]thiophen-6-yl)-3-(4-hydroxyphenyl)acrylamide (RMF-1-11)

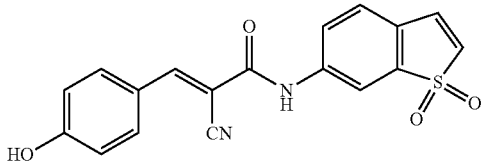 [SMILES: N#C/C(=C\c1ccc(O)cc1)C(=O)Nc1ccc2c(c1)S(=O)(=O)C=C2]

The title compound was obtained as a yellow solid (mp 306-307° C.) in 99% yield. ¹H NMR (600 MHz, DMSO-d6) δ 10.66 (s, 2H), 8.20 (s, 1H), 8.13 (t, 1H, J=0.6 Hz), 7.95 (d, 2H, J=8.4 Hz), 7.90-7.91 (m, 1H), 7.58-7.62 (m, 2H), 7.32 (d, 1H, J=6.6 Hz), 6.97-6.99 (m, 2H). ¹³C NMR (150 MHz, DMSO-d6) δ 162.3, 161.7, 151.5, 141.0, 137.0, 133.3, 132.8, 130.4, 126.5, 126.2, 124.6, 122.7, 116.8, 116.4, 112.7, 101.5. HRMS (ESI) calcd for $C_{18}H_{13}N_2O_4S$ 353.0591 (M+H)⁺, found 353.0595.

2-Cyano-N-(1,1-dioxo-1H-1λ⁶-benzo[b]thiophen-6-yl)-3-(2-methoxyphenyl)acrylamide (RMF-1-12)

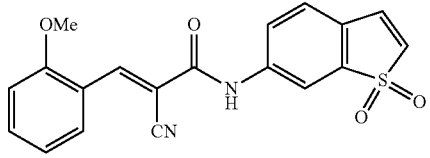 [SMILES: COc1ccccc1/C=C(\C#N)C(=O)Nc1ccc2c(c1)S(=O)(=O)C=C2]

The title compound was obtained as a yellow solid (mp 223-224° C.) in 96% yield. HPLC purity 96.0% ($t_R$=19.66 min). ¹H NMR (600 MHz, DMSO-d6) δ 10.80 (s, 2H), 8.52 (s, 1H), 8.15 (d, 1H, J=0.6 Hz), 8.07 (d, 1H, J=7.8 Hz), 7.91-7.92 (m, 1H), 7.59-7.64 (m, 3H), 7.33 (d, 1H, J=7.2 Hz), 7.23 (d, 1H, J=8.4 Hz), 7.16 (t, 1H, J=7.8 Hz), 3.92 (s, 3H). ¹³C NMR (150 MHz, DMSO-d6) δ 161.0, 158.5, 146.6, 140.7, 137.0, 134.8, 132.8, 130.5, 128.6, 126.5, 125.0, 120.8, 120.3, 116.0, 113.0, 112.1, 106.9. HRMS (ESI) calcd for $C_{19}H_{15}N_2O_4S$ 367.0747 (M+H)⁺, found 367.0750.

2-Cyano-N-(1,1-dioxo-1H-1λ⁶-benzo[b]thiophen-6-yl)-3-(4-methoxyphenyl)acrylamide (RMF-1-13)

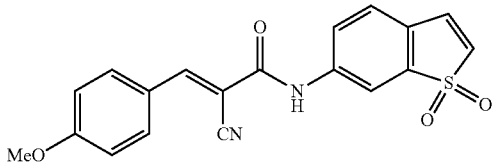 [SMILES: COc1ccc(/C=C(\C#N)C(=O)Nc2ccc3c(c2)S(=O)(=O)C=C3)cc1]

The title compound was obtained as a yellow solid (mp 275-276° C.) in 93% yield. HPLC purity 97.0% ($t_R$=19.57 min). ¹H NMR (600 MHz, DMSO-d6) δ 10.71 (s, 1H), 8.27 (s, 1H), 8.13 (d, 1H, J=1.2 Hz), 8.03-8.05 (m, 2H), 7.90-7.92 (m, 1H), 7.59-7.63 (m, 2H), 7.32 (d, 1H, J=7.2 Hz), 7.18-7.19 (m, 2H), 3.88 (s, 3H). ¹³C NMR (150 MHz, DMSO-d6) δ 163.0, 161.5, 151.2, 140.9, 137.0, 132.8, 130.4, 126.5, 126.3, 124.6, 124.2, 116.6, 115.0, 112.7, 103.0, 55.7. HRMS (ESI) calcd for $C_{19}H_{15}N_2O_4S$ 367.0747 (M+H)⁺, found 367.0740.

2-Cyano-N-(1,1-dioxo-1H-1λ⁶-benzo[b]thiophen-6-yl)-3-(2,4,6-trimethylphenyl)acrylamide (RMF-1-14)

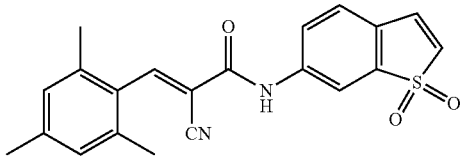 [SMILES: Cc1cc(C)c(/C=C(\C#N)C(=O)Nc2ccc3c(c2)S(=O)(=O)C=C3)c(C)c1]

The title compound was obtained as a white solid (mp 255-256° C.) in 80% yield. HPLC purity 97.4% ($t_R$=20.69 min). ¹H NMR (600 MHz, DMSO-d6) δ 10.79 (s, 1H), 8.49 (s, 1H), 8.15 (d, 1H, J=0.6 Hz), 7.93-7.95 (m, 1H), 7.61-7.64 (m, 2H), 7.34 (d, 1H, J=7.2 Hz), 7.00 (s, 2H), 2.28 (s, 3H), 2.27 (s, 6H). ¹³C NMR (150 MHz, DMSO-d6) δ 160.0, 154.0, 140.6, 139.0, 137.0, 135.6, 132.8, 130.5, 129.3, 128.6, 126.5, 124.9, 114.9, 114.5, 113.0. HRMS (ESI) calcd for $C_{21}H_{19}N_2O_3S$ 379.1111 (M+H)⁺, found 379.1106.

2-Cyano-N-(1,1-dioxo-1H-1λ⁶-benzo[b]thiophen-6-yl)-3-(3-nitrophenyl)acrylamide (RMF-1-15)

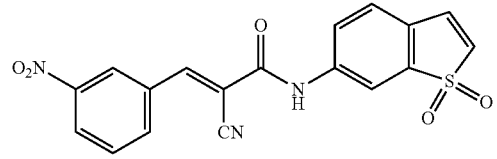 [SMILES: N#C/C(=C\c1cccc([N+](=O)[O-])c1)C(=O)Nc1ccc2c(c1)S(=O)(=O)C=C2]

The title compound was obtained as a yellow solid (mp 269-270° C.) in 87% yield. HPLC purity 99.2% ($t_R$=19.35 min). ¹H NMR (600 MHz, DMSO-d6) δ 10.94 (s, 1H), 8.83 (s, 1H), 8.51 (s, 1H), 8.44-8.46 (m, 1H), 8.39 (d, 1H, J=7.8 Hz), 8.14 (s, 1H), 7.91-7.93 (m, 2H), 7.62-7.64 (m, 2H), 7.35 (d, 1H, J=7.2 Hz). ¹³C NMR (150 MHz, DMSO-d6) δ 160.5, 149.4, 148.1, 140.5, 137.1, 135.9, 133.2, 132.7, 131.0, 130.6, 126.6, 124.8, 124.4, 115.3, 112.7, 109.5. HRMS (ESI) calcd for $C_{18}H_{12}N_3O_5S$ 382.0492 (M+H)⁺, found 382.0496.

2-Cyano-3-(4-dimethylaminophenyl)-N-(1,1-dioxo-1H-1λ⁶-benzo[b]thiophen-6-yl)acrylamide (RMF-1-16)

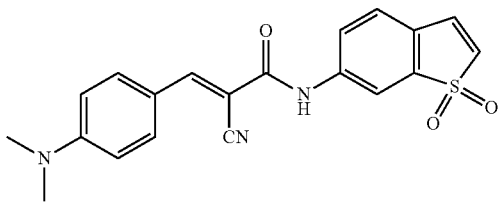 [SMILES: CN(C)c1ccc(/C=C(\C#N)C(=O)Nc2ccc3c(c2)S(=O)(=O)C=C3)cc1]

The title compound was obtained as a yellow solid (mp 279-280° C.) in 95% yield. $^1$H NMR (600 MHz, DMSO-d6) δ 10.47 (s, 1H), 8.13 (t, 2H, J=0.6 Hz), 7.94 (d, 2H, J=9.0 Hz), 7.90-7.91 (m, 1H), 7.56-7.61 (m, 2H), 7.30 (d, 1H, J=6.6 Hz), 6.86 (d, 2H, J=9.0 Hz), 3.09 (s, 6H). $^{13}$C NMR (150 MHz, DMSO-d6) δ 162.3, 153.3, 151.4, 141.3, 137.0, 133.2, 132.8, 130.2, 126.4, 125.9, 124.5, 118.5, 117.8, 112.6, 111.8, 96.8. HRMS (ESI) calcd for $C_{20}H_{18}N_3O_3S$ 380.1063 (M+H)$^+$, found 380.1061.

2-Cyano-N-(1,1-dioxo-1H-1λ$^6$-benzo[b]thiophen-6-yl)-3-(1H-pyrrolo[2,3-b]pyridin-3-yl)acrylamide (RMF-1-17)

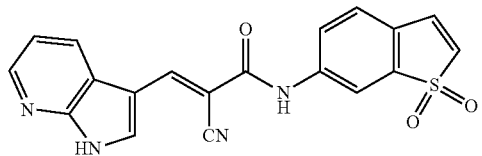 [SMILES: N#C/C(=C\c1c[nH]c2ncccc12)C(=O)Nc1ccc2c(c1)S(=O)(=O)C=C2]

The title compound was obtained as a yellow solid (mp 300-301° C.) in 87% yield. HPLC purity 99.2% ($t_R$=17.66 min). $^1$H NMR (600 MHz, DMSO-d6) δ 13.02 (s, 1H), 10.62 (s, 1H), 8.61 (d, 2H, J=16.2 Hz), 8.46-8.48 (m, 1H), 8.41-8.42 (m, 1H), 8.16 (m, 1H), 7.93-7.95 (m, 1H), 7.59-7.63 (m, 2H), 7.34-7.36 (m, 1H), 7.32 (d, 1H, J=6.6 Hz). $^{13}$C NMR (150 MHz, DMSO-d6) δ 161.8, 148.7, 145.0, 143.7, 141.1, 137.0, 132.8, 131.7, 130.3, 127.9, 126.4, 126.0, 124.5, 119.2, 118.0, 117.9, 112.7, 108.4, 98.8. HRMS (ESI) calcd for $C_{19}H_{13}N_4O_3S$ 377.0703 (M+H)$^+$, found 377.0701.

2-Cyano-3-(5-cyano-1H-indol-3-yl)-N-(1,1-dioxo-1H-1λ$^6$-benzo[b]thiophen-6-yl)acrylamide (RMF-1-19)

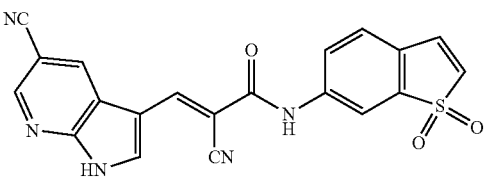 [SMILES: N#C/C(=C\c1c[nH]c2ncc(C#N)cc12)C(=O)Nc1ccc2c(c1)S(=O)(=O)C=C2]

The title compound was obtained as a yellow solid (mp 288-289° C.) in 80% yield. HPLC purity 97.7% ($t_R$=18.84 min). $^1$H NMR (600 MHz, DMSO-d6) δ 12.81 (s, 1H), 10.61 (s, 1H), 8.69 (d, 2H, J=5.4 Hz), 8.60 (s, 1H), 8.16 (s, 1H), 7.94-7.96 (m, 1H), 7.76 (d, 1H, J=8.4 Hz), 7.66-7.67 (m, 1H), 7.62 (t, 2H, J=7.2 Hz), 7.32 (d, 1H, J=6.6 Hz). $^{13}$C NMR (150 MHz, DMSO-d6) δ 161.7, 142.7, 141.1, 137.9, 137.1, 132.8, 130.3, 127.1, 126.5, 126.1, 124.6, 124.5, 120.0, 117.8, 114.3, 112.7, 110.0, 103.8, 99.9.

2-Cyano-3-cyclohexyl-N-(1,1-dioxo-1H-1λ$^6$-benzo[b]thiophen-6-yl)acrylamide (RMF-1-20)

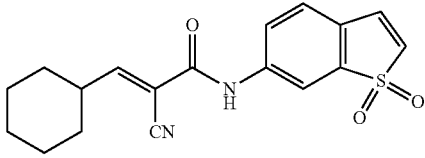 [SMILES: N#C/C(=C\C1CCCCC1)C(=O)Nc1ccc2c(c1)S(=O)(=O)C=C2]

The title compound was obtained as a white solid (mp 180-181° C.) in 59% yield. HPLC purity 98.6% ($t_R$=20.32 min). $^1$H NMR (600 MHz, DMSO-d6) δ 10.60 (s, 1H), 8.08 (d, 1H, J=0.6 Hz), 7.85-7.87 (m, 1H), 7.61 (d, 1H, J=6.6 Hz), 7.58 (d, 1H, J=7.8 Hz), 7.52 (d, 1H, J=10.2 Hz), 7.32 (d, 1H, J=6.6 Hz), 2.57-2.61 (m, 1H), 1.73-1.77 (m, 4H), 1.65-1.67 (m, 1H), 1.30-1.37 (m, 4H), 1.22-1.25 (m, 1H). $^{13}$C NMR (150 MHz, DMSO-d6) δ 163.1, 160.2, 140.6, 137.0, 132.7, 130.5, 126.5, 126.4, 124.7, 114.3, 112.8, 110.7. HRMS (ESI) calcd for $C_{18}H_{19}N_2O_3S$ 343.1111 (M+H)$^+$, found 343.1108.

2-Cyano-N-(1,1-dioxo-1H-1λ$^6$-benzo[b]thiophen-6-yl)-3-pyridin-3-yl-acrylamide (RMF-1-22)

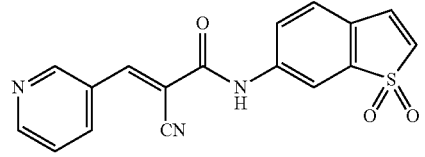 [SMILES: N#C/C(=C\c1cccnc1)C(=O)Nc1ccc2c(c1)S(=O)(=O)C=C2]

The title compound was obtained as a yellow solid (mp 255-256° C.) in 88% yield. HPLC purity 99.4% ($t_R$=17.09 min). $^1$H NMR (600 MHz, DMSO-d6) δ 10.91 (s, 1H), 9.04 (d, 1H, J=1.8 Hz), 8.77-8.78 (m, 1H), 8.44-8.46 (m, 1H), 8.41 (s, 1H), 8.14 (t, 1H, J=0.6 Hz), 7.91-7.93 (m, 1H), 7.65-7.68 (m, 1H), 7.62-7.64 (m, 2H), 7.34 (d, 1H, J=6.6 Hz). $^{13}$C NMR (150 MHz, DMSO-d6) δ 160.5, 152.7, 151.3, 148.8, 140.6, 137.1, 136.1, 132.8, 130.6, 128.0, 126.6, 124.8, 124.3, 115.6, 112.8, 109.0. HRMS (ESI) calcd for $C_{17}H_{12}N_3O_3S$ 338.0594 (M+H)$^+$, found 338.0598.

2-Cyano-N-(1,1-dioxo-1H-1λ$^6$-benzo[b]thiophen-6-yl)-3-pyridin-4-yl-acrylamide (RMF-1-23)

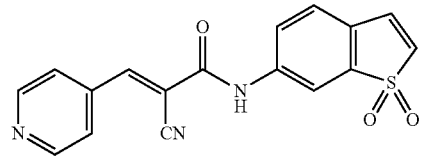 [SMILES: N#C/C(=C\c1ccncc1)C(=O)Nc1ccc2c(c1)S(=O)(=O)C=C2]

The title compound was obtained as a yellow solid (mp 288-289° C.) in 70% yield. HPLC purity 98.8% ($t_R$=17.15 min). $^1$H NMR (600 MHz, DMSO-d6) δ 10.97 (s, 1H), 8.83-8.85 (m, 2H), 8.35 (s, 1H), 8.13 (s, 1H), 7.90-7.92 (m, 1H), 7.83-7.84 (m, 2H), 7.62-7.64 (m, 2H), 7.34 (d, 1H, J=7.2 Hz). $^{13}$C NMR (150 MHz, DMSO-d6) δ 160.2, 150.9, 149.2, 140.5, 138.8, 137.1, 132.7, 130.6, 126.7, 126.6, 124.8, 122.9, 115.0, 112.8, 111.6. HRMS (ESI) calcd for $C_{17}H_{12}N_3O_3S$ 338.0594, found 338.0594.

2-Cyano-N-(1,1-dioxo-1H-1λ⁶-benzo[b]thiophen-6-yl)-3-(2-fluoro-pyridin-3-yl)acrylamide (RMF-1-24)

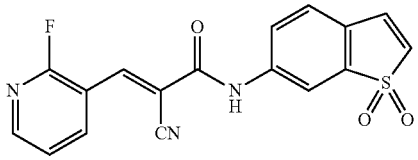 [SMILES: N#C/C(=C\c1cccnc1F)C(=O)Nc1ccc2c(c1)S(=O)(=O)C=C2]

The title compound was obtained as a yellow solid (mp 262-263° C.) in 95% yield. HPLC purity 97.2% ($t_R$=17.94 min). ¹H NMR (600 MHz, DMSO-d6) δ 10.96 (s, 1H), 8.62-8.65 (m, 1H), 8.47-8.48 (m, 1H), 8.35 (s, 1H), 8.14 (m, 1H), 7.91-7.92 (m, 1H), 7.61-7.65 (m, 3H), 7.34 (d, 1H, J=7.2 Hz). ¹³C NMR (150 MHz, DMSO-d6) δ 161.0, 159.9, 159.3, 151.2, 151.1, 142.5, 140.4, 140.4, 137.0, 132.7, 130.6, 126.7, 126.5, 125.0, 122.9, 115.1, 114.9, 113.0, 111.9. HRMS (ESI) calcd for $C_{17}H_{11}FN_3O_3S$ 356.0500 (M+H)⁺, found 356.0497.

3-(2-Chloro-pyridin-3-yl)-2-cyano-N-(1,1-dioxo-1H-1λ⁶-benzo[b]thiophen-6-yl)acrylamide (RMF-1-25)

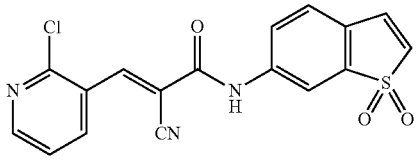 [SMILES: N#C/C(=C\c1cccnc1Cl)C(=O)Nc1ccc2c(c1)S(=O)(=O)C=C2]

The title compound was obtained as a yellow solid (mp 251-252° C.) in 92% yield. HPLC purity 98.5% ($t_R$=18.15 min). ¹H NMR (600 MHz, DMSO-d6) δ 10.95 (s, 1H), 8.61-8.62 (m, 1H), 8.45-8.47 (m, 1H), 8.44 (s, 1H), 8.15 (s, 1H), 7.92-7.94 (m, 1H), 7.69-7.71 (m, 1H), 7.62-7.64 (m, 2H), 7.35 (d, 1H, J=6.6 Hz). ¹³C NMR (150 MHz, DMSO-d6) δ 159.6, 152.3, 150.0, 146.6, 140.3, 139.0, 137.0, 132.7, 130.7, 127.4, 126.8, 126.5, 125.2, 123.7, 114.6, 113.2, 112.9. HRMS (ESI) calcd for $C_{17}H_{11}ClN_3O_3S$ 372.0204 (M+H)⁺, found 372.0201.

3-(2-Bromopyridin-3-yl)-2-cyano-N-(1,1-dioxo-1H-1λ⁶-benzo[b]thiophen-6-yl)acrylamide (RMF-1-26)

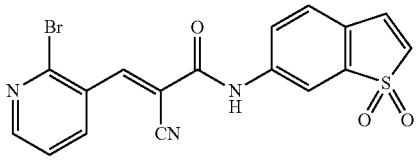 [SMILES: N#C/C(=C\c1cccnc1Br)C(=O)Nc1ccc2c(c1)S(=O)(=O)C=C2]

The title compound was obtained as a yellow solid (mp 242-243° C.) in 96% yield. HPLC purity 97.1% ($t_R$=18.32 min). ¹H NMR (600 MHz, DMSO-d6) δ 10.94 (s, 1H), 8.57-8.58 (m, 1H), 8.38 (d, 2H, J=10.2 Hz), 8.15 (s, 1H), 7.92-7.94 (m, 1H), 7.71-7.73 (m, 1H), 7.63 (t, 2H, J=6.0 Hz), 7.35 (d, 1H, J=6.6 Hz). ¹³C NMR (150 MHz, DMSO-d6) δ 159.6, 152.6, 148.6, 142.9, 140.3, 138.7, 137.0, 132.7, 130.7, 130.0, 126.8, 126.5, 125.2, 123.9, 114.6, 113.2, 112.8. HRMS (ESI) calcd for $C_{17}H_{11}BrN_3O_3S$ 415.9699 (M+H)⁺, found 415.9698.

2-Cyano-N-(1,1-dioxo-1H-1λ⁶-benzo[b]thiophen-6-yl)-3-(2-methoxy-pyridin-3-yl)acrylamide (RMF-1-27)

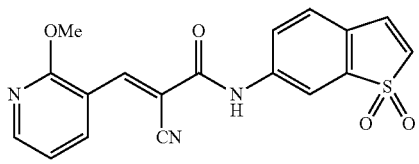 [SMILES: COc1ncccc1/C=C(\C#N)C(=O)Nc1ccc2c(c1)S(=O)(=O)C=C2]

The title compound was obtained as a yellow solid (mp 261-262° C.) in 99% yield. HPLC purity 98.3% ($t_R$=18.81 min). ¹H NMR (600 MHz, DMSO-d6) δ 10.86 (s, 1H), 8.41-8.44 (m, 3H), 8.14 (s, 1H), 7.91-7.92 (m, 1H), 7.60-7.63 (m, 2H), 7.33 (d, 1H, J=6.6 Hz), 7.24-7.26 (m, 1H), 4.00 (s, 3H). ¹³C NMR (150 MHz, DMSO-d6) δ 161.3, 160.5, 151.2, 145.4, 140.6, 138.0, 137.0, 132.7, 130.6, 126.6, 126.5, 125.0, 117.6, 115.5, 115.0, 113.1, 109.1, 54.0. HRMS (ESI) calcd for $C_{18}H_{14}N_3O_4S$ 368.0700 (M+H)⁺, found 368.0697.

2-Cyano-N-(1,1-dioxo-1H-1λ⁶-benzo[b]thiophen-6-yl)-3-(6-methoxy-pyridin-3-yl)acrylamide (RMF-1-28)

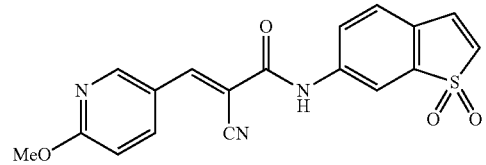 [SMILES: COc1ccc(/C=C(\C#N)C(=O)Nc2ccc3c(c2)S(=O)(=O)C=C3)cn1]

The title compound was obtained as a yellow solid (mp 255-256° C.) in 99% yield. HPLC purity 98.9% ($t_R$=18.84 min). ¹H NMR (600 MHz, DMSO-d6) δ 10.79 (s, 1H), 8.72 (d, 1H, J=2.4 Hz), 8.46-8.48 (m, 1H), 8.32 (s, 1H), 8.13 (d, 1H, J=0.6 Hz), 7.90-7.92 (m, 1H), 7.60-7.63 (m, 2H), 7.33 (d, 1H, J=6.6 Hz), 7.10 (d, 1H, J=9.0 Hz), 3.97 (s, 3H). ¹³C NMR (150 MHz, DMSO-d6) δ 165.8, 161.0, 152.0, 148.6, 140.7, 138.4, 137.1, 132.8, 130.5, 126.5, 126.4, 124.7, 121.8, 116.2, 112.8, 111.7, 105.0, 54.1. HRMS (ESI) calcd for $C_{18}H_{14}N_3O_4S$ 368.0700 (M+H)⁺, found 368.00696.

2-Cyano-N-(1,1-dioxo-1H-1λ⁶-benzo[b]thiophen-6-yl)-3-(4-fluorophenyl)acrylamide (RMF-1-29)

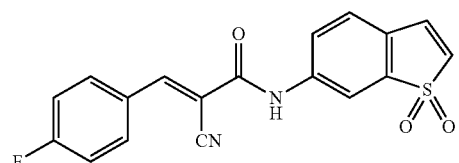

The title compound was obtained as a yellow solid (mp 271-272° C.) in 99% yield. HPLC purity 99.4% ($t_R$=19.53 min). $^1$H NMR (600 MHz, DMSO-d6) δ 10.83 (s, 1H), 8.34 (s, 1H), 8.13 (s, 1H), 8.08-8.11 (m, 2H), 7.90-7.92 (m, 1H), 7.62 (t, 2H, J=7.2 Hz), 7.49 (t, 2H, J=9.0 Hz), 7.33 (d, 1H, J=6.6 Hz). $^{13}$C NMR (150 MHz, DMSO-d6) δ 165.1, 163.4, 161.0, 150.4, 140.7, 137.1, 133.0, 132.8, 130.5, 128.4, 126.5, 126.5, 124.7, 116.7, 116.6, 115.9, 112.7, 106.4. HRMS (ESI) calcd for $C_{18}H_{12}FN_2O_3S$ 355.0547 (M+H)$^+$, found 355.0547.

2-Cyano-N-(1,1-dioxo-1H-1λ$^6$-benzo[b]thiophen-6-yl)-3-(2-fluorophenyl)acrylamide (RMF-1-30)

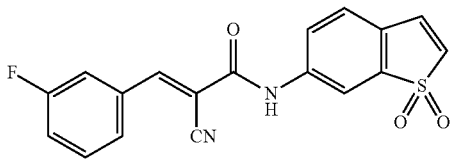 [SMILES: N#C/C(=C\c1cccc(F)c1)C(=O)Nc1ccc2c(c1)S(=O)(=O)C=C2]

The title compound was obtained as a light yellow solid (mp 253-254° C.) in 98% yield. HPLC purity 98.7% ($t_R$=19.41 min). $^1$H NMR (600 MHz, DMSO-d6) δ 10.91 (s, 1H), 8.41 (s, 1H), 8.16 (t, 2H, J=7.2 Hz), 7.91-7.92 (m, 1H), 7.68-7.72 (m, 1H), 7.62 (t, 2H, J=7.2 Hz), 7.45-7.48 (m, 2H), 7.34 (d, 1H, J=7.2 Hz). $^{13}$C NMR (150 MHz, DMSO-d6) δ 161.3, 160.4, 159.7, 143.4, 140.6, 137.0, 135.0, 134.9, 132.7, 130.6, 129.1, 126.6, 126.5, 125.3, 125.0, 119.9, 119.8, 116.5, 116.3, 115.4, 113.0, 109.9. HRMS (ESI) calcd for $C_{18}H_{12}FN_2O_3S$ 355.0547 (M+H)$^+$, found 355.0552.

2-Cyano-N-(1,1-dioxo-1H-1λ$^6$-benzo[b]thiophen-6-yl)-3-(3-fluorophenyl)acrylamide (RMF-1-31)

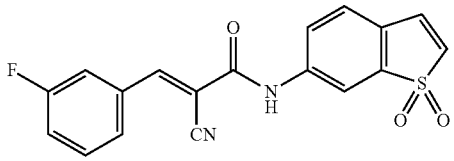 [SMILES: N#C/C(=C\c1cccc(F)c1)C(=O)Nc1ccc2c(c1)S(=O)(=O)C=C2]

The title compound was obtained as a white solid (mp 245-246° C.) in 94% yield. HPLC purity 98.0% ($t_R$=19.62 min). $^1$H NMR (600 MHz, DMSO-d6) δ 10.89 (s, 1H), 8.35 (s, 1H), 8.13 (s, 1H), 7.90-7.92 (m, 1H), 7.84 (d, 1H, J=7.2 Hz), 7.81 (d, 1H, J=9.6 Hz), 7.66-7.70 (m, 1H), 7.62 (t, 2H, J=6.6 Hz), 7.49-7.52 (m, 1H), 7.34 (d, 1H, J=7.2 Hz). $^{13}$C NMR (150 MHz, DMSO-d6) δ 162.8, 161.2, 160.7, 150.2, 140.6, 137.1, 134.0, 133.9, 132.7, 131.5, 130.5, 126.6, 126.4, 124.8, 119.9, 119.4, 116.3, 116.2, 115.6, 112.8, 108.3. HRMS (ESI) calcd for $C_{18}H_{12}FN_2O_3S$ 355.0547 (M+H)$^+$, found 355.0551.

3-(3-Bromophenyl)-2-cyano-N-(1,1-dioxo-1H-1λ$^6$-benzo[b]thiophen-6-yl)acrylamide (RMF-1-32)

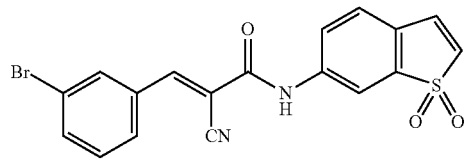 [SMILES: N#C/C(=C\c1cccc(Br)c1)C(=O)Nc1ccc2c(c1)S(=O)(=O)C=C2]

The title compound was obtained as a yellow solid (mp 250-251° C.) in 98% yield. HPLC purity 99.0% ($t_R$=20.51 min). $^1$H NMR (600 MHz, DMSO-d6) δ 10.87 (s, 1H), 8.33 (s, 1H), 8.17 (d, 1H, J=1.8 Hz), 8.13 (s, 1H), 7.99 (t, 1H, J=7.8 Hz), 7.90-7.92 (m, 1H), 7.83-7.84 (m, 1H), 7.61-7.63 (m, 2H), 7.59 (t, 1H, J=7.8 Hz), 7.34 (d, 1H, J=7.2 Hz). $^{13}$C NMR (150 MHz, DMSO-d6) δ 160.7, 150.0, 140.6, 137.1, 135.1, 134.0, 132.8, 132.4, 131.5, 130.5, 128.8, 126.6, 124.8, 122.3, 115.5, 112.7, 108.4. HRMS (ESI) calcd for $C_{18}H_{12}BrN_2O_3S$ 414.9747 (M+H)$^+$, found 414.9753.

3-(2-Chlorophenyl)-2-cyano-N-(1,1-dioxo-1H-1λ$^6$-benzo[b]thiophen-6-yl)acrylamide (RMF-1-33)

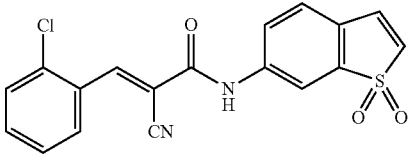 [SMILES: N#C/C(=C\c1ccccc1Cl)C(=O)Nc1ccc2c(c1)S(=O)(=O)C=C2]

The title compound was obtained as a white solid (mp 242-243° C.) in 91% yield. HPLC purity 98.3% ($t_R$=19.99 min). $^1$H NMR (600 MHz, DMSO-d6) δ 10.91 (s, 1H), 8.50 (s, 1H), 8.15 (s, 1H), 8.08 (d, 1H, J=7.8 Hz), 7.92 (d, 1H, J=8.4 Hz), 7.71 (d, 1H, J=7.8 Hz), 7.58-7.65 (m, 4H) 7.34 (d, 1H, J=6.6 Hz). $^{13}$C NMR (150 MHz, DMSO-d6) δ 160.1, 147.9, 140.5, 137.0, 134.2, 133.7, 132.7, 130.6, 130.3, 129.9, 127.9, 126.7, 126.5, 125.1, 115.1, 113.1, 111.1. HRMS (ESI) calcd for $C_{18}H_{12}ClN_2O_3S$ 371.0252 (M+H)$^+$, found 371.0254.

2-Cyano-N-(1,1-dioxo-1H-1λ$^6$-benzo[b]thiophen-6-yl)-3-(3-methoxyphenyl)acrylamide (RMF-1-35)

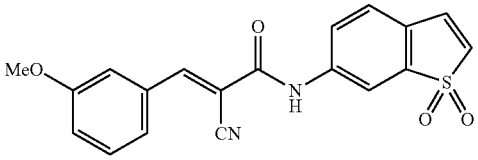 [SMILES: COc1cccc(/C=C(\C#N)C(=O)Nc2ccc3c(c2)S(=O)(=O)C=C3)c1]

The title compound was obtained as a white solid (mp 245-246° C.) in 92% yield. HPLC purity 99.4% ($t_R$=19.64 min). $^1$H NMR (600 MHz, DMSO-d6) δ 10.84 (s, 1H), 8.31 (s, 1H), 8.13 (s, 1H), 7.91-7.92 (m, 1H), 7.62 (t, 2H, J=7.2 Hz), 7.59 (t, 2H, J=1.8 Hz), 7.54 (t, 1H, J=8.4 Hz), 7.33 (d, 1H, J=7.2 Hz), 7.21-7.23 (m, 1H), 3.83 (s, 3H). $^{13}$C NMR (150 MHz, DMSO-d6) δ 161.0, 159.5 151.5, 140.7, 137.1, 133.0, 132.8, 130.5, 126.5, 126.5, 124.7, 122.7, 118.6, 115.9, 115.0, 112.8, 107.0, 55.4. HRMS (ESI) calcd for C$_{19}$H$_{15}$N$_2$O$_4$S 367.0747 (M+H)$^+$, found 367.0749.

2-Cyano-N-(1,1-dioxo-1H-1λ$^6$-benzo[b]thiophen-6-yl)-3-(2-nitrophenyl)acrylamide (RMF-1-36)

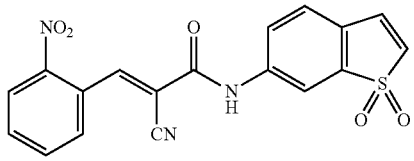 [SMILES: N#C/C(=C\c1ccccc1[N+](=O)[O-])C(=O)Nc1ccc2c(c1)S(=O)(=O)C=C2]

The title compound was obtained as a white solid (mp 254-255° C.) in 99% yield. HPLC purity 97.8% (t$_R$=18.73 min). $^1$H NMR (600 MHz, DMSO-d6) δ 10.87 (s, 1H), 8.76 (s, 1H), 8.33 (d, 1H, J=8.4 Hz), 8.16 (s, 1H), 8.00 (t, 1H, J=7.8 Hz), 7.92-7.95 (m, 2H), 7.85-7.87 (m, 1H), 7.62-7.64 (m, 2H), 7.35 (d, 1H, J=6.6 Hz). $^{13}$C NMR (150 MHz, DMSO-d6) δ 159.7, 151.3, 147.1, 140.4, 137.1, 134.8, 132.7, 132.3, 130.7, 130.6, 128.4, 126.8, 126.5, 125.3, 125.1, 114.6, 113.1, 111.3. HRMS (ESI) calcd for C$_{18}$H$_{12}$N$_3$O$_5$S 382.0492 (M+H)$^+$, found 382.0493.

2-Cyano-N-(1,1-dioxo-1H-1λ$^6$-benzo[b]thiophen-6-yl)-3-(4-nitrophenyl)acrylamide (RMF-1-37)

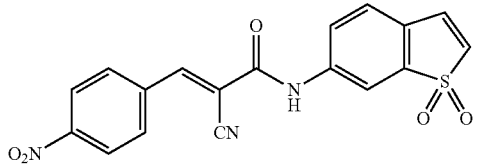 [SMILES: N#C/C(=C\c1ccc([N+](=O)[O-])cc1)C(=O)Nc1ccc2c(c1)S(=O)(=O)C=C2]

The title compound was obtained as a yellow solid (mp 272-273° C.) in 99% yield. HPLC purity 96.5% (t$_R$=19.38 min). $^1$H NMR (600 MHz, DMSO-d6) δ 10.97 (s, 1H), 8.47 (s, 1H), 8.44 (d, 2H, J=9.0 Hz), 8.19 (d, 2H, J=8.4 Hz), 8.13 (s, 1H), 7.91-7.92 (m, 1H), 7.62-7.64 (m, 2H), 7.34 (d, 1H, J=6.6 Hz). $^{13}$C NMR (150 MHz, DMSO-d6) δ 160.4, 149.2, 149.0, 140.5, 137.8, 137.1, 132.8, 131.1, 130.6, 126.7, 126.6, 124.8, 124.3, 115.2, 112.8, 110.6.

2-Cyano-N-(1,1-dioxo-1H-1λ$^6$-benzo[b]thiophen-6-yl)-3-(3,4,5-trimethoxyphenyl)acrylamide (RMF-1-38)

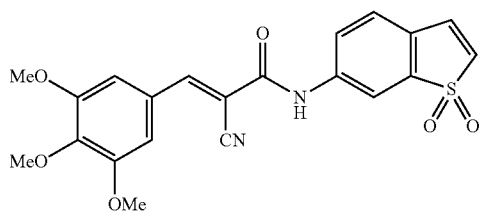 [SMILES: COc1cc(/C=C(\C#N)C(=O)Nc2ccc3c(c2)S(=O)(=O)C=C3)cc(OC)c1OC]

The title compound was obtained as a light yellow solid (mp 224-225° C.) in 99% yield. HPLC purity 97.3% (t$_R$=19.36 min). $^1$H NMR (600 MHz, DMSO-d6) δ 10.79 (s, 1H), 8.27 (s, 1H), 8.13 (s, 1H), 7.91-7.92 (m, 1H), 7.62 (t, 2H, J=7.8 Hz), 7.43 (s, 2H), 7.33 (d, 1H, J=6.6 Hz), 3.85 (s, 6H), 3.79 (s, 3H). $^{13}$C NMR (150 MHz, DMSO-d6) δ 161.2, 152.9, 151.7, 141.4, 140.8, 137.1, 132.8, 130.5, 126.9, 126.5, 126.4, 124.7, 116.4, 112.8, 108.1, 105.1, 60.4, 56.1. HRMS (ESI) calcd for C$_{21}$H$_{19}$N$_2$O$_6$S 427.0958 (M+H)$^+$, found 427.0957.

2-Cyano-N-(1,1-dioxo-1H-1λ$^6$-benzo[b]thiophen-6-yl)-3-(6-methyl-pyridin-2-yl)acrylamide (HJC-5-88)

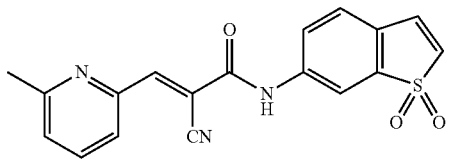 [SMILES: Cc1cccc(/C=C(\C#N)C(=O)Nc2ccc3c(c2)S(=O)(=O)C=C3)n1]

The title compound was obtained as a light white solid (mp 221-222° C.) in 97% yield. HPLC purity 97.3% (t$_R$=18.38 min). $^1$H NMR (600 MHz, DMSO-d6) δ 10.89 (s, 1H), 8.24 (s, 1H), 8.14 (d, 1H, J=0.6 Hz), 7.90-7.93 (m, 2H), 7.70 (d, 1H, J=7.8 Hz), 7.61-7.63 (m, 2H), 7.46 (d, 1H, J=7.2 Hz), 7.33 (d, 1H, J=6.6 Hz), 2.57 (s, 3H). $^{13}$C NMR (150 MHz, DMSO-d6) δ 161.2, 158.7, 149.3, 149.1, 140.7, 137.8, 137.1, 132.8, 130.5, 126.5, 126.5, 126.2, 124.7, 124.6, 115.2, 112.7, 109.4, 23.8. HRMS (ESI) calcd for C$_{18}$H$_{14}$N$_3$O$_3$S 352.0750 (M+H)$^+$, found 352.0750.

3-(3-Chlorophenyl)-2-cyano-N-(1,1-dioxo-1H-1λ$^6$-benzo[b]thiophen-6-yl)acrylamide (HJC-5-89)

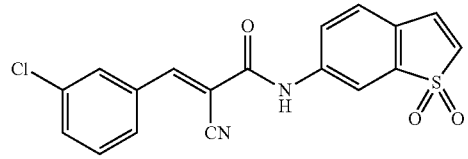 [SMILES: N#C/C(=C\c1cccc(Cl)c1)C(=O)Nc1ccc2c(c1)S(=O)(=O)C=C2]

The title compound was obtained as a light orange solid (mp 234-235° C.) in 97% yield. HPLC purity 96.5% (t$_R$=20.34 min). $^1$H NMR (600 MHz, DMSO-d6) δ 10.88 (s, 1H), 8.34 (s, 1H), 8.13 (d, 1H, J=0.6 Hz), 8.04 (s, 1H), 7.96 (d, 1H, J=7.8 Hz), 7.90-7.92 (m, 1H), 7.70-7.72 (m, 1H), 7.61-7.67 (m, 3H), 7.34 (d, 1H, J=6.6 Hz). $^{13}$C NMR (150 MHz, DMSO-d6) δ 160.7, 150.0, 140.6, 137.1, 133.9, 133.8, 132.8, 132.2, 131.3, 130.5, 129.5, 128.6, 126.6, 124.8, 115.6, 112.8, 108.4. HRMS (ESI) calcd for C$_{18}$H$_{12}$ClN$_2$O$_3$S 371.0252 (M+H)$^+$, found 371.0255.

2-Cyano-N-(1,1-dioxo-1H-1λ$^6$-benzo[b]thiophen-6-yl)-3-pyridin-2-yl-acrylamide (HJC-5-90)

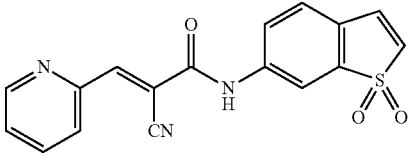 [SMILES: N#C/C(=C\c1ccccn1)C(=O)Nc1ccc2c(c1)S(=O)(=O)C=C2]

The title compound was obtained as a light yellow solid (mp 234-235° C.) in 98% yield. $^1$H NMR (600 MHz, DMSO-d6) δ 10.92 (s, 1H), 8.82 (d, 1H, J=3.6 Hz), 8.29 (s, 1H), 8.15 (s, 1H), 8.02-8.05 (m, 1H), 7.92-7.93 (m, 1H), 7.88 (d, 1H, J=7.8 Hz), 7.62 (t, 2H, J=6.6 Hz), 7.58-7.59 (m, 1H), 7.34 (d, 1H, J=7.2 Hz). $^{13}$C NMR (150 MHz, DMSO-d6) δ 161.1, 150.2, 149.8, 149.3, 140.7, 137.7, 137.1, 132.8, 130.5, 127.5, 126.5, 124.8, 115.2, 112.8, 109.6. HRMS (ESI) calcd for $C_{17}H_{12}N_3O_3S$ 338.0599 (M+H)$^+$, found 338.0599.

2-Cyano-3-(2,6-difluorophenyl)-N-(1,1-dioxo-1H-1λ$^6$-benzo[b]thiophen-6-yl)acrylamide (HJC-5-91)

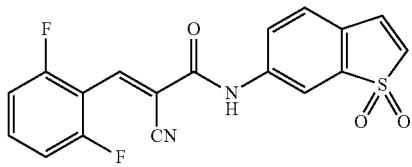 [SMILES: N#C/C(=C\c1c(F)cccc1F)C(=O)Nc1ccc2c(c1)S(=O)(=O)C=C2]

The title compound was obtained as a light orange solid (mp 253-254° C.) in 97% yield. HPLC purity 96.0% ($t_R$=19.26 min). $^1$H NMR (600 MHz, DMSO-d6) δ 10.97 (s, 1H), 8.27 (s, 1H), 8.14 (s, 1H), 7.91-7.93 (m, 1H), 7.70-7.73 (m, 1H), 7.61-7.64 (m, 2H), 7.34-7.38 (m, 3H). $^{13}$C NMR (150 MHz, DMSO-d6) δ 160.4, 159.5, 158.7, 140.4, 140.1, 137.0, 134.3, 132.7, 130.6, 126.7, 126.5, 125.1, 115.7, 114.3, 113.1, 112.6, 112.4, 110.4, 110.3, 110.2. HRMS (ESI) calcd for $C_{18}H_{11}F_2N_2O_3S$ 373.0453 (M+H)$^+$, found 373.0451.

Example 2

Anti-Cancer Properties of Compounds

In Vitro Determination of Effects of Synthesized Compounds on Cancer Cell Proliferation.

Cancer cells (breast cancer cell lines MCF-7, MDA-MB-361, SKBR3 and MDA-MB-231, pancreatic cancer cell lines AsPC-1. BxPC3 and Panc-1) were seeded in 96-well plates at a density of 1000-2000 cells/well and treated with DMSO, 0.01, 0.1, 1, 5, 10, and 100 mM of STAT3 individual inhibitors for 72 hrs. Proliferation was measured by treating cells with the 3-(4,5-dimethylthiazol-2-yl)-5-(3-carboxymethoxyphenyl)-2-(4-sulfophenyl)-2H-tetrazolium) (MTS) in a CellTiter 96t AQueous Non-Radioactive Cell Proliferation Assay kit from Promega, Madison, Wis., USA). Absorbance of all wells was determined by measuring OD at 550 nm after 1 hr incubation at 37° C. on a 96-well iMark™ Microplate Absorbance Reader (BioRad, Hercules, Calif.). Each individual compound was tested in quadruplicate wells for each concentration, and the results were reported as mean absorption±s.e.

Determination of Anti-Cancer Activity Using In Vivo Animal Models.

Female nude mice at 4 to 6 wk of age were obtained from MDACC ERO facility. The mice were maintained in a barrier unit with 12 hours light-dark switch room and all materials were autoclaved. Freshly harvested MDA-MB-231 cells (2.5×10$^6$ cells per mouse, resuspended in 100 μl PBS) were injected into the 3$^{rd}$ mammary fat pad of the mice, and then mice were randomly assigned into control and treatment groups (≥6 mice per group). Treatment started when the xenograft mammary tumors reaches a volume of 200 mm$^3$. Selected STAT3 inhibitors and positive control drugs were dissolved in DMSO, and the individual compounds was administered to nude mice bearing xenograft breast tumors via i.p. injection at dosing from 2.5-25 mg/kg or sterile DMSO daily, with a total injection volume of 100 ml. Control pups received an i.p. injection of 100 ml DMSO only. All experimental mice were treated with STAT3 compounds or vehicle for a consecutive 14 days. Mice were monitored daily for general health conditions (body weight, fur coat condition and posture) and toxicity (hair loss, skin rash, abdominal distension). Mice were sacrificed when the bearing xenograft tumors reach 1.5 cm diameter. Tumor volume was calculated as $V=W^2 \times L/2$, where L=longer diameter (mm) and W=width of short diameter (mm). All mice were sacrificed by $CO_2$ when tumor reached the maximum size allowed, in accordance with the institutional IACUC policies. Tumor volume changes were compared with DMSO and/or other positive control drugs. At the time of sacrifice, lung, intestine, stomach, heart, brain, kidney, mammary gland, and tumor tissues were collected and fixed in 4% formalin overnight, then paraffin embedded and sectioned for Hematoxylin-Eosin staining or immunohistochemistry staining. A portion of xenograft tumor was frozen for each tumor for further biomarker studies.

Figure 2:
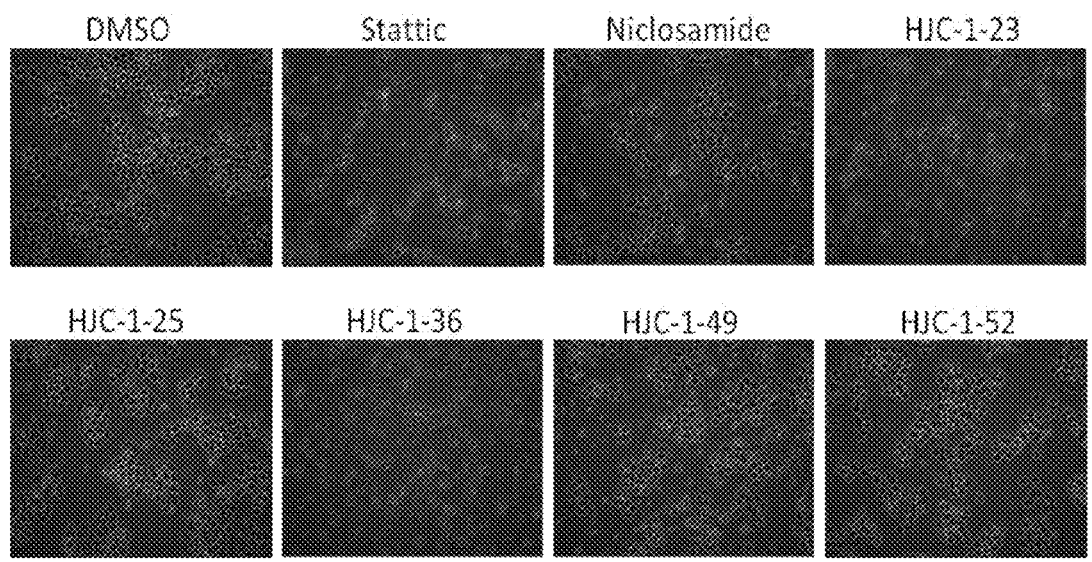
FIG. 2: Morphological changes in MCF-7 breast cancer cells after 30 hours of treatment with selected STAT3 inhibitors.

The inventors designed and chemically synthesized a class of new STAT3 inhibitors (Table 1; Detailed experimental procedures synthesizing these molecules are shown above in Example 1). Based on studies testing the effects of these compounds, a number of compounds such as HJC-1-23, HJC-1-25, HJC-1-30, HJC-1-36, HJC-1-49, HJC-1-52, HJC-3-8, HJC-3-9, HJC-3-69, HJC-3-71, HJC-3-81, HJC-3-89, HJC-3-91, HJC-4-16, HJC-4-28, HJC-4-30, and HJC-4-31 (Table 1) were identified that demonstrated significant inhibition on breast cancer cell proliferation (FIG. 1), accompanied with morphological changed in cellular appearance (FIG. 2). Also, these compounds demonstrated significant inhibition on pancreatic cancer cell proliferation (Table 1).

Figure 3:
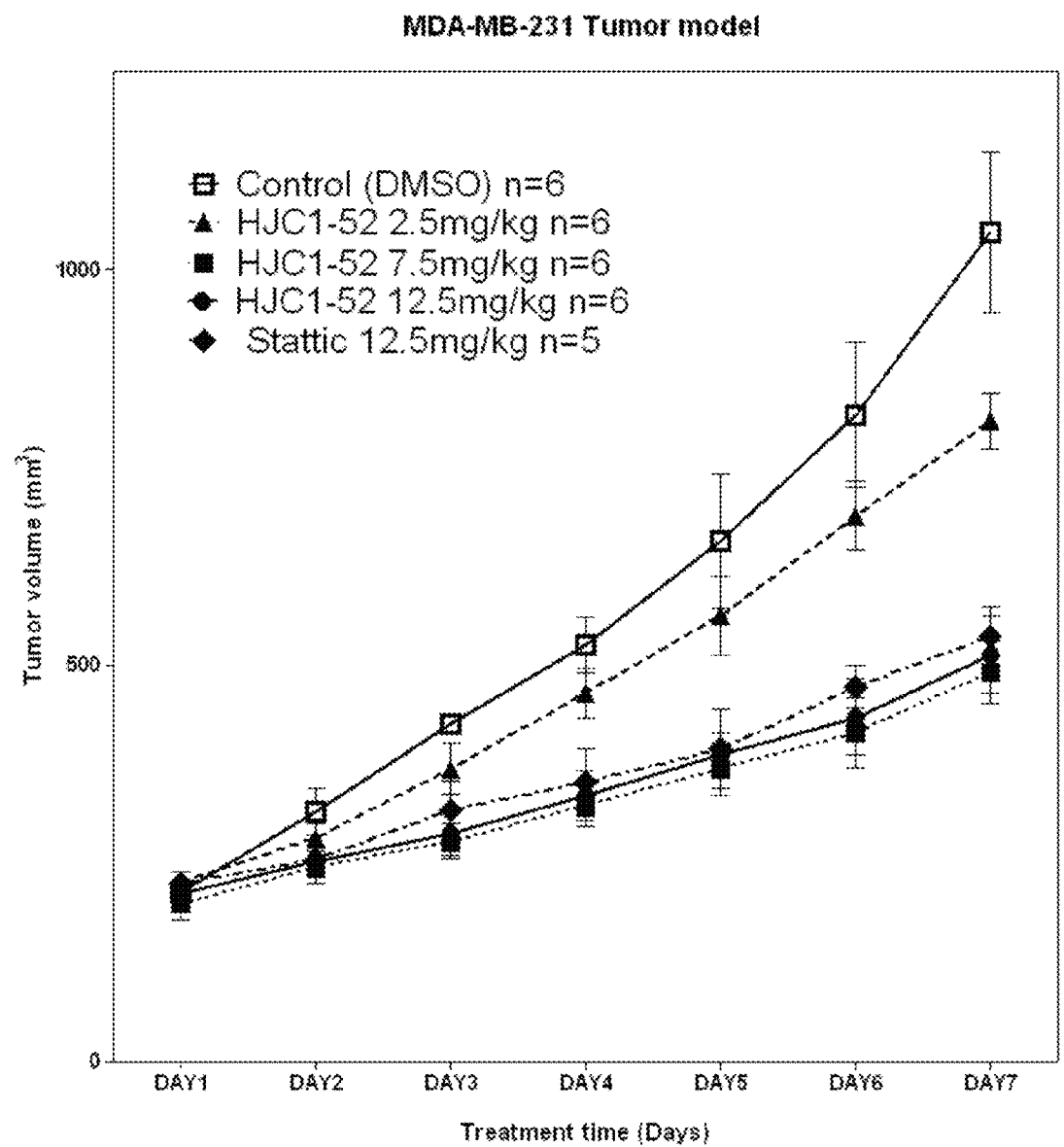
FIG. 3: In vivo efficacy of compound HJC-1-52 in inhibiting growth of xenograft tumors (Breast cancer MDA-MB-231) arose in mice.

The In vivo efficacy of compound HJC-1-52 in inhibiting growth of xenograft tumors (Breast cancer MDA-MB-231) arose in mice has been carried out (FIG. 3). HJC-1-52 significantly suppresses tumor growth and induces apoptosis in breast cancer xenografts at the dose of 2.5, 7.5 and 12.5 mg/kg, respectively. HJC-1-52 at 7.5 mg/kg showed a similar efficacy to that of Stattic or Niclosamide at 12.5 mg/kg (FIG. 3). The further in vivo evaluation of other selected drug candidates identified from the initial in vitro screening including oral administration is in progress: (1) To choose 3 drug candidates and determine their efficacy in inhibiting growth of xenograft tumors arose in mice. 2 ER-positive and 2 ER-negative breast cancer cell lines will be tested. The control and treated xenograft tumors will be compared for growth rate, tumor volume, and expression of STAT3-dependent down-stream genes and biomarkers. (2) To choose 1-2 effective STAT3 inhibitors from the xenograft studies to treat MMTV-ErbB2 transgenic mice that spontaneously develop oncogene-induced, ER-negative mammary tumors. The drug candidates' preventive and therapeutic efficacy will be determined by examining premalignant lesions, mammary tumor incidence after preventive use of the drug candidates and tumor growth when the drug candidate is given to mice with existing mammary tumors. Expression of STAT3-dependent down-stream genes and biomarkers will be compared.

Figure 4:
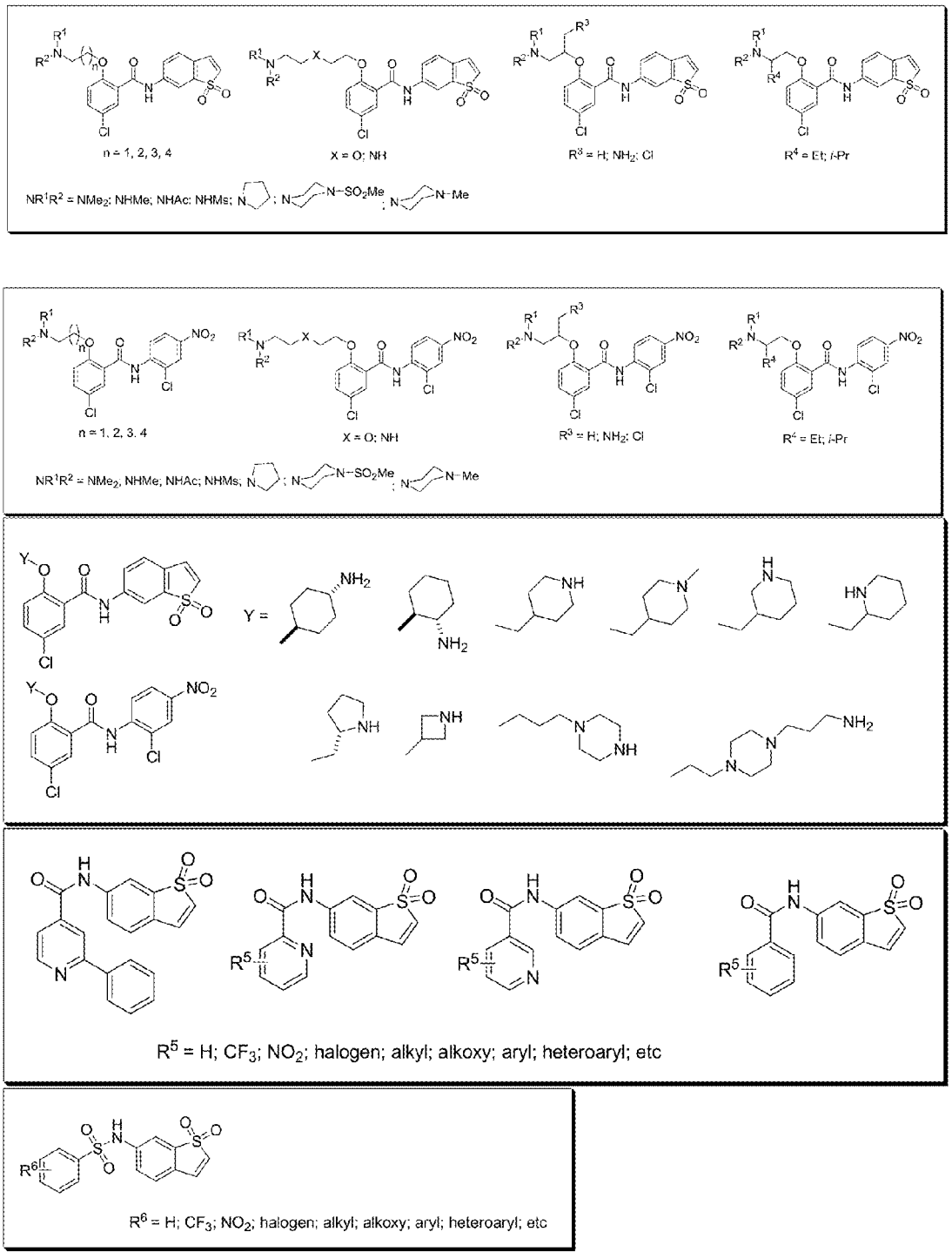
FIG. 4: Chemical structures of select compounds.
Figure 4:
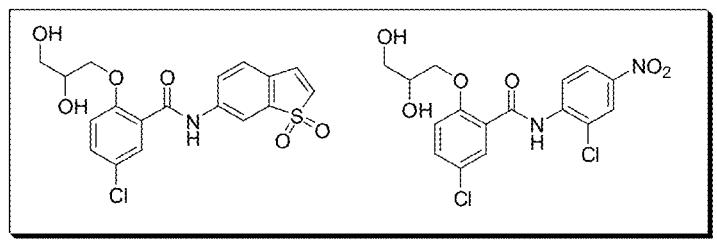

Additional small molecules are being synthesized and can be biologically investigated. Additional structures are shown in FIG. 4.

TABLE 1

List of representative compounds that have been synthesized and pharmacologically screened.
Inhibitory effects of STAT3 inhibitors on ER-positive, ER-negative breast cancer cells and pancreatic cancer cells. $IC_{50}$ values (μM) calculated from the proliferation data using MasterPlex ReaderFit 2010 software.

| Code | Structure | Breast cancer ER-Positive | | Breast cancer ER-Negative | | Pancreatic cancer | | |
|---|---|---|---|---|---|---|---|---|
| | | MCF-7 | MDA-MB-361 | MDA-MB-231 | SKBR3 | AsPC1 | BxPc-3H | Panc-1 |
| HJC-1-14 | | 9.87 | 12.55 | 17.95 | 5.1 | 73.23 | >10 | >10 |
| HJC-1-25 | | 0.25 | 0.18 | 0.29 | 0.28 | 2.76 | 0.27 | 0.54 |
| HJC-1-52 | | 0.91 | 2.37 | 1.64 | ND | 1.9 | 1.07 | 1.08 |
| HJC-2-52 | | 12.44 | | 8.66 | | | | |
| HJC-2-55 | | >10 | | >10 | | | | |

TABLE 1-continued

List of representative compounds that have been synthesized and pharmacologically screened. Inhibitory effects of STAT3 inhibitors on ER-positive, ER-negative breast cancer cells and pancreatic cancer cells. $IC_{50}$ values (μM) calculated from the proliferation data using MasterPlex ReaderFit 2010 software.

| Code | Structure | Breast cancer ER-Positive | | Breast cancer ER-Negative | | Pancreatic cancer | | |
|---|---|---|---|---|---|---|---|---|
| | | MCF-7 | MDA-MB-361 | MDA-MB-231 | SKBR3 | AsPC1 | BxPc-3H | Panc-1 |
| HJC-2-58 | | 9.37 | | 5.3 | | | | |
| HJC-3-8 | | 3.11 | | 2.61 | | 4.2 | | 3.11 |
| HJC-3-57 | | >10 | | >10 | | | | |
| HJC-3-60 | | >10 | | >10 | | | | |
| HJC-3-64 | | >10 | | >10 | | | | |
| HJC-3-65 | | >10 | | >10 | | | | |
| HJC-3-81 | | 4.11 | | 2.69 | | | | |

TABLE 1-continued

List of representative compounds that have been synthesized and pharmacologically screened.
Inhibitory effects of STAT3 inhibitors on ER-positive, ER-negative breast cancer cells and pancreatic cancer
cells. $IC_{50}$ values (μM) calculated from the proliferation data using MasterPlex ReaderFit 2010 software.

| Code | Structure | Breast cancer ER-Positive | | Breast cancer ER-Negative | | Pancreatic cancer | | |
|---|---|---|---|---|---|---|---|---|
| | | MCF-7 | MDA-MB-361 | MDA-MB-231 | SKBR3 | AsPC1 | BxPc-3H | Panc-1 |
| HJC-3-84 | | >10 | | >10 | | | | |
| HJC-3-89 | | 3.49 | | 3.1 | | 2.08 | | 4.67 |
| HJC-3-98 | | >10 | | >10 | | | | |
| HJC-4-22 | | >10 | | 5.87 | | | | |
| HJC-4-24 | | >10 | | >10 | | | | |
| HJC-4-25 | | >10 | | >10 | | | | |

TABLE 1-continued

List of representative compounds that have been synthesized and pharmacologically screened. Inhibitory effects of STAT3 inhibitors on ER-positive, ER-negative breast cancer cells and pancreatic cancer cells. $IC_{50}$ values (μM) calculated from the proliferation data using MasterPlex ReaderFit 2010 software.

| Code | Structure | Breast cancer ER-Positive | | Breast cancer ER-Negative | | Pancreatic cancer | | |
|---|---|---|---|---|---|---|---|---|
| | | MCF-7 | MDA-MB-361 | MDA-MB-231 | SKBR3 | AsPC1 | BxPc-3H | Panc-1 |
| HJC-4-26 | | >10 | | >10 | | | | |
| HJC-4-27 | | >10 | | >10 | | | | |
| HJC-4-31 | | 3.7 | | 2.37 | | | | |
| HJC-1-29 | | >10 | 14.86 | >10 | 16.12 | >10 | >10 | >10 |
| HJC-1-31 | | >10 | 42.97 | >10 | >10 | >10 | >10 | 0.84 |
| HJC-1-37 | | 11.69 | 9.23 | >10 | 9.14 | 11.59 | 13.15 | 27.88 |

TABLE 1-continued

List of representative compounds that have been synthesized and pharmacologically screened.
Inhibitory effects of STAT3 inhibitors on ER-positive, ER-negative breast cancer cells and pancreatic cancer
cells. $IC_{50}$ values (μM) calculated from the proliferation data using MasterPlex ReaderFit 2010 software.

| Code | Structure | Breast cancer ER-Positive | | Breast cancer ER-Negative | | Pancreatic cancer | | |
|---|---|---|---|---|---|---|---|---|
| | | MCF-7 | MDA-MB-361 | MDA-MB-231 | SKBR3 | AsPC1 | BxPc-3H | Panc-1 |
| HJC-1-40 | | >10 | 22.83 | 66.33 | 11.25 | 37.63 | >10 | >10 |
| HJC-4-23 | | >10 | | >10 | | | | |
| HJC-4-32 | | >10 | | >10 | | | | |
| HJC-4-35-1 | | >10 | | >10 | | | | |
| HJC-4-35-2 | | >10 | | >10 | | | | |
| HJC-1-23 | | 0.1 | 0.24 | 0.29 | 0.22 | 1.25 | 0.2 | 0.26 |

TABLE 1-continued

List of representative compounds that have been synthesized and pharmacologically screened.
Inhibitory effects of STAT3 inhibitors on ER-positive, ER-negative breast cancer cells and pancreatic cancer
cells. IC$_{50}$ values (μM) calculated from the proliferation data using MasterPlex ReaderFit 2010 software.

| Code | Structure | Breast cancer ER-Positive | | Breast cancer ER-Negative | | Pancreatic cancer | | |
|---|---|---|---|---|---|---|---|---|
| | | MCF-7 | MDA-MB-361 | MDA-MB-231 | SKBR3 | AsPC1 | BxPc-3H | Panc-1 |
| HJC-1-36 | | 0.65 | 0.23 | 0.45 | 0.2 | 0.12 | 0.27 | 0.31 |
| HJC-1-41 | | >10 | 170.23 | >10 | >10 | >10 | >10 | >10 |
| HJC-1-62 | | >10 | | >10 | | | | |
| HJC-2-15 | | 5.85 | | 4.97 | | | | |
| HJC-3-20 | | 6.7 | | >10 | | | | |
| HJC-3-76 | | 15.32 | | >10 | | | | |
| HJC-3-80 | | >10 | | >10 | | | | |

TABLE 1-continued

List of representative compounds that have been synthesized and pharmacologically screened.
Inhibitory effects of STAT3 inhibitors on ER-positive, ER-negative breast cancer cells and pancreatic cancer
cells. $IC_{50}$ values (μM) calculated from the proliferation data using MasterPlex ReaderFit 2010 software.

| Code | Structure | Breast cancer ER-Positive | | Breast cancer ER-Negative | | Pancreatic cancer | | |
|---|---|---|---|---|---|---|---|---|
| | | MCF-7 | MDA-MB-361 | MDA-MB-231 | SKBR3 | AsPC1 | BxPc-3H | Panc-1 |
| HJC-3-91 | | 2.97 | | 6.21 | | | | |
| HJC-3-95 | | 3.64 | | >10 | | | | |
| HJC-4-30 | | 3.78 | | 1.85 | | 1.3 | | 3.35 |
| HJC-1-49 | | 0.91 | 2.37 | 1.64 | 0.72 | 1.92 | 1.16 | 2.34 |
| HJC-3-9 | | 0.49 | | 5.43 | | | | |
| HJC-3-69 | | 3.5 | | 2.69 | | | | |
| HJC-3-77 | | >10 | | >10 | | | | |

TABLE 1-continued

List of representative compounds that have been synthesized and pharmacologically screened.
Inhibitory effects of STAT3 inhibitors on ER-positive, ER-negative breast cancer cells and pancreatic cancer
cells. IC$_{50}$ values (μM) calculated from the proliferation data using MasterPlex ReaderFit 2010 software.

| Code | Structure | Breast cancer ER-Positive | | Breast cancer ER-Negative | | Pancreatic cancer | | |
|---|---|---|---|---|---|---|---|---|
| | | MCF-7 | MDA-MB-361 | MDA-MB-231 | SKBR3 | AsPC1 | BxPc-3H | Panc-1 |
| HJC-3-78 | | 4.08 | | 2.86 | | | | |
| HJC-3-79 | | 3.74 | | 2.51 | | | | |
| HJC-3-82 | | 3.53 | | 2.68 | | | | |
| HJC-3-93 | | 3.47 | | 3.12 | | | | |
| HJC-3-99 | | 4 | | 4.42 | | | | |
| HJC-4-13 | | 2.56 | | 3.29 | | 1.87 | | 3.69 |
| HJC-4-15 | | 4.21 | | 2.85 | | | | |

TABLE 1-continued

List of representative compounds that have been synthesized and pharmacologically screened.
Inhibitory effects of STAT3 inhibitors on ER-positive, ER-negative breast cancer cells and pancreatic cancer
cells. IC$_{50}$ values (μM) calculated from the proliferation data using MasterPlex ReaderFit 2010 software.

| Code | Structure | Breast cancer ER-Positive | | Breast cancer ER-Negative | | Pancreatic cancer | | |
|---|---|---|---|---|---|---|---|---|
| | | MCF-7 | MDA-MB-361 | MDA-MB-231 | SKBR3 | AsPC1 | BxPc-3H | Panc-1 |
| HJC-4-16 | | 1.76 | | 1.97 | | 0.27 | | 1.88 |
| HJC-4-28 | | 3.15 | | 3.12 | | 2.05 | | 3.09 |
| HJC-3-61 | | >10 | | >10 | | | | |
| HJC-3-71 | | 3.31 | | 1.53 | | 1.54 | | 1.64 |
| HJC-4-11 | | 4.27 | | >10 | | | | |
| HJC-3-68 | | 3.45 | | 2.71 | | | | |
| HJC-3-70 | | 3.24 | | 2.66 | | 1.92 | | 2.89 |
| HJC-1-47 | | 6.07 | 9.07 | 7.05 | 4.03 | 8.46 | 6.66 | 8.39 |

TABLE 1-continued

List of representative compounds that have been synthesized and pharmacologically screened.
Inhibitory effects of STAT3 inhibitors on ER-positive, ER-negative breast cancer cells and pancreatic cancer
cells. $IC_{50}$ values (μM) calculated from the proliferation data using MasterPlex ReaderFit 2010 software.

| Code | Structure | Breast cancer ER-Positive | | Breast cancer ER-Negative | | Pancreatic cancer | | |
|---|---|---|---|---|---|---|---|---|
| | | MCF-7 | MDA-MB-361 | MDA-MB-231 | SKBR3 | AsPC1 | BxPc-3H | Panc-1 |
| HJC-1-57 | | >10 | | 13.76 | | | | |
| HJC-1-63 | | >10 | | >10 | | | | |
| HJC-2-20 | | >10 | | >10 | | | | |
| HJC-1-17 | | 15.89 | 17.44 | >10 | >10 | >10 | >10 | >10 |
| HJC-1-51 | | >10 | >10 | >10 | 42.42 | >10 | 199.83 | >10 |
| HJC-1-28 | | 2.24 | 132.32 | 85.95 | 45.93 | >10 | 16.4 | 15.38 |

TABLE 1-continued

List of representative compounds that have been synthesized and pharmacologically screened.
Inhibitory effects of STAT3 inhibitors on ER-positive, ER-negative breast cancer cells and pancreatic cancer
cells. $IC_{50}$ values (μM) calculated from the proliferation data using MasterPlex ReaderFit 2010 software.

| Code | Structure | Breast cancer ER-Positive | | Breast cancer ER-Negative | | Pancreatic cancer | | |
|---|---|---|---|---|---|---|---|---|
| | | MCF-7 | MDA-MB-361 | MDA-MB-231 | SKBR3 | AsPC1 | BxPc-3H | Panc-1 |
| HJC-1-30 | [structure] | 0.9 | 6.39 | 8.88 | 6.51 | 7.54 | 7.26 | 8.44 |

Note:
(1) Breast cancer cell lines: MCF-7, MDA-MB-361, MDA-MB-231, and SKBR3. Pancreatic cancer cell lines: ASPC1, BxPc-3H, and Panc-1.
(2) Software: MasterPlex ReaderFit 2010, MiraiBio, Inc.
(3) If a specific compound is given a value >10, indicates that a specific $IC_{50}$ cannot be calculated from the data points collected, meaning "no effect".

TABLE 2

Effects of STAT3 inhibitors (2-14) on proliferation of human breast and pancreatic cancer cell lines.

2-13

[structure]

14

[structure]

| Compound | $R^3$ | IC50 (μM)[a] | | | |
|---|---|---|---|---|---|
| | | Breast cancer ER Positive | Breast cancer ER-Negative | Pancreatic cancer | |
| | | MCF-7 | MDA-MB-231 | AsPC1 | Panc-1 |
| 1 | H | 0.91 | 1.64 | 1.92 | 2.34 |
| 2 | Br~~~ | >10[b] | >10 | ND[c] | ND |
| 3 | F~~~ | 4 | 4.42 | 1.37 | 9.53 |

TABLE 2-continued

Effects of STAT3 inhibitors (2-14) on proliferation of human breast and pancreatic cancer cell lines.

2-13

[Structure: R³O-substituted benzamide with 5-chloro group, linked via amide to benzothiophene 1,1-dioxide]

14

[Structure: 2-hydroxy-5-chloro benzamide linked via amide to 3-methoxy-2,3-dihydrobenzothiophene 1,1-dioxide]

| | | IC50 (µM)[a] | | | |
|---|---|---|---|---|---|
| | | Breast cancer ER Positive | Breast cancer ER-Negative | Pancreatic cancer | |
| Compound | R³ | MCF-7 | MDA-MB-231 | AsPC1 | Panc-1 |
| 4 | N-methylpiperidin-4-yl | 3.53 | 2.68 | 1.04 | 1.36 |
| 5 | dimethylaminoethyl | 3.5 | 2.69 | 1.14 | 3.38 |
| 6 | morpholinoethyl | 0.49 | 5.43 | 1.37 | 6.95 |
| 7 | piperidinoethyl | 3.74 | 2.51 | 1.42 | 1.81 |
| 8 | 4-methylpiperazinylethyl | 4.08 | 2.86 | 1.07 | 3.01 |
| 9 | piperazinylethyl | 2.56 | 3.29 | 1.02 | 3.69 |

TABLE 2-continued

Effects of STAT3 inhibitors (2-14) on proliferation of human breast and pancreatic cancer cell lines.

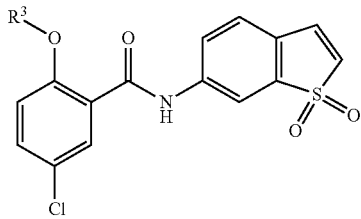

2-13

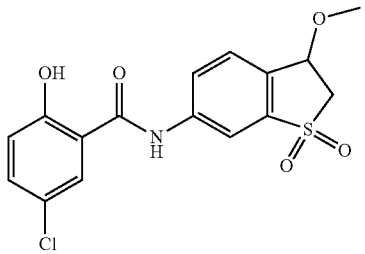 [SMILES: COC1CS(=O)(=O)c2cc(NC(=O)c3cc(Cl)ccc3O)ccc21]

14

| | | IC50 (μM)[a] | | | |
|---|---|---|---|---|---|
| | | Breast cancer ER Positive | Breast cancer ER-Negative | Pancreatic cancer | |
| Compound | R³ | MCF-7 | MDA-MB-231 | AsPC1 | Panc-1 |
| 10 | piperidinyl | 4.21 | 2.85 | 1.6 | 4.09 |
| 11 | H₂N-CH₂CH₂- | 3.47 | 3.12 | 1.05 | 2.25 |
| 12 (HJC0416) | H₂N-(CH₂)₃- | 1.76 | 1.97 | 0.04 | 1.88 |
| 13 | MeNH-CH₂CH₂- | 3.15 | 3.12 | 2.05 | 3.09 |
| 14 | | 6.07 | 7.05 | 8.46 | 8.39 |

[a]Breast cancer cell lines: MCF-7 and MDA-MB-231. Pancreatic cancer cell lines: ASPC1 and Panc-1. Software: MasterPlex ReaderFit 2010, MiraiBio, Inc.
[b]If a specific compound is given a value >10, indicates that a specific IC$_{50}$ cannot be calculated from the data points collected, meaning 'no effect'.
[c]ND: not determined.

Example 3

Discovery of O-Alkylamino Tethered Niclosamide Derivatives as Potent and Orally Bioavailable Anticancer Agents Niclosamide has been identified to potently inhibit the activation, nuclear translocation, and transactivation of STAT3. Nevertheless, the poor aqueous solubility and bioavailability of niclosamide has hindered its further clinical development for cancer therapy. To discover new molecules with enhanced drug-like properties, a series of novel O-alkylamino tethered derivatives of niclosamide have been designed, synthesized, and biologically evaluated. Among them, compound 11 (HJC0152) has been demonstrated to significantly suppress MDA-MB-231 xenograft tumor growth in vivo (i.p. & p.o.), indicating its great potential as efficacious and orally bioavailable therapeutics for human cancer.

Signal transducers and activators of transcription (STATs) are a family of transcription factors that serve as signaling transmitters for a large number of cytokines and growth factors in the regulation of critical biological processes including cell growth, proliferation, differentiation, and survival (Darnell, J. E., Jr., 1997; Bowman, T. et al., 2000; Bromberg, J. et al., 2000; Darnell, J. E., Jr., 2002; Buettner, R. et al., 2002; Yu, H. et al., 2004). Accumulating evidence has demonstrated that persistent activation of STAT3 stimulates tumor angiogenesis, promotes tumor immune evasion, and even confers resistance to apoptosis induced by conventional therapies (Becker, S. et al., 1998; Bromberg, J. F. et al., 1999; Siddiquee, K. et al., 2008; Darnell, J. E., 2005; Yue, P. et al., 2009; Haftchenary, S., 2011; Yu, H. et al., 2009). Therefore, STAT3 may be used as a therapeutic target for the treatment of various types of human cancer (Deng, J. et al., 2007; Page, B. D. et al., 2011; Debnath, B. et al., 2012).

Despite significant advances in recent discovery efforts targeting STAT3, only several STAT3 inhibitors are advanced into early phase clinical trials (Debnath, B. et al., 2012). Poor physicochemical property is one of the most significant obstacles in promoting a potent agent into clinical trials (Debnath, B. et al., 2012). For example, peptide and peptidomimetics inhibitors targeting STAT3 suffer from poor cellular permeability and stability.[17-20] Aqueous solubility plays an essential role in drug disposition and is one of the crucial molecular properties for successful drug development. Although appropriate formulation could be used to enhance solubility and absorption, the stability and manufacturing difficulties should also be taken into consideration. In addition, oral chemotherapy is obviously a preferred administrative route in cancer treatment due to its convenience, patient compliance and cost-effectiveness (O'Neill, V. J. et al., 2002; Schott, S. et al., 2011). Niclosamide, an FDA-approved anticestodal drug, has recently been identified with significant inhibition of the activation, nuclear translocation, and transactivation of STAT3 (Ren, X. et al., 2010). It inhibits the transcription of STAT3 target genes, and induces cell growth inhibition, apoptosis, and cell cycle arrest of cancer cells with constitutively active STAT3. Nevertheless, niclosamide does not have an ideal pharmacokinetic profile due to its poor water solubility and low oral bioavailability (Elkihel, L. et al., 1994; Navab, M et al., 2009). As shown herein, the inventors utilize rational chemical approaches to generate and identify novel derivatives of niclosamide with improved aqueous solubility and bioavailability as potential clinical candidates for cancer therapy. The inventors provide herein compounds with enhanced efficacy and improved drug-like properties as compared to niclosamide.

The inventors firstly modified of the hydroxyl group on phenol ring of niclosamide by introduction of O-alkylamino side chain. The amino group-containing scaffolds are important motifs of structural tuning with the capability to form the hydrogen bonding like phenol group for selective protein binding and drug-likeness enhancement (Xiong, Y. et al., 2010). These new O-alkylamino tethered analogs may provide efficient target binding for a better potency and as free bases, these molecules can also form salts for the final target compounds to have a better aqueous solubility. As shown in Scheme 3, analogs 2-6 were conveniently prepared by Mitsunobu reaction. Alkylation of the bromide intermediate 2 with a variety of amines including heterocyclic moieties introduced basic functionalities into the molecules providing niclosamide derivatives 7 and 8. Mitsunobu coupling of niclosamide with N-Boc-protected amino alcohols followed by the Boc-deprotection afforded analogues 9-15 with diversified O-alkylamino side chains. Both linear alkyl amines and heterocyclic alkyl amines have been explored for the purpose of comparison.

To examine whether the substitution of moiety groups affected biological activities of newly synthesized analogs and explore the structure-activity relationship (SAR), the inventors firstly evaluated the in vitro anticancer effects of the compounds 3-15 on the proliferation of breast cancer cell lines MCF-7 (ER-positive) and MDA-MB-231 (ER-negative and triple-negative), as well as pancreatic cancer cell lines AsPC1 and Panc-1 using MTS assays. The ability of these new analogues to inhibit the growth of cancer cells is summarized in Table 3. The results revealed that analogues 10-15 bearing the terminal amino group-containing side chain at the phenol moiety showed promising antiproliferative activities with low micromolar to nanomolar $IC_{50}$ values, while the alkyl-substituted derivatives 5-9 at the terminal amino group on the same position displayed moderate to low activities. For example, new analogues 10 and 11 exhibited a similar or significantly higher potency than niclosamide. However, compound 4 with a methylated terminal amino group in 4-O-piperidinyl moiety, displayed 10-fold loss of antiproliferative activity in comparison with analogue 10. The same trend of SAR was also found for compounds 5-8, in which the dialkylsubstitution at the terminal amino group resulted in significant loss of activities, while O-ethylpiperazinyl derivative 9 in contrast with 8 regained antiproliferative activity with $IC_{50}$ values of 12.4 µM and 8.7 µM against two breast cancer cell lines MCF-7 and MDA-MB-231, respectively. The fluorinated compound 3 that was initially designed for potential PET imaging studies displayed no significant effects against the tested cancer cells.

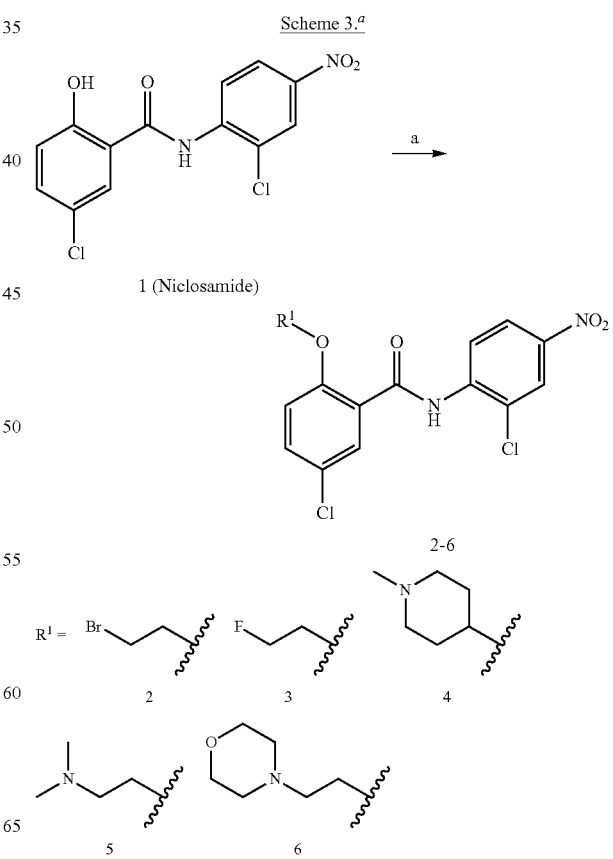

-continued

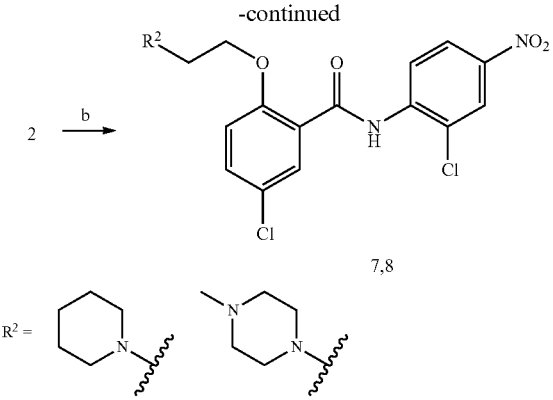

7, 8

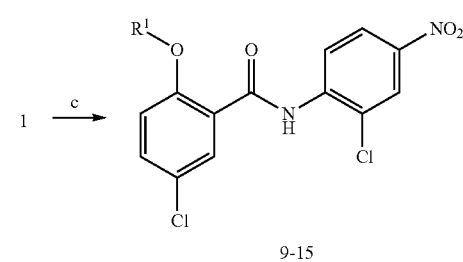

9-15

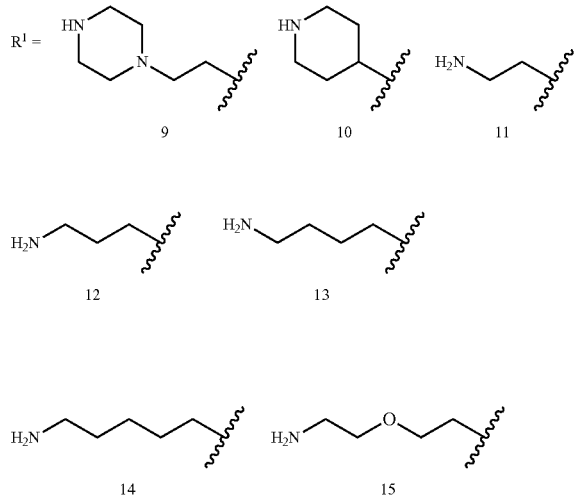

<sup>a</sup>Reagents and conditions: (a) R¹OH, Ph₃P, DIAD, THF, rt, 50-93%;
(b) R²H, KI, K₂CO₃, acetone, reflux, 55-91%; (c) (i) Boc-R¹OH, Ph₃P, DIAD, THF, rt;
(ii) TFA, CH₂Cl₂, 0° C. to rt, 34-81% (two steps).

Further modifications of nitro group in compound 10, one of the most potent analogues identified from the first SAR exploration, were also investigated. As outlined in Scheme 4, reduction of the nitro group of the intermediate 17 with zinc dust provided the corresponding amine 18. Further treatment of 18 with methanesulfonyl chloride or acetyl chloride followed by removal of the Boc group afforded the desired products 19 and 20, respectively. As shown in Table 3, replacement of the nitro group of compound 10 with methanesulfonamide (19) or acetamide (20) resulted in a significant loss of the antiproliferative activity, indicating that the nitro moiety is fairly important for potency.

Scheme 4.<sup>a</sup>

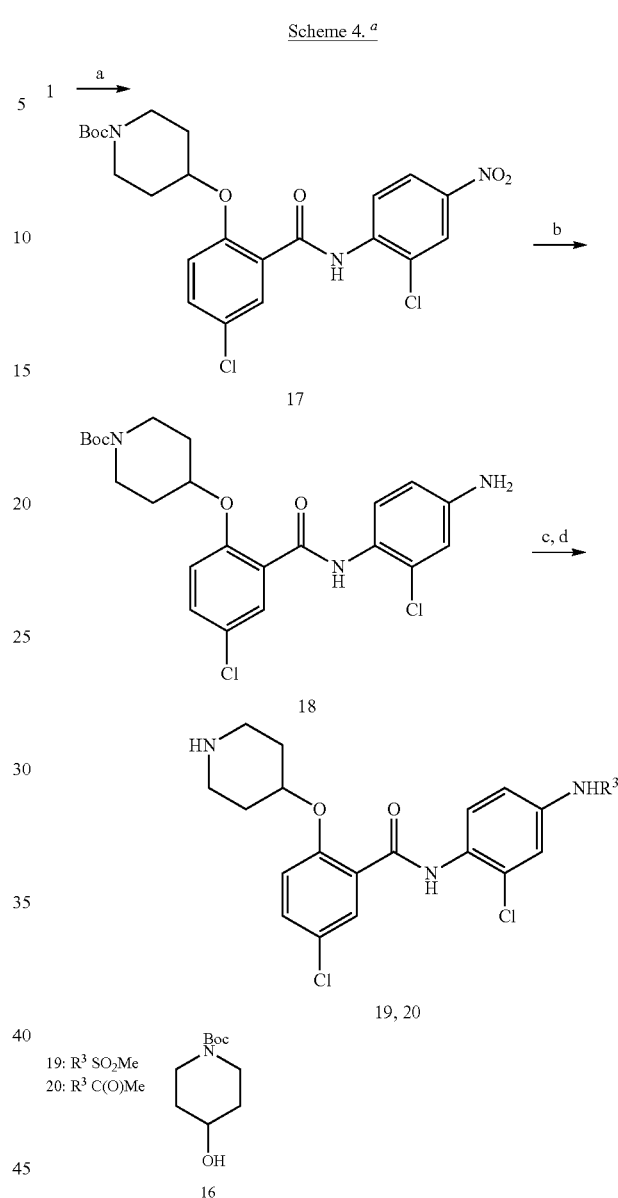

<sup>a</sup>Reagents and conditions: (a) 16, Ph₃P, DIAD, THF, rt, 58%; (b) Zn dust, sat. NH₄Cl (aq.), MeOH, rt; (c) MeC(O)Cl or MeSO₂Cl, Et₃N, CH₂Cl₂, rt; (d) TFA, CH₂Cl₂, 0° C. to rt, 31-66% (three steps).

TABLE 3

Effects of niclosamide analogues on proliferation of human breast and pancreatic cancer cell lines.

| | | IC$_{50}$ (μM) | | | |
| | | Breast Cancer | | Pancreatic cancer | |
| Compd | cLogP$^a$ | MCF-7 | MDA-MB-231 | AsPC1 | Panc-1 |
|---|---|---|---|---|---|
| 1 | 4.05 | 1.06 | 0.79 | 1.47 | 1.73 |
| 3 | 4.26 | >10 | >10 | ND$^b$ | ND |
| 4 | 4.22 | 4.11 | 2.69 | 3.51 | >10 |
| 5 | 3.77 | >10 | >10 | ND | ND |
| 6 | 3.47 | 9.87 | 18.0 | 72.2 | >10 |
| 7 | 4.73 | >10 | >10 | ND | ND |

TABLE 3-continued

Effects of niclosamide analogues on proliferation of human breast and pancreatic cancer cell lines.

| | | IC$_{50}$ (μM) | | | |
|---|---|---|---|---|---|
| | | Breast Cancer | | Pancreatic cancer | |
| Compd | cLogP$^a$ | MCF-7 | MDA-MB-231 | AsPC1 | Panc-1 |
| 8 | 3.56 | >10 | >10 | ND | ND |
| 9 | 3.20 | 12.4 | 8.7 | ND | ND |
| 10 | 3.91 | 0.25 | 0.29 | 2.76 | 0.54 |
| 11 | 3.01 | 0.91 | 1.64 | 1.9 | 1.08 |
| 12 | 3.33 | 3.11 | 2.61 | 4.2 | 3.11 |
| 13 | 3.76 | 3.7 | 2.37 | 7.4 | >10 |
| 14 | 4.15 | 3.49 | 3.1 | 2.08 | 4.67 |
| 15 | 2.87 | 9.37 | 5.3 | >10 | >10 |
| 19 | 2.95 | >10 | >10 | ND | ND |
| 20 | 3.13 | >10 | 5.87 | ND | ND |

$^a$cLogP: http://146.107.217.178/lab/alogps/start.html.
$^b$ND: not determined.

From the in vitro screening of all tested compounds, analogues 10 (HJC0125) and 11 (HJC0152) displayed an attractive anti-cancer profile and were subjected to further biological evaluation. To study the effects of these two compounds on cell growth, cellular morphological changes were examined in MDA-MB-231 breast cancer cells treated with compounds 10, 11 or niclosamide for 48 h, under light microscopy. Like niclosamide, both compounds 10 and 11 significantly inhibited cell proliferation and induced apoptosis accompanying cellular morphological changes at concentration of 1 μM, 5 μM, and 10 μM, respectively.

Figure 5:
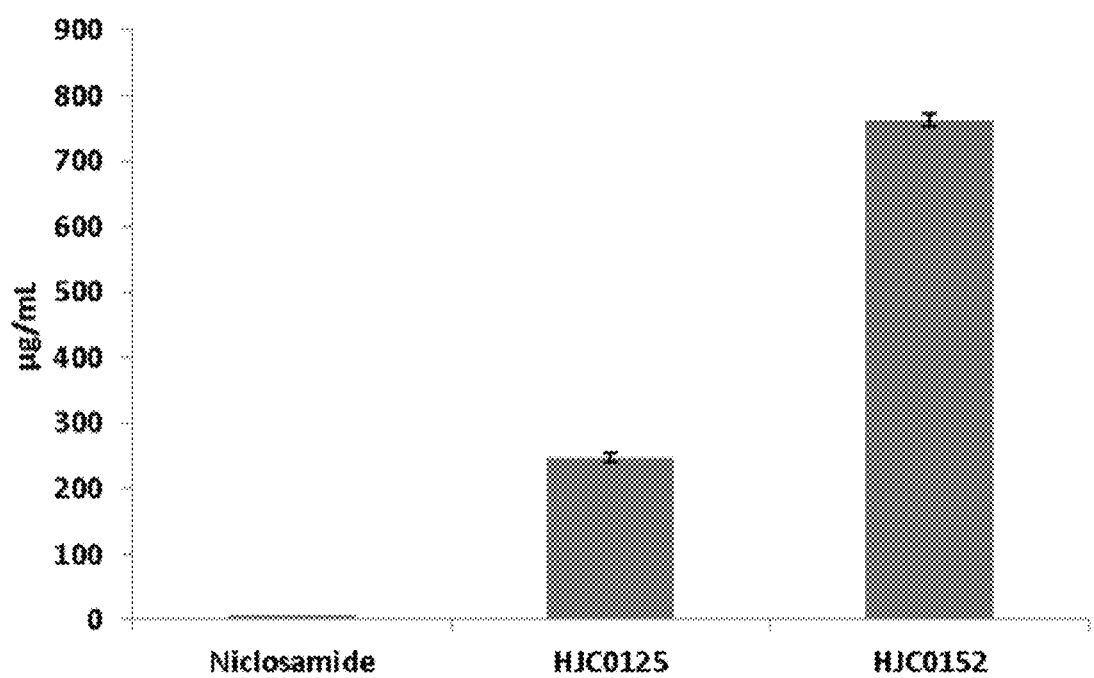
FIG. 5: Aqueous solubility of novel niclosamide analogues. Compounds 10 (HJC0125) and 11 (HJC0152) showed significantly improved solubility compared with niclosamide.

To evaluate water solubility and oral bioavailability, aqueous solubility of the new analogues 10 and 11 was determined by an HPLC method (Vogel, G. H., 2006). As expected, introduction of O-alkylamino tethered moiety not only enhanced anticancer activity, but also significantly increased the aqueous solubility. Both compounds 10 and 11 (in the form of HCl salt) demonstrated excellent water solubility, with a saturated concentration of 248 μg/mL and 762 μg/mL, respectively (FIG. 5). The O-ethylamino derivative 11 showed the most favorable solubility, which is about 3,300-fold improvement in comparison with that of niclosamide (0.23 μg/mL) (The Merck Index, 2001). The significant improvement of the aqueous solubility is expected to facilitate these compounds to be more orally bioavailable and efficacious in vivo than niclosamide, which is substantially water insoluble.

Previous studies have demonstrated that niclosamide is a potential inhibitor of STAT3 (Ren, X. et al., 2010). To determine whether the new derivatives act as potent small-molecule inhibitors of STAT3 activation, the effect of niclosamide and compound 11 was measured on promoter activity using the cell-based transient transfection and dual luciferase reporter assays. MDA-MB-231 cells were pre-treated with niclosamide or 11 at different concentrations for 24 h. The STAT3 promoter activity in MDA-MB-231 cells was determined after transient transfecting with pSTAT3-Luc vector. As shown in FIG. 6A, treatment with 10 μM of compound 11 decreased the STAT3 promoter activity in MDA-MB-231 cells by approximately 32%, increasing the dose of compound 11 to 20 μM further decreased STAT3 promoter activity by 62% compared with control. Similarly, STAT3 promoter activity in MDA-MB-231 cells was suppressed after treatment with 20 μM niclosamide, while proliferation of MDA-MB-231 cells (MTT assay) (Ren, X. et al., 2010) showed comparable to slightly more potent reduction (FIG. 6B). These results demonstrate that compound 11 inhibits STAT3 promoter activity in MDA-MB-231 cells in a dose-dependent manner and has a similar effect as niclosamide.

To further investigate the inhibitory activity of compound 11 against STAT3 pathway, the inventors examined STAT3 phosphorylation and expression of the known STAT3 target genes in MDA-MB-231 cell line. The cells were treated with different doses of compound 11 for 24 h, and levels of total STAT3 and phosphorylated STAT3 at Tyr-705 were then examined by Western blot. As shown in FIGS. 7A-B, total STAT3 was reduced after treatment with 11 or niclosamide, suggesting that these compounds may alter transcription and/or translation of STAT3. Similarly, phosphorylated STAT3 (p-STAT3) at Tyr-705 is suppressed by 11 or niclosamide, suggesting that compound 11 has a comparable potency in downregulating STAT3 protein production and phosphorylation at Tyr-705 site. Blocking STAT3 signaling in many different tumor cells leads to induce growth arrest and apoptosis (Turkson, J. et al., 2000; Bromberg, J., 2002; Zhang, X. et al., 2012). The inventors observed that compound 11 induced cleaved caspase-3 and downregulated cyclin D1 in MDA-MB-231 cells. These results support the idea that compound 11 inhibits cell cycle progression and promotes apoptosis. These results were further confirmed using annexin V-based measurement using flow cytometry. Compound 11 and niclosamide activated apoptosis in MDA-MB-231 breast cancer cells in a dose-dependent manner. Other than targeting STAT3, niclosamide has also been found to inhibit NF-kB and Wnt/β-catenin signaling (Ren, X. et al., 2010; Jin, Y. et al., 2010; Osada, T. et al., 2011). The inventors are investigating the mechanisms how compound 11 regulates STAT3 upstream targets and related signaling pathways, and transcriptional/translational regulation.

Furthermore, compound 11 was further evaluated for its antitumor activity in inhibition of tumor growth in the MDA-MB-231 xenograft model. As expected, mice treated with 7.5 mg/kg of compound 11 via i.p. showed better effect in inhibiting tumor growth compared to the mice treated with 12.5 mg/kg of niclosamide (FIG. 8A). Similarly, the MDA-MB-231 xenograft mice were treated with oral administration of compound 11 and found that the growth of xenograft tumors in mice was significantly reduced by compound 11 at the dose of 25 mg/kg, and even more efficacious than niclosamide at 75 mg/kg (FIG. 8B). This observation might be attributed to the superior solubility of compound 11, which might have resulted in an improved oral bioavailability (Lipinski, C. A., 2000; Leach, A. G. et al., 2006, Bergstrom, C. A. et al., 2007; Ishikawa, M. et al., 2011; Hann, M. M. et al., 2012) and consequently, an enhanced suppression of tumor growth in mice. It is also noteworthy that compound 11 did not show significant signs of toxicity at the dose of 75 mg/kg. These results have demonstrated that compound 11 (HJC0152) displays excellent aqueous solubility and may be used as a orally bioavailable anticancer agent.

In summary, a series of novel O-alkylamino tethered derivatives of niclosamide have been designed, synthesized, and biologically evaluated. New analogues 10 and 11 were identified to exhibit a similar or significantly higher potency than niclosamide against human breast and pancreatic cancer cells. Both compounds 10 and 11 demonstrated a superior aqueous solubility, especially the compound 11, which has about 3,300-fold improvement in water solubility in comparison with niclosamide. In MDA-MB-231 cells, compound 11 inhibited STAT3 promoter activity, increased the expression of active caspase-3, inhibited cell cycle progression and promoted apoptosis. In nude mice bearing breast tumor xenografts, compound 11 significantly suppressed MDA-MB-231 xenograft tumor growth in vivo (both i.p. & p.o.). Compound 11 (HJC0152) was observed to have a remarkably improved aqueous solubility and may be used as an orally bioavailable agent for cancer therapy.

Example 4

Identification of HJC0123, an Orally Bioavailable STAT3 Inhibitor for Cancer Therapy Systematic chemical synthesis and pharmacological evaluation of scaffolds as potent anticancer agents was performed by utilizing six privileged fragments from STAT3 inhibitors. Several molecules such as compounds 5, 12, and 19 that may act as advanced chemical leads have been identified. The most potent compound 5 (HJC0123) has demonstrated the ability to inhibit STAT3 promoter activity, downregulate phosphorylation of STAT3, increase the expression of cleaved caspase-3, inhibit cell cycle progression and promote apoptosis in breast and pancreatic cancer cells with low micromolar to nanomolar $IC_{50}$ values. Furthermore, compound 5 significantly suppressed estrogen receptor (ER)-negative breast cancer MDA-MB-231 xenograft tumor growth in vivo (p.o.), indicating its great potential as an efficacious and orally bioavailable drug candidate for human cancer therapy.

STAT3 (signal transducers and activators of transcription 3) is a member of a family of seven transcription factors (STATs 1, 2, 3, 4, 5a, 5b, and 6) that transmit signals from cell surface receptors to the nucleus, and are crucial for the signaling of many cytokines and growth factors that are mediators in the fundamental cellular and biological processes such as the immune response, angiogenesis, cell proliferation, differentiation, and apoptosis (Zhong, Z. et al., 1994; Darnell, J. E., Jr., 1997; Bromberg, J. F. et al., 1999; Bromberg, J. et al., 2000; Hirano, T. et al., 2000; Bowman, T. et al., 2000; Turkson, J. et al., 2000). It contains four functional domains that contribute to its oligomerization, DNA binding, Src homology 2 (SH2) dimerization, and transactivation, respectively. Once activated by extracellular signaling proteins, STAT3 is phosphorylated at a tyrosine residue 705 (Tyr-705) and phosphorylated STAT3 forms dimers via a reciprocal phosphotyrosines (pTyr)-SH2 domain interaction. Then the dimers translocate to the nucleus where they bind to specific DNA response elements and induce transcription (Johnston, P. A. et al., 2011). In contrast to the transient nature of STAT3 activation in normal cells, constitutive STAT3 activity has been observed and reported in many human solid and hematological tumors (Buettner, R. et al., 2002; Haura, E. B. et al., 2005). Aberrant STAT3 activation is found to be correlated with worse prognosis by promoting tumorigenesis, inducing tumor invasion and metastasis, and driving the malignant progression in many carcinomas. Thus, STAT3 is considered to be a promising target for prevention and treatment of cancer, thereby providing the rationale to develop novel anticancer agents targeting the STAT3 signaling pathway (Yu, H. et al., 2007; Yu, H. et al., 2004; Darnell, J. E., Jr., 2005; Darnell, J. E., Jr., 2002; Yu, H. et al., 2009; Germain, D. A., 2007; Costantino, L. et al., 2008; Siddiquee, K. et al., 2008).

Figure 9:
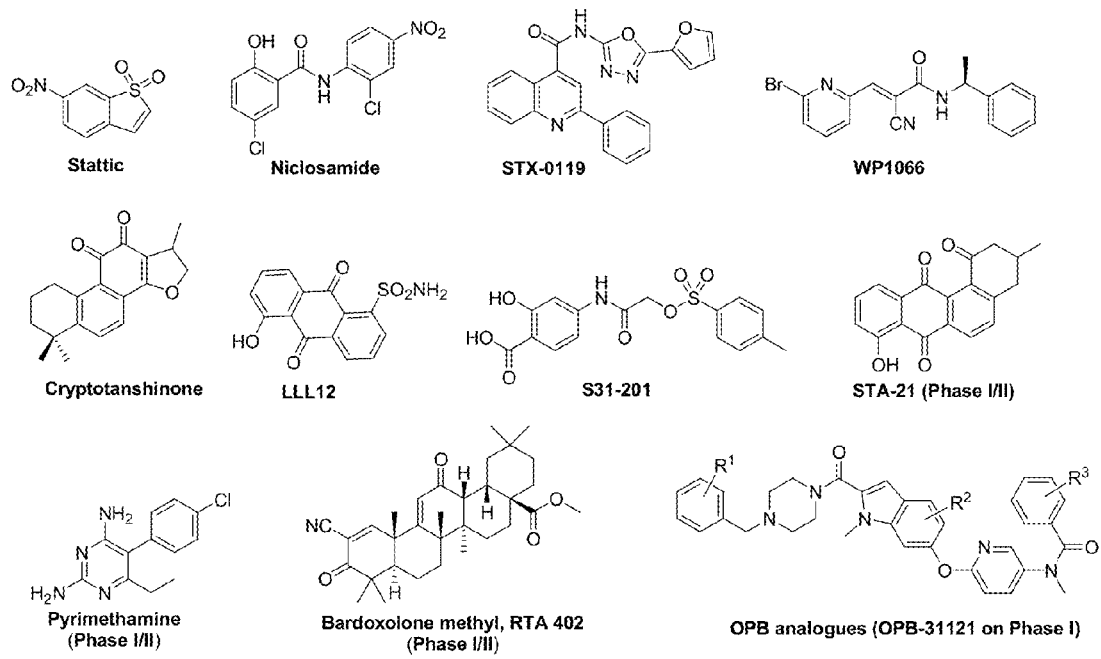
FIG. 9: Chemical structures of representative non-peptidic STAT3 inhibitors.

Over the past decade, several peptidic and non-peptidic STAT3 inhibitors that directly inhibit the different structural domains of STAT3 protein or indirectly inhibit the upstream components of the STAT3 activation (Schindler, C. W., 2002) such as PY*LKTK (Turkson, J. et al., 2001), STX-0119 (Matsuno, K. et al., 2010), and S31-201 (Siddiquee, K. et al., 2007) to inhibit STAT3 dimerization, Stattic (Schust, J. et al., 2006) to inhibit phosphorylation, CAP-1 (Turkson, J. et al., 2004) and IS3 295 (Turkson, J. et al., 2005) to inhibit DNA-binding, niclosamide (Ren, X. et al., 2010) to inhibit transcriptional function of STAT3, WP1066 (Horiguchi, A. et al., 2010) and AG490 (Iwamaru, A. et al., 2007) to inhibit the upstream Janus kinases activity have been explored (FIG. 9). Despite these significant advances, no STAT3 inhibitor drugs have reached the market. The challenges include the lack of membrane permeability and stability, low water-solubility, weak binding affinity, or low specificity of effects (Chen, J. et al., 2010; Mandall, P. K. et al., 2009; Mandal, P. K. et al., 2011; Yue, P. et al., 2009; Deng, J. et al., 2007; Zhao, M. et al., 2011; Mankan, A. K. et al., 2011; Lavecchia, A. et al., 2011; Page, B. D. et al., 2011; Debnath, B. et al., 2012). As further described below, compound 5 (HJC0123) was discovered as a potent and orally bioavailable anticancer agent.

Synthesis of Compounds

All commercially available starting materials and solvents were reagent grade, and used without further purification. Reactions were performed under a nitrogen atmosphere in dry glassware with magnetic stirring. Preparative column chromatography was performed using silica gel 60, particle size 0.063-0.200 mm (70-230 mesh, flash). Analytical TLC was carried out employing silica gel 60 F254 plates (Merck, Darmstadt). Visualization of the developed chromatograms was performed with detection by UV (254 nm). NMR spectra were recorded on a Brucker-600 ($^1$H, 600 MHz; $^{13}$C, 150 MHz) spectrometer. $^1$H and $^{13}$C NMR spectra were recorded with TMS as an internal reference. Chemical shifts were expressed in ppm, and J values were given in Hz. High-resolution mass spectra (HRMS) were obtained from Thermo Fisher LTQ Orbitrap Elite mass spectrometer. Parameters include the following: Nano ESI spray voltage was 1.8 kV; Capillary temperature was 275° C. and the resolution was 60,000; Ionization was achieved by positive mode. Melting points were measured on a Thermo Scientific Electrothermal Digital Melting Point Apparatus and uncorrected. Purity of final compounds was determined by analytical HPLC, which was carried out on a Shimadzu HPLC system (model: CBM-20A LC-20AD SPD-20A UV/VIS). HPLC analysis conditions: Waters μBondapak C18 (300× 3.9 mm); flow rate 0.5 mL/min; UV detection at 270 and 254 nm; linear gradient from 30% acetonitrile in water (0.1% TFA) to 100% acetonitrile (0.1% TFA) in 20 min followed by 30 min of the last-named solvent. All biologically evaluated compounds are >95% pure.

2-Cyano-N-(1,1-dioxo-1H-1$\lambda^6$-benzo[b]thiophen-6-yl) acetamide (4). To a solution of cyanoacetic acid (340 mg, 4.0 mmol) and 1,1-dioxo-1H-1$\lambda^6$-benzo[b]thiophen-6-ylamine (362 mg, 2.0 mmol) in 10 mL of $CH_2Cl_2$ was added DIPEA (774 mg, 6.0 mmol). HBTU (1.14 g, 3.0 mmol) was added at 0° C. The resulting mixture was stirred at r.t. for 28 h. The reaction mixture was diluted with $CH_2Cl_2$ (80 mL) and washed with water (20 mL). The organic layer was separated and dried with anhydrous $Na_2SO_4$. The solution was concentrated to give a crude product, which was purified with silica gel column (EtOAc/hexane=1/1) to obtain the desired product (400 mg, 81%) as a yellow solid (mp 207-208° C.). HPLC purity 98.6% ($t_R$=10.93 min). $^1$H NMR (600 MHz, DMSO-$d_6$) δ 10.79 (s, 1H), 8.04 (s, 1H), 7.67-7.69 (m, 1H), 7.60 (d, 1H, J=7.2 Hz), 7.57 (d, 1H, J=7.8 Hz), 7.30 (d, 1H, J=7.2 Hz), 3.98 (s, 2H). $^{13}$C NMR (150 MHz, DMSO-$d_6$) δ

162.0, 140.7, 137.3, 132.8, 130.3, 126.7, 126.1, 123.4, 115.6, 111.4, 27.0. FIRMS (ESI) calcd for $C_{11}H_{19}N_2O_3S$ 249.0328 (M+H)$^+$, found 249.0330.

2-Phenylquinoline-4-carboxylic acid (1,1-dioxo-1H-1$\lambda^6$-benzo[b]thiophen-6-yl)amide (5). Compound 5 was prepared in 39% yield by a procedure similar to that used to prepare compound 4. The title compound was obtained as a pale yellow solid (mp 277-278° C.). HPLC purity 99.2% ($t_R$=32.39 min). $^1$H NMR (600 MHz, DMSO-d$_6$) δ 11.29 (s, 1H), 8.44 (s, 1H), 8.38 (d, 2H, J=7.2 Hz), 8.34 (s, 1H), 8.20 (dd, 2H, J=5.4 Hz, 13.8 Hz), 7.98 (d, 1H, J=7.8 Hz), 7.88 (t, 1H, J=7.2 Hz), 7.54-7.70 (m, 6H), 7.34 (d, 1H, J=6.6 Hz). $^{13}$C NMR (150 MHz, DMSO-d$_6$) δ 165.8, 155.8, 147.9, 142.2, 141.2, 138.0, 137.2, 132.9, 130.5, 130.4, 130.0, 129.7, 129.0, 127.6, 127.3, 126.6, 126.3, 125.1, 124.2, 123.0, 117.1, 117.1, 112.3, 112.3. HRMS (ESI) calcd for $C_{24}H_{17}N_2O_3S$ 413.0954 (M+H)$^+$, found 413.0959.

(S)-2-Phenylquinoline-4-carboxylic acid (1-phenylethyl) amide (8). To a solution of 2-phenyl-quinoline-4-carboxylic acid (249 mg, 1.0 mmol) and L(−)-á methylbenzylamine (127 mg, 1.05 mmol) in 10 mL of CH$_2$Cl$_2$ was added DIPEA (388 mg, 3.0 mmol). HBTU (569 mg, 1.5 mmol) was added at 0° C. The resulting mixture was stirred at r.t. for 3 h. The reaction mixture was diluted with CH$_2$Cl$_2$ (80 mL) and washed with water (20 mL). The organic layer was separated and dried with anhydrous Na$_2$SO$_4$. The solution was concentrated to give a crude product, which was purified with silica gel column (EtOAc/hexane =1/3) to obtain 8 (330 mg, 94%) as a white solid (mp 157-158° C.). HPLC purity 99.8% ($t_R$=17.22 min). $^1$H NMR (600 MHz, CDCl$_3$) δ 8.03-8.07 (m, 3H), 7.97 (d, 1H, J=8.4 Hz), 7.71 (s, 1H), 7.67 (t, 1H, J=7.2 Hz), 7.28-7.48 (m, 9H), 6.78 (d, 1H, J=7.2 Hz), 5.38-5.43 (m, 1H), 1.66 (d, 3H, J=6.6 Hz). $^{13}$C NMR (150 MHz, CDCl$_3$) δ 166.9, 156.9, 148.7, 143.0, 142.6, 138.9, 130.3, 130.2, 129.8, 129.0, 127.8, 127.6, 127.4, 126.4, 125.0, 123.4, 116.4, 49.8, 21.9. HRMS (ESI) calcd for $C_{24}H_{21}N_2O$ 353.1648 (M+H)$^+$, found 353.1653.

(S)-5-Chloro-2-hydroxy-N-(1-phenylethyl)benzamide (9). Compound 9 was prepared in 39% yield by a procedure similar to that used to prepare compound 8. The title compound was obtained as a white solid (mp 124-125° C.). HPLC purity 97.1% ($t_R$=19.75 min). $^1$H NMR (600 MHz, CDCl$_3$) δ 12.22 (s, 1H), 7.28-7.48 (m, 7H), 6.93 (d, 1H, J=9.0 Hz), 6.55 (d, 1H, J=6.6 Hz), 5.29-5.34 (m, 1H), 1.64 (d, 3H, J=7.2 Hz). $^{13}$C NMR (150 MHz, CDCl$_3$) δ 168.2, 160.4, 142.3, 134.3, 129.1, 128.0, 126.3, 125.1, 123.4, 120.3, 115.3, 49.5, 21.7. HRMS (ESI) calcd for $C_{15}H_{15}ClNO_2$ 276.0786 (M+H)$^+$, found 276.0790.

3-(6-Bromopyridin-2-yl)-2-cyano-N-(1,1-dioxo-1H-1$\lambda^6$-benzo[b]thiophen-6-yl)acrylamide (10). To a solution of 4 (100 mg, 0.40 mmol) and 6-bromo-pyridine-2-carbaldehyde (112 mg, 0.60 mmol) in EtOH (5 mL) was added piperidine (3 mg, 0.04 mmol) at 0° C. The mixture was stirred at 90° C. for 0.5 h. A yellow suspension formed during the reaction. The solid was filtered and washed with H$_2$O. The desired product (120 mg, 72%) was obtained as a yellow solid (mp 219-220° C.). HPLC purity 96.0% ($t_R$=16.57 min). $^1$H NMR (600 MHz, DMSO-d$_6$) δ 10.94 (s, 1H), 8.24 (s, 1H), 8.14 (s, 1H), 7.98 (t, 1H, J=7.8 Hz), 7.91-7.93 (m, 2H), 7.84 (d, 1H, J=7.8 Hz), 7.62 (t, 2H, J=7.2 Hz), 7.34 (d, 1H, J=7.2 Hz). $^{13}$C NMR (150 MHz, DMSO-d$_6$) δ 160.7, 150.8, 147.2, 141.3, 140.8, 140.6, 137.1, 132.7, 130.9, 130.5, 126.7, 126.6, 126.6, 124.8, 114.6, 112.8, 110.8. HRMS (ESI) calcd for $C_{17}H_{11}BrN_3O_3S$ 415.9699 (M+H)$^+$, found 415.9703.

5-Chloro-N-(1,1-dioxo-1H-1$\lambda^6$-benzo[b]thiophen-6-yl)-2-hydroxybenzamide (12). A solution of 5-chloro-2-hydroxybenzoic acid (2.0 g, 11 mmol) and 4 mL of SOCl$_2$ in 4 mL of toluene was stirred at 110° C. overnight. The mixture was concentrated to give a crude product as a pale yellow oil. To the solution of pyridine (869 mg, 11 mmol) and 1,1-dioxo-1H-1ë$^6$-benzo[b]thiophen-6-ylamine (200 mg, 1.1 mmol) was added the solution of the acid chloride (500 mg, 2.6 mmol) in DMF (15 mL) dropwise at 0° C. The mixture was stirred at r.t. for 24 h. The mixture was added to the water solution dropwise. The yellow solid was formed and filtrated. To the mixture of the crude product in THF (8 mL) was added 1 N LiOH (2.2 mL, 2.2 mmol) at 0° C. The mixture was stirred at 0° C. for 30 min. The mixture was diluted with EtOAc (50 mL) and washed with 2 N HCl (10 mL). The organic layer was separated and dried with anhydrous Na$_2$SO$_4$. The solution was concentrated to afford the crude product, which was washed with CH$_2$Cl$_2$ (20 mL) to give the desired product (150 mg, 39%) as a yellow solid (mp 268-269° C.). HPLC purity 98.3% ($t_R$=17.24 min). $^1$H NMR (600 MHz, DMSO-d$_6$) δ 11.50 (s, 1H), 10.74 (s, 1H), 8.25 (s, 1H), 7.92 (d, 1H, J=8.4 Hz), 7.86 (d, 1H, J=2.4 Hz), 7.59-7.62 (m, 2H), 7.48 (d, 1H, J=9.0 Hz), 7.31 (d, 1H, J=6.6 Hz), 7.04 (d, 1H, J=8.4 Hz). $^{13}$C NMR (150 MHz, DMSO-d$_6$) δ 165.1, 156.2, 140.7, 137.1, 133.1, 132.8, 130.3, 128.6, 126.5, 126.2, 124.6, 122.8, 120.4, 119.0, 112.7. HRMS (ESI) calcd for $C_{15}H_{11}ClNO_4S$ 336.0092 (M+H)$^+$, found 336.0098.

5-Chloro-N-(5-furan-2-yl-[1,3,4]oxadiazol-2-yl)-2-hydroxybenzamide (13). Compound 13 was prepared in 50% yield by a procedure similar to that used to prepare compound 12. The title compound was obtained as a white solid (mp 196-197° C.). HPLC purity 96.0% ($t_R$=18.99 min). $^1$H NMR (600 MHz, CDCl$_3$) δ 10.11 (s, 1H), 8.13 (d, 1H, J=2.4 Hz), 8.02 (d, 1H, J=2.4 Hz), 7.64 (dd, 1H, J=2.4 Hz and 8.4 Hz), 7.49 (dd, 1H, J=2.4 Hz and 8.4 Hz), 7.21 (d, 1H, J=9.0 Hz), 6.99 (d, 1H, J=9.0 Hz). $^{13}$C NMR (150 MHz, DMSO-d$_6$) δ 164.4, 158.4, 148.3, 135.2, 133.6, 130.8, 130.6, 130.2, 126.2, 125.9, 122.6, 119.7, 115.4. HRMS (ESI) calcd for $C_{13}H_9ClN_3O_4$ 306.0276 (M+H)$^+$, found 306.0274.

N-(1,1-Dioxo-1H-1$\lambda^6$-benzo[b]thiophen-6-yl)-2,6-diphenyl-isonicotinamide (19). Compound 19 was prepared in 50% yield by a procedure similar to that used to prepare compound 4. The title compound was obtained as a pale yellow solid (mp 235-236° C.). HPLC purity 97.2% ($t_R$=22.05 min). $^1$H NMR (600 MHz, CDCl$_3$) δ 8.76 (s, 1H), 8.34 (d, 1H, J=6.6 Hz), 8.23 (d, 4H, J=7.2 Hz), 8.14 (s, 2H) 7.93 (s, 1H), 7.41-7.55 (m, 6H), 7.40 (d, 1H, J=8.4 Hz), 7.13-7.15 (m, 1H), 6.26-6.28 (m, 1H). $^{13}$C NMR (150 MHz, DMSO-d$_6$) δ 164.7, 156.6, 143.9, 141.1, 138.1, 137.1, 132.8, 130.4, 129.7, 129.0, 126.9, 126.6, 126.3, 124.6, 116.7, 112.7. FIRMS (ESI) calcd for $C_{26}H_{19}N_2O_3S$ 439.1111 (M+H)$^+$, found 439.1116.

Acridine-9-carboxylic acid (1,1-dioxo-1H-1$\lambda^6$-benzo[b]thiophen-6-yl)amide (20). Compound 20 was prepared in 39% yield by a procedure similar to that used to prepare compound 4. The title compound was obtained as a yellow solid (mp 237-238° C.). HPLC purity 99.4% ($t_R$=14.48 min). $^1$H NMR (600 MHz, DMSO-d$_6$) δ 8.71 (d, 1H, J=8.4 Hz), 8.32 (d, 2H, J=8.4 Hz), 8.08-8.13 (m, 5H), 7.97 (t, 2H, J=7.8 Hz), 7.82 (t, 1H, J=8.4 Hz), 7.68 (t, 2H, J=7.8 Hz). $^{13}$C NMR (150 MHz, DMSO-d$_6$) δ 163.4, 147.9, 136.1, 133.9, 132.9, 131.1, 129.5, 128.0, 128.0, 125.2, 121.7, 116.5, 115.5. HRMS (ESI) calcd for $C_{22}H_{15}N_2O_3S$ 387.0798 (M+H)$^+$, found 387.0802.

N-(1,1-Dioxo-1H-1$\lambda^6$-benzo[b]thiophen-6-yl)isonicotinamide (21). Compound 21 was prepared in 56% yield by a procedure similar to that used to prepare compound 4. The title compound was obtained as a pale yellow solid (mp 251-252° C.). HPLC purity 97.0% ($t_R$=8.81 min). $^1$H NMR (600 MHz, DMSO-$d_6$) δ 10.92 (s, 1H), 8.81-8.82 (m, 2H), 8.27 (s, 1H), 8.00 (d, 1H, J=7.8 Hz), 7.88 (t, 2H, J=2.4 Hz), 7.62 (t, 2H, J=6.6 Hz), 7.33 (d, 1H, J=6.6 Hz). $^{13}$C NMR (150 MHz, DMSO-$d_6$) δ 164.6, 150.4, 141.3, 141.1, 137.1, 132.8, 130.4, 126.5, 126.3, 124.5, 121.6, 112.6. HRMS (ESI) calcd for $C_{14}H_{11}N_2O_3S$ 287.0485 (M+H)$^+$, found 287.0488.

N-(1,1-Dioxo-1H-1λ$^6$-benzo[b]thiophen-6-yl)-2-phenylisonicotinamide (22). Compound 22 was prepared in 46% yield by a procedure similar to that used to prepare compound 4. The title compound was obtained as a pale yellow solid (mp 285-286° C.). HPLC purity 98.0% ($t_R$=14.72 min). $^1$H NMR (600 MHz, DMSO-$d_6$) δ 10.97 (s, 1H), 8.89 (d, 1H, J=4.8 Hz), 8.42 (s, 1H), 8.28 (s, 1H), 8.19 (d, 2H, J=7.8 Hz), 8.03-8.05 (m, 1H), 7.82 (d, 1H, J=4.8 Hz), 7.63 (d, 2H, J=7.8 Hz), 7.56 (t, 1H, J=7.2 Hz), 7.51 (t, 2H, J=7.2 Hz), 7.34 (d, 1H, J=6.6 Hz). $^{13}$C NMR (150 MHz, DMSO-$d_6$) δ 164.6, 156.9, 150.4, 142.6, 141.1, 138.1, 137.1, 132.8, 130.4, 129.6, 128.9, 126.8, 126.5, 126.3, 124.6, 120.5, 118.0, 112.7. HRMS (ESI) calcd for $C_{20}H_{15}N_2O_3S$ 363.0798 (M+H)$^+$, found 363.0791.

Quinoline-3-carboxylic acid (1,1-dioxo-1H-1λ$^6$-benzo[b]thiophen-6-yl)amide (23). Compound 23 was prepared in 48% yield by a procedure similar to that used to prepare compound 4. The title compound was obtained as a pale yellow solid (mp 209-210° C.). HPLC purity 98.8% ($t_R$=11.01 min). $^1$H NMR (600 MHz, Acetone-d6) δ 10.29 (s, 1H), 9.03 (d, 1H, J=4.2 Hz), 8.42 (s, 1H), 8.34 (d, 1H, J=8.4 Hz), 8.14 (d, 1H, J=8.4 Hz), 8.03-8.05 (m, 1H), 7.83-7.86 (m, 1H), 7.79 (d, 1H, J=4.8 Hz), 7.68-7.70 (m, 1H), 7.63 (d, 1H, J=7.8 Hz), 7.57 (d, 1H, J=7.2 Hz), 7.04 (d, 1H, J=7.2 Hz). $^{13}$C NMR (150 MHz, Acetone-d6) δ 166.7, 151.0, 149.7, 142.4, 139.1, 133.1, 131.6, 130.7, 128.5, 127.7, 127.2, 126.3, 125.1, 124.8, 124.7, 120.0, 113.3, 113.2. HRMS (ESI) calcd for $C_{18}H_{13}N_2O_3S$ 337.0641 (M+H)$^+$, found 337.0646.

Biology

In Vitro Determination of Effects of Synthesized Compounds on Cancer Cell Proliferation. Cancer cells (breast cancer cell lines MCF-7 and MDA-MB-231, pancreatic cancer cell lines AsPC-1 and Panc-1) were seeded in 96-well plates at a density of 2×10$^3$ cells/well and treated with DMSO, 0.01, 0.1, 1, 5, 10, and 100 µM of individual STAT3 inhibitors for 72 h. Proliferation was measured by treating cells with the 3-(4,5-dimethylthiazol-2-yl)-5-(3-carboxymethoxyphenyl)-2-(4-sulfophenyl)-2H-tetrazolium) (MTS) in a CellTiter 96t Aqueous Non-Radioactive Cell Proliferation Assay kit (Promega, Madison, Wis., USA). Absorbance of all wells was determined by measuring OD at 550 nm after 1 h incubation at 37° C. on a 96-well iMark™ Microplate Absorbance Reader (BioRad, Hercules, Calif.). Each individual compound was tested in quadruplicate wells for each concentration.

Molecular Docking Studies. Compound 5 was docked with the STAT3-SH2 domain using the X-ray structure (PDB code: 1BG1) and AutoDock Vina 1.1.2. Water molecules within the crystal structure were removed and polar hydrogens were added using AutoDockTools. The protein was treated as rigid. Docking runs were carried out using the standard parameters of the program for interactive growing and subsequent scoring, except for the parameters for setting grid box dimensions and center. For all of the docking studies, a grid box size of 30 Å×30 Å×30 Å, centered at coordinates 100.452 (x), 75.972 (y), and 68.790 (z) of the PDB structure.

Transient Transfection and Dual Luciferase Reporter Assays. MBA-MB-231 cells were seeded in 24-well plate at a density of 5×10$^4$ cells/well in RPMI-1640 medium containing 10% FBS and 1% penicillin-streptomycin. Transient transfections were performed 4 h after plating, using the method described previously (Rees, D. C. et al., 2004; Shen, Q. et al., 2008). Total amount of DNA for transfections was 0.5 µg/well, including pSTAT3-Luc (95%, obtained from Panomics, Cat# LR0077) and internal control vector renilla (5%, from Promega, Madison, Wis., USA). 5 h after transfection, the cells were treated with compound 5 for 24 h, then reporter activity was evaluated using dual luciferase reporter assay kit (Promega, Madison, Wis., USA) on an Omega™ Microplate Luminometer (BMG LABTECH Inc., NC, USA). Relative luciferase units were the ratio of the absolute activity of firefly luciferase to that of renilla luciferase. Experiments were conducted with triplicates and results are representatives of at least 3 independent experiments.

Western Blot Analysis. Protein levels were determined by Western blot using the previously described methods (Shen, Q. et al., 2008). Total cell lysates were prepared from MDA-MB-231 cells. Protein concentrations were measured using the BCA Protein Assay Reagent (Pierce, Rockford, Ill., USA). Equal amounts of total cellular protein extract (40 µg) were resuspended in denaturing sample loading buffer (0.5 M Tris-HCl, pH 6.8, 10% SDS, 0.1% bromophenol blue, and 20% glycerol), separated by electrophoresis on a 10% polyacrylamide SDS-PAGE gel and then electrophoretically transferred to a nitrocellulose membrane (Thermo Scientific, Ill., USA) at 100 Volts for 1 h at 4° C. The membrane was then incubated in a blocking solution containing 5% non-fat milk and 1% Tween 20 in TBS for 1 h. The membrane was then incubated with antibodies specific for: phospho-STAT3-pY705 (1:3000, Epitomics, #2236-1), STAT3 (1:2000, Cell Signaling, #4904), Caspase-3-cleaved (1:2000, Epitomics, #1476-1), Cyclin D1 (1:10000, Epitomics, #2261-1) and β-actin (1:10000, Sigma, clone AC-15). An anti-rabbit or anti-mouse secondary antibody (Amersham, Piscataway, N.J.) was used at 1:4000 dilution. The Western blotted bands were visualized using ECL procedure according to the manufacturer's instructions (Amersham).

In Vivo Antitumor Activity Assays. All procedures including mice and in vivo experiments were approved by the Institutional Animal Care and Use Committee (IACUC) of UT M.D. Anderson Cancer Center (MDACC). Female nude mice were obtained from MDACC and were used for orthotopic tumor studies at 4 to 6 weeks of age. The mice were maintained in a barrier unit with 12 h light-dark switch. Freshly harvested MDA-MB-231 cells (2.5×10$^6$ cells per mouse, resuspended in 100 µL PBS) were injected into the 3$^{rd}$ mammary fat pad of the mice, and then randomly assigned into 2 groups (6-7 mice per group). The mice were given 50 mg/kg compound 5 or vehicle five days per week when the tumor volume reached 200 mm$^3$. All drugs were dissolved in 50% DMSO with 50% polyethylene glycol for in vivo administration. Body weights and tumors volume were measured daily and tumor volume was calculated according to the formula V=0.5×L×W$^2$, where L=length (mm) and W=width (mm).

Statistical Analysis

Statistical significance was determined using student t-test in cell cycle analysis. * represents a p value less than 0.05.

Figure 10:
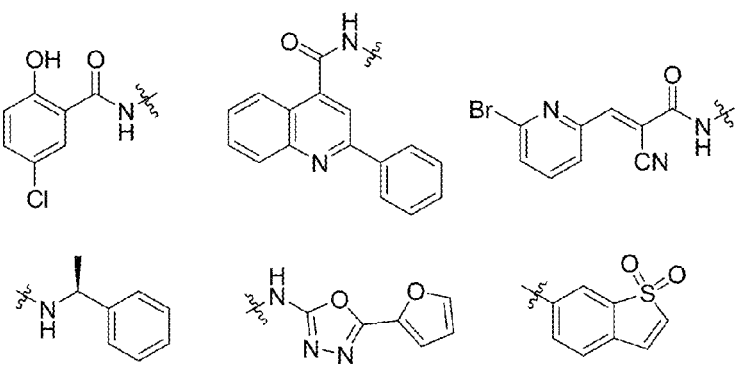
FIG. 10: Privileged fragments selected from known STAT3 inhibitors including niclosamide, STX-0119, WP1066, and stattic.

Abbreviations Used: FBDD, fragment-based drug design; STATs, signal transducers and activators of transcription; ER, estrogen receptor; HBTU, 2-(1H-benzotriazol-1-yl)-1,1,3,3-tetramethyluronium hexafluorophosphate; DIPEA, N,N-diisopropylethylamine; THF, tetrahydrofuran; SAR, Structure-Activity Relationships; RLU, Relative Luciferase Unit; MTS, 3-(4,5-dimethylthiazol-2-yl)-5-(3-carboxymethoxyphenyl)-2-(4-sulfophenyl)-2H-tetrazolium); $IC_{50}$, half maximal inhibitory concentration; PI, propidium iodide; HRMS, High-resolution mass spectrometry; HPLC, high performance liquid chromatography; TFA, trifluoroacetic acid; DMSO, dimethyl sulfoxide; TLC, thin layer chromatography; NMR, nuclear magnetic resonance; TMS, tetramethylsilane; EtOAc, ethyl acetate; DMF, dimethylformamide; PBS, phosphate-buffered saline; BCA, bicinchoninic acid; SDS-PAGE, sodium dodecyl sulfate polyacrylamide gel electrophoresis Design The inventors initiated studies with a small privileged fragment library containing six fragments selected from representative non-peptidic STAT3 inhibitors including stattic, WP1066, STX-0119, and niclosamide as potential binding pharmacophores to STAT3 (FIG. 10). The molecular weight of these fragments ranges from 120 to 251 Dalton. The inventors designed a number of novel molecules with diversified scaffolds for structure-activity relationship (SAR) studies in an attempt to identify new anticancer compounds with enhanced potency and drug-like properties.

Chemistry

As shown in Schemes 5 & 6, coupling of 1,1-dioxo-1H-1ë[6]-benzo[b]thiophen-6-ylamine (3) with cyanoacetic acid (1) or 2-phenyl-quinoline-4-carboxylic acid (2) in the presence of HBTU and DIPEA in $CH_2Cl_2$ generated the corresponding amides 4 and 5 in moderate to high yields. Condensation of L(−)-α-methylbenzylamine (7) with 2-phenylquinoline-4-carboxylic acid (2) or 5-chloro-2-hydroxybenzoic acid (6) in the same fashion provided new compounds 8 and 9, respectively. The synthesis of compound 10 was achieved in moderate yield via Knoevenagel condensation of 6-bromopyridine-2-carbaldehyde with the intermediate 4 in the presence of piperidine as the catalyst. The above mentioned coupling methods failed to give the desired compounds 12 and 13, which were successfully obtained by an alternative protocol in three steps. First, the carboxylic acid 6 was converted to the acid chloride by the treatment with $SOCl_2$ in toluene at 120° C. for 16 h. After concentration, the acid chloride, which contained some ester formed from the hydroxyl group of phenol, was used directly for next step without further purification because the hydrolysis of the ester appendage afterwards could lead to the same desired product. 1,1-Dioxo-1H-1λ[6]-benzo[b]thiophen-6-ylamine or 5-furan-2-yl-[1,3,4]oxadiazol-2-ylamine was then treated with the above acid chloride in the presence of pyridine as the base. The crude products were subsequently saponified using 1N LiOH (aq.) in THF to generate the desired compounds 12 and 13 in yield of 39% and 50% (three steps), respectively.

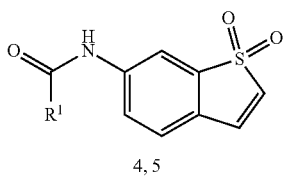

4, 5

1, 4: $R^1$ =

2, 5: $R^1$ =

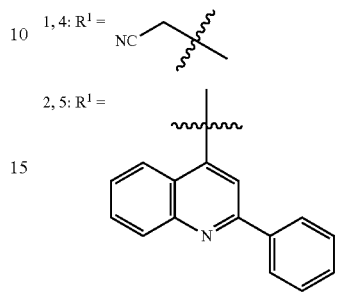

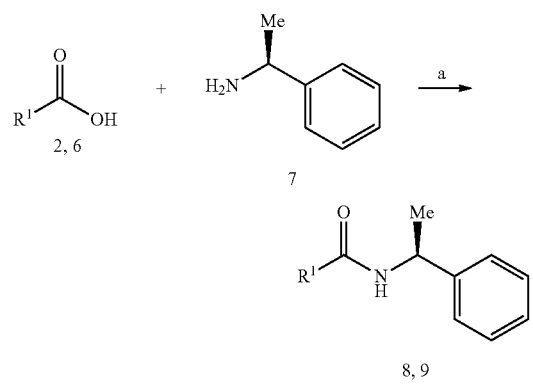

2, 6

7

8, 9

2, 8: $R^1$ =

6, 9: $R^1$ =

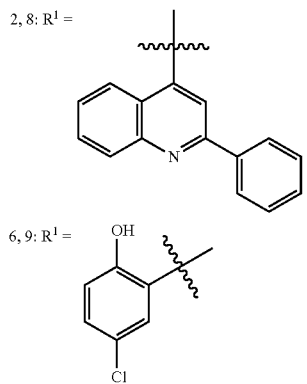

[a]Reagents and conditions: (a) HBTU, DIPEA, $CH_2Cl_2$, rt, 39-94%

Scheme 5[a]

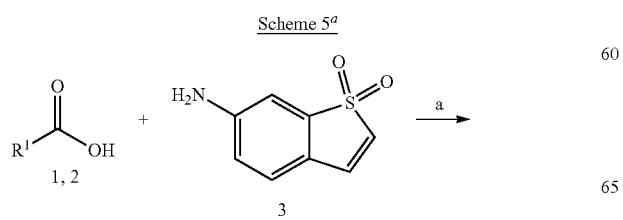

3

Scheme 6[a]

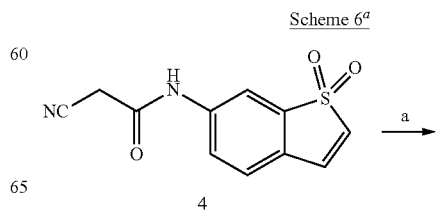

4

TABLE 4

Effects of newly synthesized compounds 4-5, 8-10 and 12-13 on proliferation of human breast and pancreatic cancer cell lines.

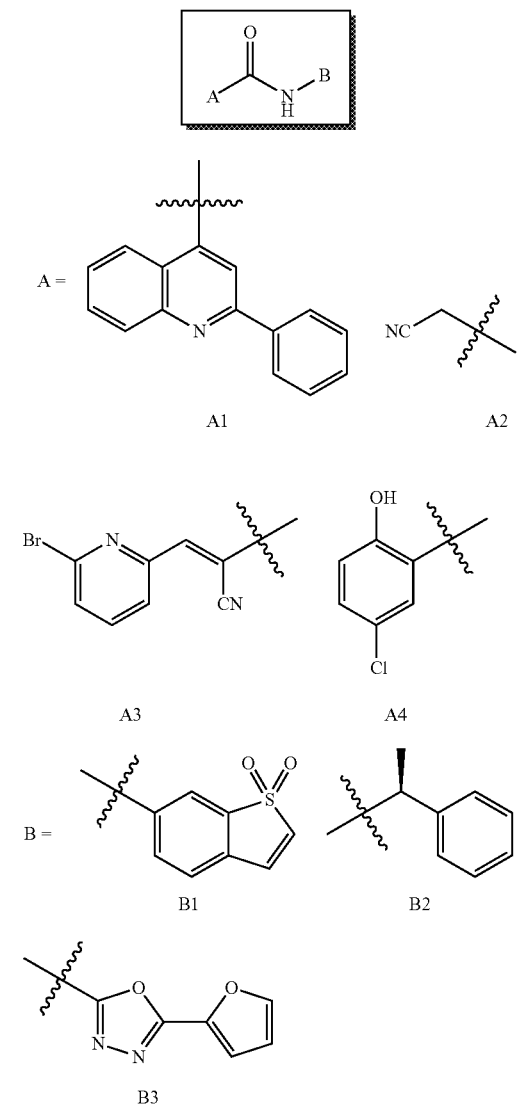

|  |  |  | IC50 (μM)[a] | | |
|---|---|---|---|---|---|
|  |  |  | Breast cancer ER Positive | Breast cancer ER-Negative | Pancreatic cancer | |
| Compound | A | B | MCF-7 | MDA-MB-231 | AsPC1 | Panc-1 |
| 4 | A2 | B1 | >10[b] | >10 | ND[c] | ND |
| 5 | A1 | B1 | 0.1 | 0.29 | 1.25 | 0.26 |
| 8 | A1 | B2 | 2.24 | 86.0 | >10 | >10 |
| 9 | A4 | B2 | 0.9 | 8.88 | 7.54 | 8.44 |
| 10 | A3 | B1 | 3.31 | 1.53 | 1.54 | 1.64 |
| 12 | A4 | B1 | 0.91 | 1.64 | 1.92 | 2.34 |
| 13 | A4 | B3 | >10 | >10 | >10 | >10 |
| niclosamide |  |  | 1.06 | 0.79 | 1.47 | 1.73 |

[a]Breast cancer cell lines: MCF-7 and MDA-MB-231. Pancreatic cancer cell lines: ASPC1 and Panc-1. Software: MasterPlex ReaderFit 2010, MiraiBio, Inc.
[b]If a specific compound is given a value >10, indicates that a specific IC50 cannot be calculated from the data points collected, meaning 'no effect'.
[c]ND: not determined.

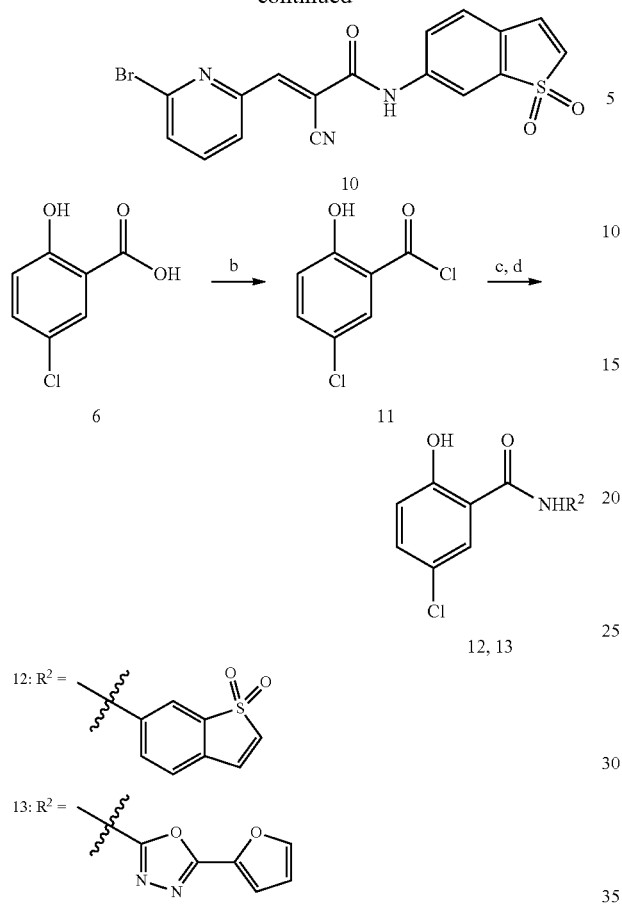

[a]Reagents and conditions: (a) 6-bromo-pyridine-2-carbaldehyde, piperidine(cat.), EtOH, 90° C., 72%; (b) SOCl$_2$, toluene, reflux; (c) R$^2$NH$_2$, pyridine, DMF, 0° C. to rt; (d) 1 N LiOH (aq.), THF, H$_2$O, 0° C. to rt, 39-50% (three steps).

Biology

To explore the SAR, the inventors first evaluated the in vitro anticancer effects of the compounds 4-5, 8-10 and 12-13 on the proliferation of human breast cancer cell lines MCF-7 (ER-positive) and MDA-MB-231 (ER-negative and triple-negative), as well as pancreatic cancer cell lines AsPC1 and Panc-1 using MTS assays as described in the Experimental Section. The ability of these new scaffolds to inhibit the growth of cancer cells is summarized in Table 4. It is noteworthy that most of the newly synthesized compounds described herein exhibited promising antiproliferative activity with low micromolar to nanomolar IC$_{50}$ values. Among them, compounds 5, 10, and 12 possessing the 1,1-dioxo-1H-1ë$^6$-benzo[b]thiophen-6-yl fragment (B1) exhibited a similar or significantly higher potency than the reference compound niclosamide. Interestingly, compound 4 containing the fragment B1 and the moiety A2 instead of the 6-bromopyridin-2-yl fragment (A3) was found inactive with a dramatic loss of antiproliferative activity in comparison with compound 10. Compounds 8 and 9 with (5)-(1-phenylethyl) amide moiety (B2) showed moderate to potent antiproliferative effects against the tested cancer cells. For example, compound 9 displayed an IC$_{50}$ value of 0.9 μM against ER-positive breast cancer cell line MCF-7. The salicylic amide compound 13 with the 5-furan-2-yl-[1,3,4] oxadiazol-2-yl moiety (B3) was found inactive, while compound 12 with the fragment B1 instead exhibited significant antiproliferative activity, indicating that fragment B1 rather than B3 is more favorable for the anticancer activity of molecules with the salicylic amide scaffold.

Figure 11:
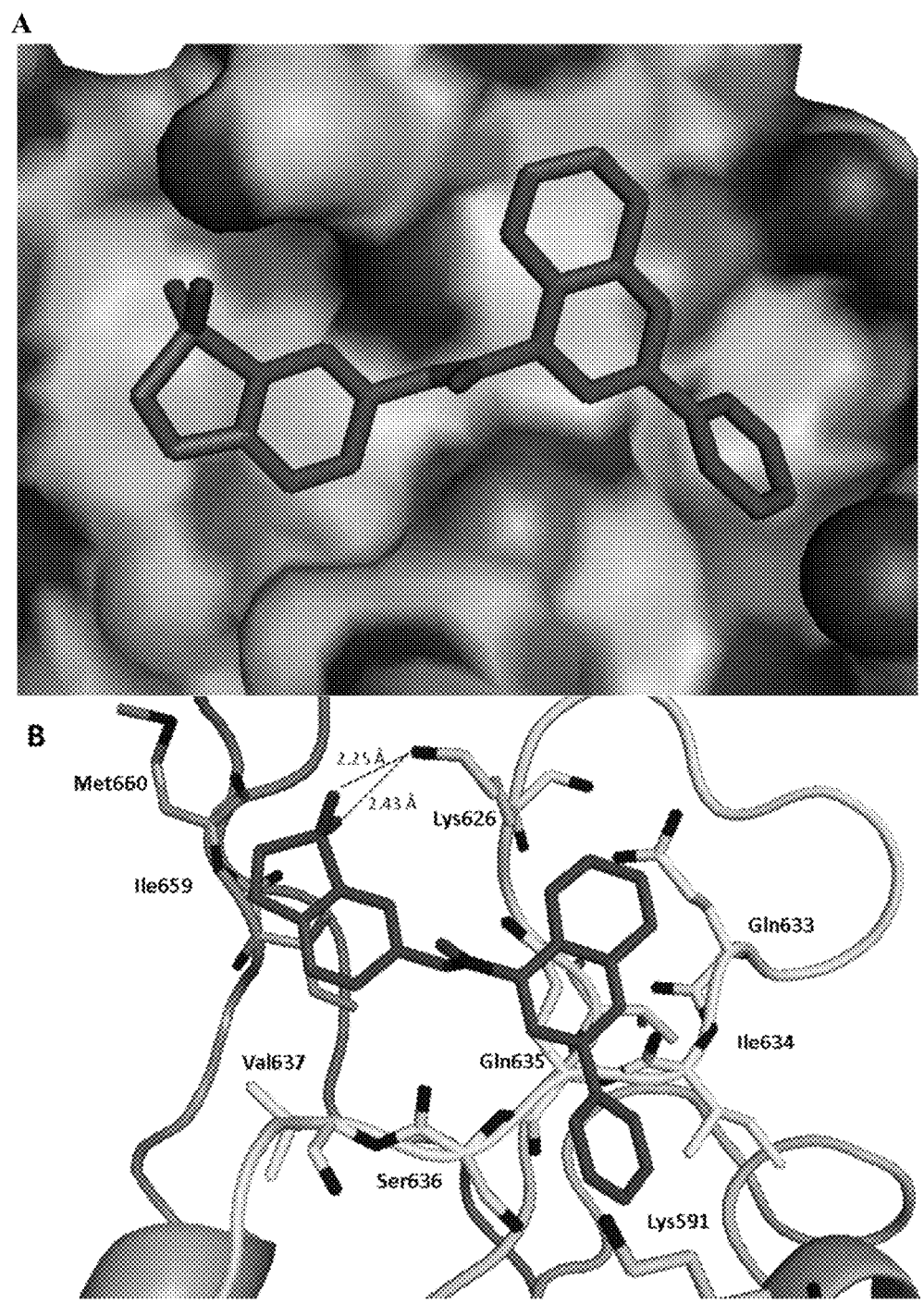
FIGS. 11A-B: Predicted binding mode for compound 5.

Among the active new scaffolds discussed above, compound 5 notably exhibited remarkable potency against all the tested cancer cells. Since STX-0119 with the 2-phenylquinoline-4-carboxylic acid amide fragment (A1) (Matsuno, K. et al., 2010; Song, H. et al., 2005) and stattic with the 1,1-dioxo-1H-1ë[6]-benzo[b]thiophen-6-yl fragment (B1) (Schust, J. et al., 2006) have been reported as the STAT3-SH2 domain inhibitors, the molecular docking studies of compound 5 with both A1 and B1 fragments were performed to investigate the possible conformations and the required spatial relationship between the scaffold and STAT3-SH2 domain (Becker, S. et al., 1998) using AutoDock Vina (Trott, O. et al., 2010) docking approach. Examination of the predicted binding model for 5 complexed with STAT3 revealed that the 2-phenyl group on the quinoline ring could fit effectively into the hydrophobic cleft around Ile634 (FIGS. 11A-B). To further verify these findings, chemical optimization of 5 was carried out to gain insights on this potential series. Additional five compounds (19-23) with different hydrophobic groups were prepared (Scheme 7), analogously to the synthesis of 4-5 described above, and their anticancer activities were evaluated in the same fashion (Table 5).

Scheme 7[a]

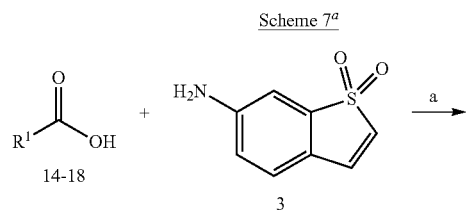

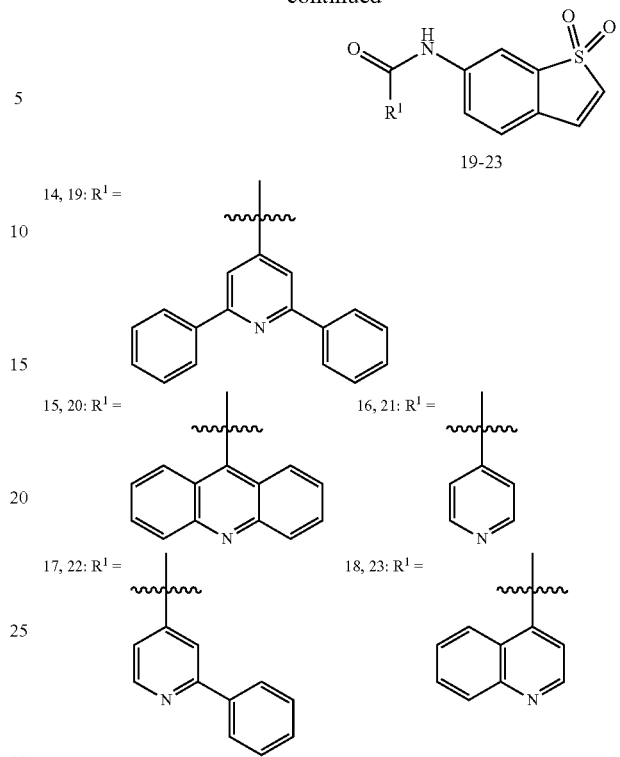

[a]Reagents and conditions: (a) HBTU, DIPEA, CH$_2$Cl$_2$, rt, 39-56%.

TABLE 5

Effects of newly synthesized compounds 19-23 on proliferation of human breast and pancreatic cancer cell lines.

| | | IC50 (μM)[a] | | | |
| --- | --- | --- | --- | --- | --- |
| | | Breast cancer ER Positive | Breast cancer ER-Negative | Pancreatic cancer | |
| Compound | R$^1$ | MCF-7 | MDA-MB-231 | AsPC1 | Panc-1 |
| 5 | | 0.1 | 0.29 | 1.25 | 0.26 |

TABLE 5-continued

Effects of newly synthesized compounds 19-23 on proliferation of human breast and pancreatic cancer cell lines.

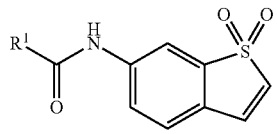

| Compound | R[1] | IC50 (μM)[a] | | | |
|---|---|---|---|---|---|
| | | Breast cancer ER Positive | Breast cancer ER-Negative | Pancreatic cancer | |
| | | MCF-7 | MDA-MB-231 | AsPC1 | Panc-1 |
| 19 | 2,6-diphenylpyridin-4-yl | 0.65 | 0.45 | 0.12 | 0.31 |
| 20 | acridin-9-yl | >10[b] | >10 | >10 | >10 |
| 21 | pyridin-4-yl | >10 | >10 | ND[c] | ND |
| 22 | 2-phenylpyridin-4-yl | 3.78 | 1.85 | 1.3 | 3.35 |
| 23 | quinolin-4-yl | 2.97 | 6.21 | 6.97 | 7.92 |

[a]Breast cancer cell lines: MCF-7 and MDA-MB-231. Pancreatic cancer cell lines: ASPC1 and Panc-1. Software: MasterPlex ReaderFit 2010, MiraiBio, Inc.
[b]If a specific compound is given a value >10, indicates that a specific IC$_{50}$ cannot be calculated from the data points collected, meaning 'no effect'.
[c]ND: not determined.

The obtained SAR results suggest that the hydrophobic substituent at C2 of the quinoline or pyridine framework is crucial for targeting STAT3. For example, compounds 20, 21 and 23 without the 2-Ph moiety displayed moderate to low antiproliferative activity against the tested cancer cells. Instead, compound 22 with 2-Ph group in contrast with compound 21 regained antiproliferative activity with low micromolar $IC_{50}$ values. Compound 19 with an additional phenyl substituent at the 6-position of pyridine ring exhibited further enhanced anticancer activity when compared with compound 22, indicating the important role of hydrophobic substituents on the quinoline and pyridine fragments.

Figure 15:
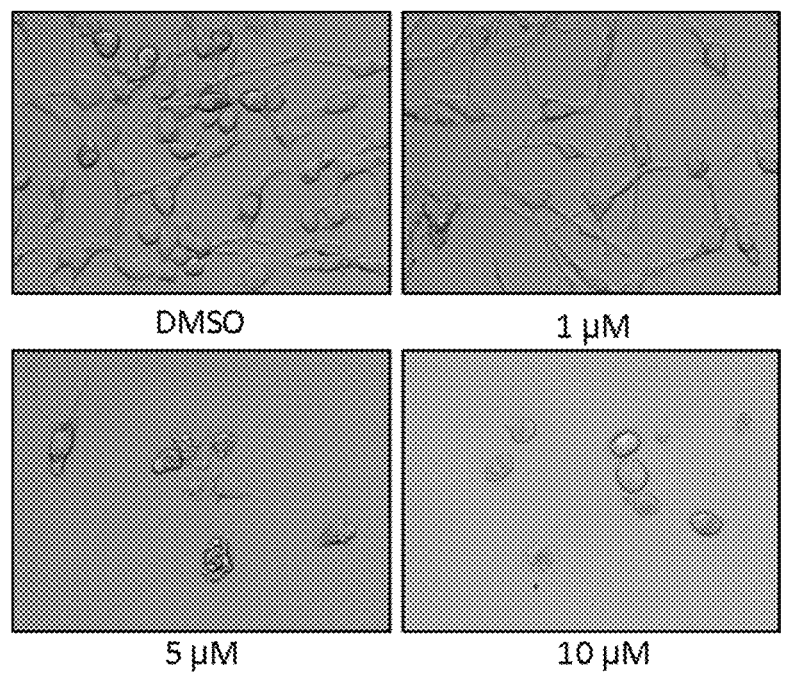
FIG. 15: Effect of 5 (HJC0123) on cell growth and cellular morphological change. Exponentially growing MDA-MB-231 breast cancer cells were incubated with HJC0123 for 48 h. Cell morphology was evaluated under light microscopy.

Through the SAR studies, compound 5 was been identified as having desirable antiproliferative activity and physicochemical parameters (see Table 6), and was subjected to further biological characterization. Cellular morphological change in MDA-MB-231 breast cancer cells treating with compound 5 for 48 h was examined under light microscopy. As shown in FIG. 15, compound 5 significantly inhibited cell proliferation and induced apoptosis accompanying cellular morphological changes in a dose-dependent manner.

TABLE 6

Physicochemical parameters[1-2] of selected novel STAT3 inhibitors

| Compound | Chemical Strcture | TPSA | cLogP | MW | HD (nOHNH) | HA (nON) |
|---|---|---|---|---|---|---|
| 5 | HJC0123 | 76.1 | 4.20 | 412.47 | 1 | 5 |
| 8 | HJC0128 | 42.0 | 5.10 | 352.437 | 1 | 3 |
| 9 | HJC0130 | 49.3 | 4.04 | 275.735 | 2 | 3 |
| 10 | HJC0371 | 99.9 | 2.63 | 416.256 | 1 | 6 |

TABLE 6-continued

Physicochemical parameters[1-2] of selected novel STAT3 inhibitors

| Compound | Chemical Strcture | TPSA | cLogP | MW | HD (nOHNH) | HA (nON) |
|---|---|---|---|---|---|---|
| 12 | HJC0149 | 83.5 | 2.88 | 335.768 | 2 | 5 |
| 19 | HJC0136 | 76.1 | 4.65 | 438.508 | 1 | 5 |
| 22 | HJC0430 | 76.1 | 2.95 | 362.41 | 1 | 5 | cLogP (Average LogP): ALOGPS 2.1 program
TPSA: molinspiration.com program

Figure 12:
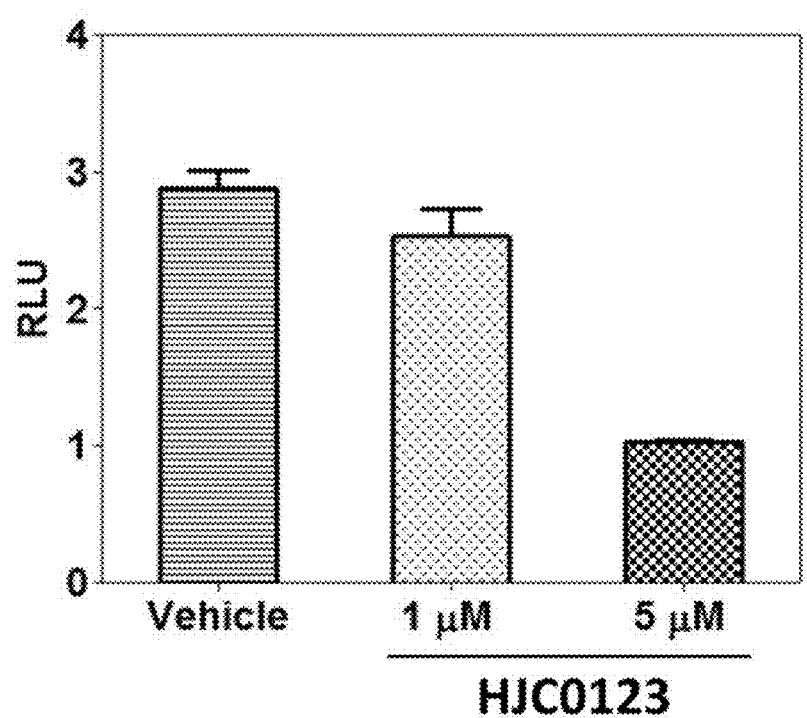
FIG. 12: Compound 5 (HJC0123) inhibited the STAT3 mediated luciferase reporter activity in MDA-MB-231 cells. STAT3 promoter activity was measured using dual luciferase assay with a STAT3 reporter. Promoter activity obtained from DMSO-treated MDA-MB-231 cells was used as control. Error bars represent standard deviation of triplicate wells. Representative experiment from at least 3 independent experiments is shown. RLU: Relative Luciferase Unit.

To determine whether compound 5 acts as a potent small-molecule inhibitor of STAT3 activation, the inventors measured the effect of 5 on promoter activity using the cell-based transient transfection and dual luciferase reporter assays. The STAT3 promoter activity in MDA-MB-231 cells was determined after transient transfecting with pSTAT3-Luc vector. As shown in FIG. 12, treatment with 5 μM of compound 5 inhibited the STAT3 promoter activity in MDA-MB-231 cells by approximately 65% compared with control.

Figure 13:
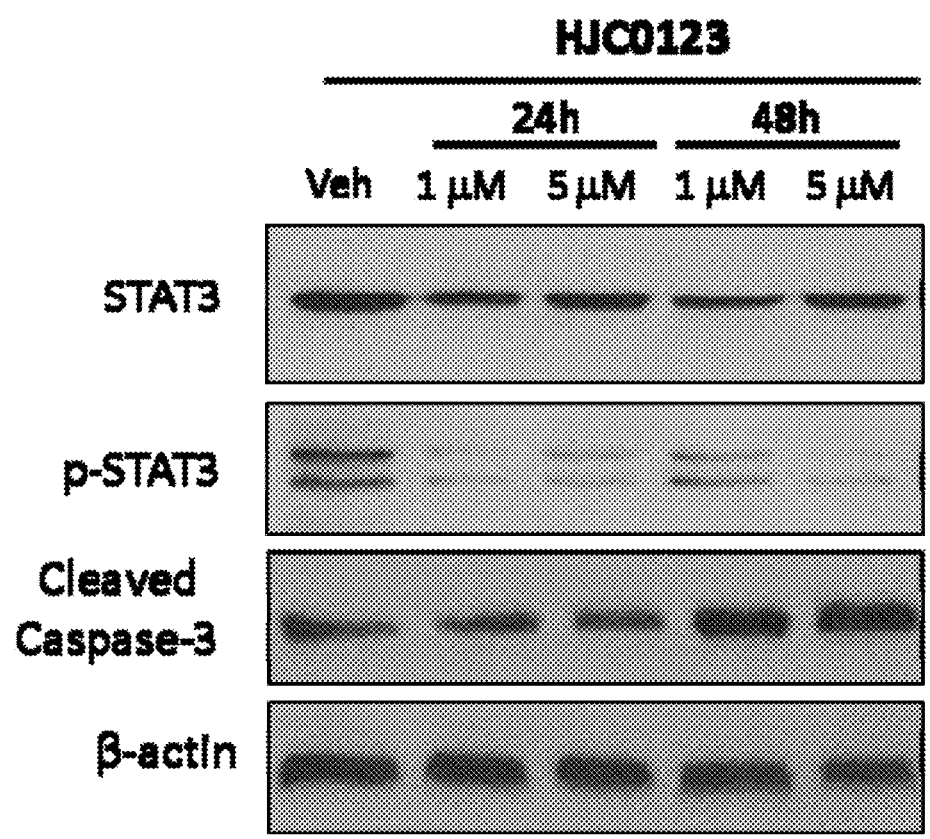
FIG. 13: Western blot analysis of biochemical markers for apoptosis induction and inhibition of STAT3 activity by compound 5 (HJC0123) in the MDA-MB-231 cell line. Cells were treated with compound 5 for 24 h and 48 h, and levels of STAT3, pSTAT3, cleaved caspase-3 were probed by specific antibodies. β-actin was used as the loading control.

To further investigate the inhibitory activity of compound 5 against the STAT3 pathway, the inventors examined STAT3 phosphorylation and expression of the known STAT3 target genes in MDA-MB-231 cell line. The cells were treated with different doses of compound 5 for 24 h and 48 h, and levels of total STAT3 and phosphorylated STAT3 at Tyr-705 were then examined by Western blot. It was found that the total STAT3 expression in these cells was reduced after the treatment with compound 5 (FIG. 13). Similarly, phosphorylated STAT3 at Tyr-705 was suppressed by compound 5. Blocking STAT3 signaling in many different tumor cells leads to growth arrest and apoptosis (Turkson, J. et al., 2000; Siddiquee, K. et al., 2007; Catlett-Falcone, R. et al., 1999; Bromberg, J., 2002; Zhang, X. et al., 2012). To investigate whether compound 5 induces apoptosis, the inventors first determined its ability in inducing cleaved caspase 3 in MDA-MB-231 breast cancer cells. As shown in FIG. 13, compound 5 induced a higher cleaved caspase-3 level in MDA-MB-231 cells, supporting the idea that compound 5 promoted the apoptosis of cancer cells. The inventors further confirmed these results using annexin V-based measurement using flow cytometry. As depicted in FIGS. 16A-B, compound 5 activated apoptosis in MDA-MB-231 breast cancer cells in a dose-dependent manner. Further flow cytometry analysis revealed that compound 5 arrested MDA-MB-231 cells at S phase in a dose-dependent manner (FIGS. 17A-B). These results support the idea that compound 5 was conferred the ability to arrest cells. The more extensive mechanism studies on compound 5 including STAT3 upstream targets and related signaling pathways may be performed.

Figure 14:
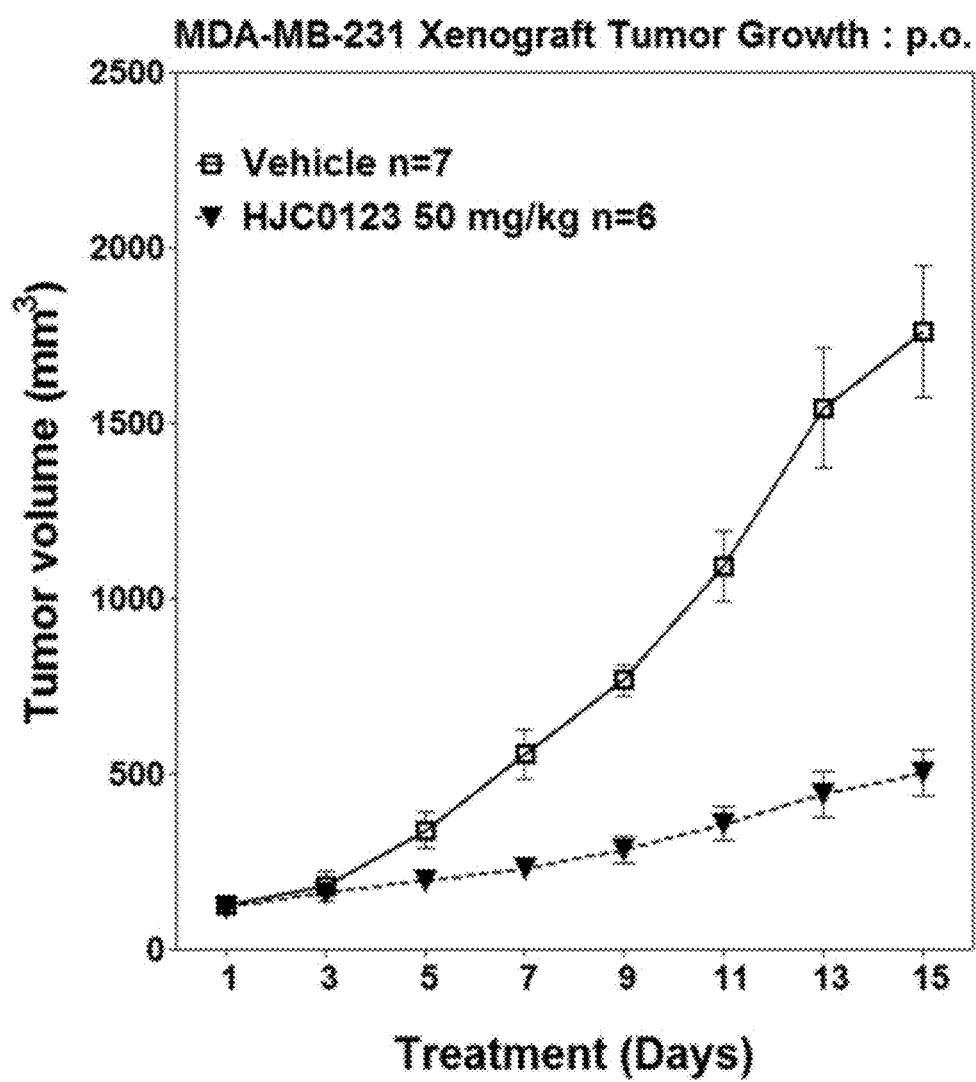
FIG. 14: In vivo efficacy of compound 5 (HJC0123) in inhibiting growth of xenograft tumors (Breast cancer MDA-MB-231) in mice (p.o.).

Compound 5 was next evaluated for its antitumor activity in inhibition of tumor growth in the MDA-MB-231 xenograft model. MDA-MB-231 xenograft tumors were developed in immunodeficient nude mice and tumor volume was measured daily in oral gavage (p.o.) group. The inventors treated the MDA-MB-231 xenograft mice through oral administration of compound 5 (50 mg/kg) and found that the growth of xenograft tumors in mice was significantly suppressed by compound 5 (FIG. 14). Notably, compound 5 did not show significant signs of toxicity even at the dose of 150 mg/kg. These results have demonstrated that compound 5 is a potent, efficacious and orally bioavailable anti-cancer drug candidate that is promising for further clinical development.

Systematic chemical synthesis and pharmacological evaluation of these scaffolds as potent anticancer agents was carried out by utilizing six privileged fragments from STAT3 inhibitors. Several molecules such as compounds 5, 12, and 19 were identified and characterized. Compound 5 was observed to have remarkable potency and was shown to inhibit STAT3 promoter activity, down-regulate phospho-STAT3, increase the expression of cleaved caspase-3, inhibit cell cycle progression, and promote apoptosis in breast and pancreatic cancer cells with low micromolar to nanomolar $IC_{50}$ values. Furthermore, compound 5 significantly suppressed ER-negative breast cancer MDA-MB-231 xenograft tumor growth in vivo (p.o.), indicating that it may be used as an efficacious and orally bioavailable drug candidate for human cancer therapy.

Example 5

Orally Active Small-Molecule STAT3 Inhibitor HJC0152 Exhibits Potent Anticancer Activity and Suppresses the Growth of Triple-Negative Breast Cancer Xenograft Tumors Materials and Methods Cells and Reagents: Breast cancer cell lines MDA-MB-231, HCC1569, and BT474 were maintained in RPMI-1640 medium (Cellgro, Va.); MDA-MB-468, MDA-MB-453, T47D, and MCF-7 in DMEM (Cellgro, Va.) supplemented with 10% heat-inactivated fetal bovine serum (Cellgro, Va.) and 1% penicillin streptomycin (Sigma, MO); and SKBr3 in McCoy's 5A medium (Cellgro, Va.). Human mammary epithelial cells (HMEC) were maintained in a serum-free medium MEBM (Lonza, Allendale, N.J.) containing MEGM SingalQuotes. MCF10A cells were maintained in DMEM/F12 HAM (Sigma, MO) containing 5% horse serum, 20 ng/mL EGF, 100 ng/mL cholera toxin, 10 ng/mL insulin, and 500 ng/mL hydrocortisone. IL-6 was obtained from Cell Signaling Inc. (#8904, Cell Signaling, MA). Niclosamide was obtained from Spectrum Inc. (NJ, USA), and compound HJC0152 was synthesized in house (Chen, H. et al., 2013).

Cell Proliferation Assay and Morphological Changes: Breast cells (MDA-MB-231, MCF10A, and HMEC) were seeded in 96-well plates at a density of $1\times10^4$ cells/well in 100 µL culture media and treated with DMSO; or 1, 5, and 10 µM of individual STAT3 inhibitors. Proliferation was measured by treating cells with 3-(4,5-dimethylthiazol-2-yl)-5-(3-carboxymethoxyphenyl)-2-(4-sulfophenyl)-2H-tetrazolium, MTS) from a CellTiter 96t AQueous Non-Radioactive Cell Proliferation Assay Kit (Promega, Madison, Wis.). Absorbance was determined by measuring OD at 560 nm after 1 h incubation at 37° C. on a 96-well plate reader. Each compound was tested in quadruplicate wells for 3 concentrations. For comparison of morphological changes, MDA-MB-231 cells were seeded in 6-well plates at a density of $2\times10^5$ cells/well and maintained in RPMI-1640 medium overnight at 37° C. in a humidified atmosphere of 95% air and 5% $CO_2$. The cells were then treated with vehicle or individual compounds. Growth media was removed 48 h after treatment and replaced with 1xPBS. Images were taken using Olympus BX41 microscope.

Colony Formation Assay: MDA-MB-468 and MDA-MB-231 cells were seeded in 6-well plates with a density of 800-3000 cells/well, respectively. After 24 h, the cells were treated with HJC0152, niclosamide (0.625 µM, 1.25 µM, 2.5 µM, 5 µM and 10 µM), or DMSO as vehicle. The culture media with the compounds were changed every 72 h. After two weeks, the wells were washed twice with PBS buffer and 2 mL of 0.01% crystal violet staining buffer was added and incubated for 10 min. The wells were then washed with PBS for 5 min for three times, and allowed to dry. Photographs were then taken and the density of the entire culture well area was digitally measured using the GelCount™ instrument (Oxford Optronix, UK). Experiments were performed in triplicate and the density data were analyzed with one-way ANOVA using GraphPad Prizm 6 software. Error bars represent standard deviation.

Transient Transfection of STAT3 Expression Vector: Transient transfection was conducted using Fugene HD reagent (Invitrogen, N.Y., USA) per manufacturer's instructions. Briefly, MDA-MB-453 and BT474 cells were seeded in 100 $mm^2$ culture dishes and incubated overnight. Culture medium was changed to FBS free media 1 h prior to transfection, and 15 µg STAT3C over-expression vector (#24983, Addgene, Mass., USA), 45 µL Fugene HD together with 879 µL opti-MEM (Invitrogen, N.Y.) was added into each dish. Eight hours after transfection, the media was removed and changed to regular media containing 10% FBS. Twelve hours later, cells were treated with either 10 µM HJC0152 or vehicle as designated. After 12 h treatment, total cell lysates were collected and proceeded to Western blot analysis.

Western blot analysis: Total cells and tissue lysates were prepared using the methods described previously (Chen, H. et al., 2013a; Chen, H. et al., 2013b). Antibodies from Epitomics (Burlingame, Calif.) were used for: STAT1 (#ab109320, phospho-STAT1(Y701)(#ab109457), phospho-STAT1 (S727)(#ab109461), STAT2(#ab134192), phospho-STAT3 (Y705)(#2236-1), phospho-STAT3(S727) (#ab32143), STAT4(#ab68156s), STAT5 (#32043), phospho-STAT5a(Y694)(#32364), phospho-STAT5a(S726) (#ab128896), STAT6 (#ab32108), cyclin D1(#2261-1), PARP1(#1072-1), cleaved PARP1(#1072-1), JAK1 (#ab133666), phosphor-JAK1(pY1022)(#ab38519, JAK2 (#ab108596), and phosphor-JAK2(pY1007+pY1008) (#ab68268). Antibodies from Cell Signal Inc: STAT3 (#4904s), cleaved caspase3(#9661s), and Bcl-xl (#ab2764). Mcl-1(#S-19) was purchased from Santa Cruz (Santa Cruz, Calif.), and β-actin (#AC-15, Sigma, MO).

IL-6 Induction of STAT3 Phosphorylation and Nuclear Translocation: A total of $5\times10^4$ MDA-MB-231 cells were seeded into each well of the chamber slides (#154526, Thermo, N.Y.) and cultured overnight. Cells were starved up to 24 h prior to the designated drug treatment. The cells were then treated with vehicle (0.1% DMSO) or HJC0152 at 5 or 10 µM concentrations for 6 h. After stimulation with IL-6 (50 ng/mL) for 1 h, the culture media were aspirated and followed by DPBS (Gibco, Auckland, NZ) wash twice. Then cells were fixed with 4% paraformaldehyde for 10 min, followed by permeabilization using 100% methanol, blocking buffer for 1 h at room temperature, and incubation with primary antibodies at 4° C. overnight. After incubation with secondary antibody for 1 h, slides were stained with DAPI (Invitrogen, CA) for 5 min, and then anti-fade mounting media added to each chamber. Cells were then analyzed under immunofluorescence microscope with laser-scanning confocal imaging system (Nikon TS100F).

Cell Cycle Assay and Apoptosis Assay: Cell cycle and apoptosis kits (#MCH100106 and #MCH100105, Millipore, Mass.) were used. MDA-MB-231 cells were incubated in 6-well plates ($2.5\times10^5$/well) in 2 mL culture media, treated with DMSO, niclosamide or HJC0152 at different concentrations. 24 and 48 h after drug treatment, both adherent and floating cells were collected, washed once with PBS and fixed in cold ethanol for at least 4 h before cell cycle analysis. The fixed cells were then washed twice with PBS and resuspended in 200 µL cell cycle detection reagent, incubated for 30 minutes in dark at room temperature. Cell cycle distribution was measured by the Muse Cell Analyzer with Muse™ Cell Cycle. Similarly, MDA-MB-231 cells with the same treatments were prepared for apoptosis assay. After washing with PBS, resuspended cells were incubated with 100 µL PBS containing 1% BSA and 100 µL Annexin V and dead cell detection reagent in dark for 20 minutes at room temperature. Apoptosis was measured immediately using the Muse Cell Analyzer with the Muse™ Apoptosis Program.

Tumor Xenografts and In Vivo Treatment Experiment: All procedures including mice and in vivo experiments were approved by the Institutional Animal Care and Use Committee of MD Anderson Cancer Center. Twenty-two female nude mice (8 wks of age) were obtained from MDACC ERC Center. Mice were maintained in a barrier unit with 12 h light-dark switch. Freshly harvested MDA-MB-231 cells were injected into the 3rd mammary fat pad of each mouse ($2.5 \times 10^6$ cells per mouse, resuspended in 100 µL PBS), and the mice were then randomized (5-10 mice/group). Mice were given 25 mg/kg of HJC0152, 75 mg/kg of niclosamide, or vehicle daily for a total of 14 days by oral gavage, starting when the tumor volume reached approximately 100 $mm^3$. All drugs were solubilized in 50:50/DMSO:Poly ethylene glycol. Body weights and tumors volume were measured daily and tumor volume calculated using the formula $V=0.5 \times L \times W^2$, where L=length (mm) and W=width (mm) of xenograft tumors. Signs of toxicity were recorded individually. Experimental mouse was sacrificed when a tumor reached 1.5 cm in diameter or at the end of experiments. Lung, colon, stomach, heart, brain, kidney, liver, and tumor tissues were collected and fixed in 4% formalin overnight, paraffin embedded and sectioned for H&E staining or immunohistochemical staining (IHC).

Immunohistochemistry (IHC): Paraffin blocks of the collected tissue were sectioned into 4 µm thickness and stained with H&E as a reference. All slides were subjected to phospho-STAT3 (Y705) IHC with ABC staining method. Rabbit or mouse IgG ABC kit was purchased from Vector Laboratories (Burlingame, Calif., USA) and ABC staining reagents were purchased from Sigma Aldrich (Louis, Mo., USA). PBS was used instead of primary antibody as a negative control.

RPPA and Bioinformatics Analysis: MDA-MB-231 cells were seeded into 6-well plates at a density of 50% confluence overnight. Cells were treated the following day with either 10 µM of HJC0152 or vehicle for 6 h when the cells reached 80% confluence. At the designated time points, culture media was aspired, dishes washed with chilled PBS buffer twice, and then 150 µL of cell lysate buffer (1% Triton X-100, 50 mM HEPES, pH 7.4, 150 mM NaCl, 1.5 mM $MgCl_2$, 1 mM EGTA, 100 mM NaF, 10 mM Sodium pyrophosphate, 1 mM $Na_3VO_4$, 10% glycerol) added (containing protease and phosphatase inhibitor). Supernatant was collected after 20 min of incubation with occasional shaking, after centrifuging at 13,300 rpm for 10 min at 4° C. Protein concentrations were determined using a BCA kit (Piece, Calif.). The protein concentrations were adjusted to 1 µg/µL in the lysates and 40 µg of protein used for RPPA analysis at the CCSG Core of MD Anderson Cancer Center. Briefly, samples were printed onto slides in five two-fold-serial dilutions (from undiluted to 1:16 dilution). Validated primary antibodies were used to probe the tissue sections and the signal was amplified by a secondary antibody, until a stable dye was precipitated (Spurrier, B. et al., 2008). Quantified data were produced from the stained slides using Microvigene® software (Vigene Tech, Carlisle, Mass.). All samples were probed with 167 validated antibodies.

Statistical analysis of RPPA data: Relative protein levels for each sample were generated from the 5 serial dilutions by Supercurve algorithms (Hu, J. et al., 2007). Normalization was the most important step in data analysis (Cai, G. et al., 2012), and quantile normalization was applied to raw values (Bolstad, B. M. et al., 2003). Analysis using unbiased clustering was performed on antibodies but with samples kept in order. $Log_2$ signals were centered by median and scaled to standard Z scores on antibodies and clustering was based on Pearson correlation distance. Differential expression of proteins was assessed using standard two sample t tests. And the false discovery rate (FDR) control was performed to account for multiple comparison adjustment (Benjamini, Y. et al., 1995). A p-value of less than 0.05 was considered significant. Comparing two conditions S1 and S2, for gene i, M (log ratios) was calculated as $M_i = \log_2 S1_i - \log_2 S2_i$ and A (mean average) was calculated as $A_i = \frac{1}{2}(\log_2 S1_i + \log_2 S2_i)$. To determine pathways and networks that were significantly regulated between conditions, the top 20 differentially expressed genes were selected as described in Table 7 and Table 8 and performed pathway enrichment analysis using Ingenuity Pathway Analysis (IPA) software. Top enriched networks, diseases and disorders, molecular and cellular functions, and physiological system development and function were identified from IPA analysis.

To search the STAT3 binding site(s) for the genes in Table 9, the UCSC Genome Browser was used. The UCSC Genome Browser is developed and maintained by the Genome Bioinformatics Group, a cross-departmental team within the Center for Biomolecular Science and Engineering (CBSE) at the University of California Santa Cruz (UCSC).

Statistical Analysis: Statistical analysis was performed on mean±standard error values of three independent experiments using GraphPad Prism 5 Software. The significance of differences between groups was determined by comparing student's t test at *P<0.05, P<0.01, and *P<0.005, 2-sided. For xenograft tumor growth experiment, ANOVA was used to compare the statistical difference of treatment with vehicle, HJC0152 or niclosamide.

Differential Expression of STAT3 and its Phosphorylation Status Among ER-Negative and ER-Positive Breast Cancer Cells.

As described in the above examples, the inventors found that HJC0152 (chemical structure shown in FIG. 18A) significantly inhibited activation of STAT3 and down-regulated STAT3 total protein level. To further characterize the effect of HJC0152 on STAT3 phosphorylation, the inventors first examined STAT3 protein level and its phosphorylation status in ER-negative and ER-positive breast cancer cells. STAT3 protein was expressed at variable levels among ER-positive and ER-negative breast cancer cells, while activated STAT3 was shown in MDA-MB-231, MDA-MB-468, HCC1569, SKBR3, MCF-7 and T47D cells, with lower level of pSTAT3 in MDA-MB-453, T47D or BT474 cells (FIG. 18B), supporting the idea that basal subtype breast cancer cells have a high STAT3 activation.

HJC0152 Inhibits IL-6 Induced STAT3 Phosphorylation and Nuclear Translocation.

To determine whether HJC0152 affects STAT3 and its phosphorylation in cells with forced STAT3 expression, STAT3-expressing vector was transiently transfected into breast cancer cells that have lower STAT3 protein levels. As shown in FIG. 18C, MDA-MB-453 and BT474 cells present lower level of pSTAT3. Forced expression of STAT3 increased STAT3 and pSTAT3 levels, and treatment of HJC0152 significantly decreased STAT3 and pSTAT3 levels. HJC0152 demonstrated stronger inhibition on pSTAT3 at the 5727 versus the Y705 residue in MDA-MB-453 cells, while both phosphorylation sites were inhibited in BT474 cells.

To determine whether HJC0152 suppresses IL-6-induced STAT3 phosphorylation and nuclear translocation, MDA-MB-231 cells were stimulated with IL-6 for 1 h and observed enhanced nuclear translocation of pSTAT3, while HJC0152 treatment for 6 h blocked the IL-6 induced nuclear translocation (FIG. 18D). These results support the idea that HJC0152 effectively reduces protein level of STAT3 and pSTAT3, and inhibits IL-6-induced pSTAT3 nuclear translocation.

Dynamic Alterations of STAT3 Phosphorylation in Triple-Negative Breast Cancer Cells after Treating with HJC0152.

To determine the dynamic patterns in protein level after treating with HJC0152, MDA-MB-231 and MDA-MB-468 cells were treated for 3, 6, 12, and 24 h with a single administration of HJC0152 or niclosamide, which served as the lead compound for HJC0152 synthesis. In MDA-MB-231 cells, HJC0152 significantly decreased pSTAT3 at Y705 residue at 6 h of treatment but gradually recovered at 24 h of treatment, while S727 residue showed a continuous inhibition to 24 h. Apoptotic marker cleaved caspase 3 was induced at 12 h of treatment, while the apoptotic protein Mc1-1 showed a decrease starting from 6 h of treatment. The expression of Bcl-xl protein and cyclin D1 was not altered for 24 h of treatment, while 72 h of treatment decreased cyclin D1 significantly as reported by the inventors (Chen, H. et al., 2013a; Chen, H. et al., 2013b), suggesting that cyclinD1 might be indirectly regulated. Other STAT proteins were next examined and it was found that there were no significant changes for STAT1 and active STAT1 at Y701 or S727 residues, and STAT2, STAT4 and STAT6 showed minimal changes after HJC0152 treatment. STAT5 showed a transient decrease at 6 h with 5 and 10 μM of HJC0152 treatment, and recovered at 12 h and beyond. The pSTAT5 showed moderate decrease at 12 and 24 h with 5 and 10 μM of HJC0152 treatment. The expression of JAKs positioned upstream of STAT3 were also examined. There were no changes in JAK1 or pJAK1 (Y1022). However, starting from 6 h of HJC0152 treatment, analysis of JAK2 and pJAK2 (Y1007 & Y1008) showed apparent down-regulation of protein with 5 μM and 10 μM of HJC0152 treatment (FIG. 19A).

Similarly, MDA-MB-468 cells showed down-regulation of STAT3 and pSTAT3 starting at 3 h and maximized to 24 h of HJC01152 treatment (FIG. 19B). Cleaved PARP1 was induced from 6 h, while Bcl-2 and cyclin D1 showed decreased level from 6 h of HJC0152 treatment. While STAT1 showed minimal changes, pSTAT1 at Y701 and S727 residues showed down-regulation starting at 6 h with high concentration of 10 μM of HJC0152. STAT5 and pSTAT5 (Y694) showed a decreased level starting at 12 h of treatment with 5 μM HJC0152. In addition, JAK1 protein showed decreased level at 12 h and 24 h of HJC0152 treatment, while pJAK1 deceased starting at 3 h of treatment, peaked at 12 h and moderately recovered at 24 h of HJC0152 treatment. JAK2 and pJAK2 showed transient down-regulation at 12 h then recovered at 24 h of HJC0152 treatment, while JAK3 showed minimal alterations. These results demonstrate that HJC0152 mainly suppresses STAT3 and its phosphorylation at both residue sites, together with moderate inhibition of STAT5, JAK2/3 in MDA-MB-231 cells; while a wider profile of inhibition of STAT5 and JAK1, in addition to STAT3 inhibition, was seen in MDA-MB-468 cells. These results support the idea that STAT3 is the predominant target with its phosphorylation as the major targeting point. In addition, these results support the notion that TNBC cells respond towards HJC0152 treatment dynamically and differentially.

HJC0152 Inhibits Proliferation and Colony Formation, and is Well Tolerated in Normal and Immortal Mammary Epithelial Cells.

Figure 20A:
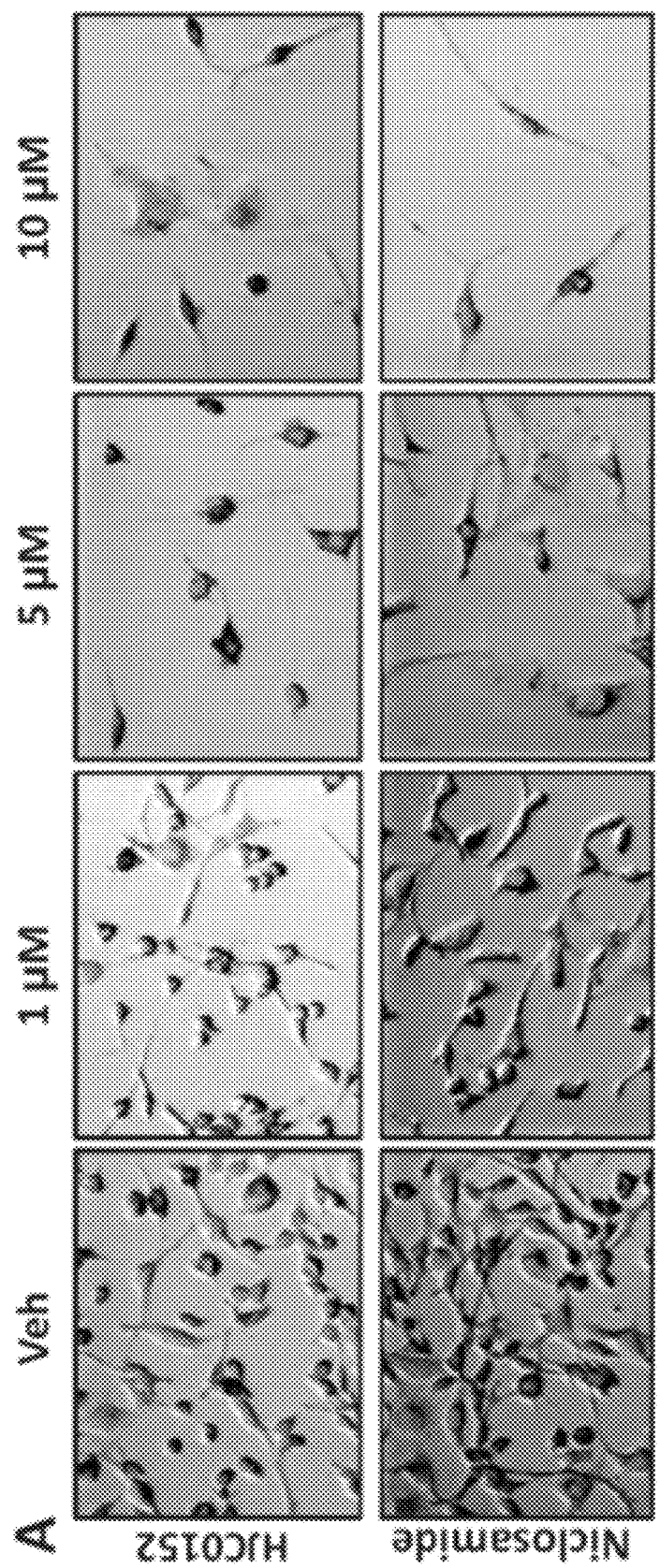
Figure 20B:
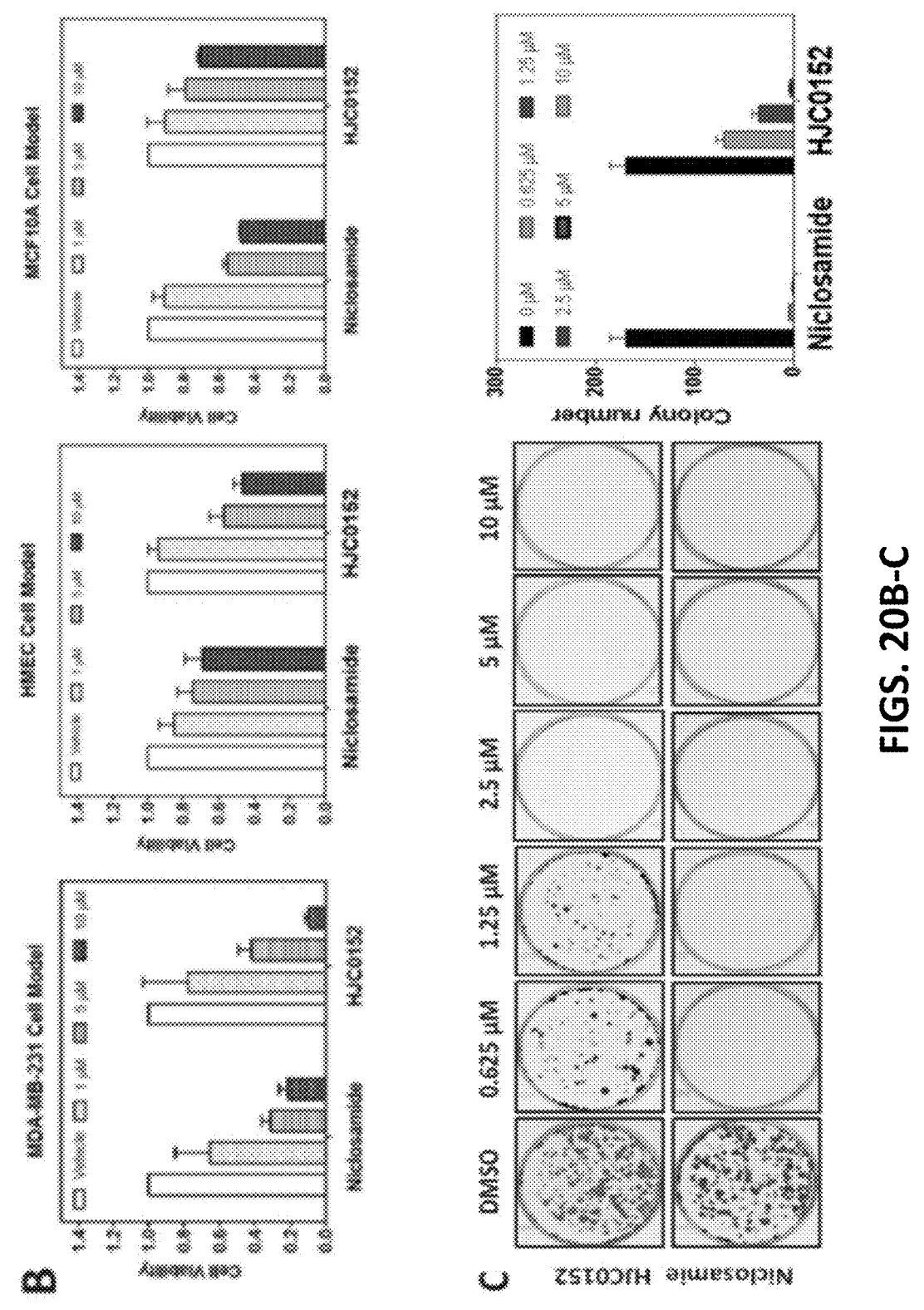

To study the effects of HJC0152 on cell growth, MTT assays were performed on HMEC, MCF-10A and MDA-MB-231 cells. The growth of MDA-MB-231 cells was suppressed in a dose-dependent manner after treating with HJC0152 and niclosamide, with similar morphological change (FIG. 20A). As shown in FIG. 20B, HJC0152 showed similar inhibition on the viability of MDA-MB-231 cells at 1 and 5 μM concentrations, more potent at a higher dose at 10 μM. However, both HMEC and MCF-10A cells showed above 50% viability compared to <15% viability in MDA-MB-231 cell after treating with 10 μM of HJC0152, supporting the idea that HJC0152 is less toxic in normal mammary epithelial cells, and thus the inventors predicted that it could be well tolerated in in vivo studies. To determine whether HJC0152 inhibits the ability of TNBC cells to form colonies, MDA-MB-231 and MDA-MB-468 cells were seeded at a low density and treated with HJC0152 or niclosamide for 15 days, both showed significant suppression of colony formation starting at a low concentration of 0.625 μM, while HJC0152 displayed a better dose-dependent response (FIG. 20C), supporting the idea that HJC0152 may have a larger dosing window for less toxicity.

HJC0152 Induces Apoptosis of TNBC Cells.

Figure 20D:
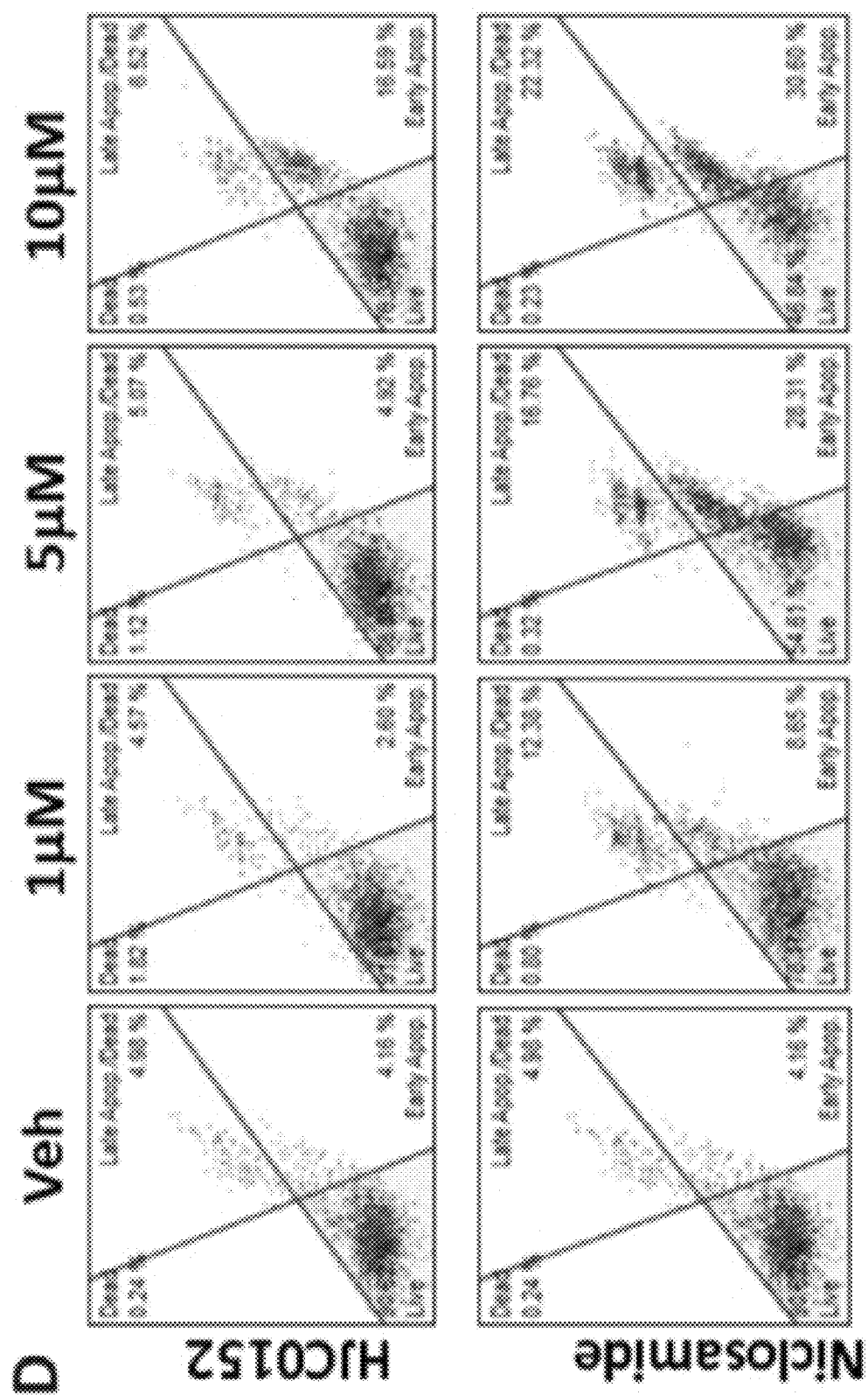

Blocking STAT3 signaling in many different tumor cells leads to induce growth arrest and apoptosis (Bromberg, J., 2002; Turkson, J., 2004; Siddiquee, K. et al., 2007; Catlett-Falcone, R. et al., 1999; Zhang, X. et al., 2012). As shown in FIGS. 19A-B, HJC0152 induced several critical apoptosis-related proteins including cleaved caspase 3, Bcl-xl, and cleaved PARP1. It was then further validated that HJC0152 induces significant apoptosis in MDA-MB-231 cells, from 8% at with 1 μM to 23% at with 10 μM concentrations (FIG. 20D). However, compared to niclosamide, the latter showed stronger induction of apoptosis in both early and late phase of apoptosis. These results support the idea that HJC0152 can induce apoptosis, in addition to its inhibitory effect on proliferation.

HJC0152 Significantly Suppresses the Growth of Xenograft Tumors Arose from TNBC Cell Line MDA-MB-231, Via Suppressing STAT3 Signaling.

To determine whether HJC0152 actually inhibits the growth of TNBC tumors, MDA-MB-231 xenograft tumors were developed in nude mice and the mice were treated with HJC0152, niclosamide or vehicle by oral gavage daily for 14 days. Tumor-bearing mice were treated with niclosamide at 75 mg/kg showed significant inhibition of tumor growth (55% reduction). At one-third of the dose of niclosamide, mice treated with HJC0152 at 25 mg/kg showed approximately 80% reduction in tumor growth. Comparing to niclosamide, HJC0152 is significantly potent in inhibiting xenograft tumor growth (p: HJC0152 vs vehicle=0.0001, niclosamide vs vehicle=0.0001, HJC0152 vs niclosamide=0.023, FIG. 21A). No toxicity signs were observed in HJC0152- or niclosamide-treated mice (FIG. 21B). The inventors observed that HJC0152 showed significant effect on reducing pSTAT3 level (Y705) as shown in (FIG. 21C). Further, both HJC0152 and niclosamide decreased STAT3 and pSTAT3 (Y705 and S727 residues), while HJC0152 has a significantly stronger effect (FIG. 21D). These results clearly support the idea that STAT3 associated signaling is a predominant target for HJC0152, and that HJC0152 may be used as an orally active anticancer agent for TNBC treatment.

Identification of Signal Molecules and Signal Transduction Pathways Mediating the Inhibitory Effect from HJC0152

To identify the signal molecules and signal transduction pathways involved after HJC0152 treatment, the protein level of 167 signal molecules was measured using RPPA analysis and a heatmap of all proteins was created. MDA-MB-231 cells were treated for 6 h for analysis. RPPA data were obtained from RPPA facility and imported into IPA software and analyzed. In Table 9, the top 20 signal proteins were identified in up-regulated or down-regulated directions are listed. Total EEF2K, cyclin D1, FoxM1, PDCD4, TEF1, p27; and active AMPK(pT172), EGFR(pY1068), NF-κB (pS536) and MEK1(pS221) were among the down-regulated proteins with statistical significance. Total Annexin VII, MEK1, MIG-6, PEA15; and active Akt(pT308 and pS473), BAD(pS112), eIF4E(pS209), p38(pT180 &Y182), and 4E-BP1(pT70) are among the top 10 up-regulated molecules. The identified genes are associated with three major signal networks: (1) cell cycle, cancer, cell morphology, (2) cancer, dermatological diseases and conditions, protein synthesis, and (3) cell death and survival, tumor morphology, and embryonic development. Cancer is the #1 disease/disorder connected to these genes, and the genes are closely related to protein synthesis, cell cycle, cell death and survival, and cell proliferation. In addition, the identified genes are also related to physiological development of hepatic, connective tissue and digestive system, and tissue and tumor morphology. Network connections for the regulated proteins are shown in Table 10. The genes and networks identified after HJC0152 treatment belong to MAPK, PI3K/Akt, PTEN, ErbB, and IL signaling pathways from IPA analysis. Taken together, HJC0152 regulates genes important to cell proliferation, apoptosis, and signal transduction pathways. The majority of the genes are direct target genes of STAT3, as these genes have STAT3 regulatory elements in the promoter region, as shown in Table. 9, supporting the idea that STAT3 is the major target of HJC0152.

TABLE 9

Down-regulated Proteins

| Gene | Protein | Function | STAT3 binding site(s) in gene promotor | M | A | p value |
| --- | --- | --- | --- | --- | --- | --- |
| PRKAA1 | AMPK_pT172 | Energy sensor protein kinase | No | 0.534205 | −0.2567 | 0.000736 |
| EEF2K | eEF2K | Protein synthesis | Yes (1) | 0.404648 | −1.36682 | 0.002087 |
| CCND1 | Cyclin_D1 | Cell cycle progression | No | 0.170533 | −0.67692 | 0.018496 |
| FOXM1 | FoxM1 | Cell proliferation | No | 0.153734 | −0.63592 | 0.021902 |
| PDCD4 | PDCD4 | Apoptosis, JNK activation | Yes (1) | 0.373667 | 0.117163 | 0.025799 |
| TFF1 | TTF1 | Not clear, expression in cancer & gastric mucose | Yes (6) | 0.096924 | −1.02753 | 0.022408 |
| EGFR | EGFR_pY1068 | Master protein kinase | Yes (24) | 0.170301 | −2.55326 | 0.040426 |
| NFKB1 | Nf-kB-p65_pS536 | Transcription regulator | Yes (1) | 0.319279 | −0.19996 | 0.041405 |
| CDKN18 | p27 | CDK inhibitor, cell cycle | No | 0.043964 | −2.1379 | 0.037485 |
| MAP2K1 | MEK1_pS217_S221 | Kinase involved in proliferation, differentiation, transcription regulation & development | Yes (4) | 0.230587 | −0.68168 | 0.047862 |

Up-regulated Proteins

| Gene | Protein | Function | STAT3 binding site(s) in gene promotor | M | A | p value |
| --- | --- | --- | --- | --- | --- | --- |
| AKT1 AKT2 AKT3 | Akt_pT308 | Protein kinase regulating metabolism, proliferation, cell survival, growth & angiogenesis | Yes (4) | −0.43522 | −1.65867 | 0.024296 |
| ANXA7 | Annexin_VII | Calcium-dependent phospholipid binding proteins, exocytosis | No | −0.1289 | 0.039204 | 0.016086 |
| BAD | Bad_pS112 | Apoptosis regulator | Yes (2) | −0.09218 | −1.5298 | 0.017081 |
| EIF4E | eIF4E_pS209 | Protein synthesis | Yes (4) | −0.25874 | −0.65622 | 0.016361 |
| MAP2K1 | MEK1 | Proliferation, differentiation, transcription regulation & development | Yes (4) | −0.11175 | −0.38455 | 0.01558 |
| ERRF11 | MIG-6 | Cell growth, negative regulator of EGFR family proteins | Yes (1) | −0.20218 | 0.35739 | 0.007262 |
| MAPK14 | p38_pT180_Y182 | Cell proliferation, differentiation, transcription regulation & development | No | −0.24499 | −0.63223 | 0.020982 |
| PEA15 | PEA15 | Regulate MAP kinase cascade & glucose metabolism | No | −0.08518 | −0.26359 | 0.025838 |
| AKT1 AKT2 AKT3 | Akt_pT473 | Protein kinase regulating metabolism, proliferation, cell survival, growth & angiogenesis | Yes (4) | −0.554 | −2.46531 | 0.033567 |
| EIF4EBP1 | 4E-BP1_pT70 | Interact with eIF-4E & mediate protein synthesis by hormones, growth factors and other stimuli that signal through the MAP kinase | Yes (1) | −0.03679 | −0.12821 | 0.051809 |

TABLE 10

Top Networks

| ID | Associated Network Functions | Score |
|---|---|---|
| 1 | Cell Cycle, Cancer, Cell Morphology | 24 |
| 2 | Cancer, Dermatological Diseases and Conditions, Protein Synthesis | 11 |
| 3 | Cell Death and Survival, Tumor Morphology, Embryonic Development | 4 |

| Name | p-value | #Molecules |
|---|---|---|
| Diseases and Disorders | | |
| Cancer | 8.60E−14-6.50E−04 | 12 |
| Hematological Disease | 3.97E−13-8.93E−04 | 13 |
| Dermatological Diseases and Conditions | 1.43E−12-8.89E−04 | 16 |
| Developmental Disorder | 3.21E−11-9.15E−04 | 17 |
| Cellular Development | 2.61E−10-9.15E−04 | 17 |
| Molecular and Cellular Functions | | |
| Protein Synthesis | 1.75E−10-2.14E−02 | 7 |
| Cell Cycle | 1.75E−10-1.99E−02 | 7 |
| Cell Death and Survival | 1.15E−08-1.89E−02 | 7 |
| Cellular Growth and Proliferation | 1.91E−08-2.04E−02 | 6 |
| Cell Death and Survival | 1.19E−07-2.09E−02 | 7 |
| Physiological System Development and Function | | |
| Hepatic System Development and Function | 3.25E−10-8.12E−04 | 7 |
| Connective Tissue Development and Function | 1.62E−08-8.93E−04 | 10 |
| Tissue Morphology | 4.05E−08-7.78E−04 | 12 |
| Tumor Morphology | 9.67E−08-9.74E−04 | 11 |
| Digestive System Development and Function | 1.06E−07-8.12E−04 | 8 |

As shown above, HJC0152 effectively inhibits STAT3 activation in STAT3-expressing cells and blocks nuclear translocation of active STAT3 in TNBC cells stimulated with IL-6, and reduces protein levels of total and phosphorylated STAT3. These changes are mediated by signal pathways associated with cell cycle, cancer, and cell morphology; protein synthesis; and cell death and survival. Thus, the results from this research support that HJC0152 may have multiple targets in signal transduction pathways, while STAT3 signaling is its major effector of its anti-cancer efficacy. The favorable aqueous solubility of HJC0152 further supports use of this compound for cancer prevention and treatment.

In xenograft tumor treatment studies, the efficacy of HJC0152 and niclosamide via oral administration was compared. Consistent with the data provided in the above examples, HJC0152 at a dose of 25 mg/kg given 5 days/week for 1-2 week(s) via i.p. or oral gavage inhibits the growth of xenograft tumors arose from MDA-MD-231 cells. The tumor-bearing nude mice were further treated with a continuous 14-day oral gavage of HJC0152 at 25 mg/kg or niclosamide at 75 mg/kg, starting the treatment when tumor volume reached approximately 100 mm$^3$. The inhibition on tumor growth with low dose of HJC0152 is significantly better than high dose of niclosamide. At 25 mg/kg dose, the mice taking oral HJC0152 maintained excellent health status without any noticeable side effects or toxicity, and the body weight maintained stable for the entire experimental period (FIG. 21B). Thus, a significantly lower dosage of HJC0152 demonstrated superior efficacy, as compared to niclosamide, in inhibiting the growth of existing xenograft tumors, without any noticeable toxicity. Orally active HJC0152 thus overcomes challenges and problems associated with use of insoluble niclosamide for the treatment of cancer, and these favorable properties of HJC0152 indicate that HJC0152 may be particularly useful for the treatment of cancer.

HJC0152 is effective and potent to suppress STAT3 activation via downregulating total STAT3 and active forms of STAT3, as demonstrated by IHC and Western blot (FIGS. 21C-D). Results from in vitro and in vivo studies reported here support the idea that STAT3 and its activation are the major target points accounting for the inhibitory effects from HJC0152. In fact, there are one or more STAT3 binding sites present in the promoter regions of STAT1 (1 binding sites), STAT3 (3), STAT5a and b (5), STAT6 (4), JAK2 (5) and JAK3 (1) (search results from UCSC Genome Bioinformatics Site and SABiosciences transcription factor search), supporting the idea that STAT3 may regulate the expression of those genes. Without wishing to be bound by any theory, this could thus explain the alterations in STATs and JAKs after HJC0152 treatment in multiple TNBC cell lines.

Figure 22:
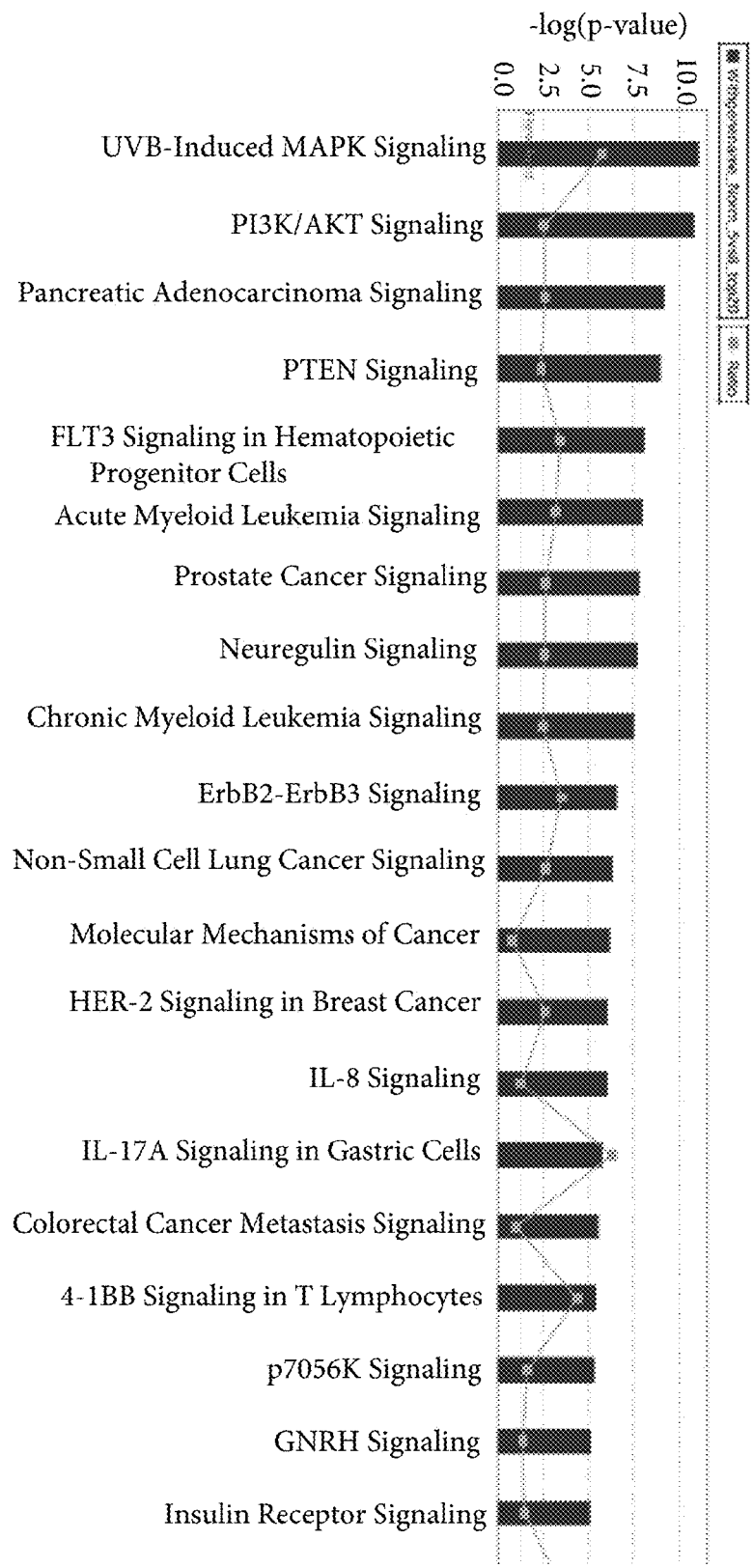
FIG. 22: Changes in cellular function group and signal transduction pathway after HJC0152 treatment. MDA-MB-231 cells were treated for 6 h as in Table 9. RPPA data were obtained from for analyzing changes in cellular functions, see method section for details. Top 20 regulated signal transduction pathways are shown according to the log p-value changes.

To evaluate the molecular networks and signal transduction pathways mediating anti-cancer effect of HJC0152, RPPA studies were performed and top regulated genes were identified in both up- and down-regulated directions. The majority of the genes identified are direct target genes of STAT3, as evidenced by the presence of STAT3 binding site(s) in their promoter regions. Particularly, AMPK, EGFR, NF-κB and MEK signaling were observed to be down-regulated, supporting the idea that the inhibitory effects of HJC0152 are mediated by these master regulators of signal transduction pathways. Without wishing to be bound by any theory, genes critical for protein synthesis and energy metabolism such as eEF2K, AMPK, eIF4E, and its binding protein 4E-BP1, and PEA15 were significantly affected, suggesting that HJC0152 may exert its inhibition via down-regulation of protein synthesis and energy balance. Three major molecular networks connect HJC0152 to the cell cycle, cell morphology, cell death and survival, and protein synthesis (FIG. 22), consistent with the genes regulated by STAT3 in normal and cancer cells (Lai, C. F. et al., 1999; Hsieh, F. C. et al., 2005). These findings are in line with the early report that niclosamide disrupt mitochondrial membrane and ATP production (Park, S. J. et al., 2011), resulting consequent decreased protein synthesis and cell proliferation.

The inventors have considered that STAT3 may or may not be the direct target for HJC0152. The results presented herein support the idea that STAT3 is a major effector of HJC0152, as evidenced by the down-regulation of total STAT3 and its active forms both at Y705 and S727 phosphorylation site in in vitro and in vivo experiments, while other STAT family members and JAK2/JAK3 may be down-regulated via STAT3 inhibition from HJC0152. Without wishing to be bound by any theory, HJC0152 may indirectly inhibit STAT3 via multiple mechanisms such as interrupting ATP synthesis and reactive oxidative species resulting in mitochondrial fragmentation. Whether STAT3 has direct interaction with HJC0152 may be tested via affinity pull-down and other approaches. HJC0152 may be used to inhibit cancer progression and/or metastasis, as STAT3 is involved in the progression of cancer to metastasis. Since STAT3 is critically involved in early carcinogenesis of breast cancer, it is anticipated that compounds disclosed herein, such as HJC0152, may be used to either treat an existing cancer, or slow or prevent the development of a cancer in a subject such as a human patient.

\* \* \*

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,629,001
U.S. Pat. No. 6,613,308
U.S. Pat. No. 5,466,468
U.S. Pat. No. 5,543,158
U.S. Pat. No. 5,641,515
U.S. Pat. No. 5,580,579
U.S. Pat. No. 5,792,451
U.S. Pat. No. 5,399,363
U.S. Pat. No. 5,466,468
U.S. Pat. No. 5,756,353
U.S. Pat. No. 5,804,212
U.S. Pat. No. 5,725,871
U.S. Pat. No. 5,780,045
Anderson, N. G., *Practical Process Research & Development—A Guide For Organic Chemists*, $2^{nd}$ ed., Academic Press, New York, 2012.
*Handbook of Pharmaceutical Salts: Properties, and Use*, Stahl and Wermuth Eds.), Verlag Helvetica Chimica Acta, 2002.
*March's Advanced Organic Chemistry: Reactions, Mechanisms, and Structure*, 2007.
*Remington: The Science and Practice of Pharmacy*, $21^{st}$ Ed. Lippincott Williams and Wilkins, 2005.
*Remington's Pharmaceutical Sciences*, $18^{th}$ Ed. Mack Printing Company, 1990.
*Remington's Pharmaceutical Sciences*, $15^{th}$ Ed., 1035-1038 and 1570-1580, 1990.
T. Ara, R. Nakata, M. A. Sheard, H. Shimada, R. Buettner, S. G. Groshen, L. Ji, H. Yu, R. Jove, R. C. Seeger, Y. A. DeClerck, Critical role of STAT3 in IL-6-mediated drug resistance in human neuroblastoma. Cancer research 73 (2013) 3852-3864.
K. Babaoglu, B. K. Shoichet, Deconstructing fragment-based inhibitor discovery. Nat. Chem. Biol. 2 (2006) 720-723.
S. Barelier, I. Krimm, Ligand specificity, privileged substructures and protein druggability from fragment-based screening. Curr. Opin. Chem. Biol. 15 (2011) 469-474.
Becker, S.; Groner, B.; Müller, C. W. Three-dimensional structure of the Stat3beta homodimer bound to DNA. Nature 1998, 394, 145-151.
Y. Benjamini, Y. Hochberg, Controlling the false discovery rate: a practical and powerful approach to multiple testing. Journal of the Royal Statistical Society Series B 57 (1995) 289-300.
Bergström, C. A.; Wassvik, C. M.; Johansson, K.; Hubatsch, I. Poorly soluble marketed drugs display solvation limited solubility. J. Med. Chem. 2007, 50, 5858-5862.
B. M. Bolstad, R. A. Irizarry, M. Astrand, T. P. Speed, A comparison of normalization methods for high density oligonucleotide array data based on variance and bias. Bioinformatics 19 (2003) 185-193.
Bowman, T.; Garcia, R.; Turkson, J.; Jove, R. STATs in oncogenesis. Oncogene 2000, 19, 2474-2488.
Bromberg, J. F.; Wrzeszczynska, M. H.; Devgan, G.; Zhao, Y.; Pestell, R. G.; Albanese, C.; Darnell, J. E., Jr. Stat3 as an oncogene. Cell 1999, 98, 295-303.
Bromberg, J.; Darnell, J. E., Jr. The role of STATs in transcriptional control and their impact on cellular function. Oncogene 2000, 19, 2468-2473.
Bromberg, J. Stat proteins and oncogenesis. J. Clin. Invest. 2002, 109, 1139-1142.
Buettner, R.; Mora, L. B.; Jove, R. Activated STAT signaling in human tumors provides novel molecular targets for therapeutic intervention. Clin. Cancer Res. 2002, 8, 945-954.
G. Cai, H. Li, Y. Lu, X. Huang, J. Lee, P. Muller, Y. Ji, S. Liang, Accuracy of RNA-Seq and its dependence on sequencing depth. BMC Bioinformatics 13 Suppl 13 (2012) S5.
R. Catlett-Falcone, T. H. Landowski, M. M. Oshiro, J. Turkson, A. Levitzki, R. Savino, G. Ciliberto, L. Moscinski, J. L. Fernandez-Luna, G. Nunez, W. S. Dalton, R. Jove, Constitutive activation of Stat3 signaling confers resistance to apoptosis in human U266 myeloma cells. Immunity 10 (1999) 105-115.
Chapman R S, Lourenco P C, Tonner E, Flint D J, Seibert S, Takeda K, et al. Suppression of epithelial apoptosis and delayed mammary gland involution in mice with a conditional knockout of Stat3. *Genes Dev* 1999 Oct. 1; 13 (19): 2604-2616.
H. Chen, Z. Yang, C. Ding, L. Chu, Y. Zhang, K. Terry, H. Liu, Q. Shen, J. Zhou, Discovery of -Alkylamino Tethered Niclosamide Derivatives as Potent and Orally Bioavailable Anticancer Agents. ACS Med Chem Lett 4 (2013) 180-185.
H. Chen, Z. Yang, C. Ding, L. Chu, Y. Zhang, K. Terry, H. Liu, Q. Shen, J. Zhou, Fragment-based drug design and identification of HJC0123, a novel orally bioavailable STAT3 inhibitor for cancer therapy. Eur J Med Chem 62 (2013) 498-507.
Chen, J.; Bai, L.; Bernard, D.; Nikolovska-Coleska, Z.; Gomez, C.; Zhang, J.; Yi, H.; Wang, S. Structure-based design of conformationally constrained, cell-permeable STAT3 inhibitors. ACS Med. Chem. Lett. 2010, 1, 85-89.
Coletta R D, Jedlicka P, Gutierrez-Hartmann A, Ford H L. Transcriptional control of the cell cycle in mammary gland development and tumorigenesis. *J Mammary Gland Biol Neoplasia* 2004 January; 9 (1): 39-53.
L. Costantino, D. Barlocco, STAT3 as a target for cancer drug discovery. Curr. Med. Chem. 15 (2008) 834-843.
Darnell, J. E., Jr. STATs and gene regulation. Science 1997, 277, 1630-1635.
Darnell, J. E., Jr. Transcription factors as targets for cancer therapy. Nat. Rev. Cancer 2002, 2, 740-749.
Darnell, J. E., Jr. Validating Stat3 in cancer therapy. Nat. Med. 2005, 11, 595-596.
Debnath, B.; Xu, S.; Neamati, N. Small molecule inhibitors of signal transducer and activator of transcription 3 (Stat3) protein. J. Med. Chem. 2012, 55, 6645-6668.

Deng, J.; Grande, F.; Neamati, N. Small molecule inhibitors of Stat3 signaling pathway. Curr. Cancer Drug Targets 2007, 7, 91-107.

Elkihel, L.; Loiseau, P. M.; Bourass, J.; Gayral, P.; Letourneux, Y. Synthesis and orally macrofilaricidal evaluation of niclosamide lymphotropic prodrugs. Arzneimittelforschung 1994, 44, 1259-1264.

D. A. Erlanson, R. S. McDowell, T. O'Brien, Fragment-based drug discovery. J. Med. Chem. 47 (2004) 3463-3482.

D. Germain, D. A. Frank, Targeting the cytoplasmic and nuclear functions of signal transducers and activators of transcription 3 for cancer therapy. Clin. Cancer Res. 13 (2007) 5665-5669.

Haftchenary, S.; Avadisian, M.; Gunning, P. T. Inhibiting aberrant Stat3 function with molecular therapeutics: a progress report. Anticancer Drugs 2011, 22, 115-127.

P. J. Hajduk, Fragment-based drug design: how big is too big? J. Med. Chem. 49 (2006) 6972-6976.

P. J. Hajduk, J. Greer, A decade of fragment-based drug design: strategic advances and lessons learned. Nat. Rev. Drug Discovery 6 (2007) 211-219.

Hann, M. M.; Keserü, G. M. Finding the sweet spot: the role of nature and nurture in medicinal chemistry. Nat. Rev. Drug Discov. 2012, 11, 355-365.

S. Haricharan, Y. Li, STAT signaling in mammary gland differentiation, cell survival and tumorigenesis. Molecular and cellular endocrinology (2013).

E. B. Haura, J. Turkson, R. Jove, Mechanisms of disease: Insights into the emerging role of signal transducers and activators of transcription in cancer. Nat. Clin. Pract. Oncol. 2 (2005) 315-324.

T. Hirano, K. Ishihara, M. Hibi, Roles of STAT3 in mediating the cell growth, differentiation and survival signals relayed through the IL-6 family of cytokine receptors. Oncogene 19 (2000) 2548-2556.

A. Horiguchi, T. Asano, K. Kuroda, A. Sato, J. Asakuma, K. Ito, M. Hayakawa, M. Sumitomo, T. Asano, STAT3 inhibitor WP1066 as a novel therapeutic agent for renal cell carcinoma. Br. J. Cancer 102 (2010) 1592-1599.

F. C. Hsieh, G. Cheng, J. Lin, Evaluation of potential Stat3-regulated genes in human breast cancer. Biochem Biophys Res Commun 335 (2005) 292-299.

J. Hu, X. He, K. A. Baggerly, K. R. Coombes, B. T. Hennessy, G. B. Mills, Non-parametric quantification of protein lysate arrays. Bioinformatics 23 (2007) 1986-1994.

Ishikawa, M.; Hashimoto, Y. Improvement in aqueous solubility in small molecule drug discovery programs by disruption of molecular planarity and symmetry. J. Med. Chem. 2011, 54, 1539-1554.

A. Iwamaru, S. Szymanski, E. Iwado, H. Aoki, T. Yokoyama, I. Fokt, K. Hess, C. Conrad, T. Madden, R. Sawaya, S. Kondo, W. Priebe, Y. Kondo, A novel inhibitor of the STAT3 pathway induces apoptosis in malignant glioma cells both in vitro and in vivo. Oncogene 26 (2007) 2435-2444.

Jin, Y.; Lu, Z.; Ding, K.; Li, J.; Du, X.; Chen, C.; Sun, X.; Wu, Y.; Zhou, J.; Pan, J. Antineoplastic mechanisms of niclosamide in acute myelogenous leukemia stem cells: inactivation of the NF-kappaB pathway and generation of reactive oxygen species. Cancer Res. 2010, 70, 2516-2527.

P. A. Johnston, J. R. Grandis, STAT3 signaling: anticancer strategies and challenges. Mol. Interv. 11 (2011) 18-26.

H. Kida, S. Ihara, A. Kumanogoh, Involvement of STAT3 in immune evasion during lung tumorigenesis. Oncoimmunology 2 (2013) e22653.

B. H. Kim, C. Won, Y. H. Lee, J. S. Choi, K. H. Noh, S. Han, H. Lee, C. S. Lee, D. S. Lee, S. K. Ye, M. H. Kim, Sophoraflavanone G induces apoptosis of human cancer cells by targeting upstream signals of STATs. Biochemical pharmacology (2013).

S. Y. Kim, J. W. Kang, X. Song, B. K. Kim, Y. D. Yoo, Y. T. Kwon, Y. J. Lee, Role of the IL-6-JAK1-STAT3-Oct-4 pathway in the conversion of non-stem cancer cells into cancer stem-like cells. Cellular signalling 25 (2013) 961-969.

C. F. Lai, J. Ripperger, Y. Wang, H. Kim, R. B. Hawley, H. Baumann, The STAT3-independent signaling pathway by glycoprotein 130 in hepatic cells. J Biol Chem 274 (1999) 7793-7802.

A. Lavecchia, C. Di Giovanni, E. Novellino, STAT-3 inhibitors: state of the art and new horizons for cancer treatment. Curr. Med. Chem. 18 (2011) 2359-2375.

Leach, A. G.; Jones, H. D.; Cosgrove, D. A.; Kenny, P. W.; Ruston, L.; MacFaul, P.; Wood, J. M.; Colclough, N.; Law, B. Matched molecular pairs as a guide in the optimization of pharmaceutical properties; a study of aqueous solubility, plasma protein binding and oral exposure. J. Med. Chem. 2006, 49, 6672-6682.

H. Li, A. Liu, Z. Zhao, Y. Xu, J. Lin, D. Jou, C. Li, Fragment-based drug design and drug repositioning using multiple ligand simultaneous docking (MLSD): identifying celecoxib and template compounds as novel inhibitors of signal transducer and activator of transcription 3 (STAT3). J. Med. Chem. 54 (2011) 5592-5596.

Lipinski, C. A. Drug-like properties and the causes of poor solubility and poor permeability. J. Pharmacol. Toxicol. Methods 2000, 44, 235-249.

Liu X, Robinson G W, Wagner K U, Garrett L, Wynshaw-Boris A, Hennighausen L. Stat5a is mandatory for adult mammary gland development and lactogenesis. *Genes Dev* 1997 Jan. 15; 11 (2): 179-186.

Mandal, P. K.; Ren, Z.; Chen, X.; Xiong, C.; McMurray, J. S. Structure-affinity relationships of glutamine mimics incorporated into phosphopeptides targeted to the SH2 domain of signal transducer and activator of transcription 3. J. Med. Chem. 2009, 52, 6126-6141.

P. K. Mandal, F. Gao, Z. Lu, Z. Ren, R. Ramesh, J. S. Birtwistle, K. K. Kaluarachchi, X. Chen, R. C. Jr. Bast, W. S. Liao, J. S. McMurray, Potent and selective phosphopeptide mimetic prodrugs targeted to the Src Homology 2 (SH2) domain of signal transducer and activator of transcription 3. J. Med. Chem. 54 (2011) 3549-3563.

A. K. Mankan, F. R. Greten, Inhibiting signal transducer and activator of transcription 3: rationality and rationale design of inhibitors. Expert Opin. Invest. Drugs 20 (2011) 1263-1275.

K. Matsuno, Y. Masuda, Y. Uehara, H. Sato, A. Muroya, O. Takahashi, T. Yokotagawa, T. Furuya, T. Okawara, M. Otsuka, N. Ogo, T. Ashizawa, C. Oshita, S. Tai, H. Ishii, Y. Akiyama, A. Asai, Identification of a new series of STAT3 inhibitors by virtual screening. ACS Med. Chem. Lett. 1 (2010) 371-375.

The Merck Index, 13th ed.; Merck: Rahway, N Y, 2001.

Navab, M.; Ruchala, P.; Waring, A. J.; Lehrer, R. I.; Hama, S.; Hough, G.; Palgunachari, M. N.; Anantharamaiah, G. M.; Fogelman, A. M. A novel method for oral delivery of apolipoprotein mimetic peptides synthesized from all L-amino acids. J. Lipid Res. 2009, 50, 1538-1547.

G. Niu, K. L. Wright, M. Huang, L. Song, E. Haura, J. Turkson, S. Zhang, T. Wang, D. Sinibaldi, D. Coppola, R. Heller, L. M. Ellis, J. Karras, J. Bromberg, D. Pardoll, R. Jove, H. Yu, Constitutive Stat3 activity up-regulates VEGF expression and tumor angiogenesis. Oncogene 21 (2002) 2000-2008.

O'Neill, V. J.; Twelves, C. J. Oral cancer treatment: developments in chemotherapy and beyond. Br. J. Cancer 2002, 87, 933-937.

Osada, T.; Chen, M.; Yang, X. Y.; Spasojevic, I.; Vandeusen, J. B.; Hsu, D.; Clary, B. M.; Clay, T. M.; Chen, W.; Morse, M. A.; Lyerly, H. K. Antihelminth compound niclosamide downregulates Wnt signaling and elicits antitumor responses in tumors with activating APC mutations. Cancer Res. 2011, 71, 4172-4182.

Page, B. D.; Ball, D. P.; Gunning, P. T. Signal transducer and activator of transcription 3 inhibitors: a patent review. Expert Opin. Ther. Pat. 2011, 21, 65-83.

J. X. Pan, K. Ding, C. Y. Wang, Niclosamide, an old antihelminthic agent, demonstrates antitumor activity by blocking multiple signaling pathways of cancer stem cells. Chin J Cancer 31 (2012) 178-184.

S. J. Park, J. H. Shin, H. Kang, J. J. Hwang, D. H. Cho, Niclosamide induces mitochondria fragmentation and promotes both apoptotic and autophagic cell death. BMB Rep 44 (2011) 517-522.

P. F. Peddi, M. J. Ellis, C. Ma, Molecular basis of triple negative breast cancer and implications for therapy. Int J Breast Cancer 2012 (2012) 217185.

Ranger J J, Levy D E, Shahalizadeh S, Hallett M, Muller W J. Identification of a Stat3-dependent transcription regulatory network involved in metastatic progression. *Cancer Res* 2009 Sep. 1; 69 (17): 6823-6830.

D. C. Rees, M. Congreve, C. W. Murray, R. Carr, Fragment-based lead discovery. Nat. Rev. Drug Discovery 3 (2004) 660-672.

Ren X, Duan L, He Q., Zhang Z., Zhou, Y., Wu D., Pan J., Pei D., Ding K. Identification of Niclosamide as a New Small-Molecule Inhibitor of the STAT3 Signaling Pathway. ACS Med. Chem. Lett. 2010; 1:454-459.

P. Sansone, J. Bromberg, Targeting the interleukin-6/Jak/stat pathway in human malignancies. Journal of clinical oncology: official journal of the American Society of Clinical Oncology 30 (2012) 1005-1014.

C. W. Schindler, Series introduction. JAK-STAT signaling in human disease. J. Clin. Invest. 109 (2002) 1133-1137.

Schott, S.; Schneeweiss, A.; Reinhardt, J.; Bruckner, T.; Domschke, C.; Sohn, C.; Eichbaum, M. H. Acceptance of oral chemotherapy in breast cancer patients—a survey study. BMC Cancer 2011, 11, 129.

Schust, J., Sperl, B., Hollis, A., Mayer, T. U., Berg, T. Stattic: A Small-Molecule Inhibitor of STAT3 Activation and Dimerization. Chemistry & Biology 2006; 13, 1235-1242.

Q. Shen, I. P. Uray, Y. Li, T. I. Krisko, T. E. Strecker, H. T. Kim, P. H. Brown, The AP-1 transcription factor regulates breast cancer cell growth via cyclins and E2F factors. Oncogene 27 (2008) 366-377.

K. Siddiquee, S. Zhang, W. C. Guida, M. A. Blaskovich, B. Greedy, H. R. Lawrence, M. L. Yip, R. Jove, M. M. McLaughlin, N. J. Lawrence, S. M. Sebti, J. Turkson, Selective chemical probe inhibitor of Stat3, identified through structure-based virtual screening, induces antitumor activity. Proc. Natl. Acad. Sci. U.S.A 104 (2007) 7391-7396.

Siddiquee, K.; Turkson, J. STAT3 as a target for inducing apoptosis in solid and hematological tumors. Cell Res. 2008, 18, 254-267.

H. Song, R. Wang, S. Wang, J. Lin, A low-molecular-weight compound discovered through virtual database screening inhibits Stat3 function in breast cancer cells. Proc. Natl. Acad. Sci. U.S.A. 102 (2005) 4700-4705.

B. Spurrier, S. Ramalingam, S. Nishizuka, Reverse-phase protein lysate microarrays for cell signaling analysis. Nat Protoc 3 (2008) 1796-1808.

Takeda K, Clausen B E, Kaisho T, Tsujimura T, Terada N, Forster I, et al. Enhanced Th1 activity and development of chronic enterocolitis in mice devoid of Stat3 in macrophages and neutrophils. *Immunity* 1999 January; 10 (1): 39-49.

Takeda K, Kaisho T, Yoshida N, Takeda J, Kishimoto T, Akira S. Stat3 activation is responsible for IL-6-dependent T cell proliferation through preventing apoptosis: generation and characterization of T cell-specific Stat3-deficient mice. *J Immunol* 1998 Nov. 1; 161 (9): 4652-4660.

O. Trott, A. J. Olson, AutoDock Vina: improving the speed and accuracy of docking with a new scoring function, efficient optimization, and multithreading. J. Comput. Chem. 31 (2010) 455-461.

Turkson, J.; Jove, R. STAT proteins: novel molecular targets for cancer drug discovery. Oncogene 2000, 19, 6613-6626.

J. Turkson, D. Ryan, J. S. Kim, Y. Zhang, Z. Chen, E. Haura, A. Laudano, S. Sebti, A. D. Hamilton, R. Jove, Phosphotyrosyl peptides block Stat3-mediated DNA binding activity, gene regulation, and cell transformation. J. Biol. Chem. 276 (2001) 45443-45455.

J. Turkson, S. Zhang, J. Palmer, H. Kay, J. Stanko, L. B. Mora, S. Sebti, H. Yu, R. Jove, Inhibition of constitutive signal transducer and activator of transcription 3 activation by novel platinum complexes with potent antitumor activity. Mol. Cancer Ther. 3 (2004) 1533-1542.

Turkson J. STAT proteins as novel targets for cancer drug discovery. *Expert Opin Ther Targets* 2004 October; 8 (5): 409-422.

J. Turkson, S. Zhang, L. B. Mora, A. Burns, S. Sebti, R. Jove, A novel platinum compound inhibits constitutive Stat3 signaling and induces cell cycle arrest and apoptosis of malignant cells. J. Biol. Chem. 280 (2005) 32979-32988.

Vogel, G. H. Determination of solubility by hyphenated HPLC methods. In Drug Discovery and Evaluation: Safety and Pharmacokinetics Assay; Springer: New York, 2006; pp 400-402.

Watson C J. Stat transcription factors in mammary gland development and tumorigenesis. *J Mammary Gland Biol Neoplasia* 2001 January; 6 (1): 115-127.

Xiong, Y.; Teegarden, B. R.; Choi, J. S.; Strah-Pleynet, S.; Decaire, M.; Jayakumar, H.; Dosa, P. I.; Casper, M. D.; Pham, L.; Feichtinger, K.; Ullman, B.; Adams, J.; Yuskin, D.; Frazer, J.; Morgan, M.; Sadeque, A.; Chen, W.; Webb, R. R.; Connolly, D. T.; Semple, G.; Al-Shamma, H. Discovery and structure-activity relationship of 3-methoxy-N-(3-(1-methyl-1H-pyrazol-5-yl)-4-(2-morpholinoethoxy)phenyl)benzamide (APD791): a highly selective 5-hydroxytryptamine2A receptor inverse agonist for treatment of arterial thrombosis. J. Med. Chem. 2010, 53, 4412-4421.

Yeh Y T, Ou-Yang F, Chen I F, Yang S F, Wang Y Y, Chuang H Y, et al. STAT3 ser727 phosphorylation and its association with negative estrogen receptor status in breast infiltrating ductal carcinoma. *Int J Cancer* 2006 Jun. 15; 118 (12): 2943-2947.

Yu H, Jove R. The STATs of cancer—new molecular targets come of age. *Nat Rev Cancer* 2004 February; 4 (2): 97-105.

H. Yu, M. Kortylewski, D. Pardoll, Crosstalk between cancer and immune cells: role of STAT3 in the tumour microenvironment. Nat. Rev. Immunol. 7 (2007) 41-51.

Yu, H.; Pardoll, D.; Jove, R. STATs in cancer inflammation and immunity: a leading role for STAT3. Nat. Rev. Cancer 2009, 9, 798-809.

Yue, P.; Turkson, J. Targeting STAT3 in cancer: how successful are we? Expert Opin. Investig. Drugs 2009, 18, 45-56.

Zhang, X.; Yue, P.; Page, B. D.; Li, T.; Zhao, W.; Namanja, A. T.; Paladino, D.; Zhao, J.; Chen, Y.; Gunning, P. T.; Turkson, J. Orally bioavailable small-molecule inhibitor of transcription factor Stat3 regresses human breast and lung cancer xenografts. Proc. Natl. Acad. Sci. U.S.A. 2012, 109, 9623-9628.

M. Zhao, B. Jiang, F. H. Gao, Small molecule inhibitors of STAT3 for cancer therapy. Curr. Med. Chem. 18 (2011) 4012-4018.

Z. Zhong, Z. Wen, J. E. Jr. Darnell, Stat3: a STAT family member activated by tyrosine phosphorylation in response to epidermal growth factor and interleukin-6. Science 264 (1994) 95-98.

The invention claimed is:

1. A compound having the following structure:

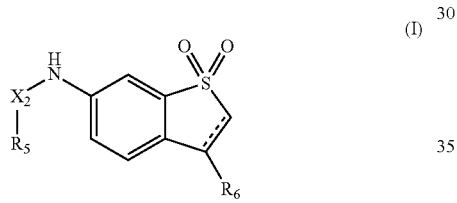

(I)

wherein $R_5$ is selected from the group consisting of alkyl$_{(C1-14)}$, substituted alkyl$_{(C1-14)}$, —H,

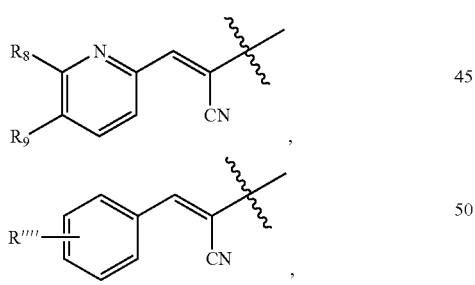

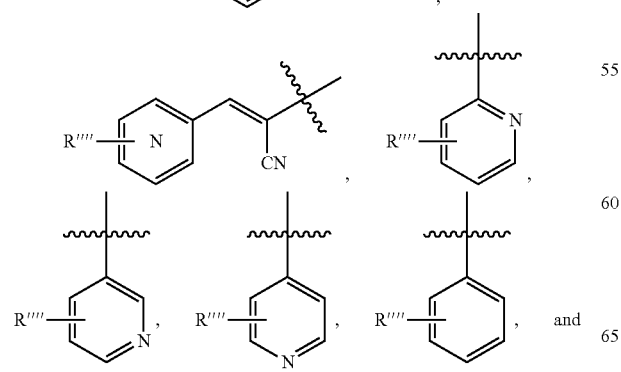

and

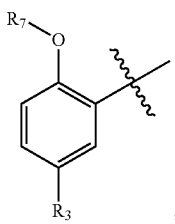

wherein $R_3$ is halogen, —OH, or —H; wherein $R_7$ is —H or $R_1$; wherein $R_8$ and $R_9$ are each independently —H or halogen; wherein $R_6$ is —H or —O—CH$_3$; wherein $X_2$ is —C(O)—; wherein R'''' is —H, —CF$_3$, —NO$_2$, —CN, halogen, alkyl$_{(C1-12)}$, alkoxy$_{(C1-12)}$, aryl$_{(C6-12)}$, heteroaryl$_{(C4-12)}$, substituted carboxylates$_{(C1-C12)}$, amido$_{(C1-C12)}$, substituted alkylamino$_{(C1-C12)}$, or —S(O)$_2$—X$_3$; wherein X$_3$ is —OH, —NH$_2$, —OCH$_3$, —OCH$_2$CH$_3$, —C(O)CH$_3$, —NHCH$_3$, —NHCH$_2$CH$_3$, —(CH$_3$)$_2$, —C(O)NH$_2$, or —OC(O)CH$_3$;

wherein $R_1$ is selected from the group consisting of substituted or unsubstituted alkyl$_{(C1-12)}$, substituted or unsubstituted heterocycloalkyl$_{(C4-12)}$, acyl$_{(C1-C6)}$, alkylamino$_{(C1-6)}$, alkoxyamino$_{(C1-6)}$,

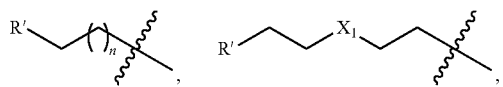

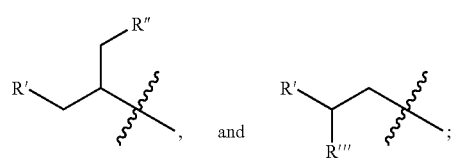

wherein $X_1$ is —O— or —NH—; wherein n=0, 1, 2, 3, 4, or 5; wherein R' is selected from the group consisting of substituted or unsubstituted alkyl$_{(C1-6)}$, alkylamino$_{(C1-6)}$, halogen, —OH, amido$_{(C1-12)}$, alkyl sulfonylamino$_{(C1-12)}$,

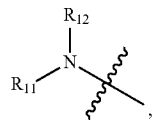

substituted or unsubstituted heterocycloalkyl$_{(C4-12)}$; wherein $R_{11}$ and $R_{12}$ are each independently —H or alkyl$_{(C1-6)}$; wherein R'' is —H, —OH, —NH$_2$, or halogen; wherein R''' is alkyl$_{(C1-6)}$;

or a salt thereof.

2. The compound of claim 1, wherein the compound is comprised in a pharmaceutical composition or a pharmaceutically acceptable carrier.

3. The compound of claim 1, wherein the compound has the structure

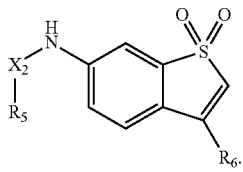

4. The compound of claim 1, wherein $R_6$ is —H.

5. The compound of claim 1, wherein $R_5$ is

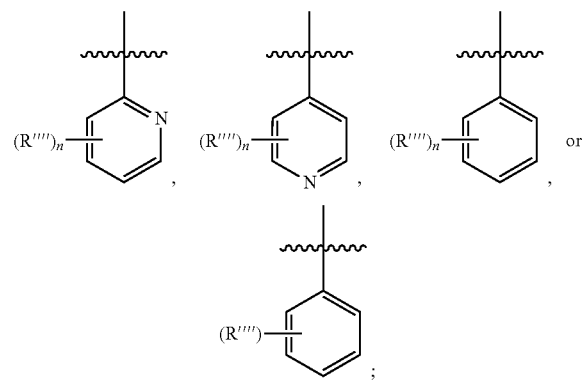

wherein n is 1, 2, 3, or 4.

6. The compound of claim 5, wherein R'''' is $aryl_{(C6-12)}$ or $heteroaryl_{(C4-12)}$, wherein said $aryl_{(C6-12)}$ or $heteroaryl_{(C4-12)}$ is fused or unfused.

7. The compound of claim 1, wherein $R_5$ is selected form the group consisting of

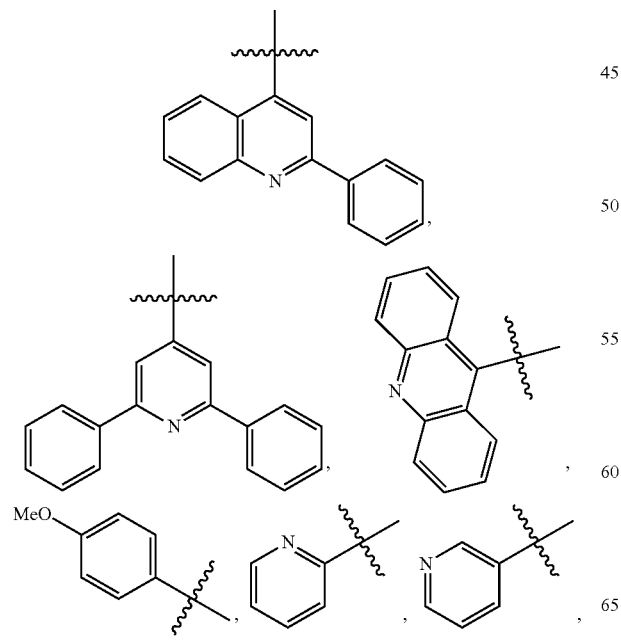

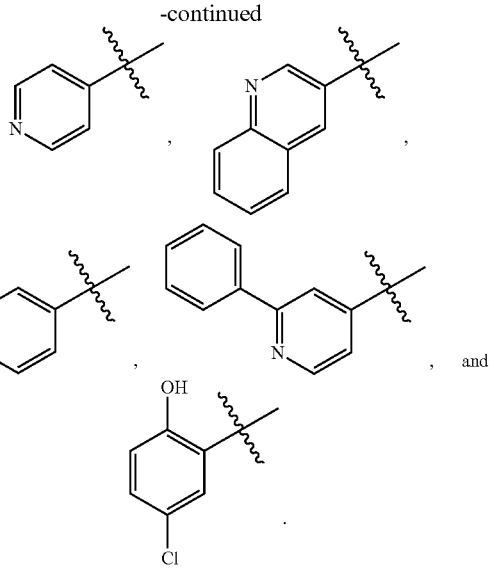

and

8. The compound of claim 1, wherein $R_5$ is

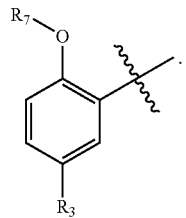

9. The compound of claim 8, wherein $R_3$ is —Cl.

10. The compound of claim 8, wherein $R_7$ is selected from the group consisting of —H, substituted $alkyl_{(C1-14)}$, substituted $heterocycloalkyl_{(C4-12)}$, substituted or unsubstituted $alkylamino_{(C1-14)}$, or $alkoxyamino_{(C1-12)}$.

11. The compound of claim 10, wherein $R_7$ is selected from the group consisting of —H,

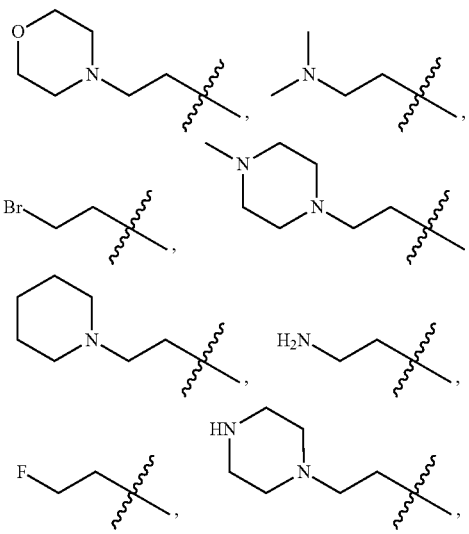

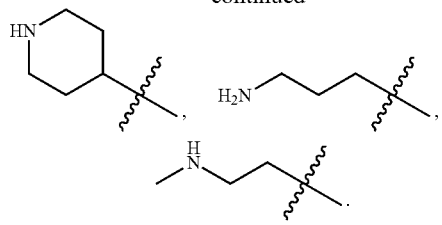
12. The compound of claim 1, wherein the compound is:
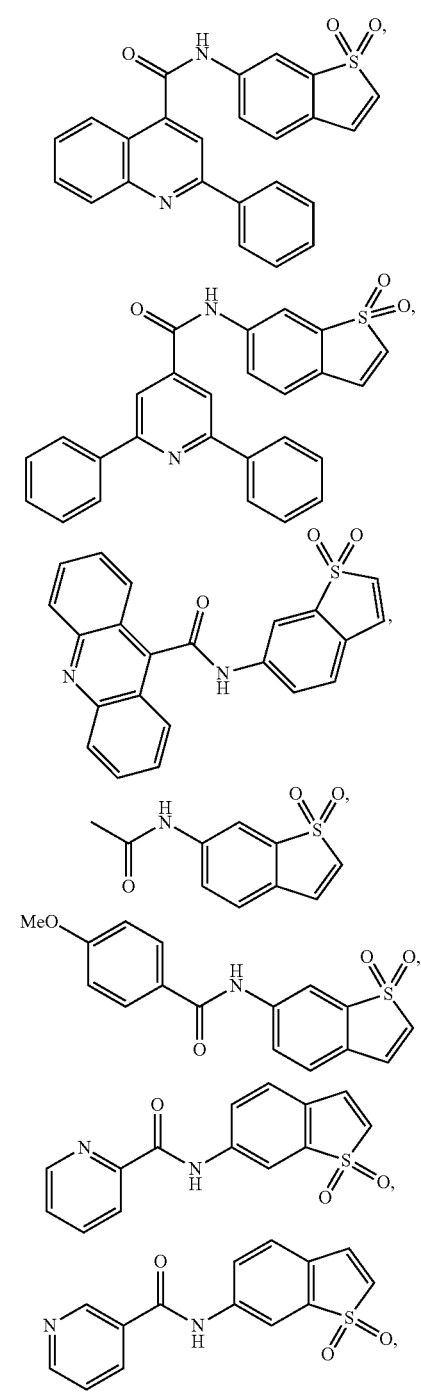
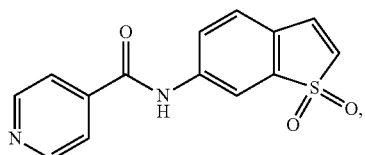
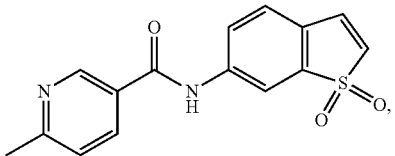
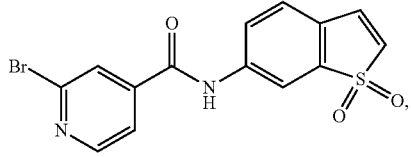
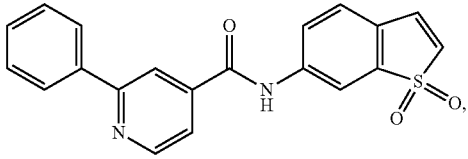
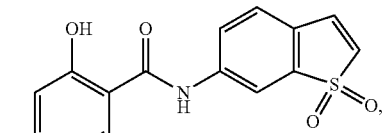
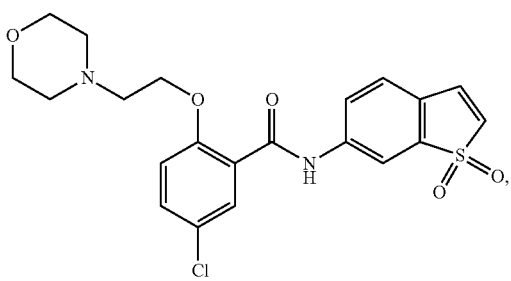
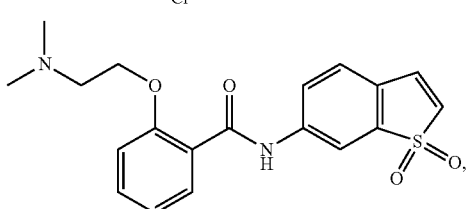
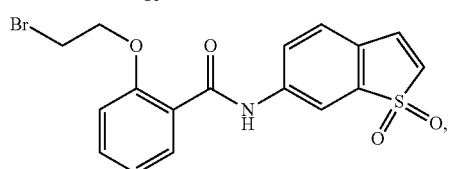

-continued
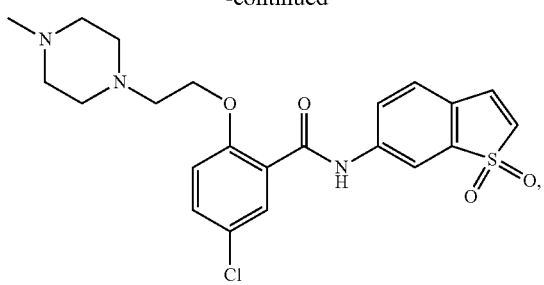
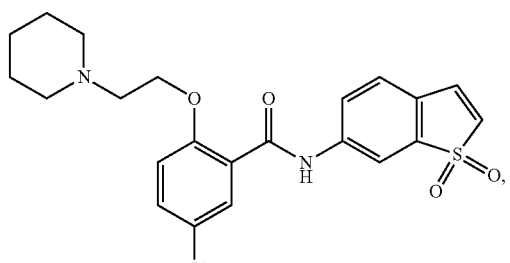
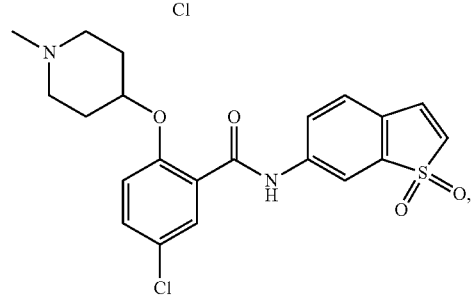
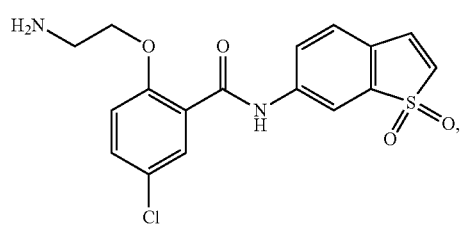
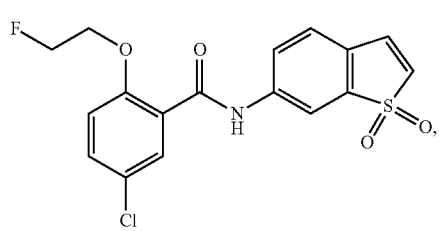
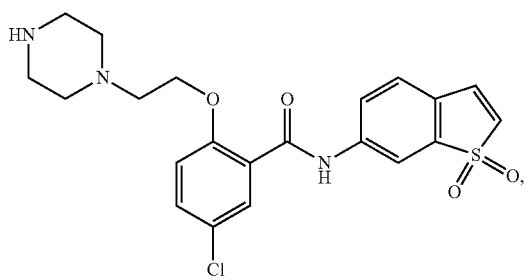
-continued
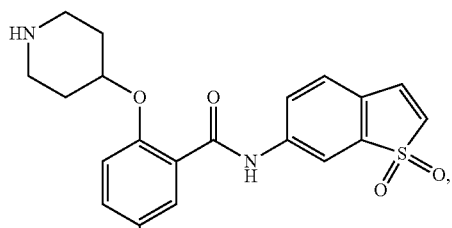
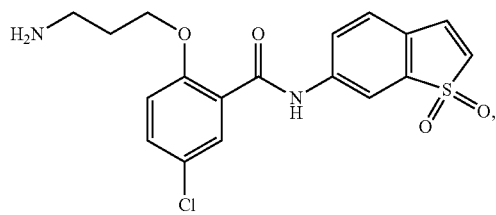
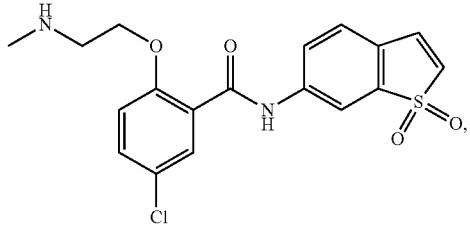
or a salt thereof.
13. The compound of claim 1, wherein the compound has the structure
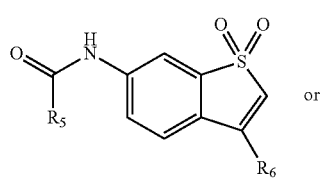
or
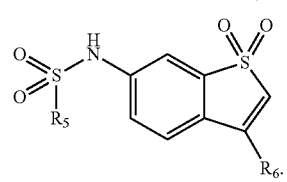
14. The compound of claim 1, wherein $R_6$ is —O—CH$_3$.
15. The compound of claim 14, wherein the compound has the structure:
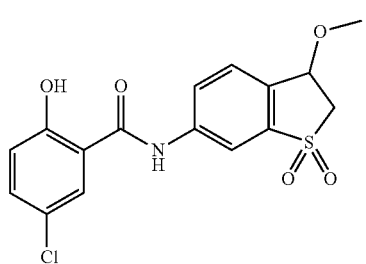
, -continued

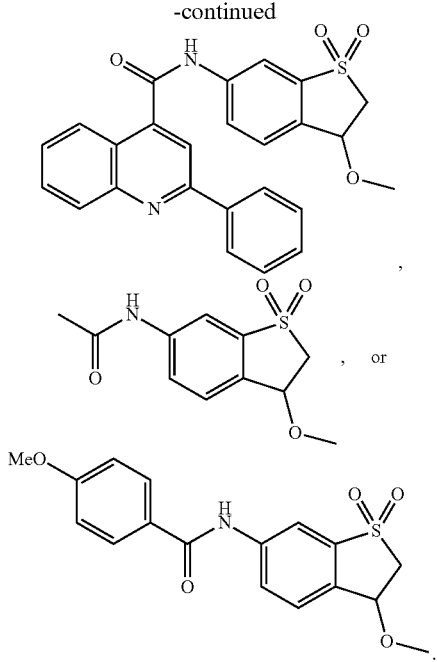

16. A method of treating cancer in a subject comprising administering a pharmaceutically effective amount of a compound of claim 1 to the subject to treat the cancer wherein the cancer is selected from pancreatic cancer, breast cancer, lung cancer, head/neck cancer, brain cancer, liver cancer, colon cancer and leukemia.

17. A method of treating inflammation in a subject comprising administering a pharmaceutically effective amount of a compound of claim 1 to the subject to treat the inflammation.

18. The compound of claim 12, wherein the compound is

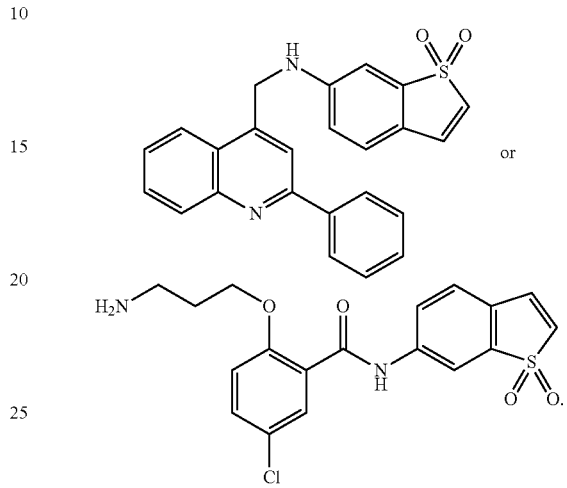

* * * * *

UNITED STATES PATENT AND TRADEMARK OFFICE
CERTIFICATE OF CORRECTION

PATENT NO. : 9,884,863 B2
APPLICATION NO. : 15/380798
DATED : February 6, 2018
INVENTOR(S) : Jia Zhou et al.

Page 1 of 2

It is certified that error appears in the above-identified patent and that said Letters Patent is hereby corrected as shown below:

In the Claims

In Claim 1, Column 184, Line 22, delete "—(CH$_3$)$_2$" and insert -- —N(CH$_3$)$_2$-- therefor.

In Claim 5, Column 185, Lines 17-25, delete second and third chemical drawings:

"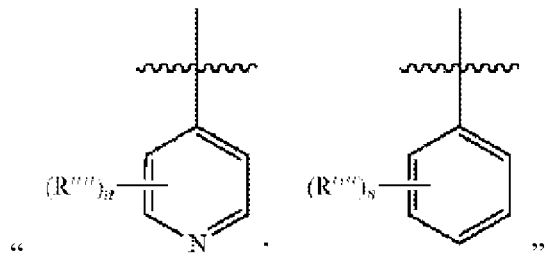"

And insert:

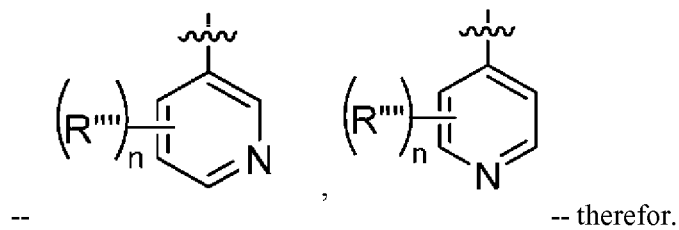

-- therefor.

Signed and Sealed this
Fifteenth Day of May, 2018

Andrei Iancu
*Director of the United States Patent and Trademark Office*

CERTIFICATE OF CORRECTION (continued)
U.S. Pat. No. 9,884,863 B2

In Claim 18, Column 192, Lines 10-20, delete chemical drawing:

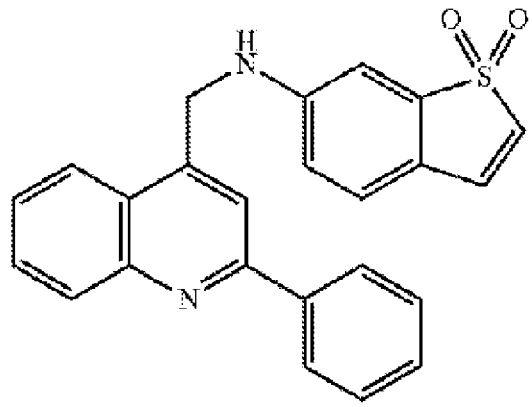

"                                                      "

And insert:

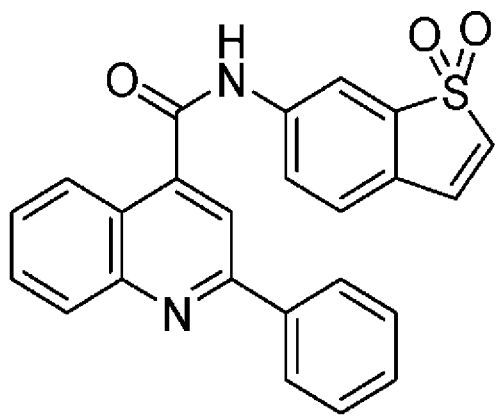

--                                                      -- therefor.